United States Patent
Johnson et al.

(10) Patent No.: US 12,414,997 B2
(45) Date of Patent: Sep. 16, 2025

(54) BRUSH PRODRUGS AND USES THEREOF

(71) Applicant: Massachusetts Institute of Technology, Cambridge, MA (US)

(72) Inventors: Jeremiah A. Johnson, Boston, MA (US); Farrukh Vohidov, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1148 days.

(21) Appl. No.: 17/047,279

(22) PCT Filed: Apr. 13, 2019

(86) PCT No.: PCT/US2019/027414
§ 371 (c)(1),
(2) Date: Oct. 13, 2020

(87) PCT Pub. No.: WO2019/200367
PCT Pub. Date: Oct. 17, 2019

(65) Prior Publication Data
US 2021/0386861 A1    Dec. 16, 2021
US 2022/0370628 A9    Nov. 24, 2022

Related U.S. Application Data

(60) Provisional application No. 62/657,715, filed on Apr. 13, 2018.

(51) Int. Cl.
*A61K 47/59*    (2017.01)
*A61K 31/138*   (2006.01)
(Continued)

(52) U.S. Cl.
CPC ............ *A61K 47/59* (2017.08); *A61K 31/138* (2013.01); *A61K 31/167* (2013.01);
(Continued)

(58) Field of Classification Search
CPC .............. C08G 61/08; C08G 2261/418; C08G 2261/136; C08G 2261/143;
(Continued)

(56) References Cited

U.S. PATENT DOCUMENTS 3,256,308 A    6/1966    Pawloski et al.
3,337,598 A    8/1967    Pawloski et al.
(Continued)

FOREIGN PATENT DOCUMENTS

CN    101412792 A    4/2009
CN    103037903 A    4/2013
(Continued)

OTHER PUBLICATIONS

Barnes, Jonathan et al "Using an RNAi Signature Assay to Guide the Design of Three-Drug-Conjugated Nanoparticles with Validated Mechanisms, In Vivo Efficacy, and Low Toxicity" Sep. 14, 2016 Journal of the American Chemical Society vol. 138 p. 12494-12501 (Year: 2016).*
(Continued)

*Primary Examiner* — Ling Siu Cho
*Assistant Examiner* — David L Miller
(74) *Attorney, Agent, or Firm* — Wolf, Greenfield & Sacks, P.C.

(57) ABSTRACT

The present disclosure provides, in some aspects, macromonomers of Formula (I), and salts thereof; methods of preparing the macromonomers, and salts thereof; Brush prodrugs (polymers); methods of preparing the Brush prodrugs; compounds of Formula (II); conjugates of Formula (III), and salts thereof; pharmaceutical compositions comprising a Brush prodrug, or a conjugate or a salt thereof; kits comprising: a macromonomer or a salt thereof, a Brush prodrug, a compound, a conjugate or a salt thereof, or a pharmaceutical composition; methods of using the Brush
(Continued)

prodrugs, or conjugates or salts thereof; and uses of the Brush prodrugs, and conjugates or salts thereof. These chemical entities may be useful in delivering pharmaceutical agents to a subject or cell.

41 Claims, 30 Drawing Sheets

(51) Int. Cl.
    *A61K 31/167*     (2006.01)
    *A61K 31/282*     (2006.01)
    *A61K 31/404*     (2006.01)
    *A61K 31/44*     (2006.01)
    *A61K 31/475*     (2006.01)
    *A61K 31/502*     (2006.01)
    *A61K 31/519*     (2006.01)
    *A61K 31/573*     (2006.01)
    *A61K 38/21*     (2006.01)
    *A61K 47/54*     (2017.01)
    *C07F 15/00*     (2006.01)
    *C08G 61/06*     (2006.01)
    *C08G 61/08*     (2006.01)

(52) U.S. Cl.
    CPC .......... *A61K 31/282* (2013.01); *A61K 31/404* (2013.01); *A61K 31/44* (2013.01); *A61K 31/475* (2013.01); *A61K 31/502* (2013.01); *A61K 31/519* (2013.01); *A61K 31/573* (2013.01); *A61K 38/212* (2013.01); *A61K 47/545* (2017.08); *C07F 15/0046* (2013.01); *C08G 61/08* (2013.01); *C08G 2261/136* (2013.01); *C08G 2261/1426* (2013.01); *C08G 2261/143* (2013.01); *C08G 2261/1432* (2013.01); *C08G 2261/418* (2013.01)

(58) Field of Classification Search
    CPC .......... C08G 2261/1432; A61K 47/545; A61K 31/138; A61K 31/167
    See application file for complete search history.

(56) References Cited

U.S. PATENT DOCUMENTS

| | | | |
|---|---|---|---|
| 4,359,425 A | 11/1982 | Totani et al. | |
| 4,510,136 A | 4/1985 | Moberg et al. | |
| 5,811,515 A | 9/1998 | Grubbs et al. | |
| 6,812,238 B1 | 11/2004 | Fukuda et al. | |
| 7,183,059 B2 | 2/2007 | Verdine et al. | |
| 8,067,505 B2 | 11/2011 | Harris et al. | |
| 8,968,920 B2 | 3/2015 | Lee et al. | |
| 9,381,253 B2 | 7/2016 | Johnson et al. | |
| 9,447,129 B2 | 9/2016 | Johnson et al. | |
| 9,822,216 B2 | 11/2017 | Mahanthappa et al. | |
| 10,023,536 B2 | 7/2018 | Johnson et al. | |
| 10,105,449 B2 | 10/2018 | Johnson et al. | |
| 10,153,513 B2 | 12/2018 | Grubbs et al. | |
| 10,159,749 B2 | 12/2018 | Johnson et al. | |
| 10,683,387 B2 | 6/2020 | Johnson et al. | |
| 10,716,858 B2 | 7/2020 | Johnson et al. | |
| 10,792,373 B2 | 10/2020 | Johnson et al. | |
| 10,793,683 B2 | 10/2020 | Johnson et al. | |
| 10,799,594 B2 | 10/2020 | Johnson et al. | |
| 10,961,338 B2 | 3/2021 | Johnson et al. | |
| 10,973,847 B2 | 4/2021 | Johnson et al. | |
| 10,988,491 B2 | 4/2021 | Johnson et al. | |
| 11,338,038 B2 | 5/2022 | Johnson et al. | |
| 11,752,221 B2 | 9/2023 | Johnson et al. | |
| 11,827,744 B2 | 11/2023 | Johnson et al. | |
| 11,897,905 B2 | 2/2024 | Johnson et al. | |
| 12,084,415 B2 | 9/2024 | Johnson et al. | |
| 2002/0183473 A1 | 12/2002 | Matyjaszewski et al. | |
| 2002/0198328 A1 | 12/2002 | L'Alloret | |
| 2003/0004364 A1 | 1/2003 | Yaghi et al. | |
| 2003/0065023 A1 | 4/2003 | Swindell et al. | |
| 2005/0109976 A1 | 5/2005 | Fuchs et al. | |
| 2008/0063937 A1 | 3/2008 | Lee et al. | |
| 2008/0248126 A1* | 10/2008 | Cheng .................. A61K 47/605 514/23 |
| 2011/0166128 A1 | 7/2011 | Remenar et al. | |
| 2011/0243848 A1 | 10/2011 | Appel et al. | |
| 2011/0300219 A1 | 12/2011 | Lippard et al. | |
| 2013/0296491 A1 | 11/2013 | Xia et al. | |
| 2013/0324666 A1 | 12/2013 | Yan et al. | |
| 2014/0024137 A1 | 1/2014 | Arya et al. | |
| 2014/0142249 A1 | 5/2014 | Cho et al. | |
| 2014/0308234 A1 | 10/2014 | Johnson et al. | |
| 2015/0225438 A1 | 8/2015 | Johnson et al. | |
| 2015/0291562 A1 | 10/2015 | Crew et al. | |
| 2016/0024246 A1 | 1/2016 | Mahanthappa et al. | |
| 2016/0289392 A1 | 10/2016 | Grubbs et al. | |
| 2016/0296631 A1 | 10/2016 | Johnson et al. | |
| 2016/0361702 A1 | 12/2016 | Cohen et al. | |
| 2017/0000909 A1 | 1/2017 | Gianneschi et al. | |
| 2017/0073311 A1 | 3/2017 | Johnson et al. | |
| 2017/0348431 A1 | 12/2017 | Johnson et al. | |
| 2018/0030213 A1 | 2/2018 | Johnson et al. | |
| 2018/0036415 A9 | 2/2018 | Johnson et al. | |
| 2018/0094099 A1 | 4/2018 | Johnson et al. | |
| 2018/0258233 A9 | 9/2018 | Johnson et al. | |
| 2018/0312634 A1 | 11/2018 | Chung et al. | |
| 2019/0030067 A1 | 1/2019 | Johnson et al. | |
| 2019/0038751 A1 | 2/2019 | Johnson et al. | |
| 2019/0038782 A1 | 2/2019 | Johnson et al. | |
| 2019/0054187 A1 | 2/2019 | Johnson et al. | |
| 2019/0192672 A1 | 6/2019 | Johnson et al. | |
| 2020/0055879 A1 | 2/2020 | Johnson et al. | |
| 2020/0123297 A1 | 4/2020 | Johnson et al. | |
| 2020/0239626 A1 | 7/2020 | Miyake et al. | |
| 2020/0261596 A1 | 8/2020 | Ali et al. | |
| 2020/0362095 A1 | 11/2020 | Johnson et al. | |
| 2020/0369685 A1 | 11/2020 | Johnson et al. | |
| 2021/0023224 A1 | 1/2021 | Johnson et al. | |
| 2021/0113701 A1 | 4/2021 | Johnson et al. | |
| 2021/0147598 A1 | 5/2021 | Johnson et al. | |
| 2021/0220391 A1 | 7/2021 | Johnson et al. | |
| 2021/0284664 A1 | 9/2021 | Johnson et al. | |
| 2021/0317143 A9 | 10/2021 | Johnson et al. | |
| 2021/0386861 A1 | 12/2021 | Johnson et al. | |
| 2023/0068959 A1 | 3/2023 | Johnson et al. | |
| 2023/0192610 A1 | 6/2023 | Johnson et al. | |
| 2024/0294555 A1 | 9/2024 | Johnson et al. | |

FOREIGN PATENT DOCUMENTS

| | | |
|---|---|---|
| CN | 103819486 A | 5/2014 |
| CN | 106132970 A | 11/2016 |
| CN | 106715437 A | 5/2017 |
| CN | 108727581 A | 11/2018 |
| DE | 2263509 A1 | 7/1974 |
| EP | 3315126 A1 | 5/2018 |
| EP | 3584245 A1 | 12/2019 |
| JP | H05-112739 A | 5/1993 |
| JP | 2004-517932 A | 6/2004 |
| JP | 2013-526549 A | 6/2013 |
| JP | 2022-549915 A | 11/2022 |
| KR | 20120113694 A | 10/2012 |
| WO | WO 2001/032652 A2 | 5/2001 |
| WO | WO 2006/052733 A1 | 5/2006 |
| WO | WO 2010/047765 A1 | 4/2010 |
| WO | WO 2011/084846 A1 | 7/2011 |
| WO | WO 2013/010676 A2 | 1/2013 |
| WO | WO 2013/116200 A1 | 8/2013 |
| WO | WO 2013/169739 A1 | 11/2013 |
| WO | WO 2014/004884 A1 | 1/2014 |
| WO | WO 2014/169073 A1 | 10/2014 |
| WO | WO 2015/117136 A1 | 8/2015 |
| WO | WO 2016/023036 A1 | 2/2016 |
| WO | WO 2016/172386 A1 | 10/2016 |
| WO | WO 2017/180834 A1 | 10/2017 |
| WO | WO 2017/205392 A1 | 11/2017 |

(56) References Cited

FOREIGN PATENT DOCUMENTS

| WO | WO 2018/073790 A1 | 4/2018 |
|---|---|---|
| WO | WO 2018/106738 A1 | 6/2018 |
| WO | WO 2018/149359 A1 | 8/2018 |
| WO | WO 2019/006426 A2 | 1/2019 |
| WO | WO 2019/200367 A1 | 10/2019 |
| WO | WO 2019/201123 A1 | 10/2019 |

OTHER PUBLICATIONS

International Search Report and Written Opinion for PCT/US2019/046872, mailed on Oct. 29, 2019.
International Preliminary Report on Patentability for PCT/US2019/046872, mailed on Mar. 4, 2021.
International Search Report and Written Opinion for PCT/US2020/023836, mailed on Jul. 7, 2020.
International Preliminary Report on Patentability for PCT/US2020/023836, mailed on Dec. 2, 2021.
Invitation to Pay Additional Fees for PCT/US2020/059827 mailed Feb. 4, 2021.
International Search Report and Written Opinion for PCT/US2020/059827 mailed Mar. 15, 2021.
International Preliminary Report on Patentability for PCT/US2020/059827 mailed Jul. 21, 2022.
Invitation to Pay Additional Fees for PCT/US2020/055862, mailed on Feb. 12, 2021.
International Search Report and Written Opinion for PCT/US2020/055862 mailed May 6, 2021.
International Preliminary Report on Patentability for PCT/US2020/055862 mailed Apr. 28, 2022.
International Search Report and Written Opinion for PCT/US2022/047333 mailed Jan. 25, 2023.
[No Author Listed], CAS Abstract of S. Masuoka et al., JP 05112739 (1993). CAS Registry File RN 150076-39-4. 2023. 7 pages.
Baslé et al., Protein chemical modification on endogenous amino acids. Chem Biol. Mar. 26, 2010;17(3):213-27. doi: 10.1016/j.chembiol.2010.02.008.
Beck et al., Strategies and challenges for the next generation of antibody-drug conjugates. Nat Rev Drug Discov. May 2017;16(5):315-337. doi: 10.1038/nrd.2016.268. Epub Mar. 17, 2017.
Blencowe et al., Ring-opening metathesis polymerization with the second generation Hoveyda-Grubbs catalyst: an efficient approach toward high-purity functionalized macrocyclic oligo(cyclooctene)s. J Am Chem Soc. Apr. 17, 2013;135(15):5717-25. doi: 10.1021/ja312418z. Epub Apr. 8, 2013.
Borke et al., Poly(glyceryl glycerol): A multi-functional hydrophilic polymer for labeling with boronic acids. Polym Chem. Jun. 1, 2017;55(11):1822-30. doi: 10.1002/pola.28497.
Burke et al., Development of Novel Quaternary Ammonium Linkers for Antibody-Drug Conjugates. Mol Cancer Ther. May 2016;15(5):938-45. doi: 10.1158/1535-7163.MCT-16-0038. Epub Mar. 4, 2016.
Cannon, J.G., Analog Design. In: Burger's Medicinal Chemistry and Drug Discovery, Fifth Edition, vol. I: Principles and Practice. 1995. Burger, Ed. Wiley Interscience. Chapter 19:783-802.
Clark et al., Dynamically Restructuring Hydrogel Networks Formed with Reversible Covalent Crosslinks. Advanced Materials. 2007;19:2503-2507. 10.1002/adma.200602649.
Collins et al., Chemical approaches to targeted protein degradation through modulation of the ubiquitin-proteasome pathway. Biochem J. Mar. 15, 2017;474(7):1127-1147. doi: 10.1042/BCJ20160762.
Corey et al., Diisopropylsilyl ditriflate and di-tert-butysilyl ditriflate: new reagents for the protection of diols. Tetrahedron Letters. 1982;23(47):4871-4874.
Dennler et al., Antibody Conjugates: From Heterogeneous Populations to Defined Reagents. Antibodies. Aug. 3, 2015;4(3):197-224. doi: 10.3390/antib4030197.
Dutta et al., Dilute solution structure of bottlebrush polymers. Soft Matter. Apr. 3, 2019;15(14):2928-2941. doi: 10.1039/c9sm00033j.
Ekladious et al., Polymer-drug conjugate therapeutics: advances, insights and prospects. Nat Rev Drug Discov. Apr. 2019;18(4):273-294. doi: 10.1038/s41573-018-0005-0.
Evans, R.A., The Rise of Azide-Alkyne 1,3-Dipolar 'Click' Cycloaddition and its Application to Polymer Science and Surface Modification. Aust J Chem. Jun. 18, 2007;60(6):384-95. doi: 10.1071/CH06457.
Fiers et al., Orthogonal Synthesis of Xeno Nucleic Acids. Chemistry. Dec. 12, 2016;22(50):17945-17948. doi: 10.1002/chem.201604386. Epub Nov. 3, 2016.
Foster et al., Getting into Shape: Reflections on a New Generation of Cylindrical Nanostructures' Self-Assembly Using Polymer Building Blocks. J Am Chem Soc. Feb. 20, 2019;141(7):2742-2753. doi: 10.1021/jacs.8b08648. Epub Feb. 8, 2019.
Fu et al., Relay Conjugation of Living Metathesis Polymers. J Am Chem Soc. Sep. 26, 2018;140(38):12181-12188. doi: 10.1021/jacs.8b07315. Epub Sep. 11, 2018.
Furstner et al., Alkyne metathesis: development of a novel molybdenum-based catalyst system and its application to the total synthesis of epothilone A and C. Chem Eur J. Dec. 17, 2001;7(24):5299-317. doi: 10.1002/1521-3765(Dec. 17, 2001)7:24<5299::aid-chem5299>3.0.co;2-x.
Furstner et al., Mo[N(t-Bu)(Ar)]$_3$ Complexes As Catalyst Precursors: In Situ Activation and Application to Metathesis Reactions of Alkynes and Diynes. J Am Chem Soc. Sep. 23, 1999;121(40):9453-4. doi: 10.1021/ja991340r.
Gallivan et al., A neutral, water-soluble olefin metathesis catalyst based on an N-heterocyclic carbene ligand. Tetrahedron Lett. Apr. 11, 2005;46(15):2577-80. doi: 10.1016/j.tetlet.2005.02.096.
Grubbs et al., Ring-Closing Metathesis and Related Processes in Organic Synthesis. Acc Chem Res. Nov. 1, 1995;28(11):446-52. doi: 10.1021/ar00059a002.
Gupta et al., Cell protective, ABC triblock polymer-based thermoresponsive hydrogels with ROS-triggered degradation and drug release. J Am Chem Soc. Oct. 22, 2014;136(42):14896-902. doi: 10.1021/ja507626y. Epub Oct. 7, 2014.
Hamblett et al., Effects of drug loading on the antitumor activity of a monoclonal antibody drug conjugate. Clin Cancer Res. Oct. 15, 2004;10(20):7063-70. doi: 10.1158/1078-0432.CCR-04-0789.
Hoye et al., Silicon tethered ring-closing metathesis reactions for self- and cross-coupling of alkenols. Tetrahedron Letters. Feb. 19, 1999;40(8):1429-1432.
Knall et al., Inverse electron demand Diels-Alder (iEDDA)-initiated conjugation: a (high) potential click chemistry scheme. Chem Soc Rev. Jun. 21, 2013;42(12):5131-42. doi: 10.1039/c3cs60049a.
Kodger, T., Mechanical Failure in Colloidal Gels. Dissertation. Harvard University. Dec. 2014. 255 pages.
Kumar et al., Multivalency in the recognition and antagonism of a HIV TAR RNA-TAT assembly using an aminoglycoside benzimidazole scaffold. Org Biomol Chem. Feb. 14, 2016;14(6):2052-6. doi: 10.1039/c5ob02016f.
Lambert et al., Ado-trastuzumab Emtansine (T-DM1): an antibody-drug conjugate (ADC) for HER2-positive breast cancer. J Med Chem. Aug. 28, 2014;57(16):6949-64. doi: 10.1021/jm500766w. Epub Jul. 10, 2014.
Li et al., Thermoresponsive PNIPAAM bottlebrush polymers with tailored side-chain length and end-group structure. Soft Matter. Mar. 28, 2014;10(12):2008-15. doi: 10.1039/c3sm52614c.
Luginbuhl et al., One-week glucose control via zero-order release kinetics from an injectable depot of glucagon-like peptide-1 fused to a thermosensitive biopolymer. Nat Biomed Eng. 2017;1:0078. doi: 10.1038/s41551-017-0078. Epub Jun. 5, 2017.
Lyon et al., Reducing hydrophobicity of homogeneous antibody-drug conjugates improves pharmacokinetics and therapeutic index. Nat Biotechnol. Jul. 2015;33(7):733-5. doi: 10.1038/nbt.3212. Epub Jun. 15, 2015.
Manyeruke et al., Synthesis and evaluation of 3-hydroxy-3-phenylpropanoate ester-AZT conjugates as potential dual-action HIV-1 Integrase and Reverse Transcriptase inhibitors. Bioorg Med Chem. Dec. 15, 2015;23(24):7521-8. doi: 10.1016/j.bmc.2015.10.039.
Nguyen et al., Scalable Synthesis of Multivalent Macromonomers for ROMP. ACS Macro Lett. Apr. 17, 2018;7(4):472-476. doi: 10.1021/acsmacrolett.8b00201. Epub Mar. 26, 2018.

(56) References Cited

OTHER PUBLICATIONS

Nishimura et al., Rhodium-Catalyzed Asymmetric Cycloisomerization of 1,6-Ene-ynamides. Adv Synth Catal. May 3, 2013;355(7):1374-82. doi: 10.1002/adsc.201300148.

Ohwada et al., Design, synthesis and antifungal activity of a novel water soluble prodrug of antifungal triazole. Bioorg Med Chem Lett. Jan. 20, 2003;13(2):191-6. doi: 10.1016/s0960-894x(02)00892-2.

Panchamoorthy et al., Targeting the human MUC1-C oncoprotein with an antibody-drug conjugate. JCI Insight. Jun. 21, 2018;3(12):e99880. doi: 10.1172/jci.insight.99880.

Qi et al., A brush-polymer conjugate of exendin-4 reduces blood glucose for up to five days and eliminates poly(ethylene glycol) antigenicity. Nat Biomed Eng. 2016;1:0002. doi: 10.1038/s41551-016-0002. Epub Nov. 28, 2016.

Qiu et al., ROMP synthesis of benzaldehyde-containing amphiphilic block polynorbornenes used to conjugate drugs for pH-responsive release. React Func Polym. Jul. 2018;128:1-15. doi: 10.1016/j.reactfunctpolym.2018.03.010.

Sakamoto et al., Protacs: chimeric molecules that target proteins to the Skp1-Cullin-F box complex for ubiquitination and degradation. Proc Natl Acad Sci U S A. Jul. 17, 2001;98(15):8554-9. doi: 10.1073/pnas.141230798. Epub Jul. 3, 2001.

Schrock et al., Tungsten(VI) neopentylidyne complexes. Organometallics. Dec. 1, 1982;1(12):1645-51. doi: 10.1021/om00072a018.

Shibuya et al., Mikto-Brush-Arm Star Polymers via Cross-Linking of Dissimilar Bottlebrushes: Synthesis and Solution Morphologies. ACS Macro Lett. Sep. 19, 2017;6(9):963-968. doi: 10.1021/acsmacrolett.7b00529. Epub Aug. 21, 2017.

Shieh et al., Tailored silyl ether monomers enable backbone-degradable polynorbornene-based linear, bottlebrush and star copolymers through ROMP. Nat Chem. Dec. 2019;11(12):1124-1132. doi: 10.1038/s41557-019-0352-4. Epub Oct. 28, 2019.

Smith et al., Modular synthesis of biologically active phosphatidic acid probes using click chemistry. Mol Biosyst. Sep. 2009;5(9):962-72. doi: 10.1039/b901420a. Epub May 7, 2009.

Sowers et al., Redox-responsive branched-bottlebrush polymers for in vivo MRI and fluorescence imaging. Nat Commun. Nov. 18, 2014;5:5460. doi: 10.1038/ncomms6460.

Staben et al., Targeted drug delivery through the traceless release of tertiary and heteroaryl amines from antibody-drug conjugates. Nat Chem. Dec. 2016;8(12):1112-1119. doi: 10.1038/nchem.2635. Epub Oct. 17, 2016.

Tian et al., Selective esterase-ester pair for targeting small molecules with cellular specificity. Proc Natl Acad Sci U S A. Mar. 27, 2012;109(13):4756-61. doi: 10.1073/pnas.1111943109. Epub Mar. 12, 2012.

Tinworth et al., Small molecule-mediated protein knockdown as a new approach to drug discovery. Med Chem Commun. Jul. 26, 2016;7:2206-16. doi: 10.1039/C6MD00347H.

Tolcher et al., Randomized phase II study of BR96-doxorubicin conjugate in patients with metastatic breast cancer. J Clin Oncol. Feb. 1999;17(2):478-84. doi: 10.1200/JCO.1999.17.2.478.

Trail et al., Cure of xenografted human carcinomas by BR96-doxorubicin immunoconjugates. Science. Jul. 9, 1993;261(5118):212-5. doi: 10.1126/science.8327892. Erratum in: Science Feb. 25, 1994;263(5150):1076.

Tu et al., Recent advances towards applications of molecular bottlebrushes and their conjugates. Curr Opin Solid State Mater Sci. Feb. 2019;23(1):50-61. doi: 10.1016/j.cossms.2019.01.003.

Venkatesh et al., Role of the development scientist in compound lead selection and optimization. J Pharm Sci. Feb. 2000;89(2):145-54. doi: 10.1002/(SICI)1520-6017(200002)89:2<145::AID-JPS2>3.0.CO;2-6.

Vohidov et al., Design of BET Inhibitor Bottlebrush Prodrugs with Superior Efficacy and Devoid of Systemic Toxicities. J Am Chem Soc. Mar. 31, 2021;143(12):4714-4724. doi: 10.1021/jacs.1c00312. Epub Mar. 19, 2021. Author Manuscript, 18 pages.

Xiao et al., Precision glycocalyx editing as a strategy for cancer immunotherapy. Proc Natl Acad Sci U S A. Sep. 13, 2016;113(37):10304-9. doi: 10.1073/pnas.1608069113. Epub Aug. 22, 2016.

Xu et al., Site-specific labeling of an anti-MUC1 antibody: probing the effects of conjugation and linker chemistry on the internalization process. RSC Adv. Jan. 15, 2019;9(4):1909-1917. doi: 10.1039/c8ra09902b.

Yan et al., The relationship among pKa, pH, and binding constants in the interactions between boronic acids and diols-it is not as simple as it appears. Tetrahedron. Nov. 29, 2004;60(49):11205-11209.

Yurkovetskiy et al., A Polymer-Based Antibody-Vinca Drug Conjugate Platform: Characterization and Preclinical Efficacy. Cancer Res. Aug. 15, 2015;75(16):3365-72. doi: 10.1158/0008-5472.CAN-15-0129. Epub Jun. 25, 2015.

Yurkovetskiy et al., Fully degradable hydrophilic polyals for protein modification. Biomacromolecules. Sep.-Oct. 2005;6(5):2648-58. doi: 10.1021/bm049210k.

Zhang et al., Convergent Synthesis of Branched Metathesis Polymers with Enyne Reagents. Macromolecules. Sep. 28, 2021;54(18):8435-8442. doi: 10.1021/acs.macromol.1c01051. Epub Sep. 8, 2021.

Zhang et al., Practical Synthesis of Functional Metathesis Initiators Using Enynes. Macromol. Aug. 16, 2018;51(16):6497-503. doi: 10.1021/acs.macromol.8b00866.

International Search Report and Written Opinion for PCT/US2019/027414, mailed on Sep. 12, 2019.

International Preliminary Report on Patentability for PCT/US2019/027414, mailed on Oct. 22, 2020.

Gao et al., Synthesis of Acid-Labile PEG and PEG-Doxorubicin-Conjugate Nanoparticles via Brush-First ROMP. ACS Macro Lett. Sep. 16, 2014;3(9):854-857. doi: 10.1021/mz5004097. Epub Aug. 13, 2014. PMID: 25243099; PMCID: PMC4165536.

Extended European Search Report for EP 14782253.0, mailed Nov. 11, 2016.

International Preliminary Report on Patentability for PCT/US2014/033554, mailed Oct. 22, 2015.

International Search Report and Written Opinion for PCT/US2014/033554, mailed Aug. 29, 2014.

International Search Report for PCT/US2017/036447, mailed Sep. 7, 2017.

International Preliminary Report on Patentability for Application No. PCT/US2017/036447 mailed Dec. 20, 2018.

International Search Report and Written Opinion for PCT/US2017/055145, mailed Jan. 23, 2018.

International Preliminary Report on Patentability for PCT/US2017/055145, mailed Apr. 18, 2019.

International Search Report and Written Opinion for PCT/US2017/064784, mailed Mar. 1, 2018.

International Preliminary Report on Patentability for PCT/US2017/064784, mailed Jun. 20, 2019.

International Search Report for PCT/US2017/48641, mailed Nov. 9, 2017.

International Preliminary Report on Patentability for Application No. PCT/US2017/48641 mailed Mar. 7, 2019.

International Search Report and Written Opinion for PCT/US2018/040488, mailed Oct. 15, 2018.

International Preliminary Report on Patentability for PCT/US2018/040488, mailed Jan. 9, 2020.

International Search Report and Written Opinion for PCT/US2018/040494, mailed Oct. 10, 2018.

International Preliminary Report on Patentability for PCT/US2018/040494, mailed Jan. 9, 2020.

Invitation to Pay Additional Fees for PCT/US2018/040496, mailed on Nov. 21, 2018.

International Search Report and Written Opinion for Application No. PCT/US2018/040496 mailed Jan. 14, 2019.

International Preliminary Report on Patentability for PCT/US2018/040496, mailed Jan. 9, 2020.

Aguirre-Chagala et al., Phenylboronic Acid-Installed Polycarbonates for the ph-Dependent Release of Diol-Containing Molecules. ACS Macro Letters. Nov. 20, 2014;3(12):1249-1253.

(56) References Cited

OTHER PUBLICATIONS

Ahn et al., Two-photon fluorescence microscopy imaging of cellular oxidative stress using profluorescent nitroxides. J Am Chem Soc. Mar. 14, 2012;134(10):4721-30. doi: 10.1021/ja210315x. Epub Mar. 1, 2012.
Aime et al., Lanthanide(III) chelates for NMR biomedical applications. Chem. Soc. Rev., 1998;27:19-29.
Aime et al., Pushing the sensitivity envelope of lanthanide-based magnetic resonance imaging (MRI) contrast agents for molecular imaging applications. Acc Chem Res. Jul. 21, 2009;42(7):822-31. doi: 10.1021/ar800192p.
Alge et al., Synthetically tractable click hydrogels for three-dimensional cell culture formed using tetrazine-norbornene chemistry. Biomacromolecules. Apr. 8, 2013;14(4):949-53. doi: 10.1021/bm4000508. Epub Mar. 8, 2013.
Altintas et al., Constructing star polymersvia modular ligation strategies. Polym. Chem., 2012;3:34-45. DOI: 10.1039/C1PY00249J.
Alvaradejo et al., Polyoxazoline-Based Bottlebrush and Brush-Arm Star Polymers via ROMP: Syntheses and Applications as Organic Radical Contrast Agents. ACS Macro Lett. Apr. 16, 2019;8(4):473-478. doi: 10.1021/acsmacrolett.9b00016. Epub Apr. 4, 2019. PMID: 31289694; PMCID: PMC6615754.
Amouri et al., Host-guest interactions: design strategy and structure of an unusual cobalt cage that encapsulates a tetrafluoroborate anion. Angew Chem Int Ed Engl. Jul. 18, 2005;44(29):4543-6.
Anderson, Late Transition Metal Complexes of Pentafluorophenylphosphino-Pincer Ligands. Doctoral Thesis. Victoria University of Wellington. 2012:ii, iii, 32.
Angelov et al., EPR and rheological study of hybrid interfaces in gold-clay-epoxy nanocomposites. Langmuir. Nov. 11, 2014;30(44):13411-21. doi: 10.1021/la503361k. Epub Oct. 30, 2014.
Angot et al., Living Radical Polymerization Immobilized on Wang Resins: Synthesis and Harvest of Narrow Polydispersity Poly(methacrylate)s. Macromolecules, 2001;34(4):768-774. DOI: 10.1021/ma0011690.
Anraku et al., Size-controlled long-circulating PICsome as a ruler to measure critical cut-off disposition size into normal and tumor tissues. Chem Commun (Camb). Jun. 7, 2011;47(21):6054-6. doi: 10.1039/c1cc11465d. Epub Apr. 26, 2011.
Arvizo et al., Modulating pharmacokinetics, tumor uptake and biodistribution by engineered nanoparticles. PLoS One. 2011;6(9):e24374. doi: 10.1371/journal.pone.0024374. Epub Sep. 13, 2011.
Aryal et al., Polymeric nanoparticles with precise ratiometric control over drug loading for combination therapy. Mol Pharm. Aug. 1, 2011;8(4):1401-7. doi: 10.1021/mp200243k. Epub Jul. 6, 2011.
Bapat et al., Dynamic-covalent nanostructures prepared by Diels-Alder reactions of styrene-maleic anhydride-derived copolymers obtained by one-step cascade block copolymerization. Polym. Chem., 2012;3:3112-3120. DOI: 10.1039/C2PY20351K.
Bapat et al., Redox-Responsive Dynamic-Covalent Assemblies: Stars and Miktoarm Stars. Macromolecules, 2013;46(6):2188-2198. DOI: 10.1021/ma400169m.
Barbour et al., An intermolecular (H2O)10 cluster in a solid-state supramolecular complex. Nature. 1998;393(6686): 671-673.
Barner et al., Synthesis of core-shell poly(divinylbenzene) microspheres via reversible addition fragmentation chain transfer graft polymerization of styrene. J. Polym. Sci. A Polym. Chem., 42: 5067-5076. doi:10.1002/pola.20328.
Barnes et al., Using an RNAi Signature Assay To Guide the Design of Three-Drug-Conjugated Nanoparticles with Validated Mechanisms, In Vivo Efficacy, and Low Toxicity. J Am Chem Soc. Sep. 28, 2016;138(38):12494-501. doi: 10.1021/jacs.6b06321. Epub Sep. 14, 2016.
Barrett et al., pH-Based Regulation of Hydrogel Mechanical Properties Through Mussel-Inspired Chemistry and Processing. Advanced Functional Materials. Mar. 6, 2013;23(9):1111-1119.

Bar-Shir et al., Single 19F Probe for Simultaneous Detection of Multiple Metal Ions Using miCEST MRI. J. Am. Chem. Soc., 2015;137(1):78-81. DOI: 10.1021/ja511313k.
Bates et al., Polarity-switching top coats enable orientation of sub-10-nm block copolymer domains. Science. Nov. 9, 2012;338(6108):775-9. doi: 10.1126/science.1226046.
Beck et al., Multistimuli, multiresponsive metallo-supramolecular polymers. J Am Chem Soc. Nov. 19, 2003;125(46):13922-3.
Bender et al., Site-isolated luminescent europium complexes with polyester macroligands: metal-centered heteroarm stars and nanoscale assemblies with labile block junctions. J Am Chem Soc. Jul. 24, 2002;124(29):8526-7.
Blencowe et al., Core cross-linked star polymers via controlled radical polymerisation. Polymer Jan. 2009;50(1):5-32.
Blinco et al., Profluorescent Nitroxides as Sensitive Probes of Oxidative Change and Free Radical Reactions. Australian Journal of Chemistry 2010;64(4):373-389. https://doi.org/10.1071/CH10442.
Boase et al., Molecular imaging with polymers. Polym. Chem., 2012,3, 1384-1389. DOI: 10.1039/C2PY20132A.
Bobko et al., Reversible reduction of nitroxides to hydroxylamines: roles for ascorbate and glutathione. Free Radic Biol Med. Feb. 1, 2007;42(3):404-12. Epub Nov. 10, 2006.
Bohbot-Raviv et al., Discovering new ordered phases of block copolymers. Phys Rev Lett. Oct. 16, 2000;85(16):3428.
Bolton et al., Synthesis and Melt Self-Assembly of PS-PMMA-PLA Triblock Bottlebrush Copolymers. Macromolecules, 2014;47(9):2864-74. DOI: 10.1021/ma500625k.
Brasch et al., Work in progress: nuclear magnetic resonance study of a paramagnetic nitroxide contrast agent for enhancement of renal structures in experimental animals. Radiology. Jun. 1983;147(3):773-9.
Brasch, Work in progress: methods of contrast enhancement for NMR imaging and potential applications. A subject review. Radiology. Jun. 1983;147(3):781-8.
Brummelhuis et al., Stimuli-responsive star polymers through thiol-yne core functionalization/crosslinking of block copolymer micelles. Polym. Chem., 2011;2:1180-1184. DOI: 10.1039/C1PY00002K.
Budil et al., Nonlinear-Least-Squares Analysis of Slow-Motion EPR Spectra in One and Two Dimensions Using a Modified Levenberg-Marquardt Algorithm. Elsevier. Journal of Magnetic Resonance, Series A. Jun. 1996;120(2):155-189.
Buerkle et al., Supramolecular gels formed from multi-component low molecular weight species. Chem Soc Rev. Sep. 21, 2012;41(18):6089-102. doi: 10.1039/c2cs35106d. Epub Jun. 7, 2012.
Bunzen et al., Self-assembly of M24L48 polyhedra based on empirical prediction. Angew Chem Int Ed Engl. Mar. 26, 2012;51(13):3161-3. doi: 10.1002/anie.201108731.
Burdynska et al., Synthesis of Star Polymers Using ARGET ATRP. Macromolecules, 2010;43(22):9227-9229. DOI: 10.1021/ma101971z.
Burnworth et al., Decoupling Optical Properties in Metallo-Supramolecular Poly (p-phenylene ethynylene)s. Macromolecules. 2008;41(6):2157-2163.
Burts et al., Brush-first and click: efficient synthesis of nanoparticles that degrade and release doxorubicin in response to light. Photochem Photobiol. Mar.-Apr. 2014;90(2):380-5. doi: 10.1111/php.12182. Epub Nov. 25, 2013.
Burts et al., Brush-first synthesis of core-photodegradable miktoarm star polymers via ROMP: towards photoresponsive self-assemblies. Macromol Rapid Commun. Jan. 2014;35(2):168-173. doi: 10.1002/marc.201300618. Epub Nov. 22, 2013.
Burts et al., Using EPR To Compare PEG-branch-nitroxide "Bivalent-Brush Polymers" and Traditional PEG Bottle-Brush Polymers: Branching Makes a Difference. Macromolecules. 2012;45(20):8310-18.
Cabral et al., Accumulation of sub-100 nm polymeric micelles in poorly permeable tumours depends on size. Nat Nanotechnol. Oct. 23, 2011;6(12):815-23. doi: 10.1038/nnano.2011.166.
Caiolfa et al., Polymer-bound camptothecin: initial biodistribution and antitumour activity studies. J Control Release. Mar. 1, 2000;65(1-2):105-19.

(56) References Cited

OTHER PUBLICATIONS

Campos-Fernández et al., A One-Pot, High-Yield Synthesis of a Paramagnetic Nickel Square from Divergent Precursors by Anion Template Assembly. Angewandte Chemie International Edition. Dec. 3, 1999;38(23):3477-3479.

Campos-Fernández et al., Fine-tuning the ring-size of metallacyclophanes: a rational approach to molecular pentagons. J Am Chem Soc. Jan. 31, 2001;123(4):773-4.

Caravan et al., Gadolinium(III) Chelates as MRI Contrast Agents: Structure, Dynamics, and Applications. Chem Rev. Sep. 8, 1999;99(9):2293-352.

Castilla et al., Stereochemistry in subcomponent self-assembly. Acc Chem Res. Jul. 15, 2014;47(7):2063-73. doi: 10.1021/ar5000924. Epub May 2, 2014.

Chambron et al., Topologically complex molecules obtained by transition metal templation: it is the presentation that determines the synthesis strategy. New Journal of Chemistry. 2013;37(1):49-57.

Chand et al., Self-assembly of a novel macrotricyclic Pd(II) metallocage encapsulating a nitrate ion. Chem Commun (Camb). Sep. 7, 2001;(17):1652-3.

Chang et al., Dose-dense chemotherapy improves mechanisms of antitumor immune response. Cancer Res. Jan. 1, 2013;73(1):119-27. doi: 10.1158/0008-5472.CAN-12-2225. Epub Oct. 29, 2012.

Chen et al., Polymeric phosphorylcholine-camptothecin conjugates prepared by controlled free radical polymerization and click chemistry. Bioconjug Chem. Dec. 2009;20(12):2331-41. doi: 10.1021/bc900339x.

Chen et al., Synthesis of superporous hydrogels: hydrogels with fast swelling and superabsorbent properties. J Biomed Mater Res. Jan. 1999;44(1):53-62.

Cheng et al., Well-defined diblock macromonomer with a norbornene group at block junction: anionic living linking synthesis and ring-opening metathesis polymerization. Macromol. Mar. 4, 2010;43(7):3153-5.

Cheon et al., Synergistically integrated nanoparticles as multimodal probes for nanobiotechnology. Acc Chem Res. Dec. 2008;41(12):1630-40. doi: 10.1021/ar800045c.

Chiang et al., Vitamin D for the prevention and treatment of pancreatic cancer. World J Gastroenterol. Jul. 21, 2009;15(27):3349-54.

Chifotides et al., Anion-π interactions in supramolecular architectures. Acc Chem Res. Apr. 16, 2013;46(4):894-906. doi: 10.1021/ar300251k. Epub Mar. 11, 2013.

Choi et al., Self-confirming "And" logic nanoparticles for fault-free MRI. J Am Chem Soc. Aug. 18, 2010;132(32):11015-7. doi: 10.1021/ja104503g.

Chou et al., In vitro and in vivo studies of FePt nanoparticles for dual modal CT/MRI molecular imaging. J Am Chem Soc. Sep. 29, 2010;132(38):13270-8. doi: 10.1021/ja1035013.

Clever et al., Inclusion of anionic guests inside a molecular cage with palladium(II) centers as electrostatic anchors. Angew Chem Int Ed Engl. 2009;48(38):7010-2. doi: 10.1002/anie.200902717.

Cok et al., Synthesis of Model Network Hydrogels via Tetrazine-Olefin Inverse Electron Demand Diels-Alder Cycloaddition. Macromolecular Symposia. Jul. 2013;329(1):108-112.

Conrad et al., Tunable, temperature-responsive polynorbornenes with side chains based on an elastin peptide sequence. Angew Chem Int Ed Engl. 2009;48(44):8328-30. doi: 10.1002/anie.200903888.

Cordier et al., Self-healing and thermoreversible rubber from supramolecular assembly. Nature. Feb. 21, 2008;451(7181):977-80. doi: 10.1038/nature06669.

Dag et al., Three-arm star ring opening metathesis polymers via alkyne-azide click reaction. J. Polym. Sci. A Polym. Chem., 47: 2344-2351. doi:10.1002/pola.23324.

Dalsin et al., Bottlebrush block polymers: Quantitative theory and experiments. ACS Nano. Nov. 6, 2015;9(12):12233-45.

Davies et al., Environmentally responsive MRI contrast agents. Chem Commun (Camb). Oct. 28, 2013;49(84):9704-21. doi: 10.1039/c3cc44268c.

Davis et al., A novel nitroxide is an effective brain redox imaging contrast agent and in vivo radioprotector. Free Radic Biol Med. Aug. 1, 2011;51(3):780-90. doi: 10.1016/j.freeradbiomed.2011.05.019. Epub May 25, 2011.

Davis et al., Atom transfer radical polymerization of tert-butyl acrylate and preparation of block copolymers. Macromol. May 30, 2000;33(11):4039-47.

Davis et al., Nanoparticle therapeutics: an emerging treatment modality for cancer. Nat Rev Drug Discov. Sep. 2008;7(9):771-82. doi: 10.1038/nrd2614.

Desmarets et al., Design, Self-Assembly, and Molecular Structures of 3D Copper(II) Capsules Templated by BF4-Guest Anions. European Journal of Inorganic Chemistry. Oct. 2009;(29-30):4396-4400. doi: 10.1002/ejic.200900606.

Detappe et al., Advanced multimodal nanoparticles delay tumor progression with clinical radiation therapy. J Control Release. Sep. 28, 2016;238:103-113. doi: 10.1016/j.jconrel.2016.07.021. Epub Jul. 14, 2016.

Dhar et al., Polyvalent oligonucleotide gold nanoparticle conjugates as delivery vehicles for platinum(IV) warheads. J Am Chem Soc. Oct. 21, 2009;131(41):14652-3. doi: 10.1021/ja9071282.

Dhar et al., Targeted delivery of a cisplatin prodrug for safer and more effective prostate cancer therapy in vivo. Proc Natl Acad Sci U S A. Feb. 1, 2011;108(5):1850-5. doi: 10.1073/pnas.1011379108. Epub Jan. 13, 2011.

Dhar et al., Targeted delivery of cisplatin to prostate cancer cells by aptamer functionalized Pt(IV) prodrug-PLGA-PEG nanoparticles. Proc Natl Acad Sci U S A. Nov. 11, 2008;105(45):17356-61. doi: 10.1073/pnas.0809154105. Epub Oct. 31, 2008.

Doane et al., The unique role of nanoparticles in nanomedicine: imaging, drug delivery and therapy. Chem Soc Rev. Apr. 7, 2012;41(7):2885-911. doi: 10.1039/c2cs15260f. Epub Jan. 27, 2012.

Duncan, The dawning era of polymer therapeutics. Nat Rev Drug Discov. May 2003;2(5):347-60.

Durr et al., Mild and Efficient Modular Synthesis of Poly(acrylonitrile-co-butadiene) Block and Miktoarm Star Copolymer Architectures. Macromolecules, 2013;46(1):49-62. DOI: 10.1021/ma302017c.

Elliott et al., Metabolism of brain tissue slices and suspensions from various mammals. J Neurophysiol. Nov. 1948;11(6):473-84.

Eryazici et al., Two Large-Pore Metal-Organic Frameworks Derived from a Single Polytopic Strut. Crystal Growth & Design. Mar. 7, 2012;12(3):1075-1080.

Feng et al., A metabonomic analysis of organ specific response to USPIO administration. Biomaterials. Sep. 2011;32(27):6558-69. doi: 10.1016/j.biomaterials.2011.05.035.

Fenlon et al., The Thread & Cut Method: Syntheses of Molecular Knot Precursors. Eur J Org Chem. Jun. 2008;2008(18):3065-3068.

Ferrauto et al., Frequency-encoded MRI-CEST agents based on paramagnetic liposomes/RBC aggregates. Nano Lett. Dec. 10, 2014;14(12):6857-62. doi: 10.1021/nl5026612. Epub Nov. 10, 2014.

Ferrauto et al., Lanthanide-loaded erythrocytes as highly sensitive chemical exchange saturation transfer MRI contrast agents. J Am Chem Soc. Jan. 15, 2014;136(2):638-41. doi: 10.1021/ja411793u. Epub Dec. 30, 2013.

Forgan et al., Chemical topology: complex molecular knots, links, and entanglements. Chem Rev. Sep. 14, 2011;111(9):5434-64. doi: 10.1021/cr200034u. Epub Jun. 21, 2011.

Foster et al., Differentially Addressable Cavities within Metal-Organic Cage-Cross-Linked Polymeric Hydrogels. J Am Chem Soc. Aug. 5, 2015;137(30):9722-9. doi: 10.1021/jacs.5b05507. Epub Jul. 23, 2015.

Fox et al., Soluble polymer carriers for the treatment of cancer: the importance of molecular architecture. Acc Chem Res. Aug. 18, 2009;42(8):1141-51. doi: 10.1021/ar900035f.

Frechet. Functional polymers and dendrimers: reactivity, molecular architecture, and interfacial energy. Science. Mar. 25, 1994;263(5154):1710-5.

Fullenkamp et al., Mussel-Inspired Histidine-Based Transient Network Metal Coordination Hydrogels. Macromolecules. Jan. 18, 2013;46(3):1167-1174.

(56) References Cited

OTHER PUBLICATIONS

Gao et al., Development of star polymers as unimolecular containers for nanomaterials. Macromol Rapid Commun. May 14, 2012;33(9):722-34. doi: 10.1002/marc.201200005. Epub Mar. 14, 2012.
Gao et al., Modular Approaches to Star and Miktoarm Star Polymers by ATRP of Cross-Linkers. Macromol. Symp., 291-292: 12-16. doi: 10.1002/masy.201050502.
Gao et al., Synthesis of Acid-Labile PEG and PEG-Doxorubicin-Conjugate Nanoparticles via Brush-First ROMP. ACS Macro Lett. Sep. 16, 2014;3(9):854-857. Epub Aug. 13, 2014.
Gao et al., Synthesis of functional polymers with controlled architecture by CRP of monomers in the presence of cross-linkers: From stars to gels. Progress in Polymer Science Apr. 2009;34(4):317-350.
Gao et al., Synthesis of Star Polymers by A New "Core-First" Method: Sequential Polymerization of Cross-Linker and Monomer. Macromolecules, 2008;41(4):1118-1125.
Ge et al., A Pyrene-functionalized Polynorbornene for Ratiometric Fluorescence Sensing of Pyrophosphate. Chem. Asian J. 2016;11:687.
Gestwicki et al., Influencing receptor-ligand binding mechanisms with multivalent ligand architecture. J Am Chem Soc. Dec. 18, 2002;124(50):14922-33.
Gilgorich et al., Palladium-catalyzed reductive coupling of styrenes and organostannanes under aerobic conditions. J Am Chem Soc. Nov. 21, 2007;129(46):14193-5. Epub Oct. 27, 2007.
Glunde et al., Magnetic resonance spectroscopy in metabolic and molecular imaging and diagnosis of cancer. Chem Rev. May 12, 2010;110(5):3043-59. doi: 10.1021/cr9004007.
Godugu et al., Abstract 2139: Effect of telmisartan on triple negative breast cancer (TNBC) and lung cancer tumor progression and intratumoral distribution of nanoparticles. Cancer Res. 2013;73(8).
Goh et al., Highly efficient synthesis of low polydispersity core cross-linked star polymers by Ru-catalyzed living radical polymerization. Macromol Rapid Commun. Mar. 2, 2011;32(5):456-61. doi: 10.1002/marc.201000641. Epub Jan. 7, 2011.
Grahovac et al., Abstract B41: The angiotensin receptor blocker telmisartan inhibits the growth of pancreatic ductal adenocarcinoma and improves survival. Cancer Res. 2016;76(24).
Grason et al., Geometric theory of diblock copolymer phases. Phys Rev Lett. Jul. 31, 2003;91(5):058304.
Greenwald et al., Effective drug delivery by PEGylated drug conjugates. Adv Drug Deliv Rev. Feb. 10, 2003;55(2):217-50.
Gumbley et al., Photoresponsive Polymers Containing Nitrobenzyl Esters via Ring-Opening Metathesis Polymerization. Macromolecules. 2011;44(20):7956-61.
Hackelbusch et al., Chain Dynamics in Supramolecular Polymer Networks. Macromolecules. 2013;46(15):6273-6286.
Hackelbusch et al., Multiresponsive Polymer Hydrogels by Orthogonal Supramolecular Chain Cross-Linking. Macromolecules. 2014;47(12):4028-4036.
Haddleton et al., Well-defined oligosaccharide-terminated polymers from living radical polymerization. Biomacromolecules. 2000 Summer;1(2):152-6.
Hafkamp et al., Organogel formation and molecular imprinting by functionalized gluconamides and their metal complexes. Chemical Communications. 1997;6:545-546. doi: 10.1039/A608266A.
Hall et al., Platinum(IV) antitumour compounds: their bioinorganic chemistry. Coord Chem Rev. 2002;232:49-67.
Hall et al., The cellular distribution and oxidation state of platinum(II) and platinum(IV) antitumour complexes in cancer cells. J Biol Inorg Chem. Sep. 2003;8(7):726-32. Epub Jul. 12, 2003.
Han et al., Recent Development of Peptide Coupling Reagents in Organic Synthesis. Tetrahedron, 2004;60:2447-2467.
Hansell et al., Additive-free clicking for polymer functionalization and coupling by tetrazine-norbornene chemistry. J Am Chem Soc. Sep. 7, 2011;133(35):13828-31. doi: 10.1021/ja203957h. Epub Aug. 11, 2011.

Hao et al., Dendrimers as scaffolds for multifunctional reversible addition—fragmentation chain transfer agents: Syntheses and polymerization. J. Polym. Sci. A Polym. Chem., 2004;42:5877-5890. doi:10.1002/pola.20434.
Harrington et al., Holdfast heroics: comparing the molecular and mechanical properties of Mytilus californianus byssal threads. J Exp Biol. Dec. 2007;210(Pt 24):4307-18.
Harrington et al., Iron-clad fibers: a metal-based biological strategy for hard flexible coatings. Science. Apr. 9, 2010;328(5975):216-20. doi: 10.1126/science.1181044. Epub Mar. 4, 2010.
Harris et al., Giant hollow M(n)L(2n) spherical complexes: structure, functionalisation and applications. Chem Commun (Camb). Aug. 4, 2013;49(60):6703-12. doi: 10.1039/c3cc43191f.
Harrison et al., A multimeric MR-optical contrast agent for multimodal imaging. Chem Commun (Camb). Oct. 9, 2014;50(78):11469-71. doi: 10.1039/c4cc05651e.
Harrison et al., Multimeric Near IR-MR Contrast Agent for Multimodal In Vivo Imaging. J Am Chem Soc. Jul. 22, 2015;137(28):9108-16. doi: 10.1021/jacs.5b04509. Epub Jul. 14, 2015.
Harvey et al., Lanthanide Complexes as Paramagnetic Probes for 19F Magnetic Resonance. Eur. J. Inorg. Chem., 2012: 2015-2022. doi:10.1002/ejic.201100894.
Hatje et al., Increases in Anthropogenic Gadolinium Anomalies and Rare Earth Element Concentrations in San Francisco Bay over a 20 Year Record. Environ Sci Technol. Apr. 19, 2016;50(8):4159-68. doi: 10.1021/acs.est.5b04322. Epub Jan. 25, 2016.
Hawker et al., Preparation of polymers with controlled molecular architecture. A new convergent approach to dendritic macromolecules. J Am Chem Soc. Oct. 1990;112(21):7638-47.
Hedrick et al., Dendrimer-like Star Block and Amphiphilic Copolymers by Combination of Ring Opening and Atom Transfer Radical Polymerization. Macromolecules, 1998;31(25):8691-8705. DOI: 10.1021/ma980932b.
Hein et al., Copper-catalyzed azide-alkyne cycloaddition (CuAAC) and beyond: new reactivity of copper(I) acetylides. Chem Soc Rev. Apr. 2010;39(4):1302-15. doi: 10.1039/b904091a. Epub Mar. 4, 2010.
Helms et al., One-Pot Reaction Cascades Using Star Polymers with Core-Confined Catalysts. Angewandte Chemie, 2005;44:6384-6387. doi:10.1002/ange.200502095.
Heroguez et al., Novel Styrene—Butadiene Copolymers by Ring-Opening Metathesis Polymerization. Macromol. Oct. 3, 2000;33(20):7241-8.
Hirakawa et al., Removal of Perchlorate Anion from an Aqueous Solution by Encapsulation in an Anion-templated Self-assembled Molecular Capsule. Chemistry Letters. 2009;38(3):290-291.
Holbrook et al., Gd(III)-Dithiolane Gold Nanoparticles for T1-Weighted Magnetic Resonance Imaging of the Pancreas. Nano Lett. May 11, 2016;16(5):3202-9. doi: 10.1021/acs.nanolett.6b00599. Epub Apr. 20, 2016.
Holliday et al., Strategies for the Construction of Supramolecular Compounds through Coordination Chemistry. Angew Chem Int Ed Engl. Jun. 1, 2001;40(11):2022-2043.
Holten-Andersen et al., Metal-coordination: using one of nature's tricks to control soft material mechanics. J. Mater. Chem. B. 2014;2:2467-2472.
Holten-Andersen et al., pH-induced metal-ligand cross-links inspired by mussel yield self-healing polymer networks with near-covalent elastic moduli. PNAS. Feb. 15, 2011;108:2651-2655.
Hoogenboom et al., 1-Lactide Polymerization Utilizing a Hydroxy-Functionalized 3,6-Bis(2-pyridyl)pyridazine as Supramolecular (Co)initiator: Construction of Polymeric [2 ×2] Grids. Macromolecules, 2003;36(13):4743-9. DOI: 10.1021/ma034119e.
Hu et al., Enhancing Gelation of Doubly Thermosensitive Hydrophilic ABC Linear Triblock Copolymers in Water by Thermoresponsive Hairy Nanoparticles. Macromolecules, 2016;49(15):5502-13. DOI: 10.1021/acs.macromol.6b01156.
Hu et al., Nanoparticle-based combination therapy toward overcoming drug resistance in cancer. Biochem Pharmacol. Apr. 15, 2012;83(8):1104-11. doi: 10.1016/j.bcp.2012.01.008. Epub Jan. 18, 2012.

(56) References Cited

OTHER PUBLICATIONS

Huang et al., Polymer-Stabilized Perfluorobutane Nanodroplets for Ultrasound Imaging Agents. J Am Chem Soc. Jan. 11, 2017;139(1):15-18. doi: 10.1021/jacs.6b08800. Epub Dec. 29, 2016.
Huinink et al., Topotecan versus paclitaxel for the treatment of recurrent epithelial ovarian cancer. J Clin Oncol. Jun. 1997;15(6):2183-93.
Huynh, Novel Polymeric Micelles via RAFT Polymerization for Platinum Drug Delivery. Doctoral Thesis. The University of New South Wales. 2012.
Hyodo et al., Assessment of tissue redox status using metabolic responsive contrast agents and magnetic resonance imaging. J Pharm Pharmacol. Aug. 2008;60(8):1049-60. doi: 10.1211/jpp.60.8.0011.
Hyodo et al., Brain redox imaging using blood-brain barrier-permeable nitroxide MRI contrast agent. J Cereb Blood Flow Metab. Jun. 2008;28(6):1165-74. doi: 10.1038/jcbfm.2008.5. Epub Feb. 13, 2008.
Hyodo et al., Probing the intracellular redox status of tumors with magnetic resonance imaging and redox-sensitive contrast agents. Cancer Res. Oct. 15, 2006;66(20):9921-8.
Iha et al., Applications of Orthogonal "Click" Chemistries in the Synthesis of Functional Soft Materials. Chem. Rev., 2009;109(11):5620-5686. DOI: 10.1021/cr900138t.
Inglis et al., Well-defined star shaped polymer-fullerene hybrids via click chemistry. Soft Matter, 2010;6:82-84. DOI: 10.1039/B920806M.
Jackson et al., pH triggered self-assembly of core cross-linked star polymers possessing thermoresponsive cores. Chem. Commun., 2011;47:6807-6809. DOI: 10.1039/C1CC11785H.
Jakubowski et al., Activators regenerated by electron transfer for atom transfer radical polymerization of styrene. Macromol. Jan. 10, 2006;39(1):39-45.
Jamieson et al., Structure, Recognition, and Processing of Cisplatin-DNA Adducts. Chem Rev. Sep. 8, 1999;99(9):2467-98.
Jeong et al., Highly tunable self-assembled nanostructures from a poly (2-vinylpyridine-b-dimethylsiloxane) block copolymer. Nano Lett. Sep. 27, 2011;11(10):4095-101.
Jesberger et al., Hyperbranched polymers as scaffolds for multifunctional reversible addition—fragmentation chain-transfer agents: A route to polystyrene-core-polyesters and polystyrene-block-poly(butyl acrylate)-core-polyesters. J. Polym. Sci. A Polym. Chem., 2003;41:3847-3861. doi:10.1002/pola.10976.
Jiang et al., Morphology and Phase Diagram of Comb Block Copolymer A m+ 1 (BC) m. J Phys Chem B. May 7, 2009;113(21):7462-7.
Johnson et al., Core-clickable PEG-branch-azide bivalent-bottle-brush polymers by ROMP: grafting-through and clicking-to. J Am Chem Soc. Jan. 26, 2011;133(3):559-66. doi: 10.1021/ja108441d. Epub Dec. 13, 2010.
Johnson et al., Drug-loaded, bivalent-bottle-brush polymers by graft-through ROMP. Macromolecules. Dec. 28, 2010;43(24):10326-10335.
Johnson et al., Efficient Synthesis of Doxorubicin Releasing Brush Polymers by Graft-Through Romp. Polymer Preprints. 2010;51(2):96-97.
Jokerst et al., Molecular imaging with theranostic nanoparticles. Acc Chem Res. Oct. 18, 2011;44(10):1050-60. doi: 10.1021/ar200106e. Epub Sep. 15, 2011.
Jokerst et al., Nanoparticle PEGylation for imaging and therapy. Nanomedicine (Lond). Jun. 2011;6(4):715-28. doi: 10.2217/nnm.11.19.
Joralemon et al., PEGylated polymers for medicine: from conjugation to self-assembled systems. Chem Commun (Camb). Mar. 7, 2010;46(9):1377-93. doi: 10.1039/b920570p. Epub Jan. 28, 2010.
Jung et al., Orientation-controlled self-assembled nanolithography using a polystyrene—polydimethylsiloxane block copolymer. Nano Lett. Jul. 11, 2007;7(7):2046-50.
Kale et al., Supramolecular assemblies of amphiphilic homopolymers. Langmuir. May 19, 2009;25(17):9660-70.
Kalyani et al., Oxidatively intercepting Heck intermediates: Pd-catalyzed 1,2- and 1,1-arylhalogenation of alkenes. J Am Chem Soc. Feb. 20, 2008;130(7):2150-1. doi: 10.1021/ja0782798. Epub Jan. 30, 2008.
Kauffman et al., Fluorescence-Based Assays for Measuring oxorubicin in Biological Systems. React Oxyg Species (Apex). 2016;2(6):432-439. doi: 10.20455/ros.2016.873. PMID: 29707647; PMCID: PMC5921830.
Kawamoto et al., Graft-through Synthesis and Assembly of Janus Bottlebrush Polymers from A-Branch-B Diblock Macromonomers. J Am Chem Soc. Sep. 14, 2016;138(36):11501-4. doi: 10.1021/jacs.6b07670. Epub Sep. 1, 2016.
Kawamoto et al., Loops versus branch functionality in model click hydrogels. Macromol. Dec. 1, 2015;48(24):8980-8.
Kean et al., Increasing the maximum achievable strain of a covalent polymer gel through the addition of mechanically invisible cross-links. Adv Mater. Sep. 10, 2014;26(34):6013-8. doi: 10.1002/adma.201401570. Epub Jul. 17, 2014.
Keana et al., Nitroxides as potential contrast enhancing agents for MRI application: influence of structure on the rate of reduction by rat hepatocytes, whole liver homogenate, subcellular fractions, and ascorbate. Magn Reson Med. Dec. 1987;5(6):525-36.
Khanna et al., Designing Miktoarm Polymers Using a Combination of "Click" Reactions in Sequence with Ring-Opening Polymerization. Macromolecules, 2010;43(13):5688-5698. DOI: 10.1021/ma100845a.
Kim et al., Anion-directed self-assembly of coordination polymer into tunable secondary structure. J Am Chem Soc. Jun. 9, 2004;126(22):7009-14.
Kirchhoff et al., Boronic acids: new coupling partners in room-temperature Suzuki reactions of alkyl bromides. Crystallographic characterization of an oxidative-addition adduct generated under remarkably mild conditions. J Am Chem Soc. Nov. 20, 2002;124(46):13662-3.
Kishi et al., An M2L4 molecular capsule with an anthracene shell: encapsulation of large guests up to 1 nm. J Am Chem Soc. Aug. 3, 2011;133(30):11438-41. doi: 10.1021/ja2037029. Epub Jul. 8, 2011.
Kokuryo et al., SPIO-PICsome: development of a highly sensitive and stealth-capable MRI nano-agent for tumor detection using SPIO-loaded unilamellar polyion complex vesicles (PICsomes). J Control Release. Aug. 10, 2013;169(3):220-7. doi: 10.1016/j.jconrel.2013.03.016. Epub Mar. 29, 2013.
Kolishetti et al., Engineering of self-assembled nanoparticle platform for precisely controlled combination drug therapy. Proc Natl Acad Sci U S A. Oct. 19, 2010;107(42):17939-44. doi: 10.1073/pnas.1011368107. Epub Oct. 4, 2010.
Kreutzer et al., Water-Soluble, Unimolecular Containers Based on Amphiphilic Multiarm Star Block Copolymers. Macromolecules, 2006;39(13):4507-4516. DOI: 10.1021/ma060548b.
Kwon et al., Block copolymer micelles as long-circulating drug vehicles. Adv Drug Delivery Rev. 1995;16:295-309.
Lammers et al., Simultaneous delivery of doxorubicin and gemcitabine to tumors in vivo using prototypic polymeric drug carriers. Biomaterials. Jul. 2009;30(20):3466-75. doi: 10.1016/j.biomaterials.2009.02.040. Epub Mar. 21, 2009.
Lee et al., Multifunctional nanoparticles for multimodal imaging and theragnosis. Chem Soc Rev. Apr. 7, 2012;41(7):2656-72. doi: 10.1039/c2cs15261d. Epub Dec. 21, 2011.
Lee et al., Mussel-Inspired Adhesives and Coatings. Annu Rev Mater Res. Aug. 1, 2011;41:99-132.
Lee et al., Novel phase morphologies in a microphase-separated dendritic polymer melt. Macromol. Jan. 12, 2009;42(3):849-59.
Lee et al., Single-molecule mechanics of mussel adhesion. Proc Natl Acad Sci U S A. Aug. 29, 2006;103(35):12999-3003. Epub Aug. 18, 2006.
Lee et al., Stimuli-responsive molecular brushes. Progress in Polymer Science (Oxford), 35(1-2), 24-44. DOI: 10.1016/j.progpolymsci.2009.11.002.
Leininger et al., Self-assembly of discrete cyclic nanostructures mediated by transition metals. Chem Rev. Mar. 8, 2000;100(3):853-908.
Li et al., Polycatechol Nanoparticle MRI Contrast Agents. Small, 2016;12(5):668-677. https://doi.org/10.1002/smll.201502754.

(56) References Cited

OTHER PUBLICATIONS

Li et al., A magnetic switch for spin-catalyzed interconversion of nuclear spin isomers. J Am Chem Soc. Mar. 31, 2010;132(12):4042-3. doi: 10.1021/ja910282p.
Li et al., Crosslinking-induced morphology change of latex nanoparticles: A study of RAFT-mediated polymerization in aqueous dispersed media using amphiphilic double-brush copolymers as reactive surfactants. J Polym Sci Part A: Polym Chem. Nov. 15, 2014;52(22):3250-9.
Li et al., Distance-Dependent Paramagnet-Enhanced Nuclear Spin Relaxation of H2@C60 Derivatives Covalently Linked to a Nitroxide Radical. J. Phys. Chem. Lett., 2010;1(14):2135-2138. DOI: 10.1021/jz100645w.
Li et al., Dynamic cylindrical assembly of triblock copolymers by a hierarchical process of covalent and supramolecular interactions. J Am Chem Soc. Jan. 4, 2011;133(5):1228-31.
Li et al., Efficient synthesis of narrowly dispersed amphiphilic double-brush copolymers through the polymerization reaction of macromonomer micelle emulsifiers at the oil-water interface. Polym Chem. 2016;7(27):4476-85.
Li et al., Facile syntheses of cylindrical molecular brushes by a sequential RAFT and ROMP "grafting-through" methodology. J Polym Sci A Polym Chem. Oct. 15, 2009;47(20):5557-5563.
Li et al., Highly fluorescent M2L4 molecular capsules with anthracene shells. Chem Commun (Camb). Aug. 14, 2011;47(30):8605-7. doi: 10.1039/c1cc12946e. Epub Jun. 28, 2011.
Li et al., Isostructural M2L4 molecular capsules with anthracene shells: synthesis, crystal structures, and fluorescent properties. Chemistry. Jul. 2, 2012;18(27):8358-65. doi: 10.1002/chem.201200155. Epub May 25, 2012.
Li et al., Pinpointing the extent of electronic delocalization in the Re(I)-to-tetrazine charge-separated excited state using time-resolved infrared spectroscopy. J Am Chem Soc. Aug. 26, 2009;131(33):11656-7. doi: 10.1021/ja903901n.
Li et al., Star Polymers via Cross-Linking Amphiphilic Macroinitiators by AGET ATRP in Aqueous Media. J. Am. Chem. Soc., 2009;131(30):10378-10379. DOI: 10.1021/ja904204g.
Li et al., Surface Properties of Bottlebrush Polymer Thin Films. Macromolecules. 2012;45(17):7118-7127.
Li et al., Synthesis of Hetero-Grafted Amphiphilic Diblock Molecular Brushes and Their Self-Assembly in Aqueous Medium. Macromolecules. 2010;43(3):1182-1184.
Li et al., Well-defined amphiphilic double-brush copolymers and their performance as emulsion surfactants. Macromol. May 18, 2012;45(11):4623-9.
Liang et al., The copper(I)-catalyzed alkyne-azide cycloaddition (CuAAC) "click" reaction and its applications. An overview. Coordination Chemistry Reviews Dec. 2011;255(23-24):2933-2945.
Liao et al., A convergent synthetic platform for single-nanoparticle combination cancer therapy: ratiometric loading and controlled release of cisplatin, doxorubicin, and camptothecin. J Am Chem Soc. Apr. 23, 2014;136(16):5896-9. doi: 10.1021/ja502011g. Epub Apr. 11, 2014.
Liao et al., A palladium-catalyzed three-component cross-coupling of conjugated dienes or terminal alkenes with vinyl triflates and boronic acids. J Am Chem Soc. Apr. 20, 2011;133(15):5784-7. doi: 10.1021/ja201358b. Epub Mar. 30, 2011.
Liao et al., Palladium-catalyzed hydroarylation of 1,3-dienes with boronic esters via reductive formation of pi-allyl palladium intermediates under oxidative conditions. J Am Chem Soc. Aug. 4, 2010;132(30):10209-11. doi: 10.1021/ja105010t.
Liao et al., Two-component control of guest binding in a self-assembled cage molecule. Chem Commun (Camb). Jul. 21, 2010;46(27):4932-4. doi: 10.1039/c0cc00234h. Epub Jun. 2010.
Lim et al., Multiplexed imaging of therapeutic cells with multispectrally encoded magnetofluorescent nanocomposite emulsions. J Am Chem Soc. Dec. 2, 2009;131(47):17145-54. doi: 10.1021/ja904472z.

Liu et al., "Brush-first" method for the parallel synthesis of photocleavable, nitroxide-labeled poly(ethylene glycol) star polymers. J Am Chem Soc. Oct. 3, 2012;134(39):16337-44. doi: 10.1021/ja3067176. Epub Sep. 24, 2012.
Liu et al., Aqueous Dispersion Polymerization of 2-Methoxyethyl Acrylate for the Synthesis of Biocompatible Nanoparticles Using a Hydrophilic RAFT Polymer and a Redox Initiator. Macromolecules, 2011;44(13):5237-5245. DOI: 10.1021/ma200984h.
Liu et al., Assembly of trigonal and tetragonal prismatic cages from octahedral metal ions and a flexible molecular clip. Inorg Chem. Jul. 23, 2007;46(15):5814-6. Epub Jan. 26, 2007.
Liu et al., Discrete M2L2 metallacycle and M2L4 cage frameworks and anion competitive reactions of Cu2L4 type receptor. Inorganic Chemistry Communications. Jun. 2009;12(6):457-460.
Liu et al., Nuts and bolts of chemical exchange saturation transfer MRI. NMR Biomed. Jul. 2013;26(7):810-28. doi: 10.1002/nbm.2899. Epub Jan. 10, 2013.
Liu et al., Particles without a Box: Brush-first Synthesis of Photodegradable PEG Star Polymers under Ambient Conditions. J Vis Exp. 2013;80:e50874, doi:10.3791/50874.
Liu et al., Synthesis of functional core, star polymers via RAFT polymerization for drug delivery applications. Macromol Rapid Commun. May 14, 2012;33(9):760-6. doi: 10.1002/marc.201200029. Epub Apr. 12, 2012.
Lock et al., One-Component Supramolecular Filament Hydrogels as Theranostic Label-Free Magnetic Resonance Imaging Agents. ACS Nano. Jan. 24, 2017;11(1):797-805.
Love et al., A practical and highly active ruthenium-based catalyst that effects the cross metathesis of acrylonitrile. Angew Chem Int Ed Engl. Nov. 4, 2002;41(21):4035-7.
Loveless et al., Chemoresponsive viscosity switching of a metallo-supramolecular polymer network near the percolation threshold. J. Mater Chem. 2007;17:56-61.
Loveless et al., Rational Control of Viscoelastic Properties in Multicomponent Associative Polymer Networks. Macromolecules. 2005;38(24):10171-10177.
Luo et al., Toroidal structures from brush amphiphiles. Chem Commun. 2014;50(5):536-8.
Ma et al., Hierarchical Responsive Nanoplatform with Two-Photon Aggregation-Induced Emission Imaging for Efficient Cancer Theranostics. ACS Appl Mater Interfaces. Dec. 18, 2019;11(50):47259-47269. doi: 10.1021/acsami.9b17587. Epub Dec. 9, 2019. PMID: 31769279.
Ma et al., Nanoparticles for combination drug therapy. ACS Nano. Nov. 26, 2013;7(11):9518-25. doi: 10.1021/nn405674m.
Mackay et al., Self-assembling chimeric polypeptide-doxorubicin conjugate nanoparticles that abolish tumours after a single injection. Nat Mater. Dec. 2009;8(12):993-9. doi: 10.1038/nmat2569. Epub Nov. 8, 2009.
Macrenaris et al., Cell-Permeable Esterase-Activated Ca(II)-Sensitive MRI Contrast Agent. Bioconjug Chem. Feb. 17, 2016;27(2):465-73. doi: 10.1021/acs.bioconjchem.5b00561. Epub Jan. 6, 2016.
Maeda et al., Polymeric drugs for efficient tumor-targeted drug delivery based on EPR-effect. Eur J Pharm Biopharm. Mar. 2009;71(3):409-19. doi: 10.1016/j.ejpb.2008.11.010. Epub Dec. 3, 2008.
Mastarone et al., A modular system for the synthesis of multiplexed magnetic resonance probes. J Am Chem Soc. Apr. 13, 2011;133(14):5329-37. doi: 10.1021/ja1099616. Epub Mar. 17, 2011.
Matson et al., Synthesis of fluorine-18 functionalized nanoparticles for use as in vivo molecular imaging agents. J Am Chem Soc. May 28, 2008;130(21):6731-3. doi: 10.1021/ja802010d. Epub May 2, 2008.
Matsumoto et al., High-resolution mapping of tumor redox status by magnetic resonance imaging using nitroxides as redox-sensitive contrast agents. Clin Cancer Res. Apr. 15, 2006;12(8):2455-62.
Matsumura et al., A new concept for macromolecular therapeutics in cancer chemotherapy: mechanism of tumoritropic accumulation of proteins and the antitumor agent smancs. Cancer Res. Dec. 1986;46(12 Pt 1):6387-92.

(56) References Cited

OTHER PUBLICATIONS

McCammant et al., Palladium-catalyzed 1,4-difunctionalization of butadiene to form skipped polyenes. J Am Chem Soc. Mar. 20, 2013;135(11):4167-70. doi: 10.1021/ja3110544. Epub Mar. 12, 2013.

McKenzie et al., Highly Efficient and Versatile Formation of Biocompatible Star Polymers in Pure Water and Their Stimuli-Responsive Self-Assembly. Macromolecules, 2014;47(22):7869-7877. DOI: 10.1021/ma502008j.

McKenzie et al., Visible Light Mediated Controlled Radical Polymerization in the Absence of Exogenous Radical Sources or Catalysts. Macromolecules, 2015;48(12):3864-3872. DOI: 10.1021/acs.macromol.5b00965.

Medarova et al., In vivo imaging of siRNA delivery and silencing in tumors. Nat Med. Mar. 2007;13(3):372-7. Epub Feb. 25, 2007.

Mendichovszky et al., Gadolinium and nephrogenic systemic fibrosis: time to tighten practice. Pediatr Radiol. May 2008;38(5):489-96; quiz 602-3. Epub Oct. 18, 2007.

Menyo et al., Versatile tuning of supramolecular hydrogels through metal complexation of oxidation-resistant catechol-inspired ligands. Soft Matter. 2013;9:10314-10323.

Meyer et al., The dynamic chemistry of molecular borromean rings and Solomon knots. Chemistry. Nov. 8, 2010;16(42):12570-81. doi: 10.1002/chem.201001806.

Mi et al., A pH-activatable nanoparticle with signal-amplification capabilities for non-invasive imaging of tumour malignancy. Nat Nanotechnol. Aug. 2016;11(8):724-30. doi: 10.1038/nnano.2016.72. Epub May 16, 2016.

Mi et al., Hydrothermally synthesized PEGylated calcium phosphate nanoparticles incorporating Gd-DTPA for contrast enhanced MRI diagnosis of solid tumors. Journal of Controlled Release Jan. 2014;174(28):63-71.

Miyake et al., Precisely tunable photonic crystals from rapidly self-assembling brush block copolymer blends. Angew Chem Int Ed Engl. Nov. 5, 2012;51(45):11246-8. doi: 10.1002/anie.201205743. Epub Sep. 13, 2012.

Moghimi et al., Long-circulating and target-specific nanoparticles: theory to practice. Pharmacol Rev. Jun. 2001;53(2):283-318.

Mukherjee et al., pH-Sensitive Nanoaggregates for Site-Specific Drug-Delivery as Well as Cancer Cell Imaging. ACS Omega, 2016;1(5):755-764. DOI: 10.1021/acsomega.6b00167.

Mukherjee et al., Site-Specific Amphiphilic Magnetic Copolymer Nanoaggregates for Dual Imaging. Macromolecules, 2015;48(19):6791-6800. DOI: 10.1021/acs.macromol.5b01716.

Mukherjee et al., Oximes as reversible links in polymer chemistry: dynamic macromolecular stars. Polym. Chem., 2014;5:6923-6931. DOI: 10.1039/C4PY01282H.

Muthukrishnan et al., Synthesis and Characterization of Glycomethacrylate Hybrid Stars from Silsesquioxane Nanoparticles. Macromolecules, 2005;38(26):10631-10642. DOI: 10.1021/ma051949e.

Na et al., Development of a T1 contrast agent for magnetic resonance imaging using MnO nanoparticles. Angew Chem Int Ed Engl. 2007;46(28):5397-401.

Na et al., Inorganic Nanoparticles for MRI Contrast Agents. Adv. Mater., 21: 2133-2148. doi:10.1002/adma.200802366.

Nair et al., Modulating mechanical properties of self-assembled polymer networks by multi-functional complementary hydrogen bonding. Soft Matter. 2011;7(2):553-559.

Nair et al., Multiresponsive Reversible Polymer Networks Based on Hydrogen Bonding and Metal Coordination. Macromolecules. 2011;44(9):3346-3357.

Nardone et al., Pediatric nephrogenic systemic fibrosis is rarely reported: a RADAR report. Pediatr Radiol. Feb. 2014;44(2):173-80. doi: 10.1007/s00247-013-2795-x. Epub Sep. 21, 2013.

Nguyen et al., Nitroxide-Based Macromolecular Contrast Agents with Unprecedented Transverse Relaxivity and Stability for Magnetic Resonance Imaging of Tumors. ACS Cent. Sci., 2017;3(7):800-811. DOI: 10.1021/acscentsci.7b00253.

Nguyen et al., Pro-organic radical contrast agents ("pro-ORCAs") for real-time MRI of pro-drug activation in biological systems. Polym Chem. Aug. 7, 2020;11(29):4768-4779. doi: 10.1039/d0py00558d. Epub Jun. 26, 2020. PMID: 33790990; PMCID: PMC8009311.

Nguyen et al., Triply Loaded Nitroxide Brush-Arm Star Polymers Enable Metal-Free Millimetric Tumor Detection by Magnetic Resonance Imaging. ACS Nano. Nov. 27, 2018;12(11):11343-11354. doi: 10.1021/acsnano.8b06160. Epub Nov. 2, 2018. PMID: 30387988; PMCID: PMC6320246.

Nicholls et al., DNA-gadolinium-gold nanoparticles for in vivo T1 MR imaging of transplanted human neural stem cells. Biomaterials. Jan. 2016;77:291-306. doi: 10.1016/j.biomaterials.2015.11.021. Epub Nov. 14, 2015.

Nishiyama et al., Novel cisplatin-incorporated polymeric micelles can eradicate solid tumors in mice. Cancer Res. Dec. 15, 2003;63(24):8977-83.

Nomura et al., Facile Controlled Synthesis of Soluble Star Shape Polymers by Ring-Opening Metathesis Polymerization (ROMP). Macromolecules, 2009;42(4):899-901. DOI: 10.1021/ma8027529.

Nomura et al., Use of Pyridine-Coated Star-Shaped ROMP Polymer As the Supporting Ligand for Ruthenium-Catalyzed Chemoselective Hydrogen Transfer Reduction of Ketones. Organometallics, 2012;31(14):5074-5080. DOI: 10.1021/om300417v.

Ohno et al., Synthesis of well-defined cyclodextrin-core star polymers. J. Polym. Sci. A Polym. Chem., 39: 2206-2214. doi:10.1002/pola.1197.

Paletta et al., Synthesis and Reduction Kinetics of Sterically Shielded Pyrrolidine Nitroxides. Org. Lett., 2012;14(20):5322-5325. DOI: 10.1021/01302506f.

Park et al.,Star Synthesis Using Macroinitiators via Electrochemically Mediated Atom Transfer Radical Polymerization. Macromolecules, 2013;46(15):5856-5860 DOI: 10.1021/ma401308e.

Patel et al., Synthesis and cell adhesive properties of linear and cyclic RGD functionalized polynorbornene thin films. Biomacromolecules. Aug. 13, 2012;13(8):2546-53. doi: 10.1021/bm300795y. Epub Jul. 27, 2012.

Patrick et al., Intracellular pH measurements using perfluorocarbon nanoemulsions. J Am Chem Soc. Dec. 11, 2013;135(49):18445-57. doi: 10.1021/ja407573m. Epub Nov. 22, 2013.

Peer et al., Nanocarriers as an emerging platform for cancer therapy. Nat Nanotechnol. Dec. 2007;2(12):751-60. doi: 10.1038/nnano.2007.387.

Petros et al., Strategies in the design of nanoparticles for therapeutic applications. Nat Rev Drug Discov. Aug. 2010;9(8):615-27. doi: 10.1038/nrd2591. Epub Jul. 9, 2010.

Plummer et al., A Phase I clinical study of cisplatin-incorporated polymeric micelles (NC-6004) in patients with solid tumours. Br J Cancer. Feb. 15, 2011;104(4):593-8. doi: 10.1038/bjc.2011.6. Epub Feb. 1, 2011.

Qiu et al., Efficient and versatile synthesis of star polymers in water and their use as emulsifiers. Chem. Commun., 2011;47:12685-12687. DOI: 10.1039/C1CC15679A.

Qiu et al., Oxidation-Responsive Polymer-Drug Conjugates with a Phenylboronic Ester Linker. Macromol Rapid Commun. Nov. 2015;36(22):2012-8. doi: 10.1002/marc.201500349. Epub Aug. 22, 2015. PMID: 26297612.

Rajca et al., Correction to organic radical contrast agents for magnetic resonance imaging. J Am Chem Soc. Feb. 26, 2014;136(8):3318. doi: 10.1021/ja413028d. Epub Feb. 17, 2014.

Rajca et al., Organic radical contrast agents for magnetic resonance imaging. J Am Chem Soc. Sep. 26, 2012;134(38):15724-7. Epub Sep. 17, 2012.

Rangadurai et al., Temporal and triggered evolution of host—guest characteristics in amphiphilic polymer assemblies. J Am Chem Soc. Jun. 10, 2016;138(24):7508-11.

Rasmussen et al., Improved numerical algorithm for exploring block copolymer mesophases. J Polym Sci Part B: Poly Phys. Aug. 15, 2002;40(16):1777-83.

Ratnakar et al., Modulation of CEST images in vivo by T1 relaxation: a new approach in the design of responsive PARACEST agents. J Am Chem Soc. Oct. 9, 2013;135(40):14904-7. doi: 10.1021/ja406738y. Epub Sep. 25, 2013.

(56) References Cited

OTHER PUBLICATIONS

Ren et al., Organic Catalyst-Mediated Ring-Opening Polymerization for the Highly Efficient Synthesis of Polyester-Based Star Polymers. ACS Macro Lett., 2012;1(6):681-686. DOI: 10.1021/mz300169m.

Ren et al., Star Polymers. Chem Rev. Jun. 22, 2016;116(12):6743-836. doi: 10.1021/acs.chemrev.6b00008. Epub Jun. 14, 2016.

Ren et al., Synthetic Strategies towards Well-Defined Complex Polymeric Architectures through Covalent Chemistry. Chemie Ingenieur Technik, 86: 2195-2214. doi:10.1002/cite.201400088.

Rizzo et al., In vivo nanotoxicity testing using the zebrafish embryo assay. J. Mater. Chem. B, 2013,1, 3918-3925. DOI: 10.1039/C3TB20528B.

Rolfe et al., Multimodal polymer nanoparticles with combined 19F magnetic resonance and optical detection for tunable, targeted, multimodal imaging in vivo. J Am Chem Soc. Feb. 12, 2014;136(6):2413-9. doi: 10.1021/ja410351h. Epub Jan. 29, 2014.

Ronson et al., Metal-organic container molecules through subcomponent self-assembly. Chem Commun (Camb). Mar. 28, 2013;49(25):2476-90. doi: 10.1039/c2cc36363a.

Rowan et al., Metal-ligand induced supramolecular polymerization: a route to responsive materials. Faraday Discuss. 2005;128:43-53.

Roy et al., Cyclic β-Peptoids. Org. Lett., 2008;10(5):921-924. DOI: 10.1021/ol7030763.

Runge et al., "Synthesis and Self-Assembly of Bottlebrush Block Copolymers" PMSEPreprints, 2005, 92, 5-6.

Rzayev et al., Molecular Bottlebrushes: New Opportunities in Nanomaterials Fabrication. ACS Macro Lett., 2012;1(9):1146-1149. DOI: 10.1021/mz300402x.

Rzayev, Synthesis of polystyrene—polylactide bottlebrush block copolymers and their melt self-assembly into large domain nanostructures. Macromol. Feb. 20, 2009;42(6):2135-41.

Saini et al., Pd(0)-catalyzed 1,1-diarylation of ethylene and allylic carbonates. Org Lett. Oct. 4, 2013;15(19):5008-11. doi: 10.1021/014023358. Epub Sep. 18, 2013.

Samuni et al., Factors influencing nitroxide reduction and cytotoxicity in vitro. Antioxid Redox Signal. Jun. 2004;6(3):587-95.

Sancey et al., Long-term in vivo clearance of gadolinium-based AGuIX nanoparticles and their biocompatibility after systemic injection. ACS Nano. Mar. 24, 2015;9(3):2477-88. doi: 10.1021/acsnano.5b00552. Epub Feb. 26, 2015.

Sanders et al., Metal-free sequential [3 + 2]-dipolar cycloadditions using cyclooctynes and 1,3-dipoles of different reactivity. J Am Chem Soc. Feb. 2, 2011;133(4):949-57. doi: 10.1021/ja1081519. Epub Dec. 23, 2010.

Sartori et al., Nitroxide paramagnet-induced para-ortho conversion and nuclear spin relaxation of H2 in organic solvents. J Am Chem Soc. Sep. 24, 2008;130(38):12752-6. doi: 10.1021/ja8037195. Epub Aug. 20, 2008.

Saunders et al., Synthesis of amphiphilic star block copolymers using ring-opening metathesis polymerization. Macromolecules, 1992;25(7):2055-2057. DOI: 10.1021/ma00033a035.

Schmidt et al., Supramolecular three-armed star polymers via cyclodextrin host-guest self-assembly. Polym. Chem., 2012;3:3139-3145. DOI: 10.1039/C2PY20293J.

Sengupta et al., Temporal targeting of tumour cells and neovasculature with a nanoscale delivery system. Nature. Jul. 28, 2005;436(7050):568-72.

Sheiko et al., Cylindrical molecular brushes: Synthesis, characterization, and properties. Progress in Polymer Science (Oxford), 33(7), 759-785. DOI: 10.1016/j.progpolymsci.2008.05.001.

Shellock et al., Safety of magnetic resonance imaging contrast agents. J Magn Reson Imaging. Sep. 1999;10(3):477-84.

Shi et al., Core cross-linked star (CCS) polymers with tunable polarity: synthesis by RAFT dispersion polymerization, self-assembly and emulsification. Polym. Chem., 2013;4:1950-1959. DOI: 10.1039/C3PY21120G.

Shibata et al., Quantitative Synthesis of Star-Shaped Poly(vinyl ether)s with a Narrow Molecular Weight Distribution by Living Cationic Polymerization. J. Am. Chem. Soc., 2006;128(23):7497-7504. DOI: 10.1021/ja057611h.

Shin et al., Recent advances in magnetic nanoparticle-based multimodal imaging. Chem Soc Rev. Jul. 21, 2015;44(14):4501-16. doi: 10.1039/c4cs00345d.

Sides et al., Parallel algorithm for numerical self-consistent field theory simulations of block copolymer structure. Polymer. Sep. 1, 2003;44(19):5859-66.

Sinturel et al., High χ -low N block polymers: how far can we go?. ACS Macro Lett. Sep. 2, 2015;4:1044-50.

Skomski et al., Redox-active on-surface assembly of metal-organic chains with single-site Pt(II). J Am Chem Soc. Jul. 16, 2014;136(28):9862-5. doi: 10.1021/ja504850f. Epub Jul. 1, 2014.

Smith et al., Nanomaterials for In Vivo Imaging. Chem Rev. Feb. 8, 2017;117(3):901-986. doi: 10.1021/acs.chemrev.6b00073. Epub Jan. 3, 2017.

Smulders et al., Building on architectural principles for three-dimensional metallosupramolecular construction. Chem Soc Rev. Feb. 21, 2013;42(4):1728-54. doi: 10.1039/c2cs35254k. Epub Oct. 2, 2012.

Sowers et al., Redox-responsive branched-bottlebrush polymers for in vivo MRI and fluorescence imaging. Nature Communications. 2014;5: Article No. 5460.

Spiniello et al., Synthesis and characterization of fluorescently labeled core cross-linked star polymers. J. Polym. Sci. A Polym. Chem., 2008;46:2422-2432. doi:10.1002/pola.22576.

Stenzel-Rosenbaum et al., Synthesis of Poly(styrene) Star Polymers Grown from Sucrose, Glucose, and Cyclodextrin Cores via Living Radical Polymerization Mediated by a Half-Metallocene Iron Carbonyl Complex. Macromolecules, 2001;34(16):5433-5438. DOI: 10.1021/ma0021803.

Su et al., Catechol polymers for pH-responsive, targeted drug delivery to cancer cells. J Am Chem Soc. Aug. 10, 2011;133(31):11850-3. doi: 10.1021/ja203077x. Epub Jul. 19, 2011. PMID: 21751810; PMCID: PMC3149454.

Su et al., Coordination-directed assembly of trigonal and tetragonal molecular boxes encapsulating anionic guests. Journal of the Chemical Society, Dalton Transactions. 2001:359-361. doi: 10.1039/B010118O.

Sulistio et al., Star polymers composed entirely of amino acid building blocks: a route towards stereospecific, biodegradable and hierarchically functionalized stars. Chem. Commun., 2011;47:1151-1153. DOI: 10.1039/C0CC03541F.

Sun et al., Multicomponent metal-ligand self-assembly. Curr Opin Chem Biol. Dec. 2002;6(6):757-64.

Sun et al., Self-assembled M24L48 polyhedra and their sharp structural switch upon subtle ligand variation. Science. May 28, 2010;328(5982): 1144-7. doi:10.1126/science.1188605. Epub Apr. 29, 2010.

Sveinbjornsson et al., Rapid self-assembly of brush block copolymers to photonic crystals. Proc Natl Acad Sci U S A. Sep. 4, 2012;109(36):14332-6. doi: 10.1073/pnas.1213055109. Epub Aug. 21, 2012.

Swaminathan et al., Nephrogenic systemic fibrosis, gadolinium, and iron mobilization. N Engl J Med. Aug. 16, 2007;357(7):720-2.

Takamizu et al., Synthesis of oligo(thiophene)-coated star-shaped ROMP polymers: unique emission properties by the precise integration of functionality. Journal of the American Chemical Society 2012;134(18):7892-7895.

Tam et al., Recent advances in metallogels. Chem Soc Rev. Feb. 21, 2013;42(4):1540-67. doi: 10.1039/c2cs35354g. Epub Jan. 8, 2013.

Terashima et al., Star-Polymer-Catalyzed Living Radical Polymerization: Microgel-Core Reaction Vessel by Tandem Catalyst Interchange. Angew. Chem., 2011;50:7892-7895. doi:10.1002/anie.201101381.

Terreno et al., Challenges for molecular magnetic resonance imaging. Chem Rev. May 12, 2010;110(5):3019-42. doi: 10.1021/cr100025t.

Theodorakis et al., Interplay between chain collapse and microphase separation in bottle-brush polymers with two types of side chains. Macromol. May 4, 2010;43(11):5137-48.

(56) References Cited

OTHER PUBLICATIONS

Thompson et al., Labelling polymers and micellar nanoparticles via initiation, propagation and termination with ROMP. Polym. Chem., 2014;5:1954-1964.
Tirotta et al., (19)F magnetic resonance imaging (MRI): from design of materials to clinical applications. Chem Rev. Jan. 28, 2015;115(2):1106-29. doi: 10.1021/cr500286d. Epub Oct. 20, 2014.
Tolmasoff et al., Superoxide dismutase: correlation with life-span and specific metabolic rate in primate species. Proc Natl Acad Sci U S A. May 1980;77(5):2777-81.
Tominaga et al., Finite, spherical coordination networks that self-organize from 36 small components. Angew Chem Int Ed Engl. Oct. 25, 2004;43(42):5621-5.
Torchilin, Tumor delivery of macromolecular drugs based on the EPR effect. Adv Drug Deliv Rev. Mar. 18, 2011;63(3):131-5. doi: 10.1016/j.addr.2010.03.011. Epub Mar. 18, 2010.
Tsuji et al., Facile Palladium catalyzed decarboxylative allylation of active methylene compounds under neutral conditions using allylic carbonates. Tetrahedron Letters. 1982;23(46):4809-12.
Tu et al., Multimodal magnetic-resonance/optical-imaging contrast agent sensitive to NADH. Angew Chem Int Ed Engl. 2009;48(35):6547-51. doi: 10.1002/anie.200900984.
Tunca et al., Novel miktofunctional initiator for the preparation of an ABC-type miktoarm star polymer via a combination of controlled polymerization techniques. J. Polym. Sci. A Polym. Chem., 42: 4228-4236. doi:10.1002/pola.20284.
Valeur et al., Amide bond formation: beyond the myth of coupling reagents. Chem. Soc. Rev., 2009;38:606-631. DOI: 10.1039/B701677H.
Verduzco et al., Correction: Structure, function, self-assembly, and applications of bottlebrush copolymers. Chem Soc Rev. Nov. 7, 2015;44(21):7916. doi: 10.1039/c5cs90099a.
Verduzco et al., Structure, function, self-assembly, and applications of bottlebrush copolymers. Chem. Soc. Rev., 2015;44:2405-20.
Verwilst et al., Recent advances in Gd-chelate based bimodal optical/MRI contrast agents. Chem Soc Rev. Apr. 7, 2015;44(7):1791-806. doi: 10.1039/c4cs00336e. Epub Jan. 27, 2015.
Villaraza et al., Macromolecules, dendrimers, and nanomaterials in magnetic resonance imaging: the interplay between size, function, and pharmacokinetics. Chem Rev. May 12, 2010;110(5):2921-59. doi: 10.1021/cr900232t.
Wang et al., Advances of cancer therapy by nanotechnology. Cancer Res Treat. Mar. 2009;41(1):1-11. doi: 10.4143/crt.2009.41.1.1. Epub Mar. 31, 2009.
Wang et al., Synthesis of Unnatural Amino Acids Functionalized with Sterically Shielded Pyrroline Nitroxides. Org Lett. Oct. 17, 2014;16(20): 5298-5300. Published online Sep. 16, 2014. doi: [10.1021/ol502449r].
Wei et al., Exceedingly small iron oxide nanoparticles as positive MRI contrast agents. Proc. Natl. Acad. Sci. USA 2017;114(9):2325-2330.
Weng et al., Control of Gel Morphology and Properties of a Class of Metallo-Supramolecular Polyers by Good/Poor Solvent Environments. Macromolecules. 2009;42(1):236-246.
Weng et al., Effect of monomer structure on the gelation of a class of metallo-supramolecular polymers. Soft Matter. 2009;5(23):4647-4657.
Weng et al., Structural origin of the thixotropic behavior of a class of metallosupramolecular gels. Tetrahedron. Jul. 30, 2007;63(31):7419-7431.
Weng et al., Understanding the mechanism of gelation and stimuli-responsive nature of a class of metallo-supramolecular gels. J Am Chem Soc. Sep. 6, 2006;128(35):11663-72.
Westhaus et al., Triggered release of calcium from lipid vesicles: a bioinspired strategy for rapid gelation of polysaccharide and protein hydrogels. Biomaterials. Mar. 2001;22(5):453-62.
Wilkinson et al., Electrophilic fluorocyclization of allyl silanes. Angew Chem Int Ed Engl. 2009;48(38):7083-7086. doi:10.1002/anie.200901795.
Wollinsky et al., Therapeutic and diagnostic applications of dendrimers for cancer treatment. Adv Drug Deliv Rev. Jun. 10, 2008;60(9):1037-55. doi: 10.1016/j.addr.2008.02.012. Epub Mar. 4, 2008.
Wong et al., Quantitative formation of core cross-linked star polymers via a one-pot two-step single electron transfer-living radical polymerization. Polym. Chem., 2013;4:4562-4565. DOI: 10.1039/C3PY00726J.
Worrell et al., Direct evidence of a dinuclear copper intermediate in Cu(I)-catalyzed azide-alkyne cycloadditions. Science. Apr. 26, 2013;340(6131):457-60. doi: 10.1126/science.1229506. Epub Apr. 4, 2013.
Xia et al., Efficient synthesis of narrowly dispersed brush copolymers and study of their assemblies: the importance of side chain arrangement. J Am Chem Soc. Dec. 30, 2009;131(51):18525-32. doi: 10.1021/ja908379q.
Xia et al., EPR study of spin labeled brush polymers in organic solvents. J Am Chem Soc. Dec. 14, 2011;133(49):19953-9. doi: 10.1021/ja2085349. Epub Nov. 21, 2011.
Xiao et al., The use of polymeric platinum(IV) prodrugs to deliver multinuclear platinum(II) drugs with reduced systemic toxicity and enhanced antitumor efficacy. Biomaterials. Nov. 2012;33(33):8657-69. doi: 10.1016/j.biomaterials.2012.08.015. Epub Aug. 28, 2012.
Xing et al., A stable metal coordination polymer gel based on a calix [4]arene and its 'uptake' of non-ionic organic molecules from the aqueous phase. Chem Commun (Camb). Feb. 21, 2002;(4):362-3.
Xing et al., Design of coordination polymer as stable catalytic systems. Chemistry. Nov. 4, 2002;8(21):5028-32.
Xing et al., Spontaneous Enrichment of Organic Molecules from Aqueous and Gas Phases into a Stable Metallogel. Langmuir. 2002;18:9654-9658.
Xu et al., Mechanism of Shear Thickening in Reversibly Cross-linked Supramolecular Polymer Networks. Macromolecules. Apr. 13, 2010;43(7):3556-3565.
Xu et al., Scaling Laws in Supramolecular Polymer Networks. Macromolecules. 2011;44(13):5465-5472.
Xu et al., Strain Hardening and Strain Softening of Reversibly Cross-linked Supramolecular Polymer Networks. Macromolecules. Sep. 27, 2011;44(18):7478-7488.
Yan et al., Hierarchical self-assembly: well-defined supramolecular nanostructures and metallohydrogels via amphiphilic discrete organoplatinum(II) metallacycles. J Am Chem Soc. Sep. 25, 2013;135(38):14036-9. doi: 10.1021/ja406877b. Epub Aug. 8, 2013.
Yan et al., Particle carriers for combating multidrug-resistant cancer. ACS Nano. Nov. 26, 2013;7(11):9512-7. doi: 10.1021/nn405632s. Epub Nov. 11, 2013.
Yan et al., Responsive supramolecular polymer metallogel constructed by orthogonal coordination-driven self-assembly and host/guest interactions. J Am Chem Soc. Mar. 26, 2014;136(12):4460-3. doi: 10.1021/ja412249k. Epub Mar. 12, 2014.
Yan et al., Supramolecular polymers with tunable topologies via hierarchical coordination—driven self-assembly and hydrogen bonding interfaces. Proc Natl Acad Sci U S A. Sep. 24, 2013;110(39):15585-90. doi: 10.1073/pnas.1307472110. Epub Sep. 9, 2013.
Yang et al., Luminescent chemodosimeters for bioimaging. Chem Rev. Jan. 9, 2013;113(1):192-270. doi: 10.1021/cr2004103. Epub Jun. 18, 2012.
Yi et al., Telmisartan attenuates hepatic fibrosis in bile ductligated rats. Acta Pharmacol Sin. Dec. 2012;33(12):1518-24. doi: 10.1038/aps.2012.115. Epub Oct. 29, 2012.
Yoneya et al., Coordination-directed self-assembly of M12L24 nanocage: effects of kinetic trapping on the assembly process. ACS Nano. Feb. 25, 2014;8(2):1290-6. doi: 10.1021/nn404595j. Epub Jan. 31, 2014.
Yoneya et al., Simulation of metal-ligand self-assembly into spherical complex M6L8. J Am Chem Soc. Sep. 5, 2012;134(35):14401-7. doi: 10.1021/ja303542r. Epub Aug. 22, 2012.
Yoshizawa et al., Molecular architectures of multi-anthracene assemblies. Chem Soc Rev. Mar. 21, 2014;43(6):1885-98. doi: 10.1039/c3cs60315f.
You et al., Manganese displacement from Zinpyr-1 allows zinc detection by fluorescence microscopy and magnetic resonance imaging. Chem Commun (Camb). Jun. 21, 2010;46(23):4139-41. doi: 10.1039/c0cc00179a. Epub May 10, 2010.

(56) References Cited

OTHER PUBLICATIONS

Yount et al., Small-molecule dynamics and mechanisms underlying the macroscopic mechanical properties of coordinatively cross-linked polymer networks. J Am Chem Soc. Oct. 19, 2005;127(41):14488-96.
Yount et al., Strong means slow: dynamic contributions to the bulk mechanical properties of supramolecular networks. Angew Chem Int Ed Engl. Apr. 29, 2005;44(18):2746-8.
Yuan et al., One-pot syntheses of amphiphilic centipede-like brush copolymers via combination of ring-opening polymerization and "click" chemistry. Macromol. Jan. 27, 2010;43(4):1739-46.
Yue et al., Macrocyclic and lantern complexes of palladium(II) with bis(amidopyridine) ligands: synthesis, structure, and host-guest chemistry. Inorg Chem. Nov. 29, 2004;43(24):7671-81.
Zhang et al., Active cross-linkers that lead to active gels. Angew Chem Int Ed Engl. Oct. 25, 2013;52(44):11494-8. doi: 10.1002/anie.201304437. Epub Sep. 12, 2013.
Zhang et al., Cyclodextrin-centred star polymers synthesized via a combination of thiol-ene click and ring opening polymerization. Chem Commun (Camb). Aug. 21, 2012;48(65):8063-5. doi: 10.1039/c2cc33742h. Epub Jul. 6, 2012.
Zhang et al., Dual-functional gadolinium-based copper(II) probe for selective magnetic resonance imaging and fluorescence sensing. Inorg Chem. Feb. 20, 2012;51(4):2325-31. doi: 10.1021/ic202322f. Epub Feb. 8, 2012.
Zhang et al., One-pot RAFT synthesis of core cross-linked star polymers of polyPEGMA in water by sequential homogeneous and heterogeneous polymerizations. Polym. Chem., 2012;3:2656-2664. DOI: 10.1039/C2PY20442H.
Zhang et al., polyMOFs: A Class of Interconvertible Polymer-Metal-Organic-Framework Hybrid Materials. Angew Chem Int Ed Engl. May 18, 2015;54(21):6152-7. doi: 10.1002/anie.201502733. Epub Apr. 29, 2015.
Zhang et al., Redox-Responsive, Core Cross-Linked Polyester Micelles. ACS Macro Lett., 2013;2(1):40-44. DOI: 10.1021/mz300522n.
Zhao et al., Polystyrene—Polylactide Bottlebrush Block Copolymer at the Air/Water Interface. Macromol. Sep. 28, 2009;42(22):9027-33.
Zhao et al., Rheological Behavoir of Shear-Responsive Metallo-Supramolecular Gels. Macromolecules. 2004;37(10):3529-3531.
Zhelev et al., Imaging of superoxide generation in the dopaminergic area of the brain in Parkinson's disease, using mito-TEMPO. ACS Chem Neurosci. Nov. 20, 2013;4(11):1439-45. doi: 10.1021/cn400159h. Epub Sep. 16, 2013.
Zhelev et al., Nitroxyl radicals as low toxic spin-labels for non-invasive magnetic resonance imaging of blood-brain barrier permeability for conventional therapeutics. Chem Commun (Camb). Jan. 7, 2009;(1):53-5. doi: 10.1039/b816878d. Epub Nov. 13, 2008.
Zhelev et al., Nitroxyl radicals for labeling of conventional therapeutics and noninvasive magnetic resonance imaging of their permeability for blood-brain barrier: relationship between structure, blood clearance, and MRI signal dynamic in the brain. Mol Pharm. Mar.-Apr. 2009;6(2):504-12. doi: 10.1021/mp800175k.
Zheng et al., Construction of Smart Supramolecular Polymeric Hydrogels Cross-linked by Discrete Organoplatinum(II) Metallacycles via Post-Assembly Polymerization. J. Am. Chem. Soc., 2016;138(14):4927-37. DOI: 10.1021/jacs.6b01089.
Zheng et al., Morphology of ABC triblock copolymers. Macromol. Oct. 1995;28(21):7215-23.
Zhou et al., Counting primary loops in polymer gels. Proc Natl Acad Sci U S A. Nov. 20, 2012;109(47):19119-24. doi: 10.1073/pnas.1213169109. Epub Nov. 6, 2012.
Zhou et al., Photo-controlled growth of telechelic polymers and end-linked polymer gels. Angew Chem Int Ed Engl. Feb. 18, 2013;52(8):2235-8. doi: 10.1002/anie.201207966. Epub Jan. 17, 2013.
PCT/US2019/027414, Sep. 12, 2019, International Search Report and Written Opinion.
PCT/US2019/027414, Oct. 22, 2020, International Preliminary Report on Patentability.
International Preliminary Report on Patentability for PCT/US2022/047333 mailed Jul. 4, 2024.
[No Author Listed], 2-Propen-1-amine, 3-(2-methoxyphenyl)-N-2-propyn-1-yl. CAS Registry File RN 1883141-01-2. STN Entry Date Mar. 10, 2016.
Amass, A.J., Ring-opening metathesis polymerization of cyclic alkenes. In: New Methods of Polymer Synthesis. 1991. J.R. Ebdon, Ed. Blackie & Son Ltd., Glasgow, Scotland. Chapter 3:76-106.
Kim et al., Anion-directed self-assembly of coordination polymer into tunable secondary structure. J Am Chem Soc. Jun. 9, 2004;126(22):7009-14. Supporting Information Experimental Section.
Kolb et al., Click Chemistry: Diverse Chemical Function from a Few Good Reactions. Angew Chem Int Ed Engl. Jun. 1, 2001;40(11):2004-2021. doi: 10.1002/1521-3773(20010601)40:11<2004::AID-ANIE2004>3.0.CO;2-5.
Pesek et al., Synthesis of bottlebrush copolymers based on poly(dimethylsiloxane) for surface active additives. Polymer. Aug. 19, 2016;98(19):495-504. Abstract Only.
Wurz et al., A "Click Chemistry Platform" for the Rapid Synthesis of Bispecific Molecules for Inducing Protein Degradation. J Med Chem. Jan. 25, 2018;61(2):453-461. doi: 10.1021/acs.jmedchem.6b01781. Epub Apr. 17, 2017.
Xia et al., Efficient Synthesis of Narrowly Dispersed Brush Polymers via Living Ring-Opening Metathesis Polymerization of Macromonomers. Macromolecules. Apr. 20, 2009;42:3761-6. doi: 10.1021/MA900280C.
Zhou et al., Efficient formation of multicompartment hydrogels by stepwise self-assembly of thermoresponsive ABC triblock terpolymers. J Am Chem Soc. Jun. 27, 2012;134(25):10365-8. doi: 10.1021/ja303841f. Epub Jun. 13, 2012.

* cited by examiner

In vitro release conditions: 37 °C, PBS

In vitro release conditions: 37 °C, PBS

MM of B1

$t_{1/2}$ = 5 hours

In vitro release conditions: 37 °C, PBS

MM of B2

$t_{1/2}$ = 4 days

In vitro release conditions: 37 °C, PBS

In vitro release conditions: 37 °C, PBS

MM of B4

$t_{1/2}$ = 6 days

In vitro release conditions: 37 °C, PBS

BRUSH PRODRUGS AND USES THEREOF

RELATED APPLICATIONS

The present application is a national stage filing under 35 U.S.C. § 371 of International Application No. PCT/US2019/027414, filed Apr. 13, 2019, which claims priority to U.S. Provisional Application No. 62/657,715, filed Apr. 13, 2018, each of which is incorporated herein by reference.

BACKGROUND OF THE DISCLOSURE

Bottlebrush polymers have found widespread applications in fields ranging from drug delivery and molecular imaging to novel materials preparation.[1-3] Graft-through ring-opening metathesis polymerization (ROMP) offers distinct advantages over other bottlebrush synthesis methods.[45] The fast-initiating Grubb's $3^{rd}$ generation catalyst (G3-Cat) has been shown to sustain propagation of polymer chains with exceptionally high tolerance towards a wide range of sterically-hindered multivalent macromonomers (MMs), reaching high degrees of polymerization and low dispersity values, even at low millimolar concentrations.[6,7] Furthermore, using G3-Cat, it is possible to control composition, morphology, and size of final macro molecules, preparing remarkable polymeric architectures such as bottlebrushes and stars.[7-11] Due to high packing density of their side-chains, the backbone of bottlebrush polymers is very rigid and adapts extended morphology with minimal side-chain entanglement.[6] Recently, self-assembly behaviors of bottlebrush block copolymers (BBCPs) have become an active area of research, as these macromolecules readily undergo phase separation and can be used to design materials with novel mechanical properties in bulk.[6,12] On the other hand, polymeric star nanoarchitectures offer several valuable features such as tunable nanoscale sizes and shapes that mimic globular biomacromolecules, allowing for extended blood circulation and efficient biodistribution and/or tumor accumulation.[13-15] These properties make star polymers particularly well-suited for biological applications.[10]

SUMMARY OF THE DISCLOSURE

The present disclosure provides, in one aspect, Brush prodrugs of pharmaceutical agents (Brush prodrugs). In certain embodiments, the pharmaceutical agents are therapeutic agents, diagnostic agents, and prophylactic agents. In certain embodiments, the therapeutic agents are bromo and extra terminal protein (BET) inhibitors (iBETs). BET inhibitors are promising anti-cancer agents, but their clinical development has been limited by hematological and gastrointestinal (GI) toxicity. For the benzodiazepine-derived inhibitor OTX-015, the dose-limiting toxicities (DLTs) are thrombocytopenia (96%), anemia (91%), and neutropenia (51%) with additional GI events (diarrhea, vomiting and mucositis) reported to limit patient compliance despite evidence of durable/objective tumor responses.

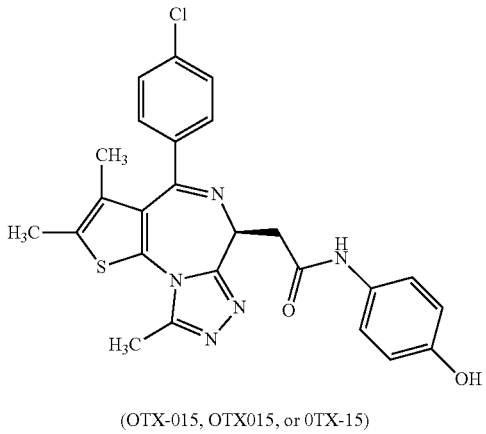 [SMILES: Cc1sc2c(c1C)C(c1ccc(Cl)cc1)=N[C@@H](CC(=O)Nc1ccc(O)cc1)c1nnc(C)n1-2]

(OTX-015, OTX015, or OTX-15)

The Brush prodrugs of BET inhibitors described herein have been found to improve the narrow therapeutic index of the free BET inhibitors, with a favorable biodistribution and release of free BET inhibitors in tumor compared to other tissues, including gut and bone marrow. Specifically, the Brush prodrugs of BET inhibitors were evaluated for myelosuppression and GI toxicity using in vitro, clinical pathology, and immunohistopathology techniques. Compared to free BET inhibitors, which showed dose-dependent body weight loss, diarrhea, and suppression of white blood cells, the Brush prodrugs of BET inhibitors spared the lymphocytes, platelets, and neutrophils, and showed minimal suppression of the reservoir of myeloid cells in the bone marrow. The release (e.g., the rate of release) of the free BET inhibitors from the Brush prodrugs of BET inhibitors may be tuned by changing one or more moieties of the Brush prodrugs of BET inhibitors.

The Brush prodrugs of other pharmaceutical agents are expected to show similar and optionally additional advantages over the free pharmaceutical agents.

The Brush prodrugs may be polymers prepared by polymerizing a macromonomer of Formula (I):

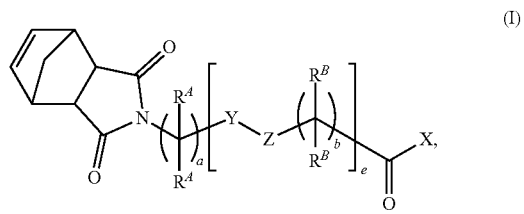

or a salt thereof, in the presence of a metathesis catalyst, wherein each instance of —Y—Z— is independently

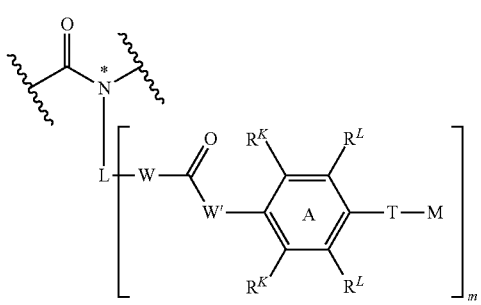

3

-continued (e.g., 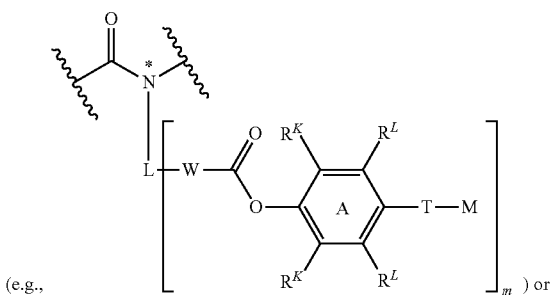 ) or

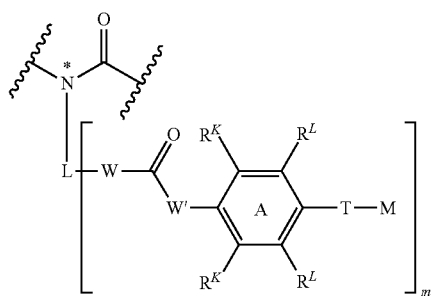

(e.g., 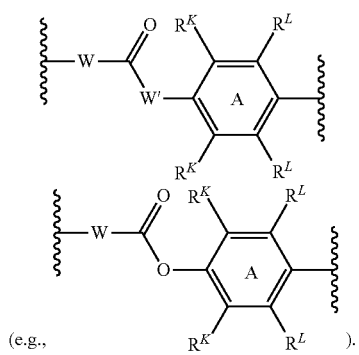 ).

In certain embodiments, the metathesis catalyst is a Grubbs catalyst.

Not bound by any particular theory, the advantages of the Brush prodrugs may be due to the moiety

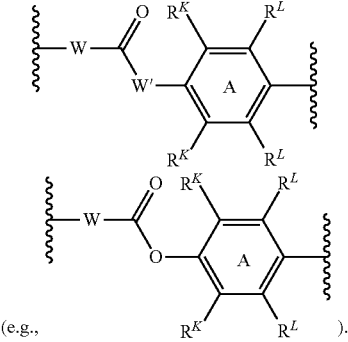

(e.g., 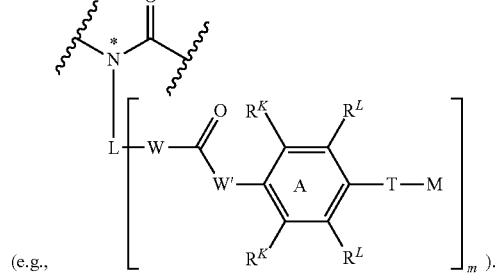 ).

The properties (e.g., release of the free pharmaceutical agents) of the Brush prodrugs may be tuned, e.g., by changing the moiety

4

For example, the size, polarity, chemical reactivity, and/or photochemical reactivity of W, $R^K$, and/or $R^L$ may affect the cleavage (e.g., rate of cleavage) of the moiety W—C (=O)—W' (e.g., the C—O bond). Bulkier $R^K$ may slow the cleavage. Bulkier $R^L$ may also slow the cleavage. Less polar $R^K$ may slow the cleavage. Less polar $R^L$ may also slow the cleavage. Smaller $R^K$ may expedite the cleavage. Smaller $R^L$ may also expedite the cleavage. More polar $R^K$ may expedite the cleavage. More polar $R^L$ may also expedite the cleavage. The moiety W—C(=O)—W' may also affect the cleavage. For example, C(=O)—O may be cleaved faster than C(=O)—N. Therefore, the cleavage may be fine tuned by modifying one or more moieties include in

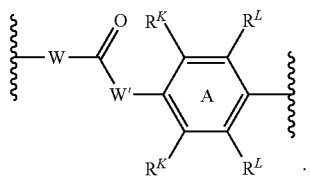

In another aspect, the present disclosure provides compounds of Formula (II):

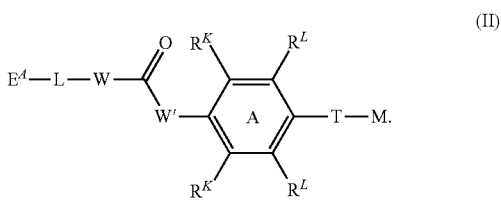

(II)

In another aspect, the present disclosure provides conjugates of Formula (III):

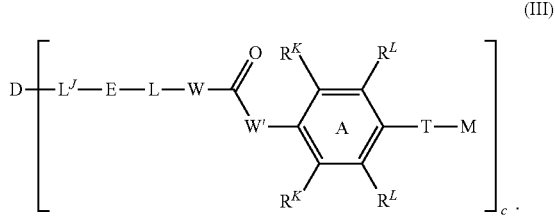

(III)

In the compounds and conjugates, each instance of T is substituted or unsubstituted methylene; and each instance of M is independently an ammonium salt or iminium salt of a pharmaceutical agent, wherein the attachment point is the $N^+$ of the ammonium salt or iminium salt. The compounds and conjugates may be useful for conjugating with a delivery vehicle a pharmaceutical agent that does not contain a conventional reaction handle. The pharmaceutical agent may be cleaved from the compounds or conjugates in the way shown in FIG. 4A. The cleavage may be fine tuned as described herein, e.g., by modifying one or more moieties include in

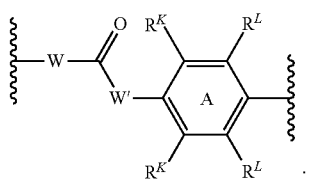

In another aspect, the present disclosure provides methods of preparing the Brush prodrugs.

In another aspect, the present disclosure provides macromonomers of Formula (I), and salts thereof.

In another aspect, the present disclosure provides methods of preparing the macromonomers, and salts thereof.

In another aspect, the present disclosure provides pharmaceutical compositions comprising a Brush prodrug and optionally a pharmaceutically acceptable excipient.

In another aspect, the present disclosure provides pharmaceutical compositions comprising a conjugate and optionally a pharmaceutically acceptable excipient.

In another aspect, the present disclosure provides kits comprising: a macromonomer, or a salt thereof, a Brush prodrug, or a pharmaceutical composition; and instructions for using the macromonomer, or a salt thereof, the polymer, or the pharmaceutical composition.

In another aspect, the present disclosure provides kits comprising a compound; and instructions for using the compound.

In another aspect, the present disclosure provides kits comprising a conjugate, or a salt thereof, or a pharmaceutical composition; and instructions for using the conjugate, or a salt thereof, or the pharmaceutical composition.

In another aspect, the present disclosure provides methods of delivering a pharmaceutical agent to a subject in need thereof comprising administering to the subject in need thereof a polymer or a pharmaceutical composition.

In another aspect, the present disclosure provides methods of delivering a pharmaceutical agent to a cell comprising contacting the cell with a polymer or a pharmaceutical composition.

In another aspect, the present disclosure provides methods of treating a disease in a subject in need thereof comprising administering to or implanting in the subject in need thereof a therapeutically effective amount of: a polymer or a pharmaceutical composition; wherein at least one instance of M is a therapeutic agent.

In another aspect, the present disclosure provides methods of preventing a disease in a subject in need thereof comprising administering to or implanting in the subject in need thereof a prophylactically effective amount of: a polymer or a pharmaceutical composition; wherein at least one instance of M is a prophylactic agent.

In another aspect, the present disclosure provides methods of diagnosing a disease in a subject comprising administering to or implanting in the subject a diagnostically effective amount of: a polymer or a pharmaceutical composition; wherein at least one instance of M is a diagnostic agent.

In another aspect, the present disclosure provides methods of delivering a pharmaceutical agent to a subject in need thereof comprising administering to the subject in need thereof a conjugate or a pharmaceutical composition.

In another aspect, the present disclosure provides methods of delivering a pharmaceutical agent to a cell comprising contacting the cell with a conjugate or a pharmaceutical composition.

In another aspect, the present disclosure provides methods of treating a disease in a subject in need thereof comprising administering to or implanting in the subject in need thereof a therapeutically effective amount of: a conjugate or a pharmaceutical composition; wherein at least one instance of M is a therapeutic agent.

In another aspect, the present disclosure provides methods of preventing a disease in a subject in need thereof comprising administering to or implanting in the subject in need thereof a prophylactically effective amount of: a conjugate or a pharmaceutical composition; wherein at least one instance of M is a prophylactic agent.

In another aspect, the present disclosure provides methods of diagnosing a disease in a subject comprising administering to or implanting in the subject a diagnostically effective amount of: a conjugate or a pharmaceutical composition; wherein at least one instance of M is a diagnostic agent.

In certain embodiments, the disease is cancer.

The present disclosure refers to various issued patent, published patent applications, journal articles, and other publications, all of which are incorporated herein by reference.

Definitions

For convenience, certain terms employed herein, in the specification, examples and appended claims are collected herein.

Unless otherwise required by context, singular terms shall include pluralities and plural terms shall include the singular.

The following definitions are more general terms used throughout the present application:

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." "About" and "approximately" shall generally mean an acceptable degree of error for the quantity measured given the nature or precision of the measurements. Exemplary degrees of error are within 20 percent (%), typically, within 10%, and more typically, within 5%, 4%, 3%, 2% or 1% of a given value or range of values.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; *Smith and March March's*

*Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

When a range of values ("range") is listed, it is intended to encompass each value and sub-range within the range. A range is inclusive of the values at the two ends of the range unless otherwise provided. For example, "an integer between 1 and 4" refers to 1, 2, 3, and 4. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "alkyl" refers to a radical of a $C_1$-$C_{1000}$ straight-chain or branched saturated hydrocarbon group. In some embodiments, an alkyl group has 1 to 200 carbon atoms ("$C_1$-$C_{200}$ alkyl"), 1 to 20 carbon atoms ("$C_1$-$C_{20}$ alkyl"), 1 to 10 carbon atoms ("$C_1$-$C_{10}$ alkyl"), 1 to 9 carbon atoms ("$C_1$-$C_9$ alkyl"), 1 to 8 carbon atoms ("$C_1$-$C_8$ alkyl"), 1 to 7 carbon atoms ("$C_1$-$C_7$ alkyl"), 1 to 6 carbon atoms ("$C_1$-$C_6$ alkyl"), 1 to 5 carbon atoms ("$C_1$-$C_5$ alkyl"), 1 to 4 carbon atoms ("$C_1$-$C_4$ alkyl"), 1 to 3 carbon atoms ("$C_1$-$C_3$ alkyl"), 1 to 2 carbon atoms ("$C_1$-$C_2$ alkyl"), or 1 carbon atom ("$C_1$ alkyl"). Examples of $C_1$-$C_6$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. $C_{30}$-$C_{1000}$ alkyl may be obtained from polymerization. Unless otherwise specified, each instance of an alkyl group is independently unsubstituted (an "unsubstituted alkyl") or substituted (a "substituted alkyl") with one or more substituents.

The term "alkenyl" refers to a radical of a straight-chain or branched hydrocarbon group having from 2 to 1000 carbon atoms and one or more carbon-carbon double bonds (e.g., 1, 2, 3, or 4 double bonds). In some embodiments, an alkenyl group has 2 to 200 carbon atoms ("$C_{2-200}$ alkenyl"). In some embodiments, an alkenyl group has 2 to 20 carbon atoms ("$C_{2-20}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl).

Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. $C_{30}$-$C_{1000}$ alkenyl may be obtained from polymerization. Unless otherwise specified, each instance of an alkenyl group is independently unsubstituted (an "unsubstituted alkenyl") or substituted (a "substituted alkenyl") with one or more substituents. In an alkenyl group, a C=C double bond for which the stereochemistry is not specified (e.g., —CH=CHCH$_3$,

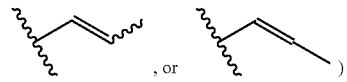

, or )

may be in the (E)- or (Z)-configuration.

The term "alkynyl" refers to a radical of a straight-chain or branched hydrocarbon group having from 2 to 1000 carbon atoms and one or more carbon-carbon triple bonds (e.g., 1, 2, 3, or 4 triple bonds) ("$C_{2-10}$ alkynyl"). In some embodiments, an alkynyl group has 2 to 200 carbon atoms ("$C_{2-200}$ alkynyl"), 2 to 20 carbon atoms ("$C_{2-20}$ alkynyl"), 2 to 9 carbon atoms ("$C_{2-9}$ alkynyl"), 2 to 8 carbon atoms ("$C_{2-8}$ alkynyl"), 2 to 7 carbon atoms ("$C_{2-7}$ alkynyl"), 2 to 6 carbon atoms ("$C_{2-6}$ alkynyl"), 2 to 5 carbon atoms ("$C_{2-5}$ alkynyl"), 2 to 4 carbon atoms ("$C_{2-4}$ alkynyl"), 2 to 3 carbon atoms ("$C_{2-3}$ alkynyl"), or 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. $C_{30}$-$C_{1000}$ alkynyl may be obtained from polymerization. Unless otherwise specified, each instance of an alkynyl group is independently unsubstituted (an "unsubstituted alkynyl") or substituted (a "substituted alkynyl") with one or more substituents.

The term "heteroalkyl" refers to an alkyl group which further includes at least one heteroatom (e.g., 1, 2, 3, 4, or more heteroatoms, as valency permits) selected from oxygen, nitrogen, phosphorus, or sulfur within (i.e., inserted between adjacent carbon atoms of) and/or placed at one or more terminal position(s) of the parent chain. In certain embodiments, a heteroalkyl group refers to a saturated group having from 1 to 1000 carbon atoms and 1 or more heteroatoms within the parent chain ("$C_1$-$C_{1000}$ heteroalkyl"), 1 to 20 carbon atoms and 1 or more heteroatoms within the parent chain ("$C_1$-$C_{20}$ heteroalkyl"), 1 to 10 carbon atoms and 1 or more heteroatoms within the parent chain ("$C_1$-$C_{10}$ heteroalkyl"), 1 to 9 carbon atoms and 1 or more heteroatoms within the parent chain ("$C_1$-$C_9$ heteroalkyl"), 1 to 8 carbon atoms and 1 or more heteroatoms within the parent chain ("$C_1$-$C_8$ heteroalkyl"), 1 to 7 carbon atoms and 1 or more heteroatoms within the parent chain ("$C_1$-$C_7$ heteroalkyl"), 1 to 6 carbon atoms and 1 or more heteroatoms within the parent chain ("$C_1$-$C_6$ heteroalkyl"), 1 to 5 carbon atoms and 1 or more heteroatoms within the parent chain ("$C_1$-$C_5$ heteroalkyl"), 1 to 4 carbon atoms and lor more heteroatoms within the parent chain ("$C_1$-$C_4$ heteroalkyl"), 1 to 3 carbon atoms and 1 or more heteroatoms within the parent chain ("$C_1$-$C_3$ heteroalkyl"), 1 to 2 carbon atoms and 1 heteroatom within the parent chain ("$C_1$-$C_2$ heteroalkyl"), or 1 carbon atom and 1 heteroatom ("$C_1$ heteroalkyl"). $C_{30}$-$C_{1000}$ heteroalkyl may be obtained from polymerization. Unless otherwise specified, each instance of a heteroalkyl group is independently unsubstituted (an "unsubstituted heteroalkyl") or substituted (a "substituted heteroalkyl") with one or more substituents.

The term "heteroalkenyl" refers to an alkenyl group, which further includes at least one heteroatom (e.g., 1, 2, 3, 4, or more heteroatoms, as valency permits) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 1000 carbon atoms, at least one double bond, and 1 or more heteroatoms within the parent chain ("hetero$C_{2-1000}$ alkenyl"). In certain embodiments, a heteroalkenyl group refers to a group having from 2 to 20 carbon atoms, at least one double bond, and 1 or more heteroatoms within the parent chain ("hetero$C_{2-20}$ alkenyl"). In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and lor 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). $C_{30}$-$C_{1000}$ heteroalkenyl may be obtained from polymerization.

Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "heteroalkynyl" refers to an alkynyl group, which further includes at least one heteroatom (e.g., 1, 2, 3, 4, or more heteroatoms, as valency permits) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 1000 carbon atoms, at least one triple bond, and 1 or more heteroatoms within the parent chain ("hetero$C_{2-1000}$ alkynyl"). In certain embodiments, a heteroalkynyl group refers to a group having from 2 to 20 carbon atoms, at least one triple bond, and 1 or more heteroatoms within the parent chain ("hetero$C_{2-20}$ alkynyl"). In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and lor 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). $C_{30}$-$C_{1000}$ heteroalkynyl may be obtained from polymerization. Unless otherwise specified, each instance of a heteroalkynyl group is independently unsubstituted (an "unsubstituted heteroalkynyl") or substituted (a "substituted heteroalkynyl") with one or more substituents.

In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" or "cycloalkyl" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"), 3 to 7 ring carbon atoms ("$C_{3-7}$ carbocyclyl"), 3 to 6 ring carbon atoms ("$C_{3-6}$ carbocyclyl"), 4 to 6 ring carbon atoms ("$C_{4-6}$ carbocyclyl"), 5 to 6 ring carbon atoms ("$C_{5-6}$ carbocyclyl"), or 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl (C$_5$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, phosphorus, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents.

In some embodiments, a heterocyclyl group is a 5-10 membered non-aromatic ring system having ring carbon atoms and 1-4 ring heteroatoms, wherein each heteroatom is independently selected from nitrogen, oxygen, phosphorus, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, phosphorus, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, phosphorus, and sulfur ("5-6 membered heterocyclyl"). In some embodiments, the 5-6 membered heterocyclyl has 1-3 ring heteroatoms selected from nitrogen, oxygen, phosphorus, and sulfur. In some embodiments, the 5-6 membered heterocyclyl has 1-2 ring heteroatoms selected from nitrogen, oxygen, phosphorus, and sulfur. In some embodiments, the 5-6 membered heterocyclyl has 1 ring heteroatom selected from nitrogen, oxygen, phosphorus, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl, and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetra-hydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C$_{6-14}$ aryl"). In some embodiments, an aryl group has 6 ring carbon atoms ("C$_6$ aryl"; e.g., phenyl). In some embodiments, an aryl group has 10 ring carbon atoms ("C$_{10}$ aryl"; e.g., naphthyl such as 1-naphthyl and 2-naphthyl). In some embodiments, an aryl group has 14 ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group be monovalent or may have more than one point of attachment to another moiety (e.g., it may be divalent, trivalent, etc), although the valency may be specified directly in the name of the group. For example, "triazoldiyl" refers to a divalent triazolyl moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

As understood from the above, alkyl, alkenyl, alkynyl, carbocyclyl, aryl, and heteroaryl groups are, in certain embodiments, optionally substituted. Optionally substituted refers to a group which may be substituted or unsubstituted (e.g., "substituted" or "unsubstituted" alkyl). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Affixing the suffix "ene" to a group indicates the group is a polyvalent (e.g., bivalent, trivalent, tetravalent, or pentavalent) moiety. In certain embodiments, affixing the suffix "ene" to a group indicates the group is a bivalent moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, —NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{aa}$, —SO$_2$OR$^{aa}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$ alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

In certain embodiments, the carbon atom substituents are independently halogen, substituted or unsubstituted C$_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)

$R^{aa}$, —OCO$_2$R$^{aa}$, —OC(=O)N(R$^{bb}$)$_2$, —NR$^{bb}$C(=O)R$^{aa}$, —NR$^{bb}$CO$_2$R$^{aa}$, or —NR$^{bb}$C(=O)N(R$^{bb}$)$_2$. In certain embodiments, the carbon atom substituents are independently halogen, substituted or unsubstituted C$_{1-6}$ alkyl, —OR$^{aa}$, —SR$^{aa}$, —N(R$^{bb}$)$_2$, —CN, —SCN, or —NO$_2$.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{aa}$, —SO$_2$OR$^{aa}$, —SO$R^{aa}$, —C(=S)N(R$^{cc}$)$_2$, —C(=O)SR$^{aa}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino) acetamide, 3-(p-hydroxyphenyl) propanamide, 3-(o-nitrophenyl) propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo) fluorenylmethyl carbamate, 9-(2,7-dibromo) fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl (o-nitrophenyl) methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido) benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmalcimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylidencamine, N-5-chlorosalicylideneamine, N-(5-chloro-2-hydroxyphenyl)phenylmethyleneamine, N-cyclohexylidencamine, N-(5,5-dimethyl-3-oxo-1-cyclohexenyl)amine, N-borane derivative, N-diphenylborinic acid derivative, N-[phenyl (pentaacylchromium- or tungsten) acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfonamide (Nps), 2,4-dinitrobenzenesulfonamide, pentachlorobenzenesulfonamide, 2-nitro-4-methoxybenzenesulfenamide, triphenylmethylsulfenamide, and 3-nitropyridinesulfonamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —C(=O)$SR^{aa}$, —C(=O)$R^{aa}$, —$CO_2R^{aa}$, —C(=O)N($R^{bb})_2$, —C(=$NR^{bb}$)$R^{aa}$, —C(=$NR^{bb}$)$OR^{aa}$, —C(=$NR^{bb}$)N($R^{bb})_2$, —S(=O)$R^{aa}$, —$SO_2R^{aa}$, —Si($R^{aa})_3$, —P($R^{cc})_2$, —P($R^{cc})_3^+X^-$, —P($OR^{cc})_2$, —P($OR^{cc})_3^+X^-$, —P(=O)($R^{aa})_2$, —P(=O)($OR^{cc})_2$, and —P(=O)(N($R^{bb})_2)_2$, wherein $X^-$, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris (benzoyloxyphenyl) methyl, 3-(imidazol-1-yl)bis(4',4''-dimethoxyphenyl) methyl, 1,1-bis(4-methoxyphenyl)-1'-pyrenylmethyl, 9-anthryl, 9-(9-phenyl) xanthenyl, 9-(9-phenyl-10-oxo) anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio) pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio)ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy) butyrate, 2-(methylthiomethoxymethyl)benzoate, 2,6-dichloro-4-methylphenoxyacetate, 2,6-dichloro-4-(1,1,3,3-tetramethylbutyl) phenoxyacetate, 2,4-bis(1,1-dimethylpropyl) phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —C(=O)$SR^{aa}$, —C(=O)$R^{aa}$, —$CO_2R^{aa}$, —C(=O)N($R^{bb})_2$, —C(=$NR^{bb}$)$R^{aa}$, —C(=$NR^{bb}$)$OR^{aa}$, —C(=$NR^{bb}$)N($R^{bb})_2$, —S(=O)$R^{aa}$, —$SO_2R^{aa}$, —Si($R^{aa})_3$, —P($R^{cc})_2$, —P($R^{ee})_3^+X^-$, —P($OR^{cc})_2$, —P($OR^{cc})_3^+X^-$, —P(=O)($R^{aa})_2$, —P(=O)($OR^{cc})_2$, and —P(=O)(N($R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

The term "halo" or "halogen" refers to fluorine (fluoro, —F), chlorine (chloro, —C$_1$), bromine (bromo, —Br), or iodine (iodo, —I).

The term "hydroxyl" or "hydroxy" refers to the group —OH.

The term "thiol" or "thio" refers to the group —SH.

The term "amine" or "amino" refers to the group —NH— or —NH$_2$.

As used herein, the term "polyethylene glycol" or "PEG" refers to an ethylene glycol polymer that contains about 20 to about 2,000,000 linked monomers, typically about 50-1,000 linked monomers, usually about 100-300. Polyethylene glycols include ethylene glycol polymer containing various numbers of linked monomers, e.g., PEG20, PEG30, PEG40, PEG60, PEG80, PEG100, PEG115, PEG200, PEG300, PEG400, PEG500, PEG600, PEG1000, PEG1500, PEG2000, PEG3350, PEG4000, PEG4600, PEG5000, PEG6000, PEG8000, PEG11000, PEG12000, PEG2000000 and any mixtures thereof.

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "leaving group" is given its ordinary meaning in the art of synthetic organic chemistry and refers to an atom or a group capable of being displaced by a nucleophile. Examples of suitable leaving groups include halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other examples of leaving groups are water, ammonia, alcohols, ether moieties, thioether moieties, zinc halides, magnesium moieties, diazonium salts, and copper moieties.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay and/or prevent recurrence.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population of subjects.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactically effective amount. In certain embodiments, an effective amount is the amount of a compound or pharmaceutical composition described herein in a single dose. In certain embodiments, an effective amount is the combined amounts of a compound or pharmaceutical composition described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "therapeutic agent" includes an agent that is capable of providing a local or systemic biological, physiological, or therapeutic effect in the biological system to which it is applied. For example, a therapeutic agent can act to control tumor growth, control infection or inflammation, act as an analgesic, promote anti-cell attachment, and enhance bone growth, among other functions. Other suitable therapeutic agents can include anti-viral agents, hormones, antibodies, or therapeutic proteins. Other therapeutic agents include prodrugs, which are agents that are not biologically active when administered but, upon administration to a subject are converted to biologically active agents through metabolism or some other mechanism.

The term "prodrug" refer to a compound that becomes active, e.g., by solvolysis, reduction, oxidation, or under physiological conditions, to provide a pharmaceutically active compound, e.g., in vivo. A prodrug can include a derivative of a pharmaceutically active compound, such as, for example, to form an ester by reaction of the acid, or acid anhydride, or mixed anhydrides moieties of the prodrug moiety with the hydroxyl moiety of the pharmaceutical active compound.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than 2,000 g/mol. In certain embodiments, the molecular weight of a small molecule is not more than 1,500 g/mol. In certain embodiments, the molecular weight of a small molecule is not more than 1,000 g/mol, not more than 900 g/mol, not more than 800 g/mol, not more than 700 g/mol, not more than 600 g/mol, not more than 500 g/mol, not more than 400 g/mol, not more than 300 g/mol, not more than 200 g/mol, or not more than 100 g/mol. In certain embodiments, the molecular weight of a small molecule is at least 100 g/mol, at least 200 g/mol, at least 300 g/mol, at least 400 g/mol, at least 500 g/mol, at least 600 g/mol, at least 700 g/mol, at least 800 g/mol, or at least 900 g/mol, or at least 1,000 g/mol. Combinations of the above ranges (e.g., at least 200 g/mol and not more than 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

A "protein," "peptide," or "polypeptide" comprises a polymer of amino acid residues linked together by peptide bonds. The term refers to proteins, polypeptides, and peptides of any size, structure, or function. A protein may refer to an individual protein or a collection of proteins. Proteins preferably contain only natural amino acids, although non-natural amino acids (i.e., compounds that do not occur in nature but that can be incorporated into a polypeptide chain) and/or amino acid analogs as are known in the art may alternatively be employed. In certain embodiments, the amino acid residues of a peptide are alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and/or valine, in D and/or L form. In certain embodiments, the amino acid residues of a peptide are alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and/or valine, in L form. One or more of the amino acids in a protein may be protected. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these. In certain embodiments, a protein comprises between 2 and 10, between 10 and 30, between 30 and 100, between 100 and 300, or between 300 and 1,000, inclusive, amino acids. In certain embodiments, the amino acids in a protein are natural amino acids. In certain embodiments, the amino acids in a protein are unnatural amino acids. In certain embodiments, the amino acids in a protein are a combination of natural amino acids and unnatural amino acids.

The disclosure is not intended to be limited in any manner by the above exemplary listing of substituents. Additional terms may be defined in other sections of this disclosure.

BRIEF DESCRIPTION OF THE DRAWINGS

The figures are exemplary and do not limit the scope of the present disclosure.

FIG. 2A shows the macromolecule (MM) used for preparing T1 and the $t_{1/2}$ of T1. FIG. 2B shows the MM used for preparing T2 and the $t_{1/2}$ of T2. FIG. 2C shows the MM used for preparing T3 and the tin of T3. FIG. 2D shows the MM used for preparing T4 and the $t_{1/2}$ of T4. FIG. 2E shows the MM used for preparing T5 and the $t_{1/2}$ of T5. FIG. 2F shows the MM used for preparing T6 and the tin of T6.

FIG. 3A shows the MM used for preparing B1 and the fin of B1. FIG. 3B shows the MM used for preparing B2 and the 112 of B2. FIG. 3C shows the MM used for preparing B3 and the tin of B3. FIG. 3D shows the MM used for preparing B4 and the fun of B4.

FIG. 5A shows the tumor volume, and FIG. 5B shows the tumor weight, after B4 doses, or API (OTX-015 (OTX015 or OTX-15), as a competitor) doses (b.i.d. daily as a PO bolus). At the 500 mpk dose (both 4× and 6×) B4 was as effective in reducing final tumor weight at a lower cumulative dose than the tolerated dose of API. No weight loss was observed in any of the B4 regimens, while even the tolerated dose of API at 100 mpk BID shows minor weight loss (FIG. 5C). Similar dosing regimen was followed for T2, and the tumor volumes are shown in FIG. 5D. At the 500 mpk dose (both 4× and 6×) T2 was as effective in reducing final tumor weight (stats) at a lower cumulative dose than the tolerated dose of API (FIG. 5E). No weight loss was observed in any of the T2 regimens, while even the tolerated doses of API at 5 mpk and 10 mpk show minor weight loss (FIG. 5F). In FIGS. 5D to 5F, "iBET" refers to OTX-015.

FIG. 6A shows biodistribution of the B4 quantified using fluorescence signal (n=5) in homogenized tissue samples. FIG. 6B shows that B4 displayed favorable accumulation in tumors compared to other organs. A representative whole organ fluorescent imaging shows accumulation of OTX-015 in tumor. FIG. 6C shows tumor pharmacokinetics of B4 in mice treated with B4. B4 provides sustained release of OTX-015 at the tumor site. FIG. 6D shows assessment of free drug in whole blood of mice administered OTX-015 or B4 (n=5), and that linker design modulated serum stability.

FIG. 7A shows significant reduction of OTX-015-caused toxicity in gut is achieved with B4 compared to free OTX-015 as evident by preservation of c-Myc production in cell of gut lining. Concurrently, in-tumor efficacy of B4 is comparable to free OTX-015 as shown by modulation of c-Myc, CD180, and HEXIM1. FIG. 7B shows B4 prevents systemic toxicity associated with BET inhibition in bone marrow. Platelets, reticulocytes, and white blood cells (WBC) levels are not affected in mice treated with B4 (n=5) compared to group treated with free OTX-015.

DETAILED DESCRIPTION OF CERTAIN EMBODIMENTS OF THE DISCLOSURE

Figure 1A:
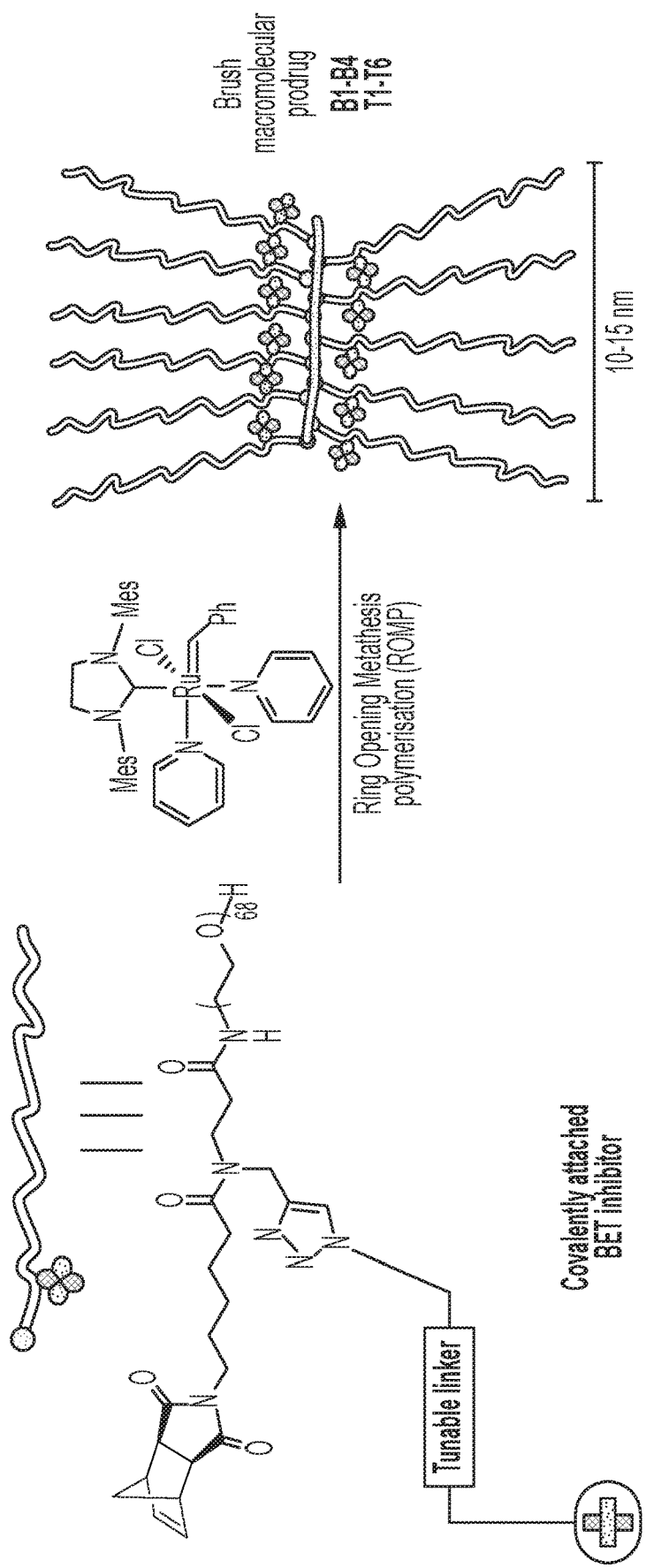
FIGS. 1A and 1B show an exemplary synthesis of Brush macromolecular prodrugs (FIG. 1A) and modulating release kinetics of the BET inhibitors from Brush prodrugs via tuning linker structure (FIG. 1B).
Figure 1B:
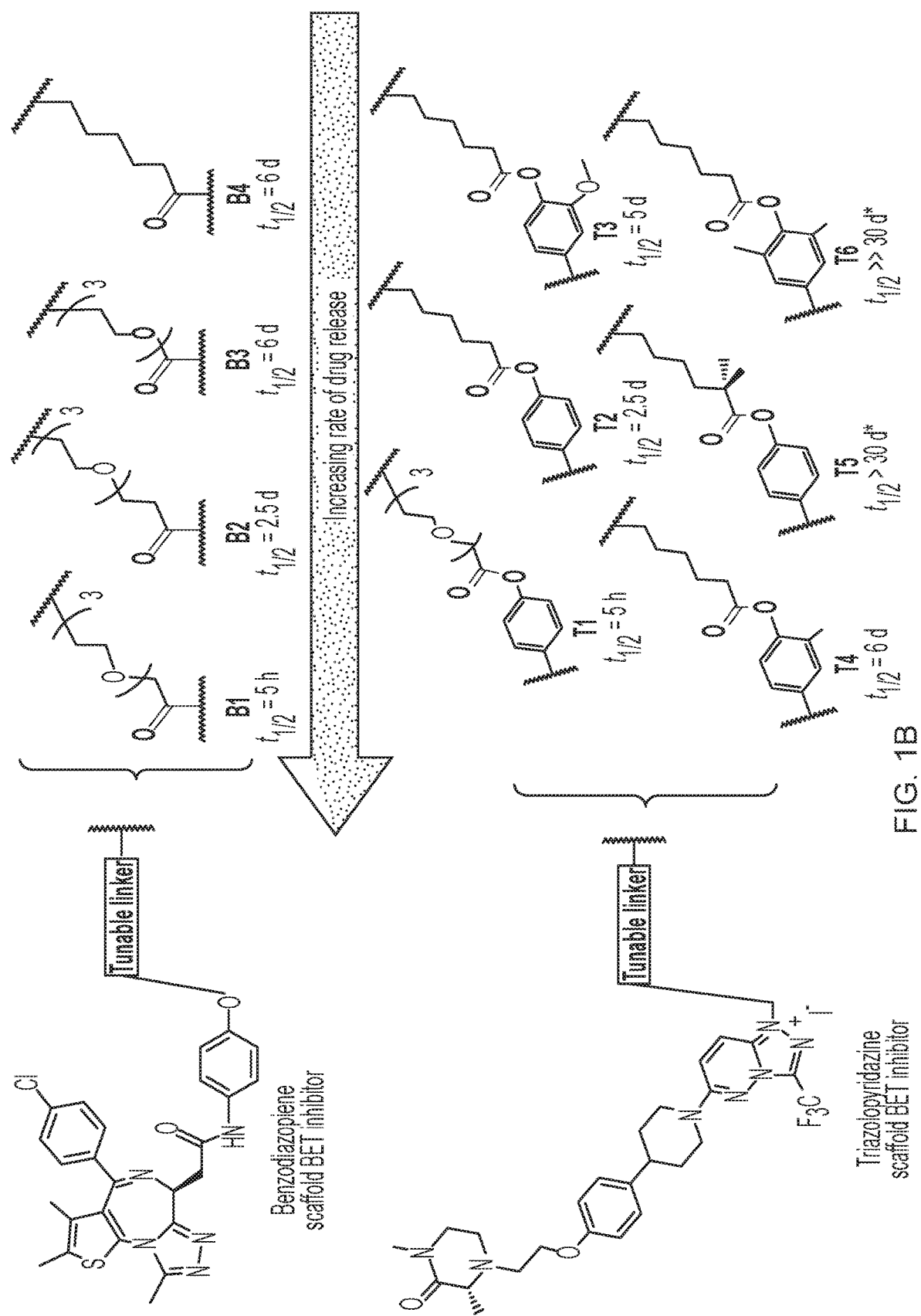
Figure 2A:
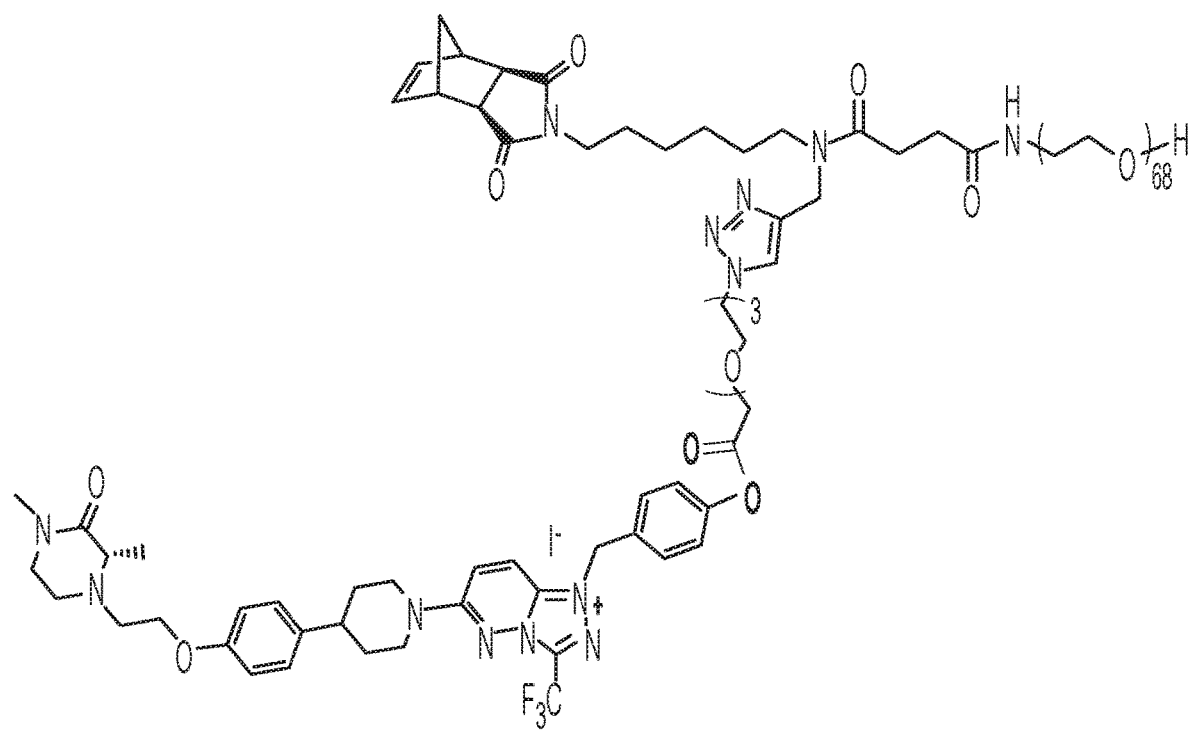
FIGS. 2A to 2F show the in vitro release profile of Brush prodrugs T1 to T6.
Figure 2B:
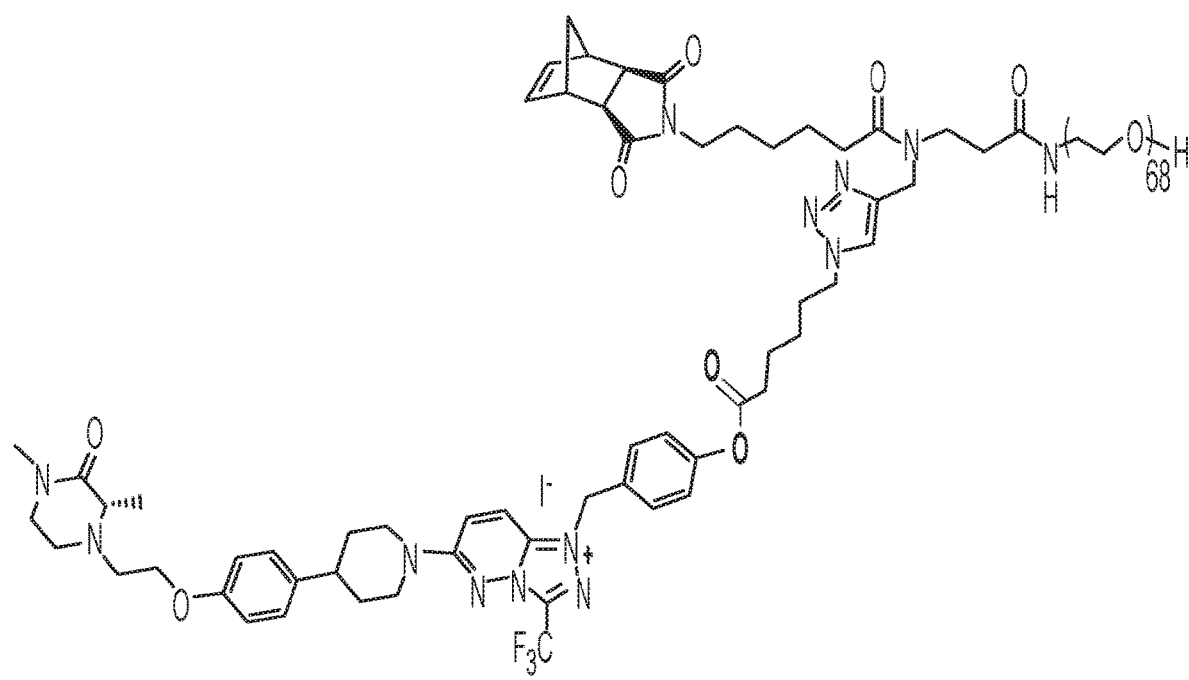
Figure 2C:
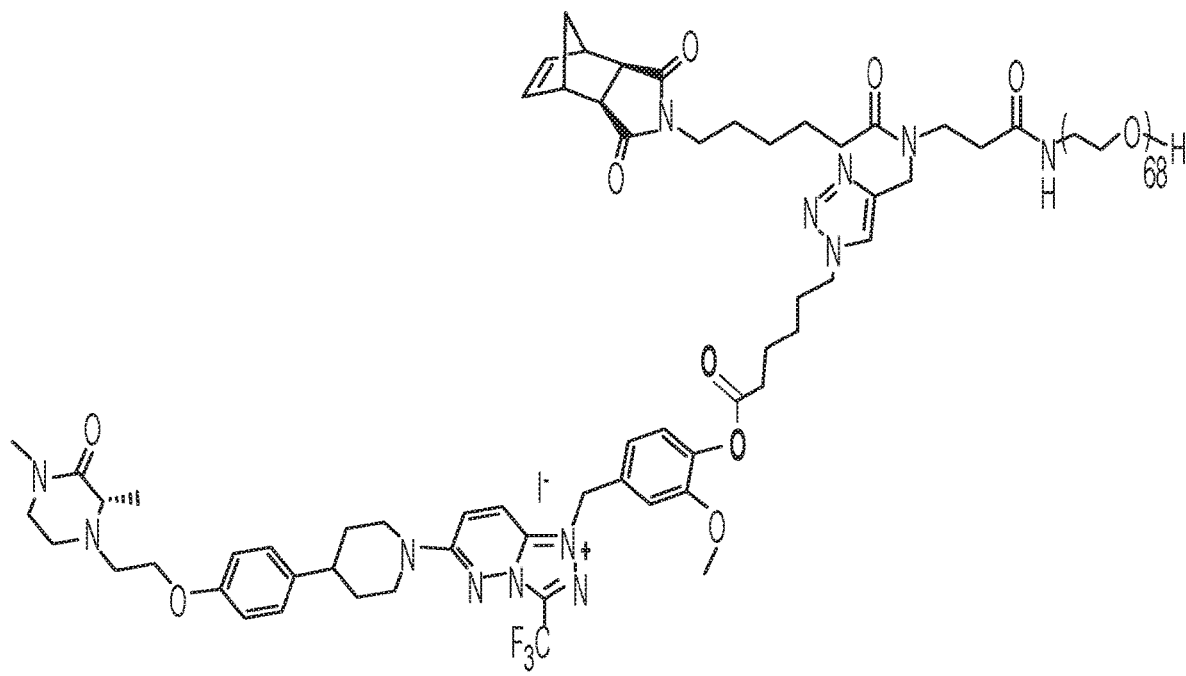
Figure 2D:
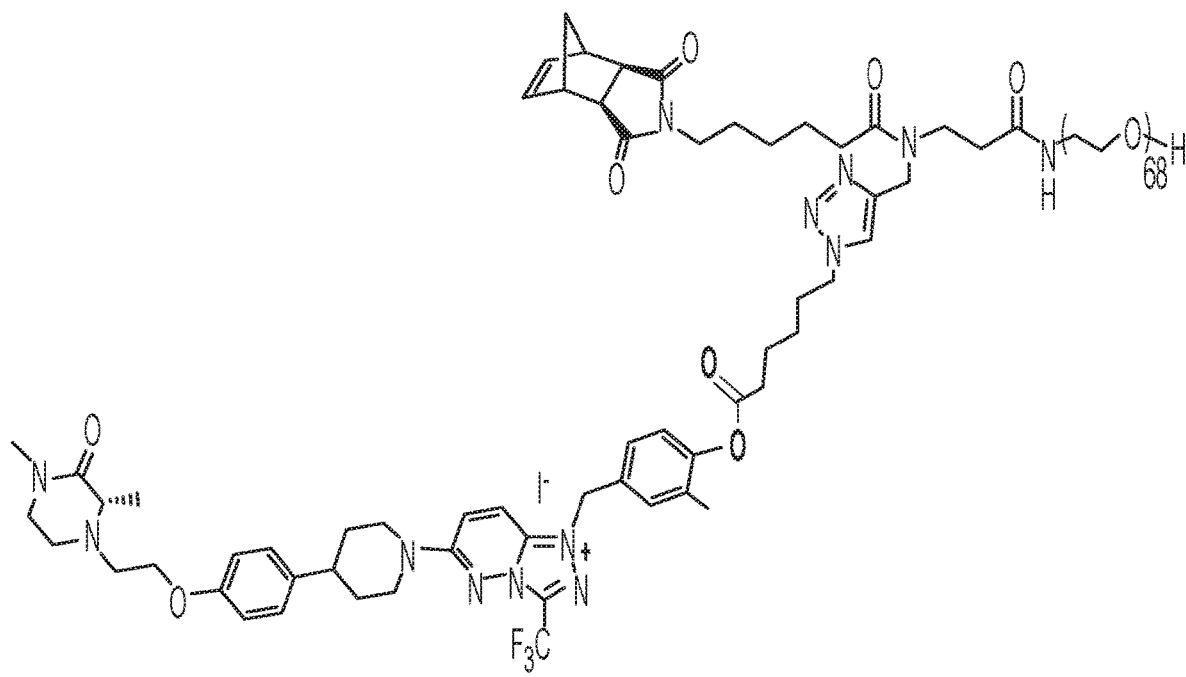
Figure 2E:
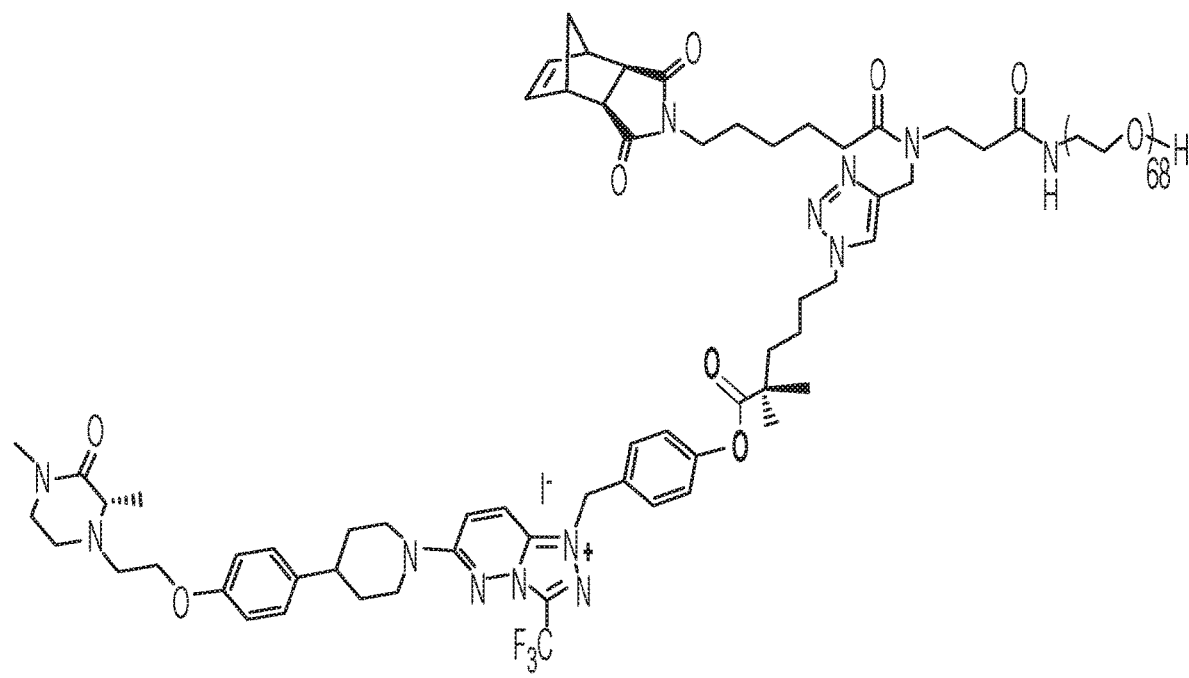
Figure 2F:
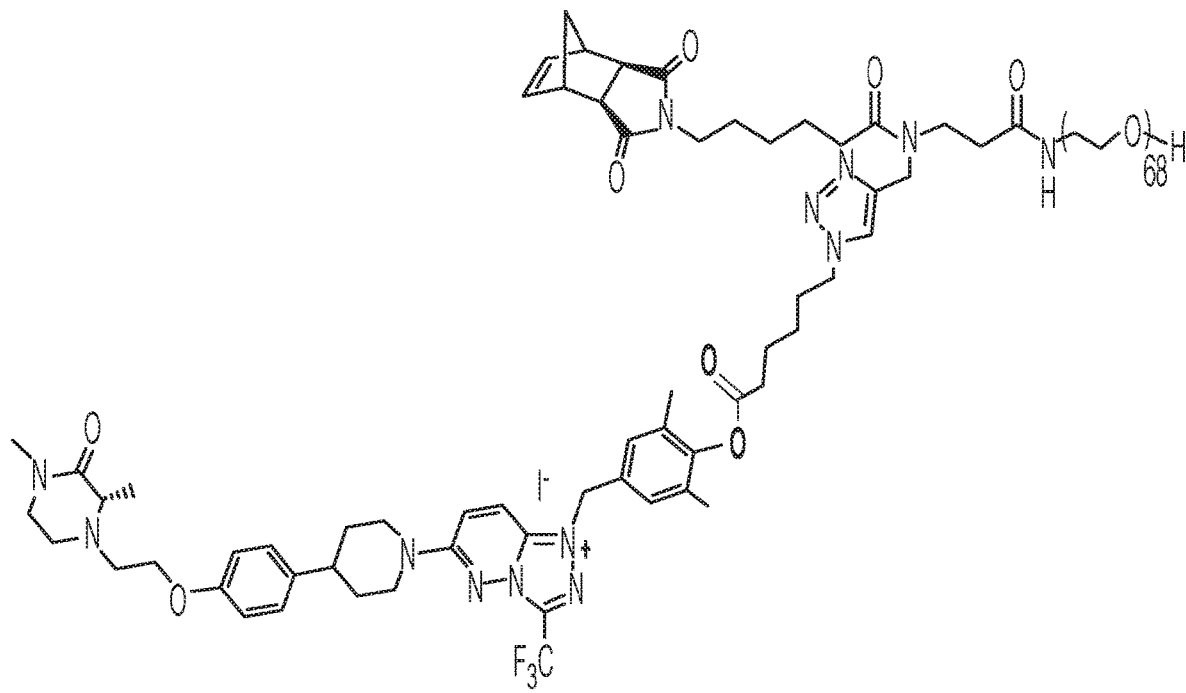
Figure 3A:
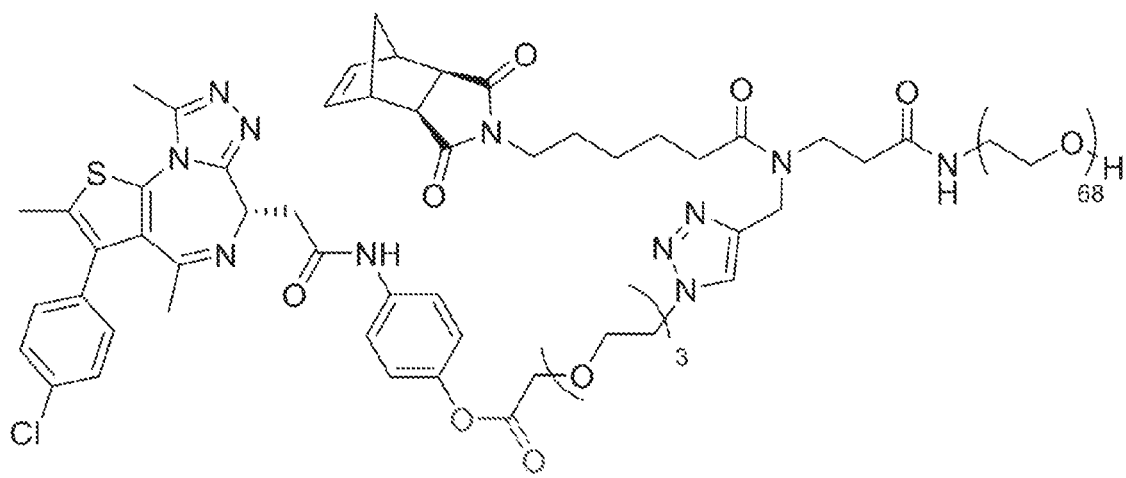
FIGS. 3A to 3D show the in vitro release profile of Brush prodrugs B1 to B4.
Figure 3B:
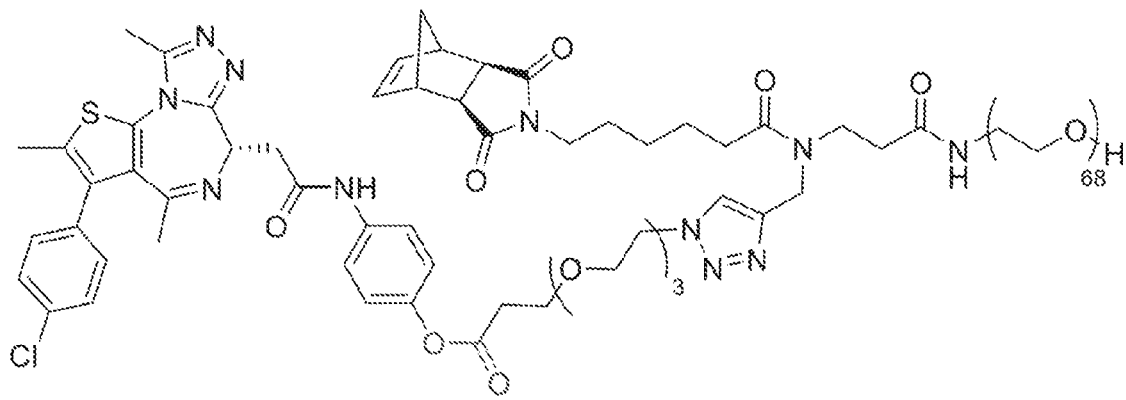
Figure 3C:
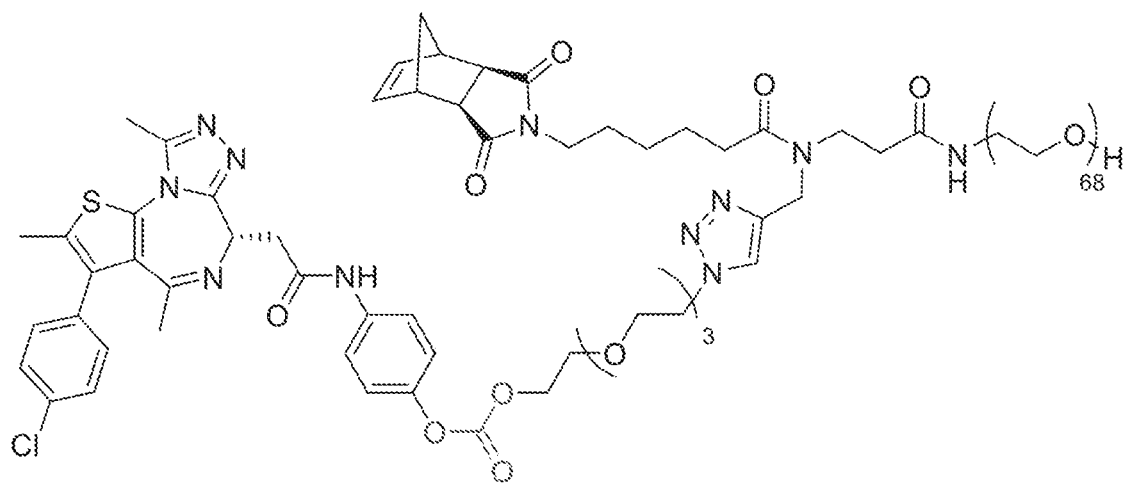
Figure 3D:
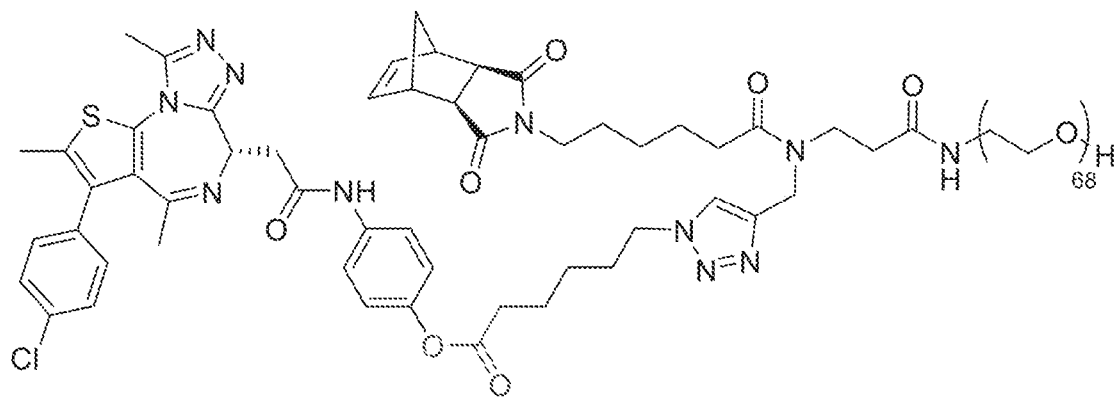

The present disclosure provides, in some aspects, macromonomers, and salts thereof; methods of preparing the macromonomers, and salts thereof; Brush prodrugs (polymers); methods of preparing the Brush prodrugs; pharmaceutical compositions comprising a Brush prodrug; kits comprising: a macromonomer, or a salt thereof, a Brush prodrug, or a pharmaceutical composition; methods of using the Brush prodrugs; and uses of the Brush prodrugs.

Macromonomers

In one aspect, the present disclosure provides macromonomers of Formula (I):

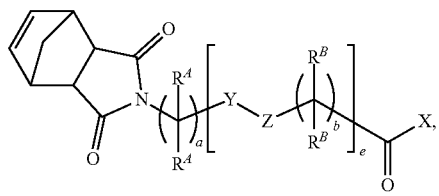

and salts thereof, wherein:
each instance of $R^A$ is independently hydrogen, halogen, or substituted or unsubstituted, $C_{1-6}$ alkyl;
a is an integer from 1 to 20, inclusive;
each instance of —Y—Z— is independently

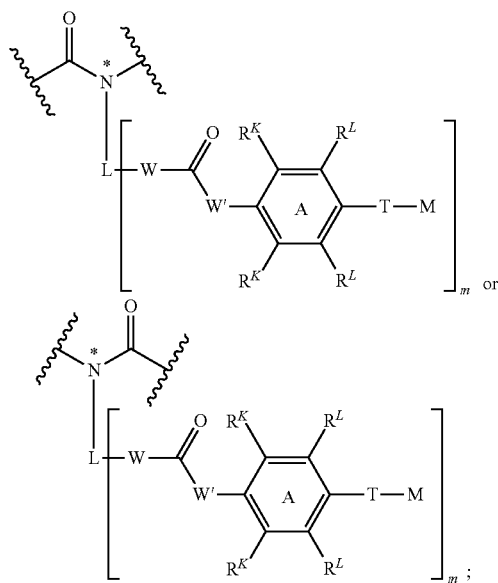

each instance of M is independently hydrogen or a pharmaceutical agent;
each instance of m is independently an integer from 1 to 10, inclusive;
each instance of L is independently substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or $C_{2-200}$ heteroalkynylene, wherein:
optionally one or more carbons in each instance of the substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, and $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene; and
optionally one or more heteroatoms in each instance of the substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;
provided that when each instance of M is hydrogen, at least one instance of -L(M)$_m$ comprises a click-chemistry handle;
each instance of W is independently a single bond, —O—, —S—, or —NR$^E$—;
each instance of $R^E$ is independently hydrogen, substituted or unsubstituted $C_{1-6}$ alkyl, or a nitrogen protecting group;
each instance of W' is independently —O—, —S—, or —NR$^J$—;
each instance of $R^J$ is independently hydrogen, substituted or unsubstituted $C_{1-6}$ alkyl, or a nitrogen protecting group;
each instance of $R^K$ and $R^L$ is independently hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, 3- to 7-membered, monocyclic carbocyclyl, substituted or unsubstituted, 3- to 7-membered, monocyclic heterocyclyl, substituted or unsubstituted phenyl, substituted or unsubstituted, 5- or 6-membered, monocyclic heteroaryl, —OR$^{aa}$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;
each instance of $R^a$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, 3- to 7-membered, monocyclic carbocyclyl, substituted or unsubstituted, 3- to 7-membered, monocyclic heterocyclyl, substituted or unsubstituted phenyl, substituted or unsubstituted, 5- or 6-membered, monocyclic heteroaryl, an oxygen protecting group when attached to an oxygen atom, a sulfur protecting group when attached to a sulfur atom, or a nitrogen protecting group when attached to a nitrogen atom; or two instances of $R^a$ attached to the same nitrogen atom are joined to form substituted or unsubstituted, 3- to 7-membered, monocyclic heterocyclyl, or substituted or unsubstituted, 5- or 6-membered, monocyclic heteroaryl;
each instance of T is independently a single bond, substituted or unsubstituted, $C_{1-20}$ alkylene, substituted or unsubstituted, $C_{2-20}$ alkenylene, or unsubstituted, $C_{2-20}$ alkynylene, substituted or unsubstituted, $C_{2-20}$ heteroalkylene, substituted or unsubstituted, $C_{2-20}$ heteroalkenylene, or $C_{2-20}$ heteroalkynylene, wherein:
optionally one or more carbons in each instance of the substituted or unsubstituted, $C_{1-20}$ alkylene, substituted or unsubstituted, $C_{2-20}$ alkenylene, substituted or unsubstituted, $C_{2-20}$ alkynylene, substituted or unsubstituted, $C_{2-20}$ heteroalkylene, substituted or unsubstituted, $C_{2-20}$ heteroalkenylene, and $C_{2-20}$ heteroalkynylene are independently replaced with substituted or unsubstituted carbocyclylene, substituted or unsubstituted heterocyclylene, substituted or unsubstituted arylene, or substituted or unsubstituted heteroarylene; and optionally one or more heteroatoms in each instance of the substituted or unsubstituted, $C_{2-20}$ heteroalkylene, substituted or unsubstituted, $C_{2-20}$ heteroalkenylene, and substituted or unsubstituted, $C_{2-20}$ heteroalkynylene are independently replaced with substituted or unsubstituted carbocyclylene, substituted or unsubstituted heterocyclylene, substituted or unsubstituted arylene, or substituted or unsubstituted heteroarylene;

each instance of $R^B$ is independently hydrogen, halogen, or substituted or unsubstituted, $C_{1-6}$ alkyl;

each instance of b is independently an integer from 1 to 20, inclusive;

e is an integer from 1 to 10, inclusive; and

X is $OR^C$ or $N(R^D)_2$, wherein:

$R^C$ is hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, an oxygen protecting group, or a leaving group; and each instance of $R^D$ is independently hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, or a nitrogen protecting group.

In certain embodiments, the macromonomers of the disclosure are macromonomers of Formula (I), and salts thereof, wherein:

each instance of $R^A$ is independently hydrogen, halogen, or substituted or unsubstituted, $C_{1-6}$ alkyl;

a is an integer from 1 to 20, inclusive;

each instance of —Y—Z— is independently

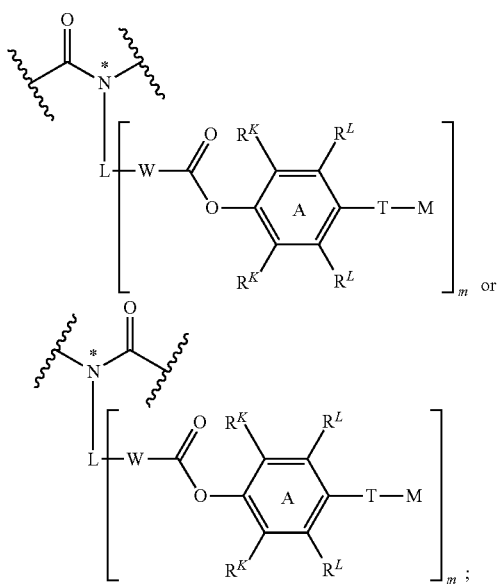

each instance of M is independently hydrogen or a pharmaceutical agent;

each instance of m is independently an integer from 1 to 10, inclusive;

each instance of L is independently substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or $C_{2-200}$ heteroalkynylene, wherein:

optionally one or more carbons in each instance of the substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, and $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene; and optionally one or more heteroatoms in each instance of the substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;

provided that when each instance of M is hydrogen, at least one instance of -L(M)$_m$ comprises a click-chemistry handle;

each instance of W is independently a single bond or —O—;

each instance of $R^K$ and $R^L$ is independently hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, 3- to 7-membered, monocyclic carbocyclyl, substituted or unsubstituted, 3- to 7-membered, monocyclic heterocyclyl, substituted or unsubstituted phenyl, substituted or unsubstituted, 5- or 6-membered, monocyclic heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^aC$(=O)$R^a$, —$NR^aC$(=O)$OR^a$, —$NR^aC$(=O)N($R^a$)$_2$, —OC(=O)$R^a$, —OC(=O)$OR^a$, or —OC(=O)N($R^a$)$_2$;

each instance of $R^a$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, 3- to 7-membered, monocyclic carbocyclyl, substituted or unsubstituted, 3- to 7-membered, monocyclic heterocyclyl, substituted or unsubstituted phenyl, substituted or unsubstituted, 5- or 6-membered, monocyclic heteroaryl, an oxygen protecting group when attached to an oxygen atom, a sulfur protecting group when attached to a sulfur atom, or a nitrogen protecting group when attached to a nitrogen atom; or two instances of $R^a$ attached to the same nitrogen atom are joined to form substituted or unsubstituted, 3- to 7-membered, monocyclic heterocyclyl, or substituted or unsubstituted, 5- or 6-membered, monocyclic heteroaryl;

each instance of T is independently a single bond, substituted or unsubstituted, $C_{1-20}$ alkylene, substituted or unsubstituted, $C_{2-20}$ alkenylene, substituted or unsubstituted, $C_{2-20}$ alkynylene, substituted or unsubstituted, $C_{2-20}$ heteroalkylene, substituted or unsubstituted, $C_{2-20}$ heteroalkenylene, or $C_{2-20}$ heteroalkynylene, wherein:

optionally one or more carbons in each instance of the substituted or unsubstituted, C$_{1-20}$ alkylene, substituted or unsubstituted, C$_{2-20}$ alkenylene, substituted or unsubstituted, C$_{2-20}$ alkynylene, substituted or unsubstituted, C$_{2-20}$ heteroalkylene, substituted or unsubstituted, C$_{2-20}$ heteroalkenylene, and C$_{2-20}$ heteroalkynylene are independently replaced with substituted or unsubstituted carbocyclylene, substituted or unsubstituted heterocyclylene, substituted or unsubstituted arylene, or substituted or unsubstituted heteroarylene; and optionally one or more heteroatoms in each instance of the substituted or unsubstituted, C$_{2-20}$ heteroalkylene, substituted or unsubstituted, C$_{2-20}$ heteroalkenylene, and substituted or unsubstituted, C$_{2-20}$ heteroalkynylene are independently replaced with substituted or unsubstituted carbocyclylene, substituted or unsubstituted heterocyclylene, substituted or unsubstituted arylene, or substituted or unsubstituted heteroarylene;

each instance of R$^B$ is independently hydrogen, halogen, or substituted or unsubstituted, C$_{1-6}$ alkyl;

each instance of b is independently an integer from 1 to 20, inclusive;

e is an integer from 1 to 10, inclusive; and

X is OR$^C$ or N(R$^D$)$_2$, wherein:

R$^C$ is hydrogen, substituted or unsubstituted, C$_{1-1000}$ alkyl, substituted or unsubstituted, C$_{2-1000}$ alkenyl, substituted or unsubstituted, C$_{2-1000}$ alkynyl, substituted or unsubstituted, C$_{1-1000}$ heteroalkyl, substituted or unsubstituted, C$_{2-1000}$ heteroalkenyl, substituted or unsubstituted, C$_{2-1000}$ heteroalkynyl, an oxygen protecting group, or a leaving group; and each instance of R$^D$ is independently hydrogen, substituted or unsubstituted, C$_{1-1000}$ alkyl, substituted or unsubstituted, C$_{2-1000}$ alkenyl, substituted or unsubstituted, C$_{2-1000}$ alkynyl, substituted or unsubstituted, C$_{1-1000}$ heteroalkyl, substituted or unsubstituted, C$_{2-1000}$ heteroalkenyl, substituted or unsubstituted, C$_{2-1000}$ heteroalkynyl, or a nitrogen protecting group.

In certain embodiments, the macromonomer is of the formula:

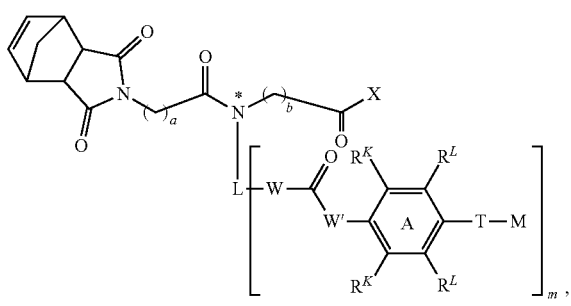

or a salt thereof.

In certain embodiments, the macromonomer is of the formula:

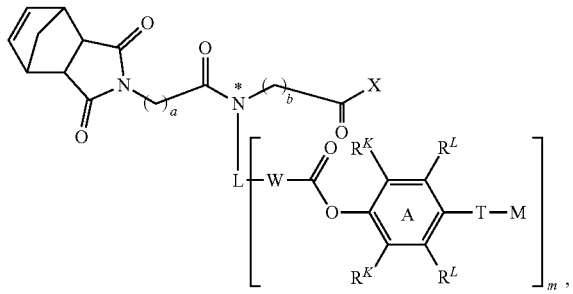

or a salt thereof.

In certain embodiments, the macromonomer is of the formula:

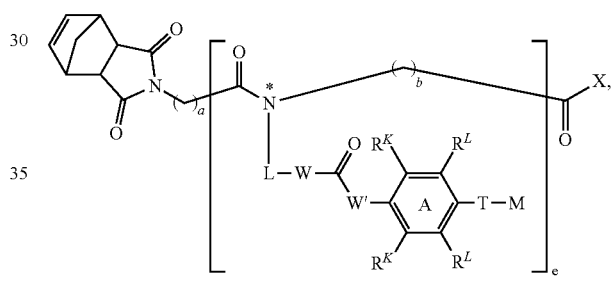

or a salt thereof.

In certain embodiments, the macromonomer is of the formula:

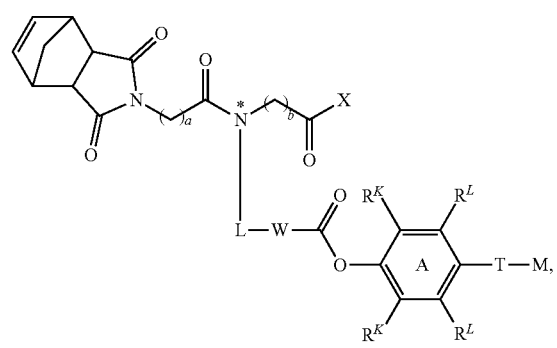

or a salt thereof.

In certain embodiments, the macromonomer is of the formula:

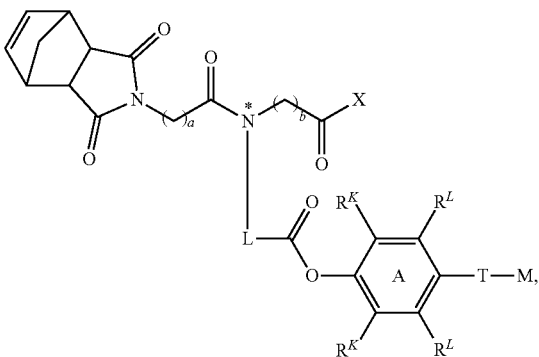

or a salt thereof.

In certain embodiments, the macromonomer is of the formula:

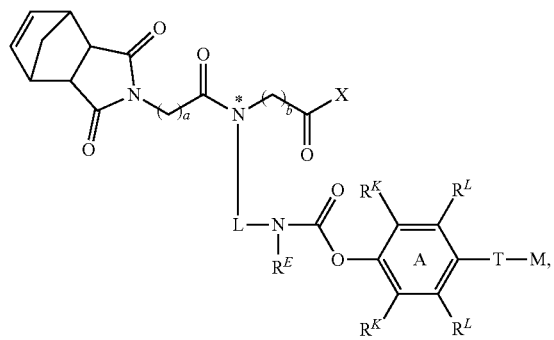

or a salt thereof.

In certain embodiments, the macromonomer is of the formula:

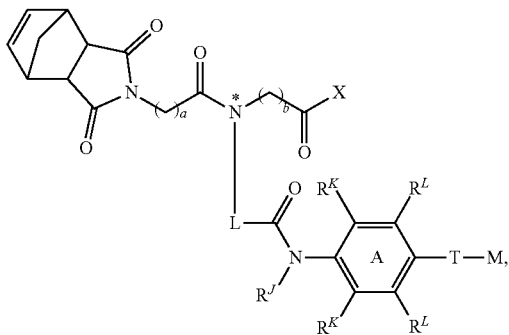

or a salt thereof.

When Formula (I) includes two or more instances of a moiety, the two or more instances of the moiety are independent from each other (e.g., any two of them may be the same or different).

In certain embodiments, at least one instance of $R^A$ is hydrogen. In certain embodiments, each instance of $R^A$ is hydrogen. In certain embodiments, at least one instance of $R^A$ is halogen (e.g., F). In certain embodiments, at least one instance of $R^A$ is substituted or unsubstituted, $C_{1-6}$ alkyl (e.g., unsubstituted, $C_{1-6}$ alkyl, e.g., Me).

In certain embodiments, a is 1. In certain embodiments, a is an integer from 2 to 20, inclusive. In certain embodiments, a is 3, 4, 5, 6, or 7. In certain embodiments, a is 4, 5, or 6. In certain embodiments, a is 5.

In certain embodiments, at least one instance of —Y—Z— is

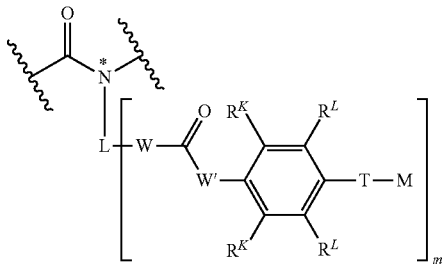

In certain embodiments, at least one instance of —Y—Z— is (e.g., 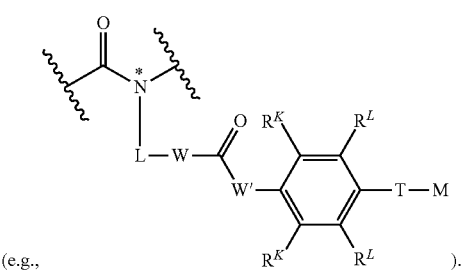 ).

In certain embodiments, at least one instance of —Y—Z— is

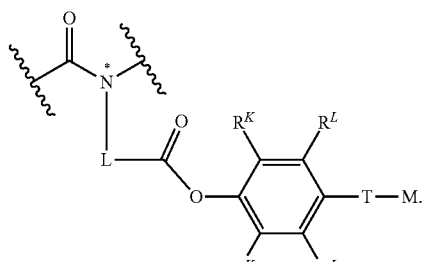

In certain embodiments, at least one instance of —Y—Z— is

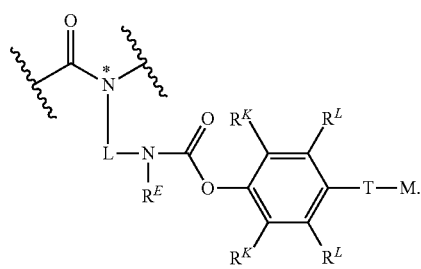

In certain embodiments, at least one instance of —Y—Z— is

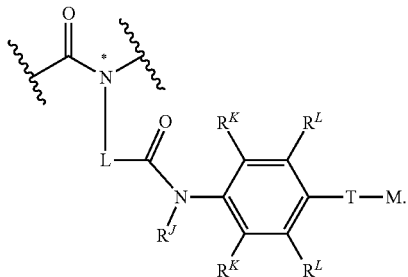

In certain embodiments, at least one instance of —Y—Z— is

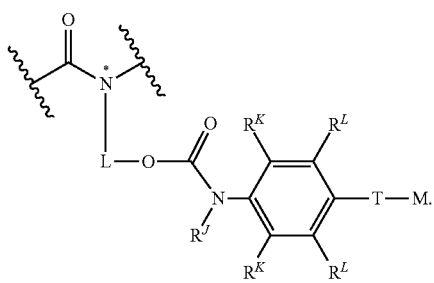

In certain embodiments, at least one instance of —Y—Z— is

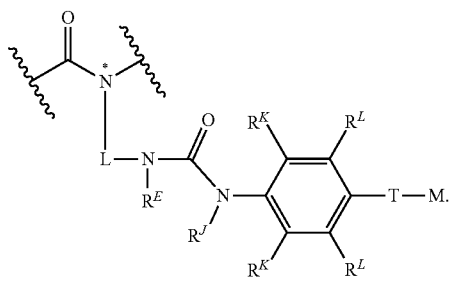

In certain embodiments, at least one instance of —Y—Z— is

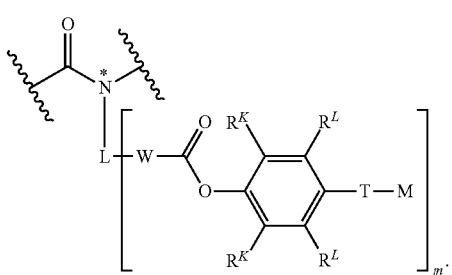

In certain embodiments, each instance of —Y—Z— is independently

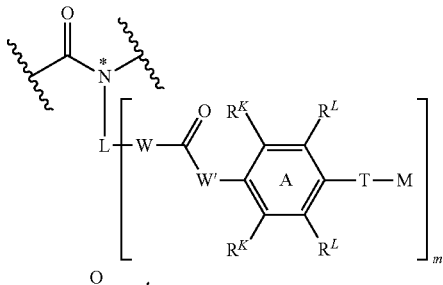

(e.g., 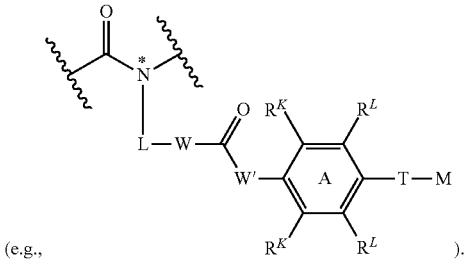).

In certain embodiments, at least one instance of —Y—Z— is

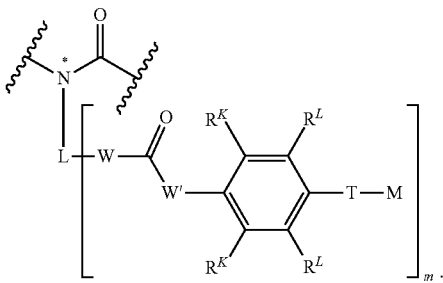

(e.g. 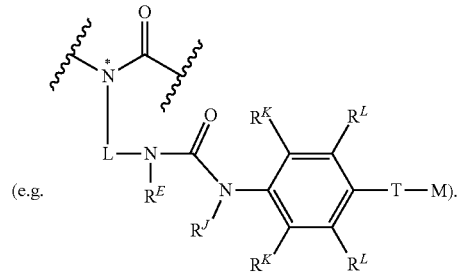).

In certain embodiments, at least one instance of —Y—Z— is

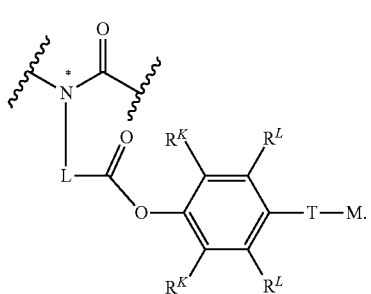

In certain embodiments, at least one instance of —Y—Z— is

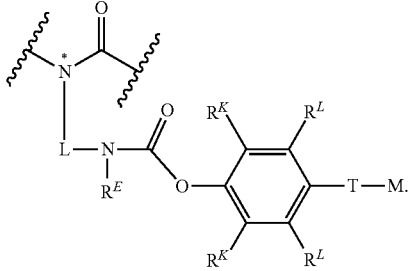

In certain embodiments, at least one instance of —Y—Z— is

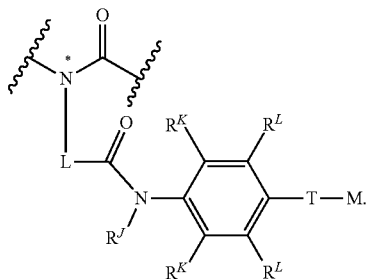

In certain embodiments, at least one instance of —Y—Z— is

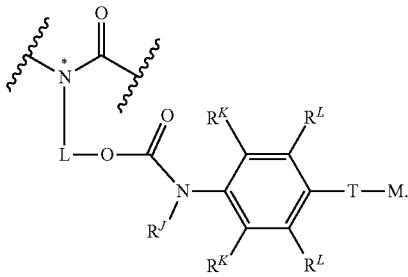

In certain embodiments, at least one instance of —Y—Z— is

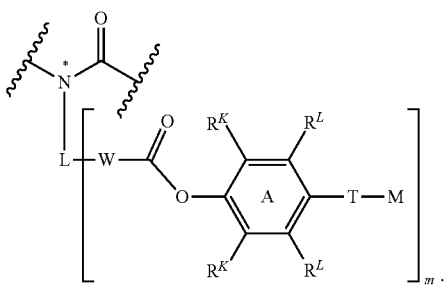

-continued

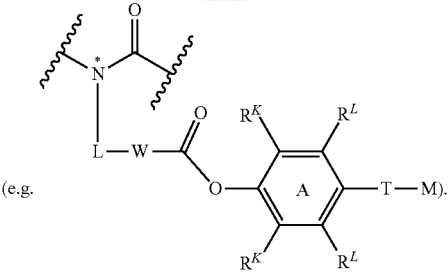

(e.g.

In certain embodiments, at least one instance of —Y—Z— is

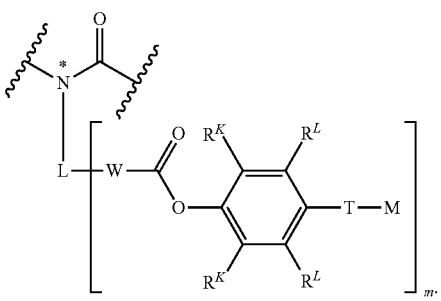

In certain embodiments, each instance of —Y—Z— is independently

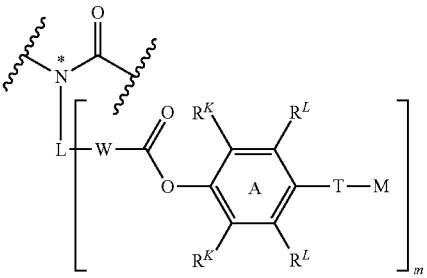

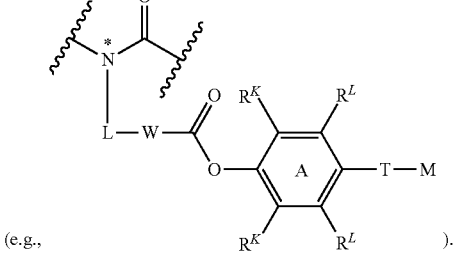

(e.g.,                                              ).

In certain embodiments, at least one instance of M is hydrogen. In certain embodiments, each instance of M is hydrogen. In certain embodiments, no instance of M is hydrogen. In certain embodiments, at least one instance of M is a pharmaceutical agent. In certain embodiments, each instance of M is independently a pharmaceutical agent. The pharmaceutical agents include chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof.

In some embodiments, the pharmaceutical agent is a small molecule. In some embodiments, the pharmaceutical agent is a peptide or protein. Exemplary pharmaceutical agents include, but are not limited to, those found in *Harrison's Principles of Internal Medicine*, 13th Edition, Eds. T. R. Harrison et al. McGraw-Hill N.Y., NY; Physicians' Desk Reference, 50th Edition, 1997, Oradell New Jersey, Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

In certain embodiments, at least one instance of M is a therapeutic agent. In certain embodiments, each instance of M is a therapeutic agent. In some embodiments, exemplary therapeutic agents include, but are not limited to, one or more of the agents listed in Paragraph 0148 of U.S. Pat. No. 9,381,253, incorporated by reference herein. In other embodiments, exemplary therapeutic agents include, but are not limited to, one or more of the therapeutic agents listed in WO 2013/169739, including the anti-hypertensive and/or a collagen modifying agents ("AHCM") disclosed, e.g., in Paragraphs 40-49, 283, 286-295; the microenvironment modulators disclosed, e.g., in Paragraphs 113-121, of WO 2013/169739, incorporated herein by reference. Examples of therapeutic agents also include, but are not limited to, antimicrobial agents, analgesics, antiinflammatory agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anticancer properties, or a combination thereof. Other suitable therapeutic agents include contraceptives and vitamins as well as micro- and macronutrients. Still other examples include antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

In certain embodiments, at least one instance of the therapeutic agent is an anti-cancer agent. Anti-cancer agents encompass biotherapeutic anti-cancer agents as well as chemotherapeutic agents. Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g., HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents include, but are not limited to, anti-estrogens (e.g., tamoxifen, raloxifene, and megestrol), LHRH agonists (e.g., goscrclin and leuprolide), anti-androgens (e.g., flutamide and bicalutamide), photodynamic therapies (e.g., vertoporfin (BPD-MA), phthalocyanine, photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g., dacarbazine, temozolomide), platinum containing compounds (e.g., cisplatin, carboplatin, oxaliplatin), vinca alkaloids (e.g., vincristine, vinblastine, vindesine, and vinorelbine), taxoids (e.g., paclitaxel or a paclitaxel equivalent) docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonucleotide reductase inhibitors (e.g., hydroxyurea and deferoxamine), uracil analogs (e.g., 5-fluorouracil (5-FU), floxuridine, doxifluridine, raltitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLA- DIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe), and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine. In certain embodiments, the anti-cancer agent is abiraterone acetate (e.g., ZYTIGA), ABVD, ABVE, ABVE-PC, AC, AC-T, ADE, ado-trastuzumab emtansine (e.g., KADCYLA), afatinib dimaleate (e.g., GILOTRIF), aldesleukin (e.g., PROLEUKIN), alemtuzumab (e.g., CAMPATH), anastrozole (e.g., ARIMIDEX), arsenic trioxide (e.g., TRISENOX), asparaginase Erwinia chrysanthemi (e.g., ERWINAZE), axitinib (e.g., INLYTA), azacitidine (e.g., MYLOSAR, VIDAZA), BEACOPP, belinostat (e.g., BELEODAQ), bendamustine hydrochloride (e.g., TREANDA), BEP, bevacizumab (e.g., AVASTIN), bicalutamide (e.g., CASODEX), bleomycin (e.g., BLENOXANE), blinatumomab (e.g., BLINCYTO), bortezomib (e.g., VELCADE), bosutinib (e.g., BOSULIF), brentuximab vedotin (e.g., ADCETRIS), busulfan (e.g., BUSULFEX, MYLERAN), cabazitaxel (e.g., JEVTANA), cabozantinib-s-malate (e.g., COMETRIQ), CAF, capecitabine (e.g., XELODA), CAPOX, carboplatin (e.g., PARAPLAT, PARAPLATIN), carboplatin-taxol, carfilzomib (e.g., KYPROLIS), carmustine (e.g., BECENUM, BICNU, CARMUBRIS), carmustine implant (e.g., GLIADEL WAFER, GLIADEL), ceritinib (e.g., ZYKADIA), cetuximab (e.g., ERBITUX), chlorambucil (e.g., AMBOCHLORIN, AMBOCLORIN, LEUKERAN, LINFOLIZIN), chlorambucil-prednisone, CHOP, cisplatin (e.g., PLATINOL, PLATINOL-AQ), clofarabine (e.g., CLOFAREX, CLOLAR), CMF, COPP, COPP-ABV, crizotinib (e.g., XALKORI), CVP, cyclophosphamide (e.g., CLAFEN, CYTOXAN, NEOSAR), cytarabine (e.g., CYTOSAR-U, TARABINE PFS), dabrafenib (e.g., TAFINLAR), dacarbazine (e.g., DTIC-DOME), dactinomycin (e.g., COSMEGEN), dasatinib (e.g., SPRYCEL), daunorubicin hydrochloride (e.g., CERUBIDINE), decitabine (e.g., DACOGEN), degarelix, denileukin diftitox (e.g., ONTAK), denosumab (e.g., PROLIA, XGEVA), Dinutuximab (e.g., UNITUXIN), docetaxel (e.g., TAXOTERE), doxorubicin hydrochloride (e.g., ADRIAMYCIN PFS, ADRIAMYCIN RDF), doxorubicin hydrochloride liposome (e.g., DOXIL, DOX-SL, EVACET, LIPODOX), enzalutamide (e.g., XTANDI), epirubicin hydrochloride (e.g., ELLENCE), EPOCH, erlotinib hydrochloride (e.g., TARCEVA), etoposide (e.g., TOPOSAR, VEPESID), etoposide phosphate (e.g., ETOPOPHOS), everolimus (e.g., AFINITOR DISPERZ, AFINITOR), exemestane (e.g., AROMASIN), FEC, fludarabine phosphate (e.g., FLUDARA), fluorouracil (e.g., ADRUCIL, EFUDEX, FLUOROPLEX), FOLFIRI, FOLFIRI-BEVACIZUMAB, FOLFIRI-CETUXIMAB, FOLFIRINOX, FOLFOX, FU-LV, fulvestrant (e.g., FASLODEX), gefitinib (e.g., IRESSA), gemcitabine hydrochloride (e.g., GEMZAR), gemcitabine-cisplatin, gemcitabine-oxaliplatin, goserelin acetate (e.g., ZOLADEX), Hyper-CVAD, ibritumomab tiuxetan (e.g., ZEVALIN), ibrutinib (e.g., IMBRUVICA), ICE, idelalisib (e.g., ZYDELIG), ifosfamide (e.g., CYFOS, IFEX, IFOSFAMIDUM), imatinib mesylate (e.g., GLEEVEC), imiquimod (e.g., ALDARA), ipilimumab (e.g., YERVOY), irinotecan hydrochloride (e.g., CAMPTOSAR), ixabepilone (e.g., IXEMPRA), lanreotide acetate (e.g., SOMATULINE DEPOT), lapatinib ditosylate (e.g., TYKERB), lenalidomide (e.g., REVLIMID), lenvatinib (e.g., LENVIMA), letrozole (e.g., FEMARA), leucovorin calcium (e.g., WELLCOVORIN), leuprolide acetate (e.g., LUPRON DEPOT, LUPRON DEPOT-3 MONTH, LUPRON DEPOT-4 MONTH, LUPRON DEPOT-PED, LUPRON, VIADUR), liposomal cytarabine (e.g., DEPOCYT), lomustine (e.g., CEENU), mechlorethamine hydrochloride (e.g., MUSTARGEN), megestrol acetate (e.g., MEGACE), mercaptopurine (e.g., PURINETHOL, PURIXAN), methotrexate (e.g., ABITREXATE, FOLEX PFS, FOLEX, METHOTREXATE LPF, MEXATE, MEXATE-AQ), mitomycin c (e.g., MITOZYTREX, MUTAMYCIN), mitoxantrone hydrochloride, MOPP, nelarabine (e.g., ARRANON), nilotinib (e.g., TASIGNA), nivolumab (e.g., OPDIVO), obinutuzumab (e.g., GAZYVA), OEPA, ofatumumab (e.g., ARZERRA), OFF, olaparib (e.g., LYNPARZA), omacetaxine mepesuccinate (e.g., SYNRIBO), OPPA, OTX-015, oxaliplatin (e.g., ELOXATIN), paclitaxel (e.g., TAXOL), paclitaxel albumin-stabilized nanoparticle formulation (e.g., ABRAXANE), PAD, palbociclib (e.g., IBRANCE), pamidronate disodium (e.g., AREDIA), panitumumab (e.g., VECTIBIX), panobinostat (e.g., FARYDAK), pazopanib hydrochloride (e.g., VOTRIENT), pegaspargase (e.g., ONCASPAR), peginterferon alfa-2b (e.g., PEG-INTRON), peginterferon alfa-2b (e.g., SYLATRON), pembrolizumab (e.g., KEYTRUDA), pemetrexed disodium (e.g., ALIMTA), pertuzumab (e.g., PERJETA), plerixafor (e.g., MOZOBIL), pomalidomide (e.g., POMALYST), ponatinib hydrochloride (e.g., ICLUSIG), pralatrexate (e.g., FOLOTYN), prednisone, procarbazine hydrochloride (e.g., MATULANE), radium 223 dichloride (e.g., XOFIGO), raloxifene hydrochloride (e.g., EVISTA, KEOXIFENE), ramucirumab (e.g., CYRAMZA), R—CHOP, recombinant HPV bivalent vaccine (e.g., CERVARIX), recombinant human papillomavirus (e.g., HPV) nonvalent vaccine (e.g., GARDASIL 9), recombinant human papillomavirus (e.g., HPV) quadrivalent vaccine (e.g., GARDASIL), recombinant interferon alfa-2b (e.g., INTRON A), regorafenib (e.g., STIVARGA), rituximab (e.g., RITUXAN), romidepsin (e.g., ISTODAX), ruxolitinib phosphate (e.g., JAKAFI), siltuximab (e.g., SYLVANT), sipuleucel-t (e.g., PROVENGE), sorafenib tosylate (e.g., NEXAVAR), STANFORD V, sunitinib malate (e.g., SUTENT), TAC, tamoxifen citrate (e.g., NOLVADEX, NOVALDEX), temozolomide (e.g., METHAZOLASTONE, TEMODAR), temsirolimus (e.g., TORISEL), thalidomide (e.g., SYNOVIR, THALOMID), thiotepa, topotecan hydrochloride (e.g., HYCAMTIN), toremifene (e.g., FARESTON), tositumomab and iodine I 131 tositumomab (e.g., BEXXAR), TPF, trametinib (e.g., MEKINIST), trastuzumab (e.g., HERCEPTIN), VAMP, vandetanib (e.g., CAPRELSA), VEIP, vemurafenib (e.g., ZELBORAF), vinblastine sulfate (e.g., VELBAN, VELSAR), vincristine sulfate (e.g., VINCASAR PFS), vincristine sulfate liposome (e.g., MARQIBO), vinorelbine tartrate (e.g., NAVELBINE), vismodegib (e.g., ERIVEDGE), vorinostat (e.g., ZOLINZA), XELIRI, XELOX, ziv-aflibercept (e.g., ZALTRAP), or zoledronic acid (e.g., ZOMETA), or a pharmaceutically acceptable salt thereof. In certain embodiments, at least one instance of the therapeutic agent is a bromodomain inhibitor. In certain embodiments, at least one instance of the therapeutic agent is a bromo and extra terminal protein (BET) inhibitor. In certain embodiments, at least one instance of the therapeutic agent is a bromodomain-containing protein 2 (BRD2) inhibitor, bromodomain-containing protein 3 (BRD3) inhibitor, bromodomain-containing protein 4 (BRD4) inhibitor, TBP (TATA box binding protein)-associated factor protein (TAF) (e.g., TAF1 or TAF1L) inhibitor, CREB-binding protein (CBP) inhibitor, or E1A binding protein p300 (EP300) inhibitor. In certain embodiments, at least one instance of M is a PARP inhibitor, ALK inhibitor, or STING ligand. In certain embodiments, at least one instance of the therapeutic agent is OTX-015. In certain embodiments, at least one instance of M is

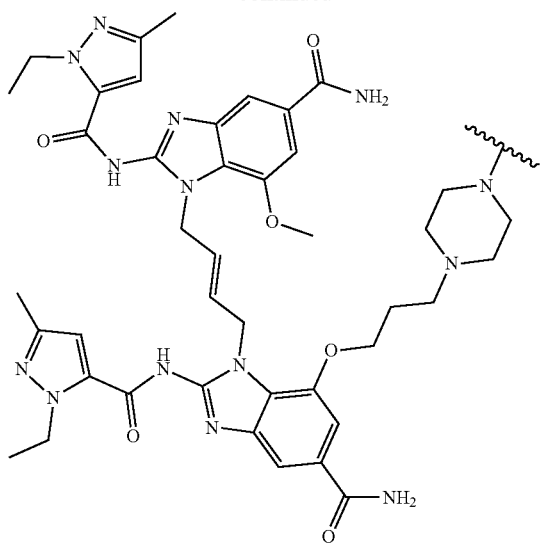

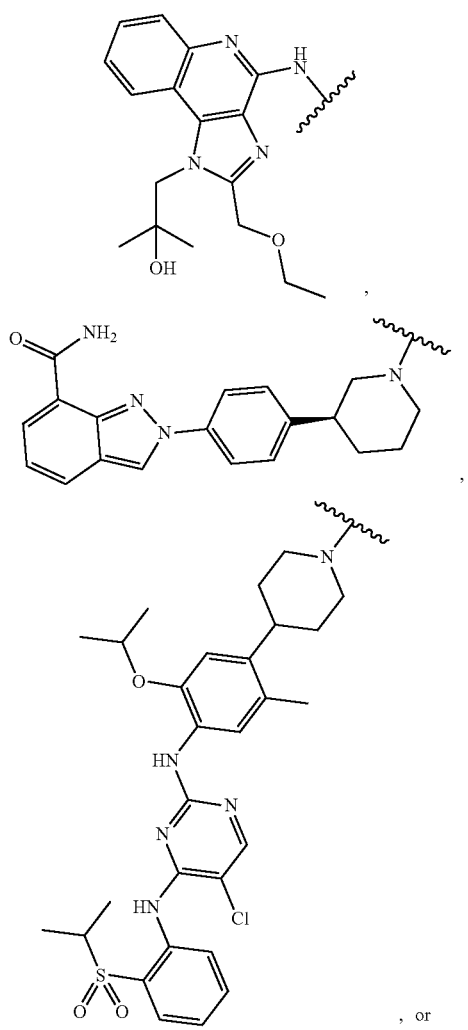

, or

In certain embodiments, at least one instance of M is of the formula:

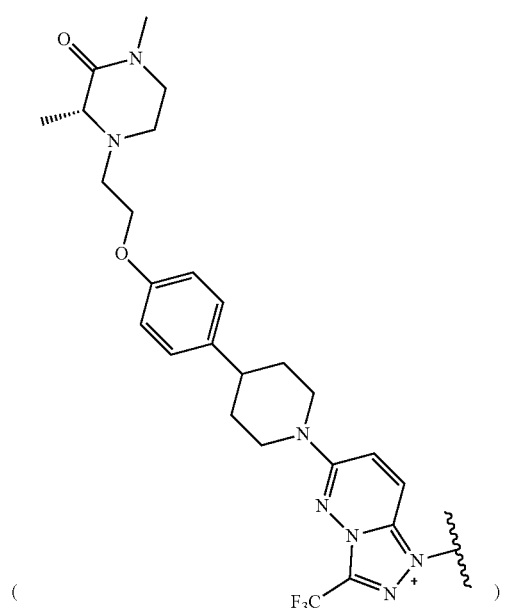

( (an anionic counterion) ) or

-continued

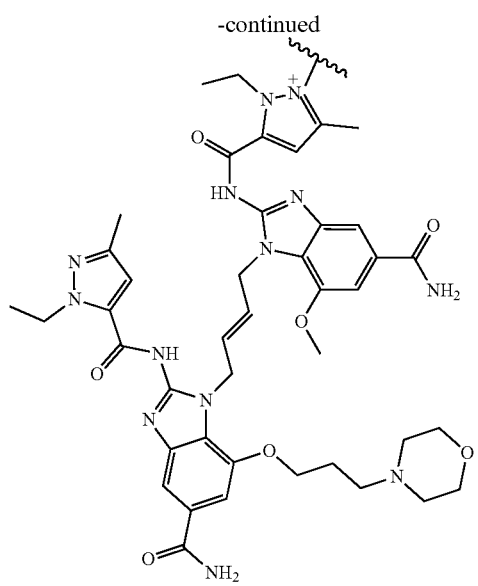

( ) (an anionic counterion)

In certain embodiments, at least one instance of -T-M is:

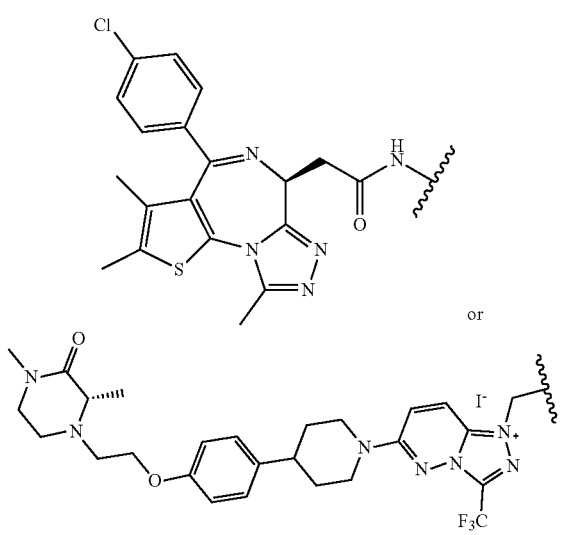

or

In certain embodiments, at least one instance of M is a prophylactic agent. In certain embodiments, each instance of M is a prophylactic agent. Prophylactic agents that can be included in the conjugates of the invention include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Prophylactic agents may be combined with interleukins, interferon, cytokines, and adjuvants such as cholera toxin, alum, Freund's adjuvant.

In certain embodiments, at least one instance of M is a diagnostic agent. In certain embodiments, each instance of M is a diagnostic agent. Exemplary diagnostic agents include, but are not limited to, fluorescent molecules; gases; metals; imaging agents, such as commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials. In certain embodiments, the diagnostic agent is used in magnetic resonance imaging (MRI), such as iron oxide particles or gadolinium complexes. Gadolinium complexes that have been approved for clinical use include gadolinium chelates with DTPA, DTPA-BMA, DOTA and HP-DO3A which are reviewed in Aime, et al. (Chemical Society Reviews (1998), 27:19-29), the entire teachings of which are incorporated herein by reference.

In certain embodiments, the diagnostic agent is a metal, inorganic compound, organometallic compound, organic compound, or salt thereof. In certain embodiments, the imaging agent contains a metal selected from the group consisting of scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, meitnerium, gadolinium, gallium, thallium, and barium. In certain embodiments, the diagnostic agent is an organic compound. In certain embodiments, the diagnostic agent is metal-free. In certain embodiments, the diagnostic agent is a metal-free organic compound.

In certain embodiments, the imaging agent is a magnetic resonance imaging (MRI) agent. In certain embodiments, the MRI agent is gadolinium. In certain embodiments, the MRI agent is a nitroxide radical-containing compound.

In certain embodiments, the imaging agent is a nuclear medicine imaging agent. In certain embodiments, the nuclear medicine imaging agent is selected from the group consisting of $^{64}$Cu diacetyl-bis (N$^4$-methylthiosemicarbazone)($^{64}$Cu-ASTM), $^{18}$F-fluorodeoxyglucose (FDG), $^{18}$F-fluoride, 3'-deoxy-3'-[$^{18}$F]fluorothymidine (FLT), $^{18}$F-fluoromisonidazole (FMISO), gallium, technetium-99m, and thallium.

In certain embodiments, the imaging agent is radiographic imaging agent. In certain embodiments, the radiographic imaging agent is selected from the group consisting of barium, gastrografin, and iodine contrast agent.

In certain embodiments, the imaging agent the diagnostic agent is a radical-containing compound. In certain embodiments, the imaging agent is a nitroxide radical-containing compound. In certain embodiments, the imaging agent the diagnostic agent is of the formula:

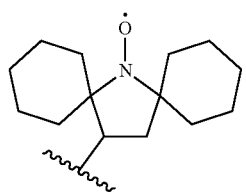

In certain embodiments, the imaging agent the diagnostic agent is an organic compound. In certain embodiments, the imaging agent is a salt of an organic compound. In certain embodiments, the imaging agent the diagnostic agent is of the formula:

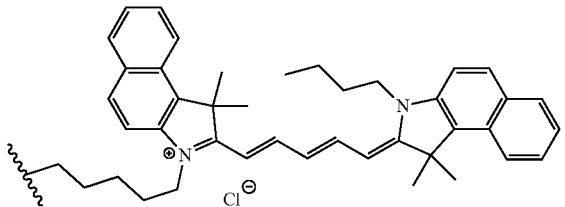

In certain embodiments, the diagnostic agent may comprise a fluorescent molecule, a metal chelate, a contrast agent, a radionuclide, or a positron emission tomography (PET) imaging agent, an infrared imaging agent, a near-IR imaging agent, a computer assisted tomography (CAT) imaging agent, a photon emission computerized tomography imaging agent, an X-ray imaging agent, or a magnetic resonance imaging (MRI) agent.

In some embodiments, the diagnostic agent is a fluorescent molecule. In some embodiments, the fluorescent molecule comprises an acridine dye, a cyanine dye, a rhodamine dye, a BODIPY dye, a fluorescein dye, a dansyl dye, an Alexa dye, an atto dye, a quantum dot, or a fluorescent protein. In some embodiments, the fluorescent molecule is a cyanine dye (e.g., Cy3, Cy 3.5, Cy5, Cy5.5, Cy7, or Cy7.5).

In some embodiments, the diagnostic agent is an MRI agent (e.g., a contrast agent). Examples of suitable materials for use as MRI agents (e.g., contrast agents) include gadolinium chelates, as well as iron, magnesium, manganese, copper, and chromium.

In some embodiments, the diagnostic agent is a CAT imaging agent or an X-ray imaging agent. Examples of materials useful for CAT and X-ray imaging include iodine-based materials.

In some embodiments, the diagnostic agent is a PET imaging agent. Examples of suitable PET imaging agents include compounds and compositions comprising the positron emitting radioisotopes $^{18}F$, $^{15}O$, $^{13}N$, $^{11}C$, $^{82}Rb$, $^{64}Cu$, and $^{68}Ga$, e.g., fludeoxyglucose ($^{18}F$-FDG), $^{68}Ga$-DOTA-pseudopeptides (e.g., $^{68}Ga$-DOTA-TOC), $^{11}C$-metomidate, $^{11}C$-acetate, $^{11}C$-methionine, $^{11}C$-choline, $^{18}F$-fluciclovine, $^{18}F$-fluorocholine, $^{18}F$-fluorodeoxysorbitol, $^{18}F$-3'-fluoro-3'-deoxythymidine, $^{11}C$-raclopride, and $^{18}F$-desmethoxyfallypride.

In some embodiments, the diagnostic agent is a near-IR imaging agent. Examples of near-IR imaging agents include Pz 247, DyLight 750, DyLight 800, cyanine dyes (e.g., Cy5, Cy5.5, Cy7), AlexaFluor 680, AlexaFluor 750, IRDye 680, IRDye 800CW, and Kodak X⁻ SIGHT dyes.

In some embodiments, the agent can be a radionuclide, e.g., for use as a therapeutic, diagnostic, or prognostic agents. Among the radionuclides used, gamma-emitters, positron-emitters, and X-ray emitters are suitable for diagnostic and/or therapy, while beta emitters and alpha-emitters may also be used for therapy. Suitable radionuclides for forming use with various embodiments of the present invention include, but are not limited to, $^{123}I$, $^{125}I$, $^{130}I$, $^{131}I$, $^{133}I$, $^{135}I$, $^{47}Sc$, $^{72}As$, $^{72}Sc$, $^{90}Y$, $^{88}Y$, $^{97}Ru$, $^{100}Pd$, $^{101m}Rh$, $^{119}Sb$, $^{128}Ba$, $^{197}Hg$, $^{211}At$, $^{212}Bi$, $^{212}Pb$, $^{109}Pd$, $^{111}In$, $^{67}Ga$, $^{68}Ga$, $^{67}Cu$, $^{75}Br$, $^{77}Br$, $^{99m}Tc$, $^{14}C$, $^{13}N$, $^{15}O$, $^{32}P$, $^{33}P$, or $^{18}F$.

In certain embodiments, at least one instance of the diagnostic agent is a contrast agent. In certain embodiments, at least one instance of the contrast agent is a magnetic-resonance signal enhancing agent, X-ray attenuating agent, ultrasound scattering agent, or ultrasound frequency shifting agent.

In certain embodiments, M being a pharmaceutical agent refers to M being a monovalent radical of the pharmaceutical agent. In certain embodiments, the monovalent radical of the pharmaceutical agent is formed by removing a hydrogen atom from the moiety HV of the pharmaceutical agent. In certain embodiments, V is a carbon atom. In certain embodiments, V is a heteroatom. In certain embodiments, V is an oxygen atom. In certain embodiments, V is a sulfur atom. In certain embodiments, V is a nitrogen atom. In certain embodiments, the monovalent radical of the pharmaceutical agent is formed further by changing the atom V of the pharmaceutical agent to substituted or unsubstituted U, wherein each of V and U is a heteroatom, and V and U are different from each other.

In certain embodiments, M being a pharmaceutical agent refers to M being an ammonium (e.g., a quaternary ammonium) salt or iminium (e.g., tertiary iminium) salt of the pharmaceutical agent, wherein the attachment point is the $N^+$ of the ammonium salt or iminium salt. In certain embodiments, the nitrogen atom of the $N^+$ of the ammonium salt or iminium salt is part of the pharmaceutical agent.

In certain embodiments, M is electrically neutral.

In certain embodiments, all instances of M are the same. In certain embodiments, at least two instances of M (e.g., all instances of M) are different from each other.

In certain embodiments, at least one instance of m is 1. In certain embodiments, each instance of m is 1. In certain embodiments, at least one instance of m is an integer from 2 to 10, inclusive. In certain embodiments, at least one instance of m is 2, 3, 4, or 5.

When a first divalent moiety comprises a second divalent moiety, the second divalent moiety is part of the backbone of the first divalent moiety. For example, when $L^F$ comprises —S—S—, —S—S— is part of the backbone of $L^F$.

In certain embodiments, at least one instance of L is substituted or unsubstituted, $C_{1-200}$ alkylene. In certain embodiments, at least one instance of L is substituted or unsubstituted, $C_{3-30}$ alkylene. In certain embodiments, at least one instance of L is substituted or unsubstituted, $C_{2-200}$ alkenylene. In certain embodiments, at least one instance of L is substituted or unsubstituted, $C_{2-200}$ alkynylene. In certain embodiments, at least one instance of L is substituted or unsubstituted, $C_{2-200}$ heteroalkylene. In certain embodiments, at least one instance of L is substituted or unsubstituted, $C_{3-30}$ heteroalkylene. In certain embodiments, at least one instance of L is substituted or unsubstituted, $C_{2-200}$ heteroalkenylene. In certain embodiments, at least one instance of L is substituted or unsubstituted, $C_{2-200}$ heteroalkynylene. In certain embodiments, at least one instance of L is substituted or unsubstituted, $C_{2-200}$ heteroalkylene, wherein one or more carbons and/or one or more heteroatoms, of the substituted or unsubstituted, $C_{2-200}$ heteroalkylene, are independently replaced with substituted or unsubstituted heteroarylene. In certain embodiments, at least one instance of L is substituted or unsubstituted, $C_{2-200}$ heteroalkylene (e.g., substituted or unsubstituted, $C_{3-30}$ heteroalkylene), wherein one or two carbons and/or one or two heteroatoms, of the substituted or unsubstituted, $C_{2-200}$ heteroalkylene (e.g., substituted or unsubstituted, $C_{3-30}$ heteroalkylene) are independently replaced with substituted or unsubstituted arylene (e.g., phenylene) or substituted or unsubstituted heteroarylene (e.g., substituted or unsubstituted, monocyclic, 5- or 6-membered heteroarylene). In certain embodiments, at least one instance of L is substituted or unsubstituted, $C_{2-200}$ heteroalkylene, wherein one or more carbons and/or one or more heteroatoms, of the substituted or unsubstituted, $C_{2-200}$ heteroalkylene, are independently replaced with

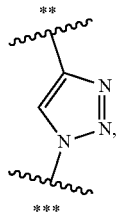

wherein the nitrogen atom labeled with "*" is closer to the attachment point labeled with "" than the attachment point labeled with "*". In certain embodiments, at least one instance of L is substituted or unsubstituted, $C_{2-200}$ heteroalkylene, wherein one carbon or one heteroatom, of the substituted or unsubstituted, $C_{2-200}$ heteroalkylene, is replaced with

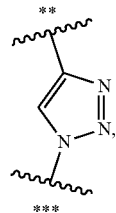

wherein the nitrogen atom labeled with "*" is closer to the attachment point labeled with "" than the attachment point labeled with "*". In certain embodiments, at least one instance of L comprises

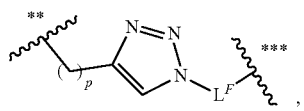

wherein:
  each instance of p is independently an integer from 1 to 10, inclusive;
  each instance of $L^F$ is independently substituted or unsubstituted, $C_{2-180}$ heteroalkylene; and
  the nitrogen atom labeled with "*" is closer to the attachment point labeled with "" than the attachment point labeled with "*". In certain embodiments, at least one instance of L is

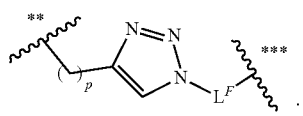

In certain embodiments, at least one instance of L comprises

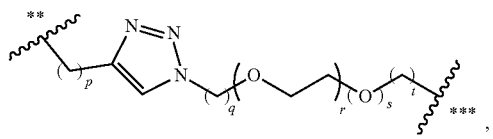

wherein:
  each instance of p is independently an integer from 1 to 10, inclusive;
  each instance of q is independently an integer from 1 to 10, inclusive;
  each instance of r is independently an integer from 0 to 10, inclusive;
  each instance of s is independently 0 or 1;
  each instance of t is independently an integer from 0 to 10, inclusive; and
  the nitrogen atom labeled with "*" is closer to the attachment point labeled with "" than the attachment point labeled with "*".

In certain embodiments, at least one instance of $L^F$ is substituted or unsubstituted, $C_{3-30}$ heteroalkylene. In certain embodiments, at least one instance of $L^F$ comprises —S—S—. In certain embodiments, at least one instance of $L^F$ is substituted or unsubstituted, $C_{3-30}$ heteroalkylene comprising one —S—S— and no other heteroatoms in the backbone. In certain embodiments, at least one instance of $L^F$ comprises a peptide comprising between 1 and 20 (e.g., between 1 and 4), inclusive, amino acid residues.

In certain embodiments, at least one instance of L is

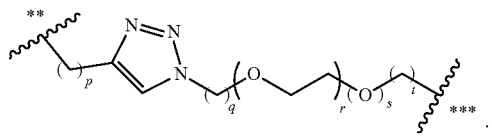

In certain embodiments, at least one instance of L is

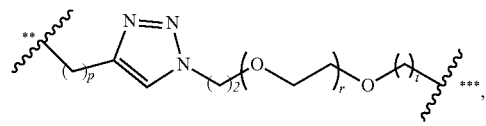

wherein r is 1, 2, or 3; and t is 1 or 2. In certain embodiments, at least one instance of L comprises

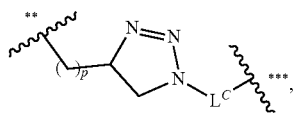

wherein:
  each instance of p is independently an integer from 1 to 10, inclusive;
  each instance of $L^C$ is independently substituted or unsubstituted, $C_{1-180}$ alkylene; and
  the nitrogen atom labeled with "*" is closer to the attachment point labeled with "" than the attachment point labeled with "*". In certain embodiments, at least one instance of L is

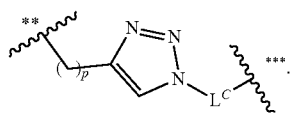

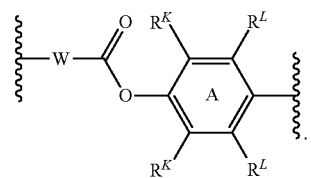

In certain embodiments, at least one instance of $L^C$ is substituted or unsubstituted $C_{1-12}$ alkylene. In certain embodiments, at least one instance of $L^C$ is unsubstituted $C_{1-12}$ alkylene. In certain embodiments, each instance of $L^C$ is independently $C_{1-180}$ alkylene substituted with one or more instances of: substituted or unsubstituted phenyl and/or substituted or unsubstituted, $C_{1-6}$ alkyl. In certain embodiments, at least one instance of L comprises a polymer. In certain embodiments, at least one instance of the polymer is substituted or unsubstituted polyethylene (e.g., unsubstituted polystyrene). In certain embodiments, the weight-average molecular weight of at least one instance of the polymer is between 300 and 10,000, between 300 and 3,000, between 300 and 1,000, between 1,000 and 10,000, between 1,000 and 3,000, or between 3,000 and 10,000, inclusive, g/mol. In certain embodiments, at least one instance of L comprises an amino acid or a peptide. In certain embodiments, at least one instance the peptide consists of between 3 and 60, between 3 and 30, between 3 and 10, between 10 and 60, between 10 and 30, or between 30 and 60, inclusive, amino acids. In certain embodiments, each instance of the amino acid is a natural amino acid. In certain embodiments, at least one instance of the amino acid is an unnatural amino acid.

A cleavable linker is "cleaved" or "degraded" when one or more bonds of the cleavable linker are broken, e.g., resulting in release of an agent, e.g., from the Brush prodrug or particle. Linker cleavage or agent release need not be 100%, e.g., a cleavage or release of at least 10%, 20%, 30%, 40%, 50%, 60%, 70%, 80%, 90%, 95% or higher, e.g., over a period of seconds, minutes, hours (e.g., 6 hours, 12 hours, or 24 hours), days (e.g., 2 days or 7 days), weeks, or months is encompassed by this term. In certain embodiments, at least 50% of all instances of the L that is cleavable is cleaved after about 10 minutes, about 1 hour, about 6 hours, about 12 hours, about 1 day, about 2 days, about 3 days, about 5 days, or about 7 days of the ultraviolet irradiation, hydrolysis, reduction, oxidation, or contact with the enzyme. In some embodiments, the cleavable linker is cleavable by or is sensitive to an enzyme (e.g., an esterase or a protease), pH (e.g., acidic pH, basic pH), light (e.g., ultraviolet light), a nucleophile, reduction, or oxidation. In some embodiments, the cleavable linker is cleavable by or is sensitive to an enzyme (e.g., an esterase or a protease) or pH (e.g., acidic pH, basic pH). In some embodiments, the cleavable linker is not cleavable by light (e.g., ultraviolet light). In certain embodiments, at least one instance of L is cleavable by ultraviolet irradiation. In certain embodiments, at least one instance of L is cleavable by hydrolysis, reduction, or oxidation. In certain embodiments, at least one instance of L is cleavable by contacting with an enzyme. In certain embodiments, no instance of L comprises in the backbone of L a linker that is more easily cleaved than the bond C—O in The cleavable linker may include an atom or a part of a moiety that is derived in part from the agent (e.g., a therapeutic agent).

In some embodiments, the cleavable linker is cleaved or degraded, e.g., preferentially cleaved or degraded, upon exposure to a first set of conditions relative to a second set of conditions. For example, the cleavable linker can be "preferentially cleaved" or "preferentially degraded" in a first set of conditions relative to a second set of conditions if at least 10%, 20%, 30%, 40%, 50%, 60%, 70%, 80%, 90%, 95% or more of a bond or bonds of the cleavable linker are broken, or the agent is released, in the first set of conditions relative to the second set of conditions.

In some embodiments, the cleavable linker is degraded or hydrolyzed at physiological conditions. In some embodiments, the linker is pH sensitive or cleaved at a certain pH. In some embodiments, the linker is degraded or hydrolyzed through the action of an enzyme (e.g., a protease or esterase). For example, in some embodiments, the cleavable linker is preferentially cleaved in a tissue microenvironment, e.g., a tumor microenvironment, which is referred to herein as a "tissue microenvironment cleavable linker." In embodiments, the tissue (e.g., tumor) microenvironment cleavable linker is preferentially cleaved or degraded upon exposure to a first desired tissue or tumor microenvironment relative to a second tissue or non-tumor tissue. A tissue (e.g., tumor) microenvironment cleavable linker can be preferentially cleaved if at least 10%, 20%, 30%, 40%, 50%, 60%, 70%, 80%, 90%, 95% or more of a bond or bonds of the linker are broken, or the agent is released, in a desired tissue or tumor microenvironment relative to another tissue or non-tumor tissue. In one embodiment, the tissue (e.g., tumor) microenvironment cleavable linker is preferentially cleaved or degraded if one or more of the bonds of the linker are broken, or the agent is released, at least 2, 5, 10, 20, 30, 40, 50, 60, 70, 80, or 100 times faster upon exposure to a first desired tissue or tumor microenvironment relative to a second tissue or non-tumor tissue. The tissue (e.g., tumor) microenvironment can have a particular set of conditions, e.g., pH, enzymes, that cause the cleavage or degradation of the linker.

In certain embodiments, at least two instances of L are different from each other. In all instances of L are the same.

In one embodiment, the tissue (e.g., tumor) microenvironment cleavable linker is cleavable by an enzyme. In some embodiments, the enzyme comprises an esterase or a protease. Exemplary proteases include MMP-1, MMP-2, MMP-3, MMP-8, MMP-9, MMP-14, plasmin, PSA, PSMA, CATHEPSIN D, CATHEPSIN K, CATHEPSIN S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, or TACE.

In other embodiments, the tissue microenvironment cleavable linker is cleavable at a particular pH. In some embodiments, the tissue microenvironment cleavable linker is cleavable at a pH between about 5.0 and about 7.4, between 5.0 and 7.0, between 5.0 and 6.5, between 5.0 and 5.5, or between 5.9 and 6.2. In one embodiment, the tissue microenvironment cleavable linker is cleavable at a pH between about 6.0 and about 7.0, between about 6.2 and about 6.9, between about 6.5 and about 6.8, or between about 6.5 and about 6.7. In one embodiment, the tissue microenvironment cleavable linker is cleavable at a pH between about 5.5 and about 6.5, e.g., between 5.9 and 6.2. In one embodiment, the tissue microenvironment cleavable linker is cleavable at a hypoxic pH, e.g., a pH about 6.7 to 6.9, e.g., compared to a physiological pH of about 7.4.

In some embodiments, the tissue microenvironment cleavable linker is cleavable is cleaved at a pH of no more than 7.4, no more than 7.0, no more than 6.9, no more than 6.8, no more than 6.7, no more than 6.6, no more than 6.5, no more than 6.4, no more than 6.3, no more than 6.2, no more than 6.1, no more than 6.0, no more than 5.5 or lower.

In one embodiment, the tissue microenvironment cleavable linker is preferentially cleaved or degraded upon exposure to a first pH relative to a second pH. In one embodiment, the tissue microenvironment cleavable linker is cleaved or degraded at least 2, 5, 10, 20, 30, 40, 50, 60, 70, 80, or 100 times faster upon exposure to a first pH relative to a second pH. In other embodiments, the tissue microenvironment cleavable linker shows a greater release or degradation rate at a first acidic pH (e.g., pH=6.7) relative to a second more basic pH (e.g., pH=7.4). In one embodiment, ratio of release or degradation rate of the tissue microenvironment cleavable linker at pH=6.7 relative to pH=7.4 is greater than 1, 1.2, 1.4, 1.6, 1.8, 2, 2.2, 2.4, 2.6, 2.8, 3 or higher. In one embodiment, ratio of release or degradation rate of the tissue microenvironment cleavable linker at pH=6.7 relative to pH=7.4 is greater than 2.

In one embodiment, the tissue microenvironment cleavable linker shows increased pH-sensitivity in a hypoxic microenvironment, e.g., in a tumor, or fibrotic tissue.

In some embodiments, the tissue microenvironment cleavable linker exhibits an increased release rate or increased release yield of the agent at a desired site (e.g., a tumor), e.g., relative to the release rate or release yield at another site. In one embodiment, the tissue microenvironment cleavable linker comprises an electron withdrawing group (e.g., an electron withdrawing group that enhances the cleavage rate or yield, e.g., upon exposure to a first set of conditions relative to a second set of conditions). When an instance of m is an integer from 2 to 10, inclusive, the m instances of

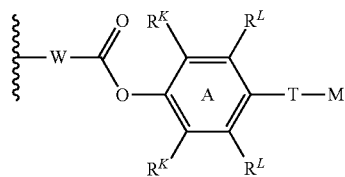

may be attached to L at the same atom and/or different atoms, as valency permits.

In certain embodiments, at least one substituent in at least one instance of L is =O, halogen (e.g., F), or substituted or unsubstituted $C_{1-6}$ alkyl.

When each instance of M is hydrogen, at least one instance of -L(M)$_m$ comprises a click-chemistry handle. "Click chemistry" reaction includes Huisgen alkyne-azide cycloaddition. Any "click chemistry" reaction known in the art can be used to this end. Click chemistry is a chemical approach introduced by Sharpless in 2001 and describes chemistry tailored to generate substances quickly and reliably by joining small units together. See, e.g., Kolb, Finn and Sharpless *Angewandte Chemie International Edition* (2001) 40:2004-2021; Evans, *Australian Journal of Chemistry* (2007) 60:384-395). Exemplary coupling reactions (some of which may be classified as "click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgen cycloaddition; thiol-yne addition; imine formation; Michael additions (e.g., maleimide addition); and Diels-Alder reactions (e.g., tetrazine [4+2] cycloaddition). In certain embodiments, at least one instance of the click-chemistry handle comprises C≡C or C=C. In certain embodiments, at least one instance of the click-chemistry handle comprises C≡CH, C=CH, CH=CH, C=CH$_2$, or CH=CH$_2$. In certain embodiments, at least one instance of the click-chemistry handle is —C≡CH, substituted or unsubstituted cyclooctynyl optionally fused independently with one or more instances of substituted or unsubstituted phenyl, substituted or unsubstituted cyclopropenyl, substituted or unsubstituted cyclobutenyl, substituted or unsubstituted trans-cyclooctenyl optionally fused independently with one or more instances of substituted or unsubstituted phenyl, or substituted or unsubstituted

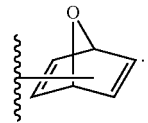

In certain embodiments, each instance of the click-chemistry handle is —C≡CH.

In certain embodiments, at least one (e.g., each) instance of W is a single bond. In certain embodiments, at least one (e.g., each) instance of W is —O—. In certain embodiments, at least one (e.g., each) instance of W is —S—. In certain embodiments, at least one (e.g., each) instance of W is —NR$^E$— (e.g., —NH—). In certain embodiments, at least one instance of R$^E$ is hydrogen. In certain embodiments, at least one instance of R$^E$ is substituted or unsubstituted, $C_{1-6}$ alkyl. In certain embodiments, at least one instance of R$^E$ is Me. In certain embodiments, at least one instance of R$^E$ is Et, Pr, Bu, substituted methyl, substituted ethyl, substituted propyl, or substituted butyl. In certain embodiments, at least one instance of R$^E$ is a nitrogen protecting group (e.g., Bn, Boc, Cbz, Fmoc, trifluoroacetyl, triphenylmethyl, acetyl, or Ts).

In certain embodiments, at least one (e.g., each) instance of W' is —O—. In certain embodiments, at least one (e.g., each) instance of W' is —S—. In certain embodiments, at least one (e.g., each) instance of W' is —NR$^J$— (e.g., —NH—).

In certain embodiments, at least one instance of R$^J$ is hydrogen. In certain embodiments, at least one instance of R$^J$ is substituted or unsubstituted, $C_{1-6}$ alkyl. In certain embodiments, at least one instance of R$^J$ is Me. In certain embodiments, at least one instance of R$^J$ is Et, Pr, Bu, substituted methyl, substituted ethyl, substituted propyl, or substituted butyl. In certain embodiments, at least one instance of R$^J$ is a nitrogen protecting group (e.g., Bn, Boc, Cbz, Fmoc, trifluoroacetyl, triphenylmethyl, acetyl, or Ts).

In certain embodiments, each instance of $R^K$ on at least one instance of

(Ring A) is hydrogen. In certain embodiments, one instance of $R^K$ on at least one instance of

is substituted or unsubstituted $C_{1-6}$ alkyl or —O(substituted or unsubstituted $C_{1-6}$ alkyl). In certain embodiments, one instance of $R^K$ on at least one instance of

is hydrogen, and the other instance of $R^K$ on the at least one instance of

is unsubstituted $C_{1-6}$ alkyl (e.g., Me, Et, i-Pr). In certain embodiments, one instance of $R^K$ on at least one instance of

is hydrogen, and the other instance of $R^K$ on the at least one instance of

is —O(unsubstituted $C_{1-6}$ alkyl) (e.g., —OMe, —OEt, —O(i-Pr)). In certain embodiments, one instance of $R^K$ on at least one instance of

is hydrogen, and the other instance of $R^K$ on the at least one instance of

is halogen (e.g., Cl, Br, I). In certain embodiments, each instance of $R^K$ on at least one instance of

is independently halogen (e.g., Cl, Br, or I), substituted or unsubstituted $C_{1-6}$ alkyl, or —O(substituted or unsubstituted $C_{1-6}$ alkyl). In certain embodiments, each instance of $R^K$ on at least one instance of

is independently substituted or unsubstituted $C_{1-6}$ alkyl or —O(substituted or unsubstituted $C_{1-6}$ alkyl). In certain embodiments, each instance of $R^K$ on at least one instance of

is independently unsubstituted $C_{1-6}$ alkyl (e.g., Me, Et, i-Pr) or —O(unsubstituted $C_{1-6}$ alkyl) (e.g., —OMe, —OEt, —O(i-Pr)). In certain embodiments, at least one instance of $R^K$ is substituted or unsubstituted $C_{2-6}$ alkenyl, or substituted or unsubstituted $C_{2-6}$ alkynyl. In certain embodiments, at least one instance of $R^K$ is substituted or unsubstituted, 3- to 7-membered, monocyclic carbocyclyl, substituted or unsubstituted, 3- to 7-membered, monocyclic heterocyclyl, substituted or unsubstituted phenyl, or substituted or unsubstituted, 5- or 6-membered, monocyclic heteroaryl. In certain embodiments, at least one instance of $R^K$ is —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$. In certain embodiments, no instance of $R^K$ is an electron-withdrawing group (e.g., F).

In certain embodiments, each instance of $R^L$ on at least one instance of

is hydrogen. In certain embodiments, each instance of $R^L$ on at least one instance of

is halogen (e.g., Cl, Br, I), substituted or unsubstituted $C_{1-6}$ alkyl, or —O(substituted or unsubstituted $C_{1-6}$ alkyl). In certain embodiments, each instance of $R^L$ on at least one instance of

is halogen (e.g., Cl, Br, I), unsubstituted $C_{1-6}$ alkyl (e.g., Me, Et, i-Pr), or —O(unsubstituted $C_{1-6}$ alkyl) (e.g., —OMe, —OEt, —O(i-Pr)). In certain embodiments, no instance of $R^L$ is an electron-withdrawing group (e.g., F).

In certain embodiments, at least one (e.g., each) instance of $R^a$ is hydrogen. In certain embodiments, at least one instance of $R^a$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted, 3- to 7-membered, monocyclic carbocyclyl, substituted or unsubstituted, 3- to 7-membered, monocyclic heterocyclyl, substituted or unsubstituted phenyl, substituted or unsubstituted, 5- or 6-membered, monocyclic heteroaryl, an oxygen protecting group when attached to an oxygen atom, a sulfur protecting group when attached to a sulfur atom, or a nitrogen protecting group when attached to a nitrogen atom. In certain embodiments, two instances of $R^a$ attached to the same nitrogen atom are joined to form substituted or unsubstituted, 3- to 7-membered, monocyclic heterocyclyl, or substituted or unsubstituted, 5- or 6-membered, monocyclic heteroaryl.

In certain embodiments, at least one (e.g., each) instance of T is a single bond, substituted or unsubstituted, $C_{1-20}$ alkylene, or substituted or unsubstituted, $C_{2-20}$ heteroalkylene. In certain embodiments, at least one (e.g., each) instance of T is a single bond; unsubstituted, $C_{1-20}$ alkylene; $C_{1-20}$ alkylene substituted with one or more halogen and/or one or more unsubstituted $C_{1-6}$ alkyl; unsubstituted $C_{2-20}$ heteroalkylene; $C_{2-20}$ heteroalkylene substituted on one or more carbons with one or more =O, one or more halogen, and/or one or more unsubstituted $C_{1-6}$ alkyl. In certain embodiments, at least one (e.g., each) instance of T is a single bond. In certain embodiments, at least one (e.g., each) instance of T is unsubstituted, $C_{1-20}$ alkylene (e.g., unsubstituted, $C_{1-6}$ alkylene). In certain embodiments, at least one (e.g., each) instance of T is substituted or unsubstituted methylene. In certain embodiments, at least one (e.g., each) instance of T is —CH$_2$—. In certain embodiments, at least one (e.g., each) instance of T is —CH($R^a$)—. In certain embodiments, at least one (e.g., each) instance of T is —CH(CH$_3$)—. In certain embodiments, at least one (e.g., each) instance of T is substituted or unsubstituted, $C_{2-20}$ heteroalkylene, wherein the backbone heteroatoms of the $C_{2-20}$ heteroalkylene are oxygen atoms. In certain embodiments, at least one (e.g., each) instance of T is *-(substituted or unsubstituted methylene)-O—C(=O)—, *-(substituted or unsubstituted methylene)-O—C(=O)—O—, *-(substituted or unsubstituted methylene)-O—C(=O)—N($R^N$)—, *-(substituted or unsubstituted methylene)-N($R^N$)—C(=O)—, *-(substituted or unsubstituted methylene)-N($R^N$)—C(=O)—O—, or *-(substituted or unsubstituted methylene)-N($R^N$)—C(=O)—N($R^N$)—, wherein the attachment point labeled with "*" is attached to Ring A, and each instance of $R^N$ is independently hydrogen, substituted or unsubstituted $C_{1-6}$ alkyl, or a nitrogen protecting group. In certain embodiments, at least one (e.g., each) instance of T is *—CH$_2$—O—C(=O)— or *—CH$_2$—O—C(=O)—N($R^N$)—. In certain embodiments, at least one instance (e.g., each instance) of T is more stable (e.g., between 30% and 100%, between 1-fold and 10-fold, between 10-fold and 100-fold, between 100-fold and 1,000-fold, between 1,000-fold and 10,000-fold, or between 10,000-fold and 1,000,000-fold, inclusive, more stable) than the moiety-W—C(=O)—W'-attached to the same Ring A to which the at least one instance of T is attached. In certain embodiments, being more stable refers to being more chemically stable. In certain embodiments, being more stable refers to being more stable under physiological conditions. In certain embodiments, being more stable refers to being more slowly cleaved by hydrolysis. In certain embodiments, being more stable refers to being more slowly cleaved by light (e.g., ultraviolet light), reduction, or oxidation. In certain embodiments, being more stable refers to being more slowly cleaved by contacting with an enzyme.

In certain embodiments, each instance of $R^B$ is hydrogen.

In certain embodiments, each instance of b is independently an integer from 2 to 20, inclusive. In certain embodiments, each instance of b is independently 2, 3, 4, 5, or 6.

In certain embodiments, e is 1. In certain embodiments, e is an integer from 2 to 10, inclusive. In certain embodiments, e is 2 or 3.

In certain embodiments, X is $OR^C$. In certain embodiments, X is $N(R^D)_2$. In certain embodiments, $R^C$ is hydrogen, substituted or unsubstituted, $C_{1-6}$ alkyl, an oxygen protecting group, or a leaving group; and at least one instance of $R^D$ is hydrogen, substituted or unsubstituted, $C_{1-6}$ alkyl, or a nitrogen protecting group. In certain embodiments, X is —$OR^C$, wherein $R^C$ is an oxygen protecting group or a leaving group. In certain embodiments, X is —OH. In certain embodiments, X is

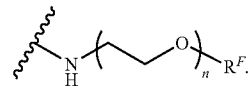

In certain embodiments, X is

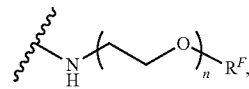

wherein n is an integer from 40 to 100, inclusive; and $R^F$ is hydrogen or unsubstituted $C_{1-6}$ alkyl.

In certain embodiments, $R^C$ or at least one instance of $R^D$ is substituted or unsubstituted, $C_{50-1000}$ heteroalkyl. In certain embodiments, $R^C$ or at least one instance of $R^D$ is

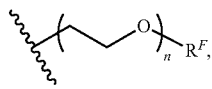

wherein:
n is an integer from 1 to 300, inclusive; and
$R^F$ is hydrogen, substituted or unsubstituted, $C_{1-6}$ alkyl, or an oxygen protecting group.

$R^C$ or at least one instance of $R^D$ is

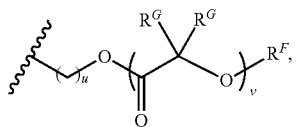

wherein:
u is 1, 2, 3, 4, 5, or 6;
each instance of $R^G$ is independently hydrogen, halogen, or substituted or unsubstituted, $C_{1-6}$ alkyl;
v is an integer from 1 to 300, inclusive; and
$R^F$ is hydrogen, substituted or unsubstituted, $C_{1-6}$ alkyl, or an oxygen protecting group.

In certain embodiments,

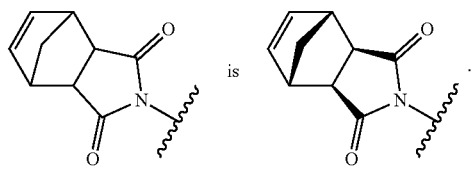

Exemplary macromonomers may be described by a number of properties, including molecular weight (kDa) and hydrodynamic diameter (nm). In some embodiments, the molecular weight of the macromonomer is between about 1 kDa and about 10 kDa, e.g., between about 2 kDa and about 8 kDa or about 3 kDa and about 6 kDa, e.g., as detected by mass spectrometry. In some embodiments, the molecular weight of the macromonomer is between about 3 kDa and about 6 kDa. In some embodiments, the molecular weight of the macromonomer is about 2 kDa, about 3 kDa, about 4 kDa, about 5 kDa, or about 6 kDa. In some embodiments, the hydrodynamic diameter of the macromonomer is between about 0.5 nm and about 3 nm, e.g., about 1 nm and about 2 nm, e.g., as detected by dynamic light scattering.

Compounds of Formula (II)

In another aspect, the present disclosure provides compounds of Formula (II):

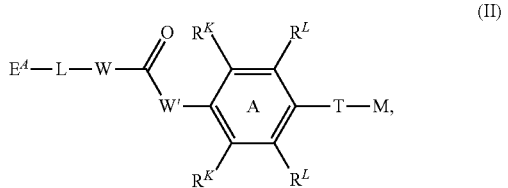

wherein:
$E^A$ is a first reaction handle;
L is substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or $C_{2-200}$ heteroalkynylene,
optionally one or more carbons in the substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, and $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;
optionally one or more heteroatoms in the substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;
W is a single bond, —O—, —S—, or —NR$^E$—;
$R^E$ is hydrogen, substituted or unsubstituted $C_{1-6}$ alkyl, or a nitrogen protecting group;
W' is —O—, —S—, or —NR$^J$—;
$R^J$ is hydrogen, substituted or unsubstituted $C_{1-6}$ alkyl, or a nitrogen protecting group;
each instance of $R^K$ and $R^L$ is independently hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, 3- to 7-membered, monocyclic carbocyclyl, substituted or unsubstituted, 3- to 7-membered, monocyclic heterocyclyl, substituted or unsubstituted phenyl, substituted or unsubstituted, 5- or 6-membered, monocyclic heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;
each instance of $R^a$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, 3- to 7-membered, monocyclic carbocyclyl, substituted or unsubstituted, 3- to 7-membered, monocyclic heterocyclyl, substituted or unsubstituted phenyl, substituted or unsubstituted, 5- or 6-membered, monocyclic heteroaryl, an oxygen protecting group when attached to an oxygen atom, a sulfur protecting group when attached to a sulfur atom, or a nitrogen protecting group when attached to a nitrogen atom; or two instances of $R^a$ attached to the same nitrogen atom are joined to form substituted or unsubstituted, 3- to 7-membered, monocyclic heterocyclyl, or substituted or unsubstituted, 5- or 6-membered, monocyclic heteroaryl;
T is substituted or unsubstituted methylene; and
M is an ammonium salt or iminium salt of a pharmaceutical agent, wherein the attachment point is the N$^+$ of the ammonium salt or iminium salt.

Unless otherwise provided, the moieties included in a compound of Formula (II) are as described herein (e.g., in the "Macromonomers" and/or the "Conjugates of Formula (III)" subsections).

Figure 4A:
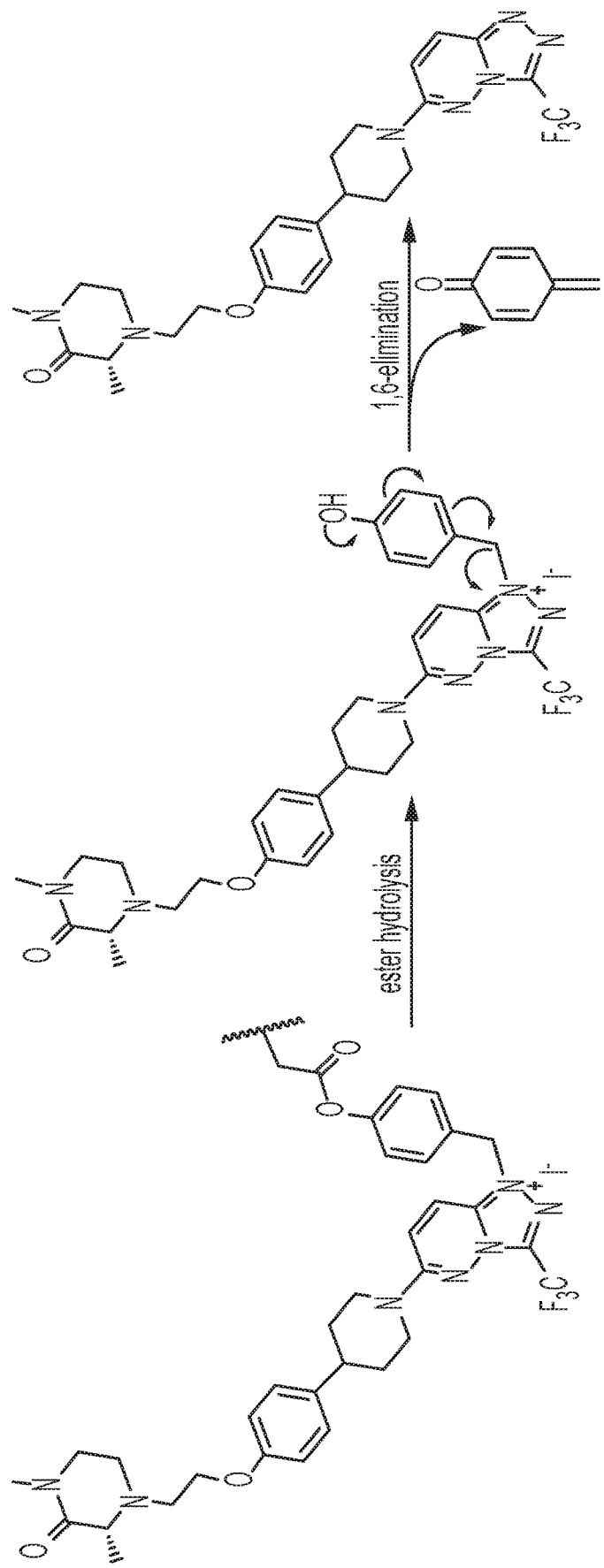
FIG. 4A shows an exemplary release of a pharmaceutical agent from a Brush prodrug.
Figure 4B:
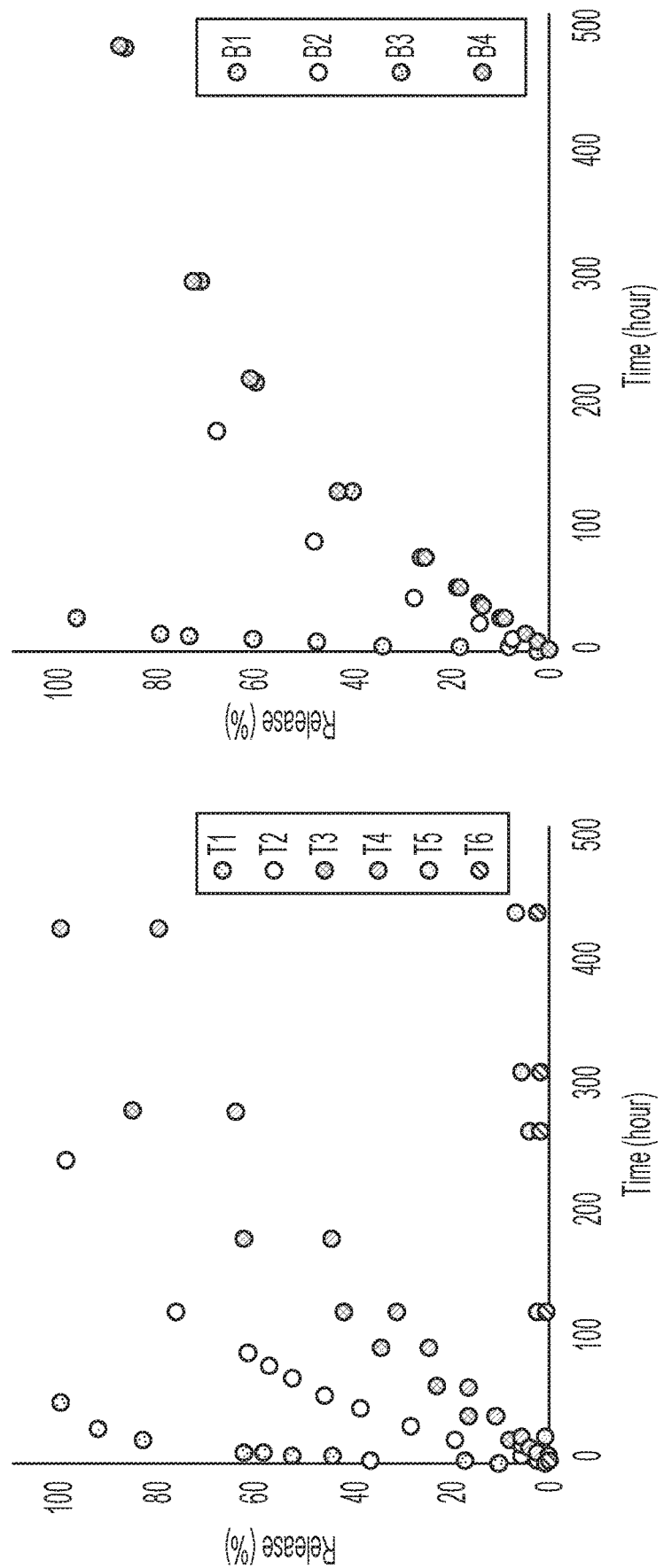
FIG. 4B shows that the release of the pharmaceutical agents from the Brush prodrugs is tunable.
Figure 5A:
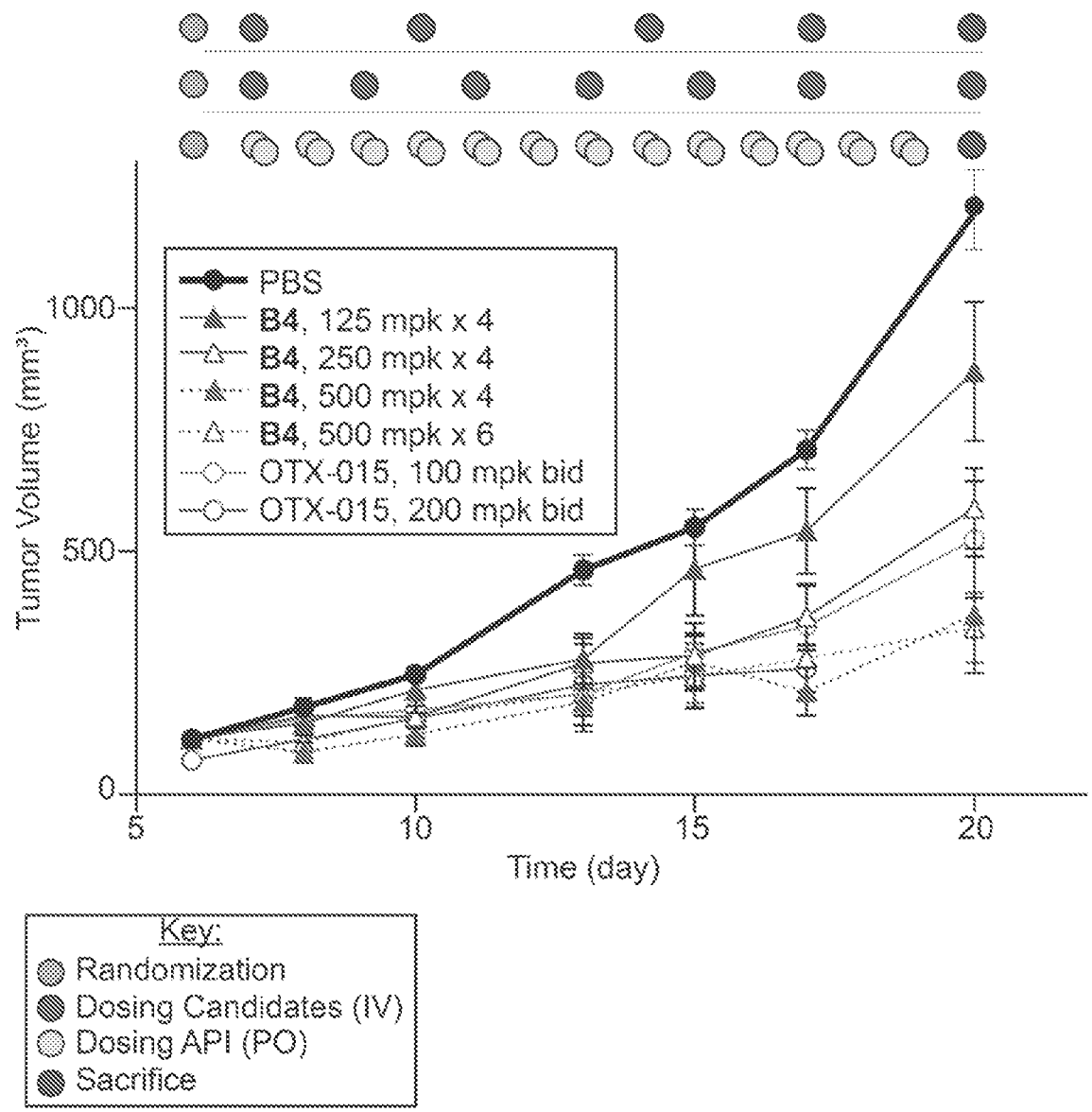
FIGS. 5A to 5F show the efficacy of Brush prodrug B4 in orthotopic, syngeneic tumor.
Figure 5B:
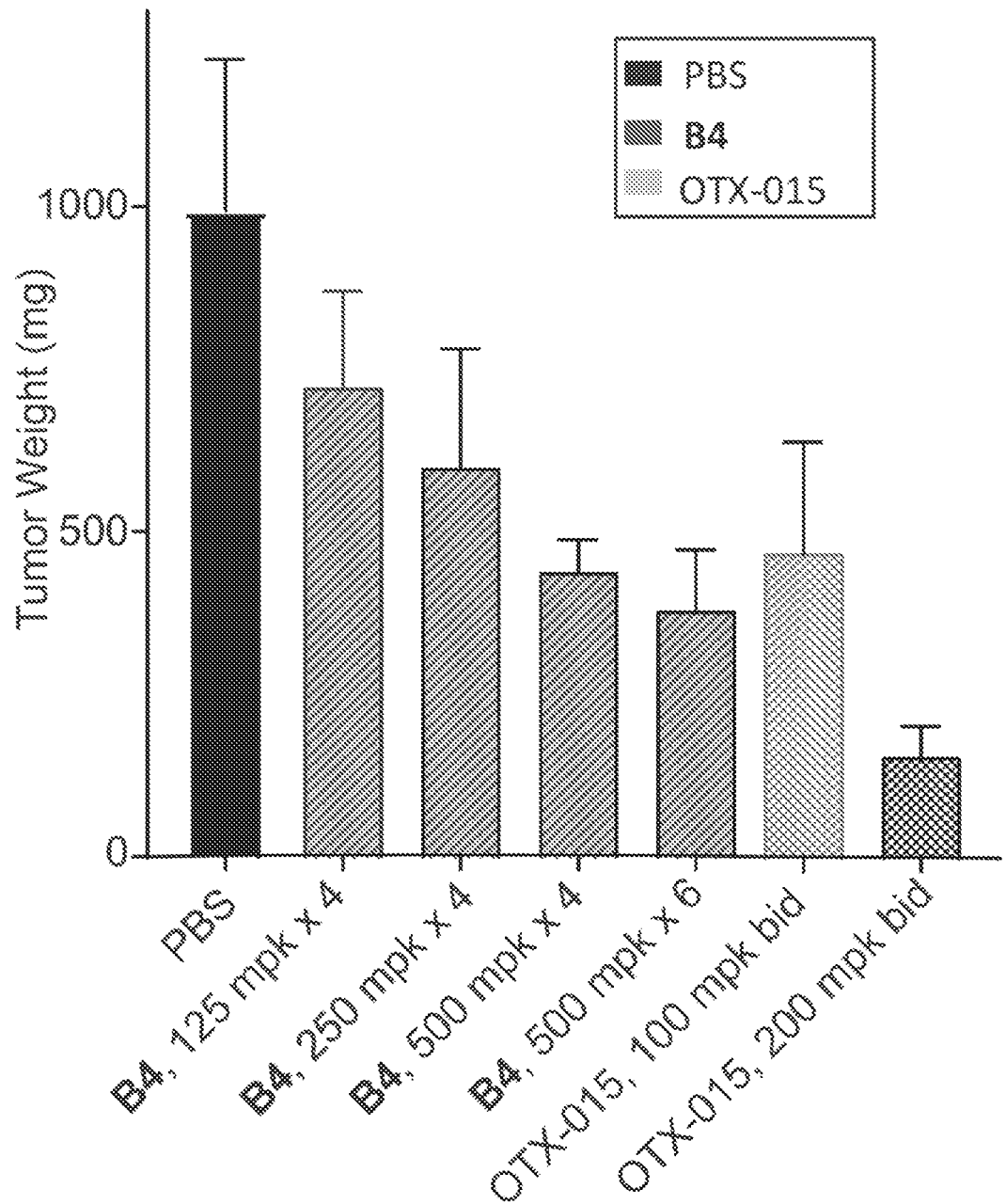
Figure 5C:
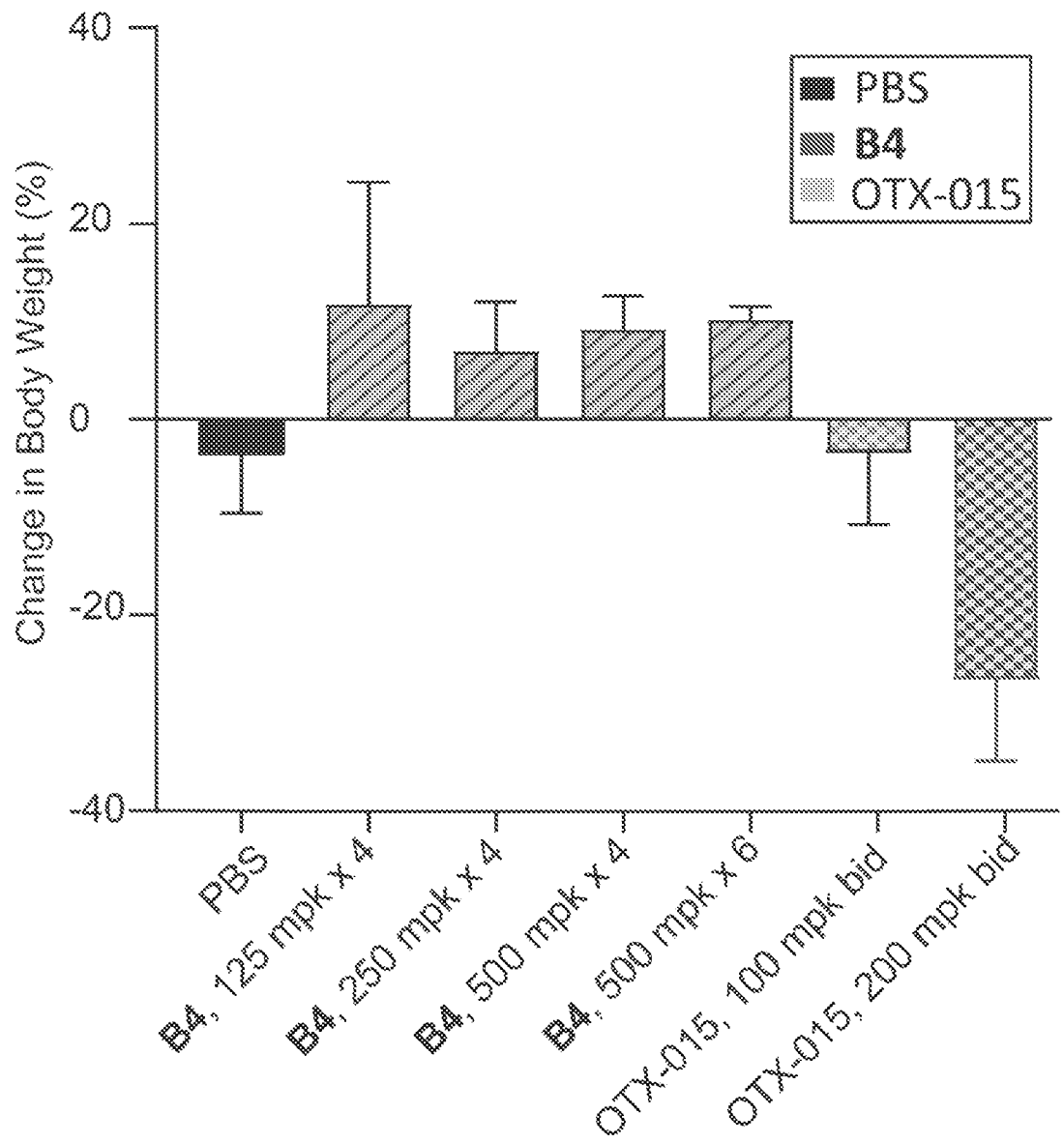
Figure 5D:
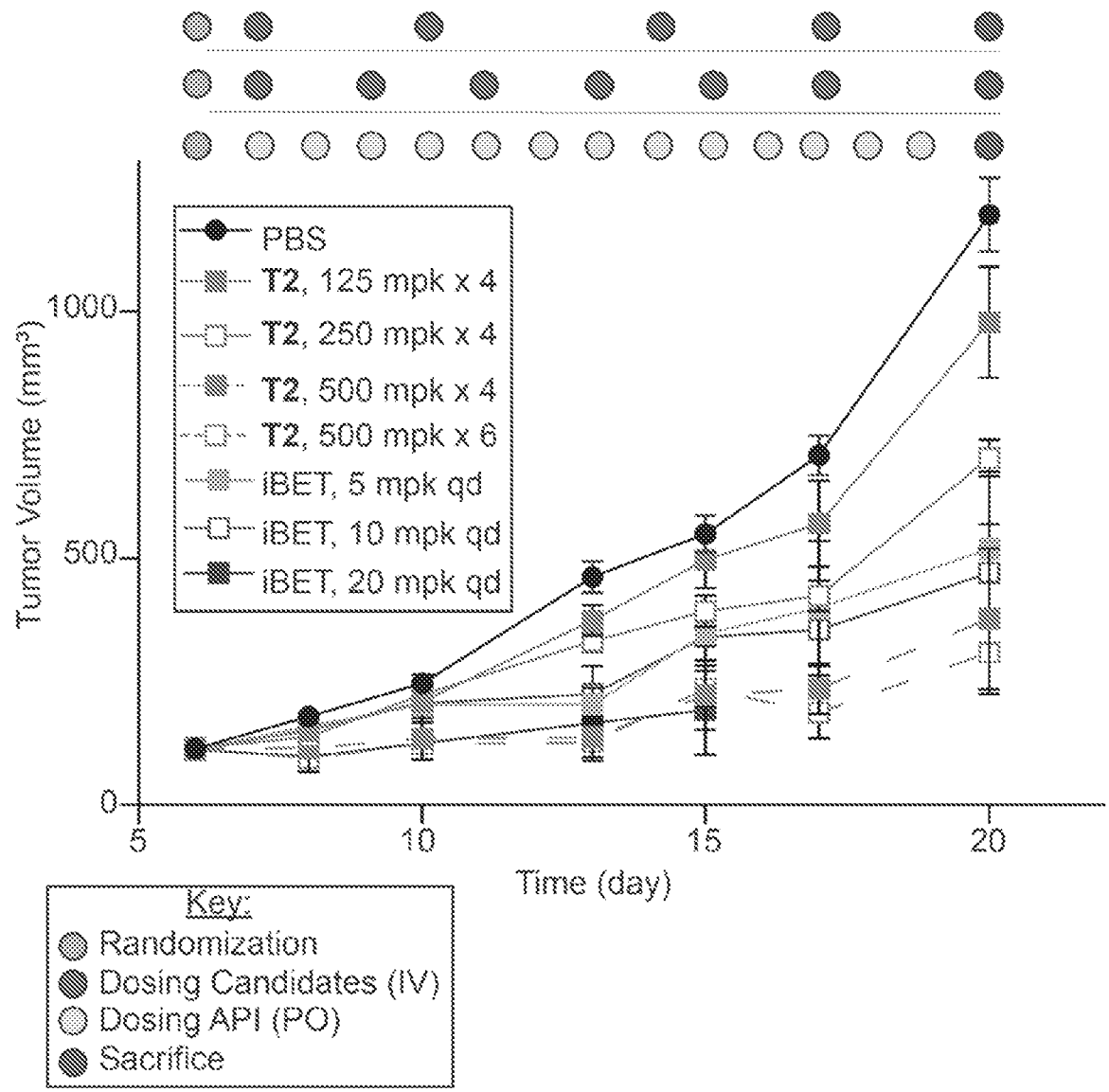
Figure 5E:
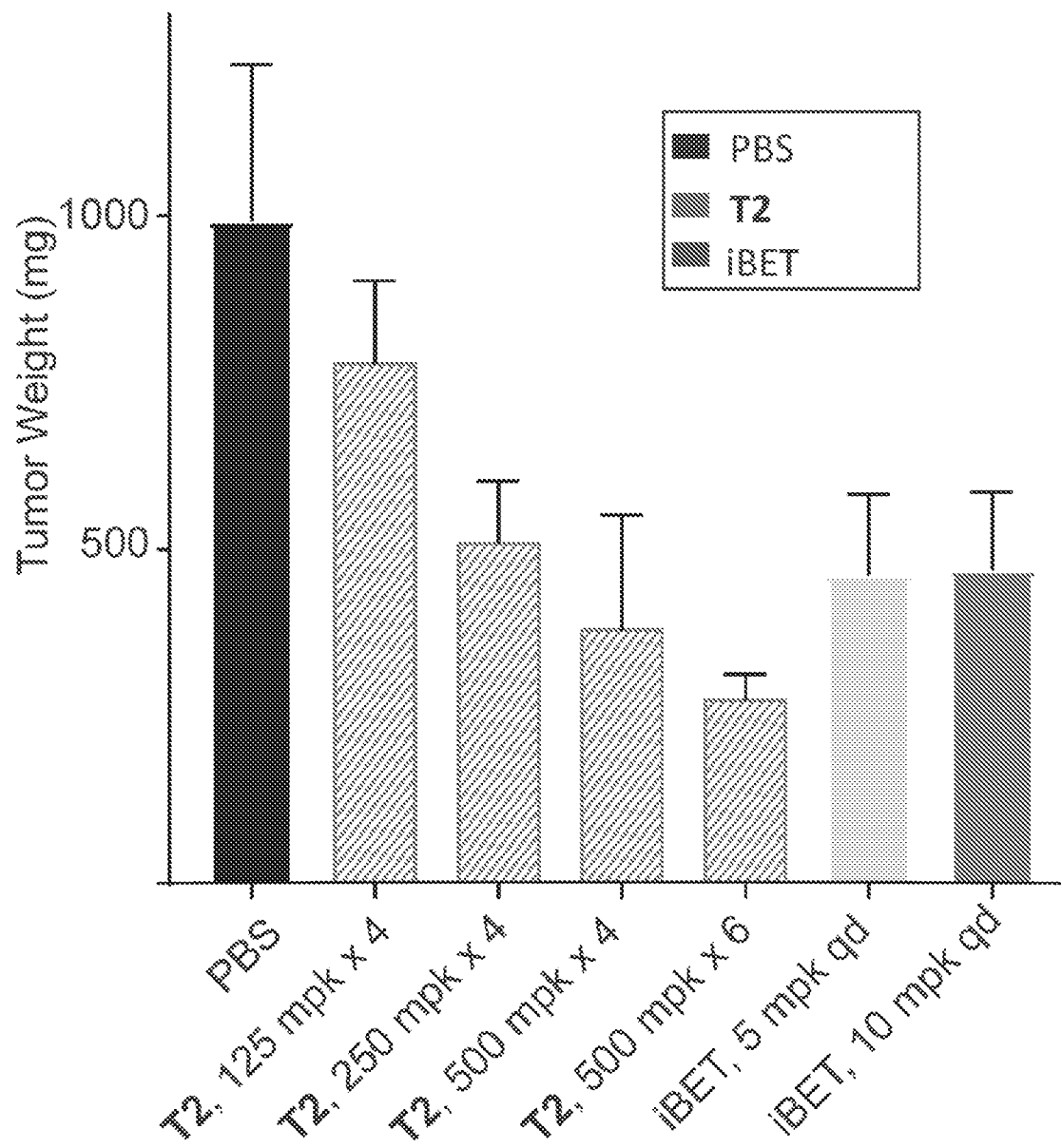
Figure 5F:
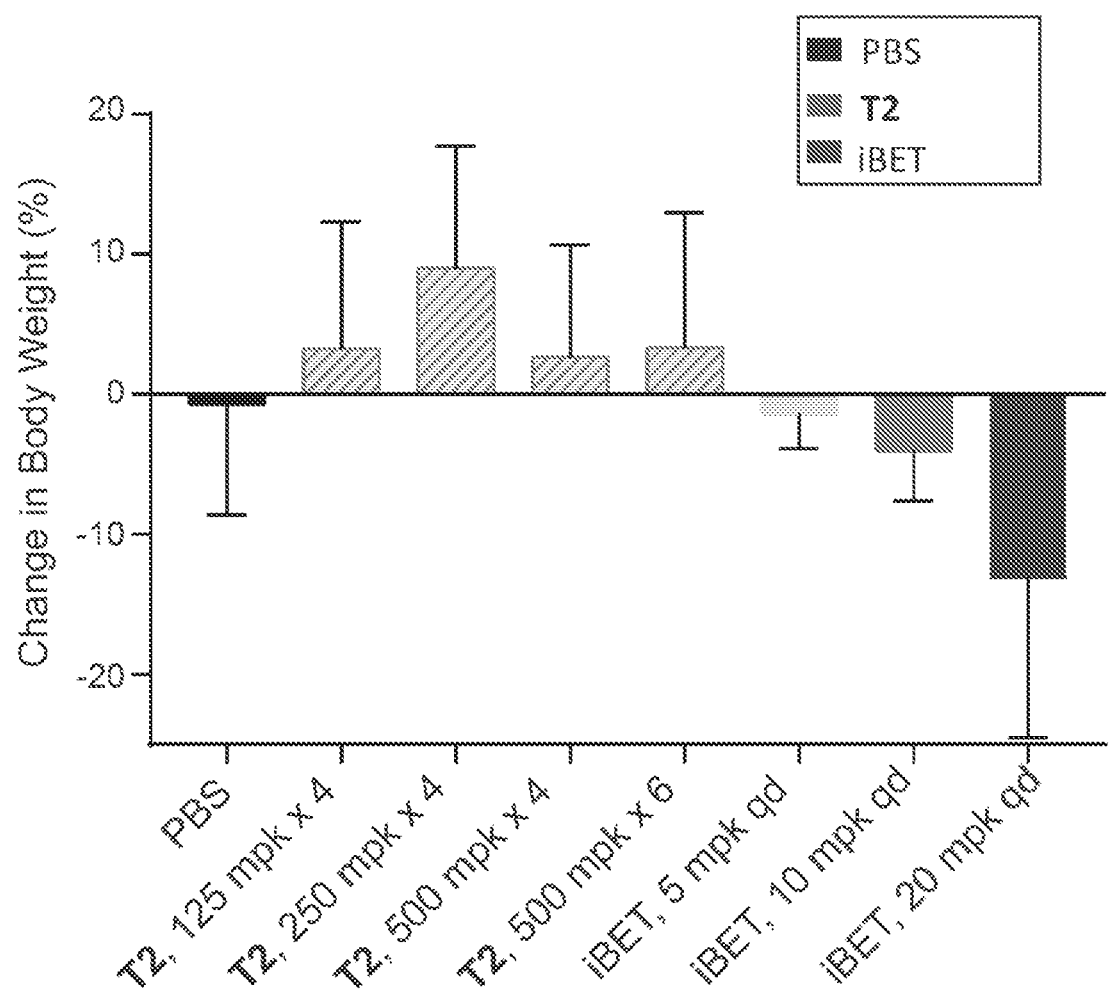
Figure 6A:
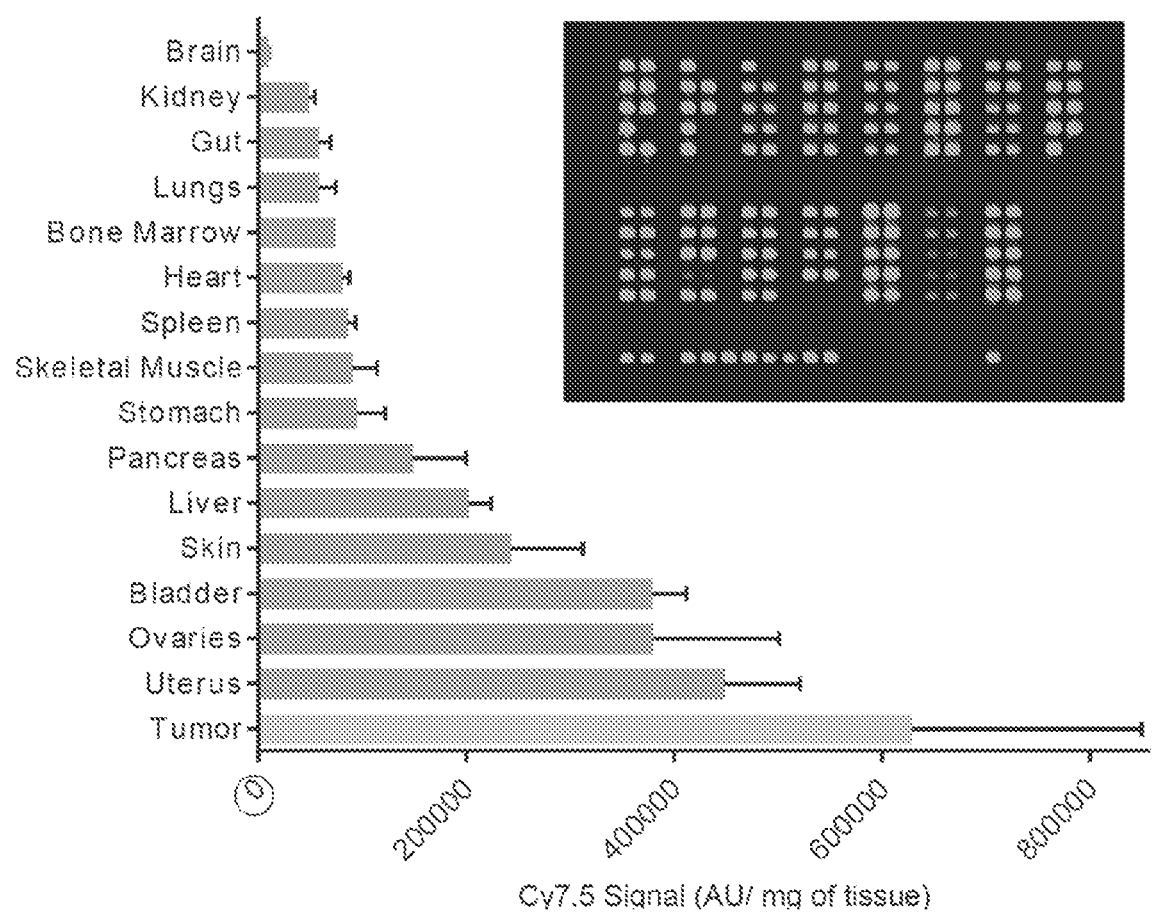
FIGS. 6A to 6D show the biodistribution and pharmacokinetics of Brush prodrug B4.
Figure 6B:
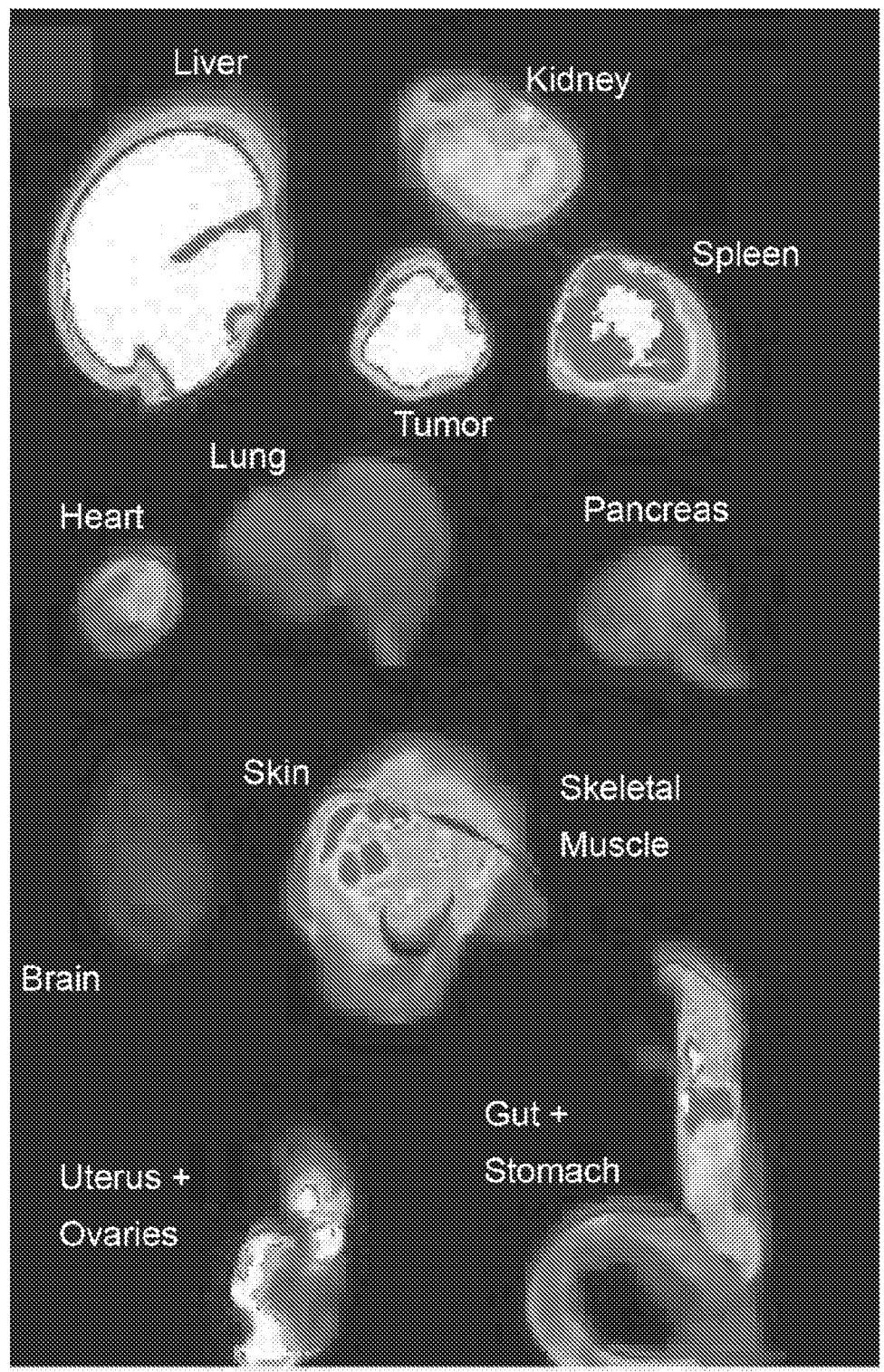
Figure 6C:
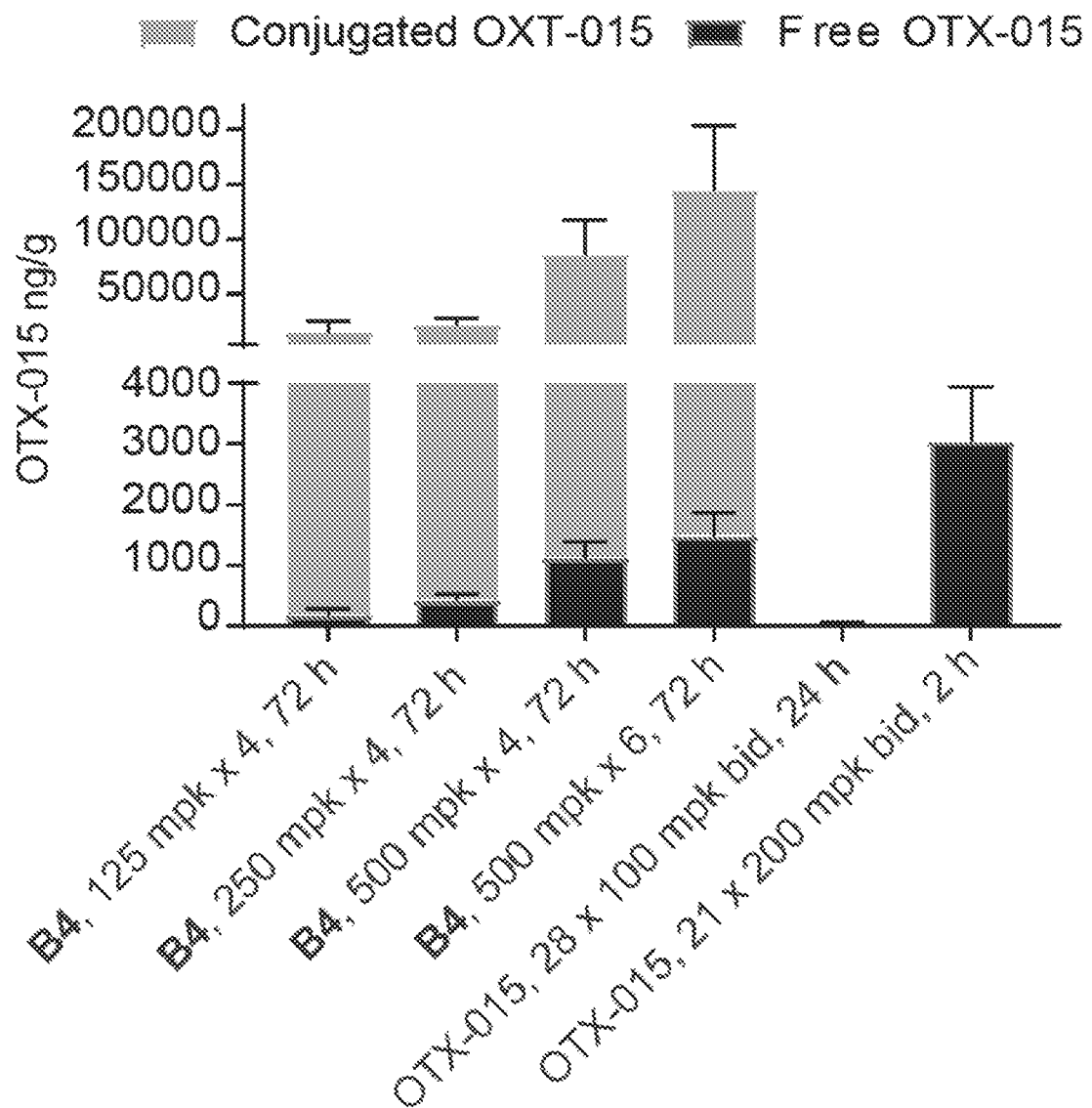
Figure 6D:
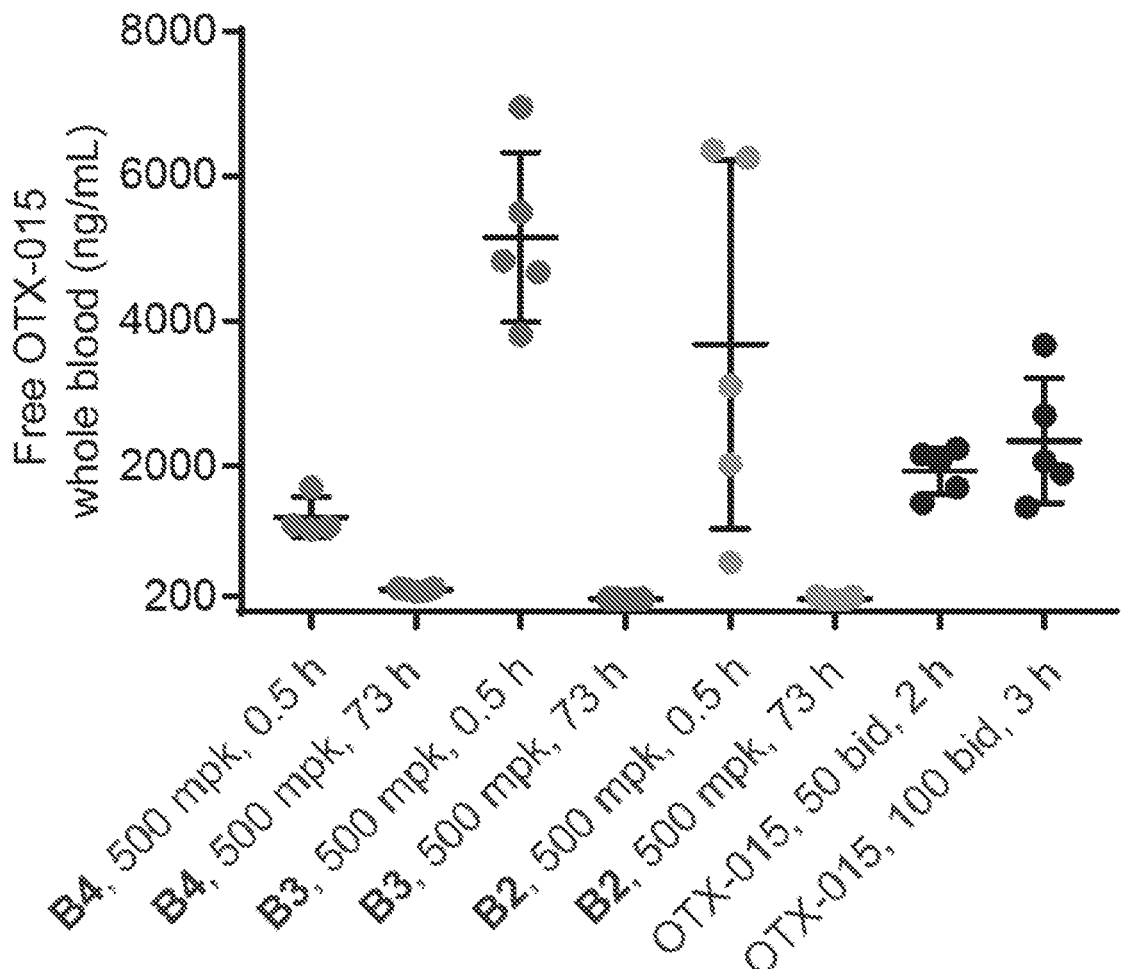

The compounds and conjugates may be useful for conjugating with a delivery vehicle (e.g., the moiety D) a pharmaceutical agent that does not contain a conventional reaction handle. In certain embodiments, the conventional reaction handle is a nucleophile, an electrophile, a leaving group, substituted or unsubstituted $C_{2-6}$ alkenyl, substituted or unsubstituted $C_{2-6}$ alkynyl, —OH, —SH, —NHR$^a$, —N$_3$, —C(=O)OH, —C(=NR$^a$) OH, —S(=O)OH, —S(=O)$_2$ OH, —C(=O)-(a leaving group), —C(=NR$^a$)-(a leaving group), —S(=O)-(a leaving group), or —S(=O)$_2$-(a leaving group). In certain embodiments, the conventional reaction handle is a nucleophile, an electrophile, a leaving group, —OH, —SH, —NHR$^a$, —N$_3$, —C(=O)OH, —C(=NR$^a$) OH, —S(=O)OH, —S(=O)$_2$OH, —C(=O)-(a leaving group), —C(=NR$^a$)-(a leaving group), —S(=O)-(a leaving group), or —S(=O)$_2$-(a leaving group). In certain embodiments, the pharmaceutical agent, before conjugation to form the compounds or conjugates, comprises tertiary amino or secondary imine. In certain embodiments, the tertiary amino or secondary imine is the conjugation site when the pharmaceutical agent is conjugated to form the compounds or conjugates. In certain embodiments, the pharmaceutical agent, after conjugation to form the compounds or conjugates, comprises a quaternary ammonium salt or tertiary iminium salt. The pharmaceutical agent may be released from the compounds or conjugates in the way shown in FIG. 4A. Related drug delivery technologies are reported in References (16) to (18).

Conjugates of Formula (III)

In another aspect, the present disclosure provides conjugates of Formula (III):

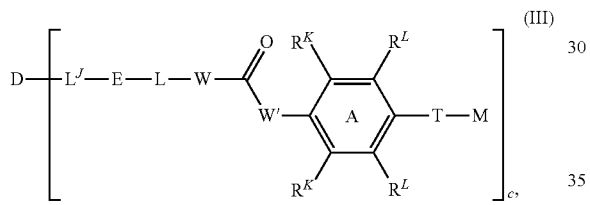

and salts thereof, wherein:
  D is a polymeric moiety, dendrimeric moiety, antibody, particle, bead, nanostructure, liposome, micelle, or vesicle;
  each instance of $L^J$ is independently substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or $C_{2-200}$ heteroalkynylene,
  optionally one or more carbons in the substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, and $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;
  optionally one or more heteroatoms in the substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;
  each instance of E is a moiety formed by reacting $E^A$ with $E^B$;
  each instance of $E^A$ is a first reaction handle;
  each instance of $E^B$ is a second reaction handle, wherein the second reaction handle is able to react with the first reaction handle;
  each instance of L is independently substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or $C_{2-200}$ heteroalkynylene,
  each instance of W is independently a single bond, —O—, —S—, or —NR$^E$—;
  each instance of $R^E$ is independently hydrogen, substituted or unsubstituted $C_{1-6}$ alkyl, or a nitrogen protecting group;
  each instance of W' is independently —O—, —S—, or —NR$^J$—;
  each instance of $R^J$ is independently hydrogen, substituted or unsubstituted $C_{1-6}$ alkyl, or a nitrogen protecting group;
  each instance of $R^K$ and $R^L$ is independently hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, 3- to 7-membered, monocyclic carbocyclyl, substituted or unsubstituted, 3- to 7-membered, monocyclic heterocyclyl, substituted or unsubstituted phenyl, substituted or unsubstituted, 5- or 6-membered, monocyclic heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;
  each instance of $R^a$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, 3- to 7-membered, monocyclic carbocyclyl, substituted or unsubstituted, 3- to 7-membered, monocyclic heterocyclyl, substituted or unsubstituted phenyl, substituted or unsubstituted, 5- or 6-membered, monocyclic heteroaryl, an oxygen protecting group when attached to an oxygen atom, a sulfur protecting group when attached to a sulfur atom, or a nitrogen protecting group when attached to a nitrogen atom; or two instances of $R^a$ attached to the same nitrogen atom are joined to form substituted or unsubstituted, 3- to 7-membered, monocyclic heterocyclyl, or substituted or unsubstituted, 5- or 6-membered, monocyclic heteroaryl;
  each instance of T is substituted or unsubstituted methylene;
  each instance of M is independently an ammonium salt or iminium salt of a pharmaceutical agent, wherein the attachment point is the N$^+$ of the ammonium salt or iminium salt; and
  c is an integer between 1 and 1000, inclusive.

Unless otherwise provided, the moieties included in a conjugate of Formula (III) are as described herein (e.g., in the "Macromonomers" subsection).

The compounds may be conjugated with D, which may be a delivery vehicle, to form the conjugates. The conjugates may be useful for, e.g., delivering the pharmaceutical agent.

In certain embodiments, D is a brush polymeric moiety or brush-arm star polymeric moiety. In certain embodiments, D is a nanoparticle or microparticle. In certain embodiments, D is an antibody.

In certain embodiments, at least one instance of E is a moiety formed by reacting two click-chemistry handles (e.g., two orthogonal click-chemistry handles). In certain embodiments, at least one instance of E is a single bond, —O—, —S—, —NR$^a$—, —C(=O)O—, —C(=NR$^a$)O—, —S(=O)O—, —S(=O)$_2$O—, —C(=O)NR$^a$—, —C(=NR$^a$) NR$^a$—, —S(=O)NR$^a$—, —S(=O)$_2$NR$^a$—, —OC(=O)—, —OC(=NR$^a$)—, —OS(=O)—, —OS(=O)$_2$—, —NR$^a$C(=O)—, —NR$^a$C(=NR$^a$)—, —NR$^a$S(=O)—, —NR$^a$S(=O)$_2$—, —OC(=O)O—, —OC(=NR$^a$)O—, —OS(=O)O—, —OS(=O)$_2$O—, —NR$^a$C(=O)O—, —NR$^a$C(=NR$^a$)O—, —NR$^a$S(=O)O—, —NR$^a$S(=O)$_2$O—, —OC(=O)NR$^a$—, —OC(=NR$^a$)NR$^a$—, —OS(=O)NR$^a$—, —OS(=O)$_2$NR$^a$—, —NR$^a$C(=O)NR$^a$—, —NR$^a$C(=NR$^a$) NR$^a$—, —NR$^a$S(=O)NR$^a$—, —NR$^a$S(=O)$_2$NR$^a$—, —C(=O)—, —C(=NR$^a$)—, —S(=O)—, or —S(=O)$_2$—.

In certain embodiments, at least one instance of $E^A$ is a polymerization handle. In certain embodiments, at least one instance of $E^A$ is an addition polymerization handle or condensation polymerization handle. In certain embodiments, at least one instance of $E^A$ is a metathesis polymerization handle. In certain embodiments, at least one instance of $E^A$ is substituted or unsubstituted $C_{2-6}$ alkenyl or substituted or unsubstituted $C_{2-6}$ alkynyl. In certain embodiments, at least one instance of $E^A$ is —OH, —NH$_2$, —C(=O)OH, or —C(=O)H. In certain embodiments, at least one instance of $E^A$ is a nucleophile, an electrophile, a leaving group, substituted or unsubstituted $C_{2-6}$ alkenyl, substituted or unsubstituted $C_{2-6}$ alkynyl, —OH, —SH, —NHR$^{aa}$, —N$_3$, —C(=O)OH, —C(=O)N(R$^a$)$_2$, —C(=NR$^a$) OH, —S(=O)OH, —S(=O)$_2$OH, —C(=O)-(a leaving group), —C(=NR$^a$)-(a leaving group), —S(=O)-(a leaving group), or —S(=O)$_2$-(a leaving group). In certain embodiments, at least one instance of $E^A$ is a click-chemistry handle. In certain embodiments, at least one instance of $E^A$ is —N$_3$.

In certain embodiments, at least one instance of $E^B$ is a click-chemistry handle. In certain embodiments, at least one instance of $E^B$ is a nucleophile, an electrophile, a leaving group, substituted or unsubstituted $C_{2-6}$ alkenyl, substituted or unsubstituted $C_{2-6}$ alkynyl, —OH, —SH, —NHR$^a$, —N$_3$, —C(=O)OH, —C(=O)N(R$^a$)$_2$, —C(=NR$^a$) OH, —S(=O)OH, —S(=O)$_2$OH, —C(=O)-(a leaving group), —C(=NR$^a$)-(a leaving group), —S(=O)-(a leaving group), or —S(=O)$_2$-(a leaving group). In certain embodiments, $E^B$ is —C≡CH.

In certain embodiments, at least one instance of $L^J$ is substituted or unsubstituted, $C_{1-12}$ alkylene, or substituted or unsubstituted, $C_{2-12}$ heteroalkylene. In certain embodiments, at least one instance of $L^J$ is substituted (e.g., substituted with one or more of: halogen, substituted or unsubstituted $C_{1-6}$ alkyl, —OR$^{aa}$, and/or oxo) or unsubstituted, $C_{1-12}$ alkylene. In certain embodiments, at least one instance of $L^J$ is or substituted (e.g., substituted with one or more of: halogen, substituted or unsubstituted $C_{1-6}$ alkyl, —OR$^{aa}$, and/or oxo) or unsubstituted, $C_{2-12}$ heteroalkylene.

In certain embodiments, c is an integer between 1 and 100 (e.g., between 1 and 10, between 11 and 30, between 31 and 100), inclusive. In certain embodiments, c is an integer between 100 and 300, inclusive. In certain embodiments, c is an integer between 300 and 1000, inclusive.

In certain embodiments, a conjugate includes salts thereof.

Methods of Preparing the Macromonomers, and Salts Thereof

In another aspect, the present disclosure provides methods of preparing the macromonomers, and salts thereof.

In certain embodiments, a method of preparing a macromonomer, or a salt thereof, comprises coupling a compound of the formula:

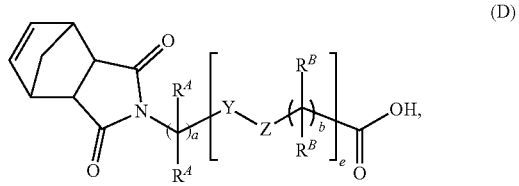

(D)

or a salt thereof, with a compound of the formula: HOR$^C$ or HN(R$^D$)$_2$, or a salt thereof. In certain embodiments, the step of coupling is performed in the presence of a reagent for coupling a carboxylic acid with an alcohol or amine.

In certain embodiments, the method of preparing a macromonomer, or a salt thereof, further comprises:
coupling a compound of the formula:

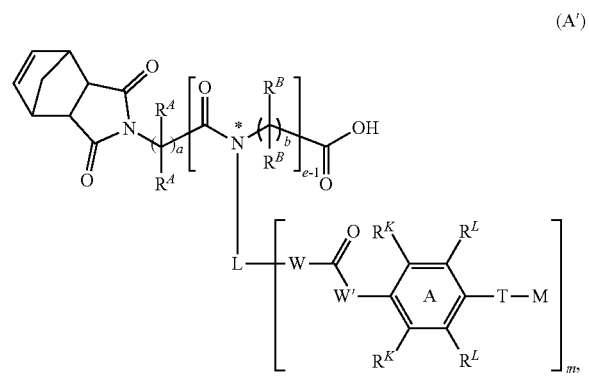

(A′)

or a salt thereof, with a compound of the formula:

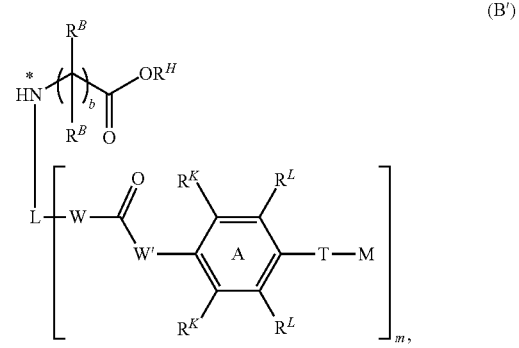

(B′)

or a salt thereof, to provide a compound of the formula:

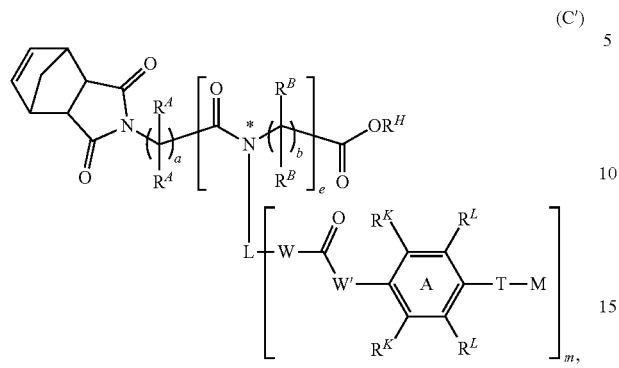

(C')

or a salt thereof, wherein $R^H$ is an oxygen protecting group; and deprotecting the compound of Formula (C'), or a salt thereof, to provide the compound of Formula (D), or a salt thereof, wherein each instance of —Y—Z— is independently

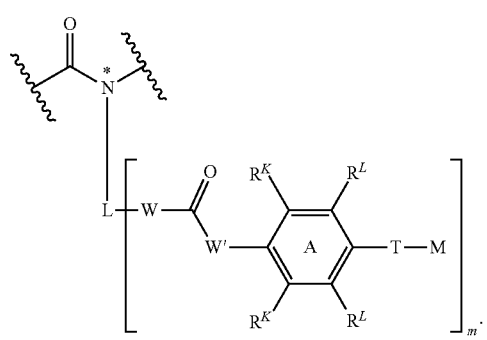

In certain embodiments, the method of preparing a macromonomer, or a salt thereof, further comprises:

coupling a compound of the formula:

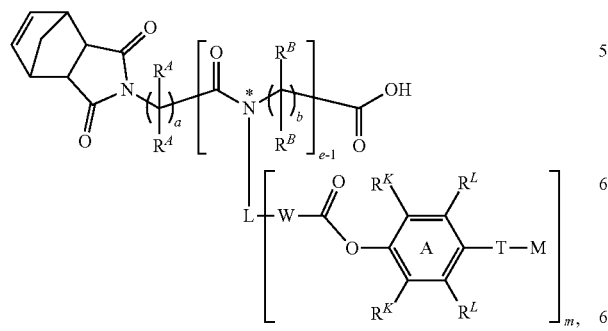

(A)

or a salt thereof, with a compound of the formula:

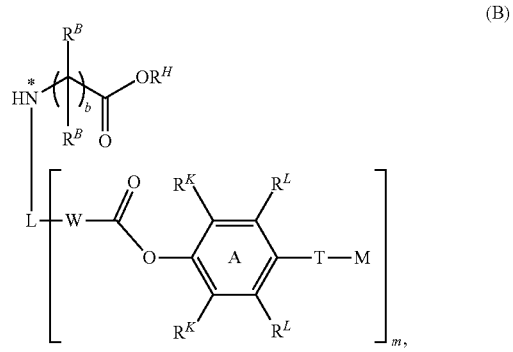

(B)

or a salt thereof, to provide a compound of the formula:

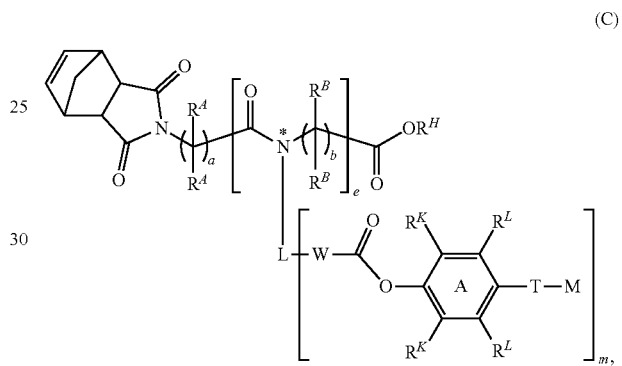

(C)

or a salt thereof, wherein $R^H$ is an oxygen protecting group; and deprotecting the compound of Formula (C), or a salt thereof, to provide the compound of Formula (D), or a salt thereof, wherein each instance of —Y—Z— is independently

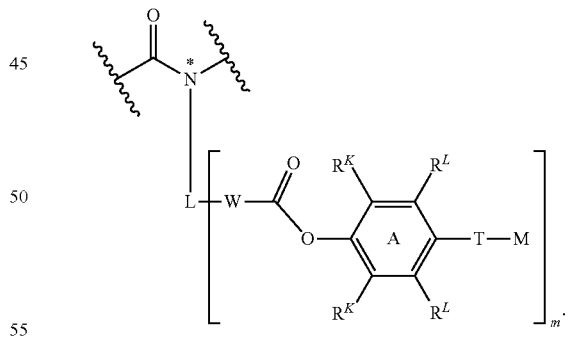

M can be conjugated to the macromonomer using any suitable conjugation technique. For instance, EDC-NHS chemistry (1-ethyl-3-(3-dimethylaminopropyl) carbodiimide hydrochloride and N-hydroxysuccinimide), or a reaction involving a maleimide or a carboxylic acid, which can be conjugated to one end of a thiol, an amine, or a similarly functionalized polyether. The conjugation can be performed in an organic solvent, such as, but not limited to, methylene chloride, acetonitrile, chloroform, dimethylformamide, tetrahydrofuran, acetone, or the like. Specific reaction conditions can be determined by those of ordinary skill in the art using no more than routine experimentation.

In another set of embodiments, a conjugation reaction may be performed by reacting the agent that includes a hydroxyl, thiol, or amino group with a polymer comprising a carboxylic acid functional group. Such a reaction may occur as a single-step reaction, i.e., the conjugation is performed with or without using intermediates such as N-hydroxysuccinimide or a maleimide. The conjugation reaction between the amine-containing, thiol-containing, or hydroxyl-containing moiety and the carboxylic acid-terminated polymer may be achieved in one embodiment, by adding the amine-containing, thoil-containing, or hydroxyl-containing moiety, solubilized in an organic solvent such as, but not limited to, dichloromethane, acetonitrile, chloroform, tetrahydrofuran, acetone, formamide, dimethylformamide, pyridines, dioxane, or dimethylsulfoxide, to a solution containing the carboxylic acid-terminated polymer. The carboxylic acid-terminated polymer may be contained within an organic solvent such as, but not limited to, dichloromethane, acetonitrile, chloroform, dimethylformamide, tetrahydrofuran, or acetone. Reaction between the amine-containing moiety and the carboxylic acid-terminated polymer may occur spontaneously in some cases. Unconjugated macromonomers may be washed away after such reactions, and the polymer may be precipitated in solvents such as, for instance, ethyl ether, hexane, methanol, or ethanol.

In certain embodiments, a reagent for coupling a carboxylic acid with an alcohol or amine is N-(3-dimethylaminopropyl)-N'-ethylcarbodiimide (EDC), dicyclohexylcarbodiimide (DCC), 1-ethyl-3-(3-dimethylaminopropyl) carbodiimide hydrochloride (WSC/HCl), diphenylphosphorylazide (DPPA), carbonyldiimidazole (CDI), diethylcyanophosphonate (DEPC), benzotriazole-1-yloxy-trispyrrolidinophosphonium (DIPCI), benzotriazole-1-yloxy-trispyrrolidinophosphonium hexafluorophosphate (PyBOP), 1-hydroxybenzotriazole (HOBt), hydroxysuccinimide (HOSu), dimethylaminopyridin (DMAP), 1-hydroxy-7-azabenzotriazole (HOAt), hydroxyphthalimide (HOPht), pentafluorophenol (Pfp-OH), 2-(1H-benzotriazole-1-yl)-1,1,3,3-tetramethyluronium hexafluorophosphate (HBTU), O-(7-azabenzotriazole-1-yl)-1,1,3,3-tetramethyluronium hexafluorophosphonate (HATU), O-benzotriazole-1-yl-1,1,3,3-tetramethyluronium tetrafluoroborate (TBTU), or 3,4-dihydro-3-hydrodi-4-oxa-1,2,3-benzotriazine (Dhbt), or a salt thereof; or a combination (e.g., a combination of two) thereof. In certain embodiments, the reagent for coupling a carboxylic acid with an alcohol or amine is DCC. In certain embodiments, the reagent for coupling a carboxylic acid with an alcohol or amine is EDC, or a salt thereof.

The reagent for coupling a carboxylic acid with an alcohol or amine is used in an amount of about 1 to 20 equivalents of the compound of Formula (D). In certain embodiments, the reagent for coupling a carboxylic acid with an alcohol or amine is used in an amount of about 1 to 10 equivalents. In certain embodiments, the activator is used in an amount of about 1 to 5 equivalents.

Examples of useful solvents in the coupling reaction are DMSO, DMF, and methylene chloride. Additional exemplary solvents include acetonitrile, chloroform, tetrahydrofuran, and acetone.

The coupling reaction can be conducted at 0 to 50° C. In certain embodiments, the coupling reaction is conducted at room temperature for about 10 min to about 30 hours. In certain embodiments, the coupling reaction is conducted for about 15 minutes to about 24 hours.

Brush Prodrug (Polymers) and Methods of Preparing the Brush Prodrugs

In another aspect, the present disclosure provides Brush prodrugs (polymers). In certain embodiments, the Brush prodrugs are prepared by polymerizing a macromonomer, or a salt thereof, in the presence of a metathesis catalyst. In certain embodiments, at least one instance of M of the first macromonomer is different from at least one instance of M of the second macromonomer. In certain embodiments, the metathesis catalyst is a transition metal metathesis catalyst (e.g., ruthenium metathesis catalyst) or Grubbs catalyst. In certain embodiments, the metathesis catalyst is of the formula:

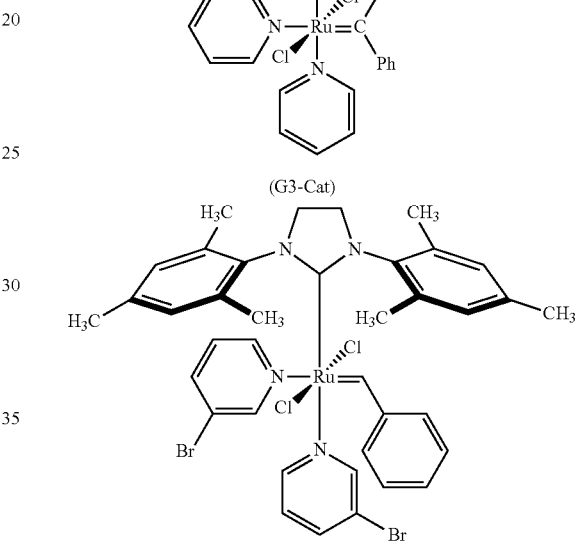

(G3-Cat).

The methods for preparing the Brush prodrugs described herein may involve ring-opening metathesis polymerization (ROMP) (Liu et al. *J. Am. Chem. Soc.* 2012, 134, 16337; Liu, J.; Gao, A. X.; Johnson, J. A. *J Vis Exp* 2013, e50874). In certain embodiments, the Brush prodrugs described herein are prepared by polymerization of norbornene-terminated macromonomers followed by in situ crosslinking with bis-norbornene crosslinkers. The preparation methods described herein are versatile and have little limitations, e.g., in terms of the different agents that can be built into the Brush prodrugs. In certain embodiments, an agent that can be built into the Brush prodrugs includes addressable functional groups that are compatible with ROMP.

In certain embodiments, the metathesis catalyst (e.g., ROMP catalyst) is a tungsten (W), molybdenum (Mo), or ruthenium (Ru) catalyst. In certain embodiments, the ROMP catalyst is a ruthenium catalyst. ROMP catalysts useful in the synthetic methods described herein include catalysts as depicted below, and as described in Grubbs et al., *Acc. Chem. Res.* 1995, 28, 446-452; U.S. Pat. No. 5,811,515; Schrock et al., *Organometallics* (1982) 1 1645; Gallivan et al., *Tetrahedron Letters* (2005) 46:2577-2580; Furstner et al., *J. Am. Chem. Soc.* (1999) 121:9453; and *Chem. Eur. J.* (2001) 7:5299; the entire contents of each of which are incorporated herein by reference.

In certain embodiments, the ROMP catalyst is a Grubbs catalyst. In certain embodiments, the Grubbs catalyst is selected from the group consisting of:

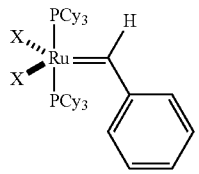

X = Cl; Br; I
Cy = cyclohexyl

Benzylidenebis-(tricyclohexylphosphine)-dichlororuthenium (X=Cl);
Benzylidenebis-(tricyclohexylphosphine)-dibromoruthenium (X=Br);
Benzylidenebis-(tricyclohexylphosphine)-diiodoruthenium (X=I);

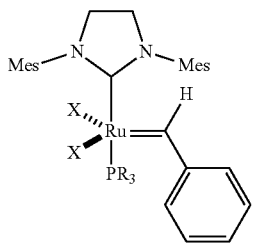

X = Cl; Br; I
R = cyclohexyl (Cy); phenyl (Ph); benzyl (Bn)

1,3-(Bis(mesityl)-2-imidazolidinylidene)dichloro-(phenylmethylene) (tricyclohexyl-phosphine)ruthenium (X=Cl; R=cyclohexyl);
1,3-(Bis(mesityl)-2-imidazolidinylidene)dibromo-(phenylmethylene) (tricyclohexyl-phosphine)ruthenium (X=Br; R=cyclohexyl);
1,3-(Bis(mesityl)-2-imidazolidinylidene)diiodo-(phenylmethylene) (tricyclohexyl-phosphine)ruthenium (X=I; R=cyclohexyl);
1,3-(Bis(mesityl)-2-imidazolidinylidene)dichloro-(phenylmethylene) (triphenylphosphine)ruthenium (X=Cl; R=phenyl);
1,3-(Bis(mesityl)-2-imidazolidinylidene)dichloro-(phenylmethylene) (tribenzylphosphine)ruthenium (X=Cl; R=benzyl);

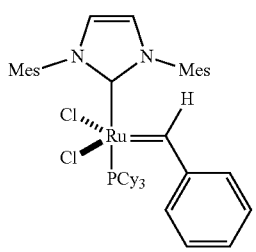 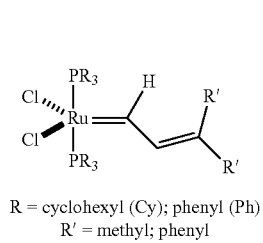

R = cyclohexyl (Cy); phenyl (Ph)
R' = methyl; phenyl

-continued

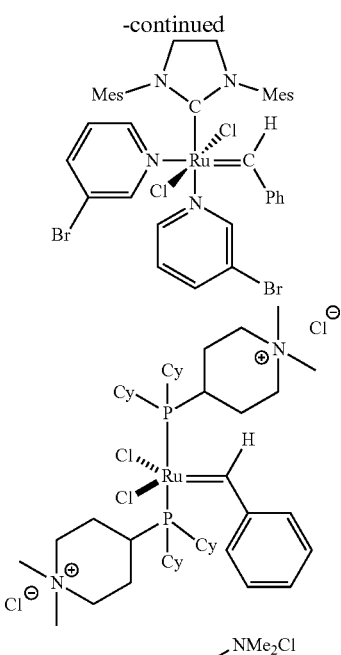

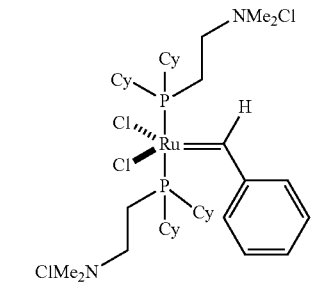

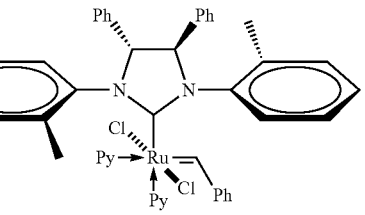

Py = pyridine
Ph = phenyl

In certain embodiments, the ROMP catalyst is a Grubbs-Hoveyda catalyst. In certain embodiments, the Grubbs-Hoveyda catalyst is selected from the group consisting of:

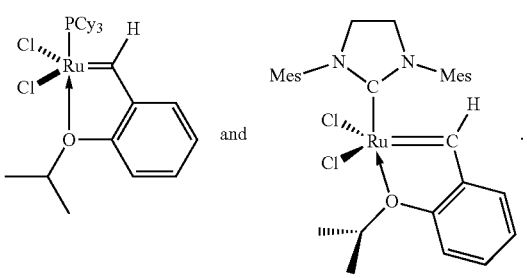 and 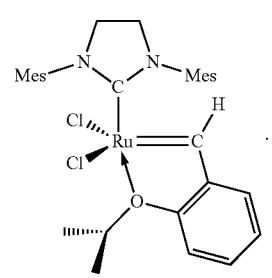

In certain embodiments, the ROMP catalyst is selected from the group consisting of:

Blechart Catalyst

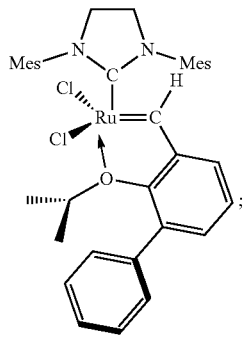

Neolyst™ M1

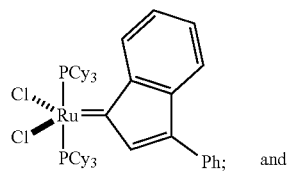

Furstner Catalyst

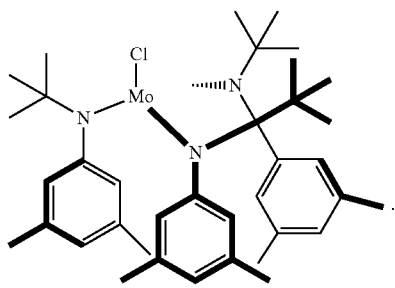

In certain embodiments, the ROMP catalyst is of the formula:

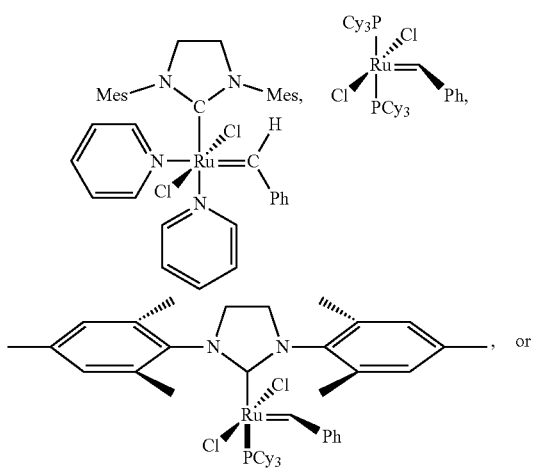

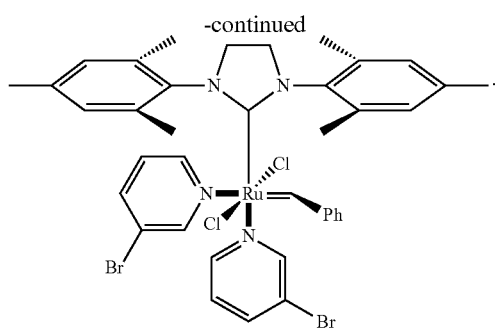

The ROMP can be conducted in one or more aprotic solvents. The term "aprotic solvent" means a non-nucleophilic solvent having a boiling point range above ambient temperature, preferably from about 25° C. to about 190° C. at atmospheric pressure. In certain embodiments, the aprotic solvent has a boiling point from about 80° C. to about 160° C. at atmospheric pressure. In certain embodiments, the aprotic solvent has a boiling point from about 80° C. to about 150° C. at atmospheric pressure. Examples of such solvents are methylene chloride, acetonitrile, toluene, DMF, diglyme, THF, and DMSO.

The ROMP can be quenched with a vinyl ether of the formula

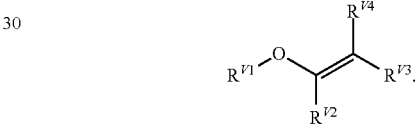

Each of $R^{V1}$, $R^{V2}$, $R^{V3}$, and $R^{V4}$ is independently optionally substituted alkyl, optionally substituted alkenyl, optionally substituted alkynyl, optionally substituted carbocyclyl, optionally substituted phenyl, optionally substituted heterocyclyl, or optionally substituted heteroaryl. In certain embodiments, $R^{V1}$ is optionally substituted alkyl, and $R^{V2}$, $R^{V3}$, and $R^{V4}$ are hydrogen. In certain embodiments, $R^{V1}$ is unsubstituted alkyl, and $R^{V2}$, $R^{V3}$, and $R^{V4}$ are hydrogen. In certain embodiments, $R^{V1}$ is substituted alkyl, and $R^{V2}$, $R^{V3}$, and $R^{V4}$ are hydrogen. In certain embodiments, $R^{V1}$ is methyl, and $R^{V2}$, $R^{V3}$, and $R^{V4}$ are hydrogen. In certain embodiments, $R^{V1}$ is ethyl, and $R^{V2}$, $R^{V3}$, and $R^{V4}$ are hydrogen. In certain embodiments, $R^{V1}$ is propyl, and $R^{V2}$, $R^{V3}$, and $R^{V4}$ are hydrogen. In certain embodiments, $R^{V1}$ is optionally substituted alkenyl, and $R^{V2}$, $R^{V3}$, and $R^{V4}$ are hydrogen. In certain embodiments, $R^{V1}$ is unsubstituted alkenyl, and $R^{V2}$, $R^{V3}$, and $R^{V4}$ are hydrogen. In certain embodiments, $R^{V1}$ is vinyl, and $R^{V2}$, $R^{V3}$, and $R^{V4}$ are hydrogen. In certain embodiments, at least one of $R^{V1}$, $R^{V2}$, $R^{V3}$, and $R^{V4}$ is conjugated with a diagnostic agent as defined above. In certain embodiments, the ROMP is quenched by ethyl vinyl ether. Excess ethyl vinyl ether can be removed from the Brush prodrugs by vacuum.

In another aspect, the present disclosure provides methods of preparing the Brush prodrug prodrugs.

The Brush prodrugs may be described by a number of properties, including average molecular weight (kDa), average hydrodynamic diameter (nm), and polydispersity.

The term "average molecular weight" may encompass the number average molecular weight (Mn), weight average molecular weight (Mw), higher average molecular weight (Mz or Mz+1), GPC/SEC-determined average molecular weight (Mp), and viscosity average molecular weight (Mv). In certain embodiments, the average molecular weight is Mw. In certain embodiments, the Mn is determined with gel permeation chromatography, viscometry via the (Mark-Houwink equation), colligative methods (such as vapor pressure osmometry), end-group determination, or proton NMR. In certain embodiments, the Mw is determined with static light scattering, small angle neutron scattering, X-ray scattering, and sedimentation velocity. In some embodiments, the average molecular weight of the Brush prodrug is between about 10 kDa and about 100 kDa, e.g., between about 15 kDa and about 85 kDa, about 20 kDa and about 60 kDa, or about 30 kDa and about 50 kDa, e.g., as determined by gel permeation chromatography. In one embodiment, the average molecular weight of the Brush prodrug is between about 20 kDa and about 60 kDa. In one embodiment, the average molecular weight of the Brush prodrug is between about 30 kDa and about 50 kDa.

In some embodiments, the average molecular weight of the Brush prodrug is less than about 100 kDa (e.g., less than about 95 kDa, about 90 kDa, about 85 kDa, about 80 kDa, about 75 kDa, about 70 kDa, about 65 kDa, about 60 kDa, about 55 kDa, or about 50 kDa), e.g., as determined by gel permeation chromatography. In some embodiments, the average molecular weight of the Brush prodrug is less than about 75 kDa (e.g., less than about 70 kDa, about 65 kDa, about 60 kDa, about 55 kDa, or about 50 kDa).

In some cases, the Brush prodrugs are of the form of particles (e.g., nanoparticles, i.e., the particle have a characteristic dimension of less than about 1 micrometer). In certain embodiments, the characteristic dimension of a particle is the diameter of a perfect sphere having the same volume as the particle. In certain embodiments, the Brush prodrug particle has a characteristic dimension of less than about 300 nm. In certain embodiments, the Brush prodrug particle has a characteristic dimension of less than about 200 nm. In certain embodiments, the Brush prodrug particle has a characteristic dimension of less than about 150 nm. In certain embodiments, the Brush prodrug particle has a characteristic dimension of less than about 100 nm. In certain embodiments, the Brush prodrug particle has a characteristic dimension of less than about 50 nm. In certain embodiments, the Brush prodrug particle has a characteristic dimension of less than about 30 nm. In certain embodiments, the Brush prodrug particle has a characteristic dimension of less than about 20 nm. In certain embodiments, the Brush prodrug particle has a characteristic dimension of less than about 10 nm. In certain embodiments, the Brush prodrug particle has a characteristic dimension between 6 and 250 nm, inclusive. In certain embodiments, the Brush prodrug particle has a characteristic dimension between 8 and 200 nm, inclusive. In certain embodiments, the Brush prodrug particle has a characteristic dimension between 12 and 200 nm, inclusive. In certain embodiments, the Brush prodrug particle has a characteristic dimension between 50 and 200 nm, inclusive. The term "average hydrodynamic diameter" as used herein refers to the average size of a Brush prodrug or particle. The average hydrodynamic diameter may or may not encompass the solvation layers of Brush prodrug or particle, and may be determined through a number of methods including dynamic light scattering, electron microscopy (e.g., scanning electron microscopy, transmission electron microscopy), atomic force microscopy, and X-ray diffraction. In some embodiments, the average hydrodynamic diameter of the Brush prodrug is less than 50 nm (e.g., less than about 45 nm, about 40 nm, about 35 nm, about 25 nm, about 20 nm, about 15 nm, about 10 nm, about 7.5 nm, or less), e.g., as determined by dynamic light scattering. In some embodiments, the average hydrodynamic diameter of the Brush prodrug is between about 1 nm and about 20 nm (e.g., between about 2.5 nm and about 17.5 nm, or about 5 nm and about 15 nm). In some embodiments, the average hydrodynamic diameter of the Brush prodrug is between about 5 nm and about 15 nm.

In some embodiments, the average hydrodynamic diameter of the particle is less than 100 nm (e.g., less than about 90 nm, about 80 nm, about 75 nm, about 70 nm, about 65 nm, about 60 nm, about 55 nm, about 50 nm, about 45 nm, about 40 nm, about 35 nm, about 25 nm, or less), e.g., as determined by dynamic light scattering. In some embodiments, the average hydrodynamic diameter of the particle is between about 5 nm and about 100 nm (e.g., between about 7.5 nm and about 75 nm, about 10 nm and about 50 nm, about 12.5 nm and about 40 nm, or about 15 nm and about 30 nm). In some embodiments, the average hydrodynamic diameter of the particle is between about 10 nm and about 50 nm. In some embodiments, the average hydrodynamic diameter of the particle is between about 15 nm and about 30 nm.

The term "average polydispersity" as used herein refers to a measure of the distribution of molecular size in a mixture, e.g., as determined by a chromatographic method, such as gel permeation chromatography or size exclusion chromatography, or through dynamic light scattering. In some embodiments, the average polydispersity of the Brush prodrug or particle is less than about 0.5 (e.g., less than about 0.4, about 0.35, about 0.3, about 0.25, about 0.2, about 0.15, or less). In some embodiments, the average polydispersity of the Brush prodrug or particle is less than about 0.3. In some embodiments, the average polydispersity of the Brush prodrug or particle is less than about 0.2. In some embodiments, the average polydispersity of the Brush prodrug or particle is less than about 0.15. In some embodiments, the Brush prodrug or particle is monodisperse. In some embodiments, the Brush prodrug or particle is about 50% monodisperse (e.g., about 55%, about 60%, about 65%, about 70%, about 75%, about 80%, about 85%, about 90%, about 95%, about 99%, or about 99.9% monodisperse).

In some embodiments, the Brush prodrug or particle is substantially soluble in water (e.g., hydrophilic). In some embodiments, the Brush prodrug or particle is substantially insoluble in water (e.g., hydrophobic). In some embodiments, the Brush prodrug or particle is substantially insoluble in water and greater than about 10,000 parts water are required to dissolve 1 part polymer. In one embodiment, the Brush prodrug or particle is amphiphilic. In one embodiment, the Brush prodrug or particle comprises a segment that is hydrophobic and a segment that is hydrophilic.

Pharmaceutical Compositions and Kits

The present disclosure provides compositions (e.g., pharmaceutical compositions) comprising a polymer described herein, and optionally an excipient (e.g., pharmaceutically acceptable excipient). The present disclosure also provides compositions (e.g., pharmaceutical compositions) comprising a conjugate described herein, and optionally an excipient (e.g., pharmaceutically acceptable excipient). In certain embodiments, the pharmaceutical composition described herein comprises a polymer described herein and a pharmaceutically acceptable excipient. In certain embodiments, the pharmaceutical composition described herein comprises a conjugate described herein and a pharmaceutically acceptable excipient.

In certain embodiments, the pharmaceutical compositions are useful for delivering an agent (e.g., to a subject or cell). In certain embodiments, the pharmaceutical compositions are useful for treating a disease in a subject in need thereof. In certain embodiments, the pharmaceutical compositions are useful for preventing a disease in a subject.

In certain embodiments, the polymer or conjugate described herein is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a proliferative disease in a subject in need thereof. In certain embodiments, the effective amount is an amount effective for preventing a proliferative disease in a subject in need thereof. In certain embodiments, the effective amount is an amount effective for treating a hematological disease in a subject in need thereof. In certain embodiments, the effective amount is an amount effective for preventing a hematological disease in a subject in need thereof. In certain embodiments, the effective amount is an amount effective for treating a neurological disease in a subject in need thereof. In certain embodiments, the effective amount is an amount effective for preventing a neurological disease in a subject in need thereof. In certain embodiments, the effective amount is an amount effective for treating a in a painful condition subject in need thereof. In certain embodiments, the effective amount is an amount effective for preventing a painful condition in a subject in need thereof. In certain embodiments, the effective amount is an amount effective for treating a psychiatric disorder in a subject in need thereof. In certain embodiments, the effective amount is an amount effective for preventing a psychiatric disorder in a subject in need thereof. In certain embodiments, the effective amount is an amount effective for treating a metabolic disorder in a subject in need thereof. In certain embodiments, the effective amount is an amount effective for preventing a metabolic disorder in a subject in need thereof. In certain embodiments, the effective amount is an amount effective for reducing the risk of developing a disease (e.g., proliferative disease, hematological disease, neurological disease, painful condition, psychiatric disorder, or metabolic disorder) in a subject in need thereof. In certain embodiments, the effective amount is an amount effective for inhibiting the activity (e.g., aberrant activity, such as increased activity) of a protein kinase in a subject or cell.

In certain embodiments, the cell is in vitro. In certain embodiments, the cell is in vivo.

Pharmaceutical compositions described herein can be prepared by any method known in the art of pharmacology. In general, such preparatory methods include bringing the polymer or conjugate described herein (which may includes a therapeutic agent (the "active ingredient")) into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan monostearate (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, *Litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (c) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a polymer or conjugate described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the polymer or conjugate in powder form through the outer layers of the skin to the dermis are suitable.

Formulations suitable for topical administration include liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Polymers provided herein are typically formulated in dosage unit form for case of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The polymers, conjugates, and compositions provided herein can be administered by any route, including enteral (e.g., oral), parenteral, intravenous, intramuscular, intraarterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the polymer, conjugate, or pharmaceutical composition described herein is suitable for topical administration to the eye of a subject.

The exact amount of a polymer or conjugate required to achieve an effective amount will vary from subject to subject, depending, for example, on species, age, and general condition of a subject, severity of the side effects or disorder, identity of the particular polymer or conjugate, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a polymer or conjugate described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a polymer or conjugate described herein. In certain embodiments, a dose described herein includes independently between 1 mg and 3 mg, inclusive, of a polymer or conjugate described herein. In certain embodiments, a dose described herein includes independently between 3 mg and 10 mg, inclusive, of a polymer or conjugate described herein. In certain embodiments, a dose described herein includes independently between 10 mg and 30 mg, inclusive, of a polymer or conjugate described herein. In certain embodiments, a dose described herein includes independently between 30 mg and 100 mg, inclusive, of a polymer or conjugate described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

A polymer, conjugate, or composition, as described herein, can be administered in combination with one or more additional pharmaceutical agents (e.g., therapeutically and/or prophylactically active agents). The polymers, conjugates, or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof, and/or in inhibiting the activity of a protein kinase in a subject or cell), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a polymer or conjugate described herein and an additional pharmaceutical agent shows a synergistic effect that is absent in a pharmaceutical composition including one of the polymer/conjugate and the additional pharmaceutical agent, but not both.

The polymer, conjugate, or composition can be administered concurrently with, prior to, or subsequent to one or more additional pharmaceutical agents, which are different from the polymer, conjugate, or composition and may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the polymer, conjugate, or composition described herein in a single dose or administered separately in different doses. The particular combination to employ in a regimen will take into account compatibility of the polymer or conjugate described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include anti-proliferative agents, anti-cancer agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In certain embodiments, the additional pharmaceutical agent is a binder or inhibitor of a protein kinase. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the polymers or conjugates described herein or pharmaceutical compositions can be administered in combination with an anti-cancer therapy including surgery, radiation therapy, transplantation (e.g., stem cell transplantation, bone marrow transplantation), immunotherapy, and chemotherapy.

Also encompassed by the disclosure are kits (e.g., pharmaceutical packs). In certain embodiments, the kits comprise: a macromonomer, or a salt thereof, a Brush prodrug, or a pharmaceutical composition; and instructions for using the macromonomer, or a salt thereof, the polymer, conjugate, or the pharmaceutical composition.

The kits provided may comprise a pharmaceutical composition, conjugate, or polymer described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition, conjugate, or polymer described herein. In some embodiments, the pharmaceutical composition, conjugate, or polymer described herein provided in the first container and the second container are combined to form one unit dosage form.

In some embodiments, the percentage of the conjugates (e.g., in a particle) that comprise an agent is between about 1 and about 100% (e.g., about 1%, about 2%, about 3%, about 4%, about 5%, about 10%, about 15%, about 20%, about 30%, about 40%, about 50%, about 60%, about 70%, about 80%, about 90%, or about 100%). In some embodiments, the percentage of the conjugates that comprise an agent is less than about 50%, e.g., less than about 40%, less than about 35%, less than about 30%, less than about 25%, less than about 20%, less than about 15%, or less than about 10%. In some embodiments, the percentage of the conjugates (e.g., in a particle) that comprise an agent is between about 5% and about 50%, about 5% and about 40%, about 5% and about 30%, about 5% and about 25%, or about 5% and about 20%. In some embodiments, the percentage of the conjugates (e.g., in a particle) that comprise an agent is between about 5% and 90%. In some embodiments, the percentage of the conjugates (e.g., in a particle) that comprise an agent is between about 5% and about 75%. In the some embodiments, the conjugates (e.g., in a particle) that comprise an agent is between about 5% and about 50%. In the some embodiments, the percentage of the conjugates (e.g., in a particle) that comprise an agent is between about 10% and about 25%.

In some embodiments, the total amount of the agent present in the Brush prodrug or particle is greater than about 5% (e.g., about 6%, about 7%, about 8%, about 9%, about 10%, about 12%, about 15%, about 20%, about 25%, about 30%, or more) of the total size or weight of the Brush prodrug or particle. In some embodiments, the total amount of the agent present in the Brush prodrug or particle is greater than about 10% (e.g., about 12%, about 15%, about 20%, about 25%, about 30%, or more) of the total size or weight of the Brush prodrug or particle.

Without being bound by theory, the conjugates or particles disclosed herein may improve the efficiency of an agent by one or more of increasing the localization and/or release (e.g., preferential release) of the agent to a target cell (e.g., a cancer or a fibrotic cell; a cell associated with a hypoxic environment), or increasing the half life of the agent, thus resulting in a significantly higher amount of a released agent at a target site (e.g., a tumor or liver (e.g., cirrhotic cell). According, the conjugates and particles disclosed herein can be more effective therapeutically than the free agent (e.g., due to enhanced drug uptake in the target tissue) and/or allow for a lower therapeutic dose of the agent, e.g., without substantially compromising the resulting drug concentration at a target tissue. In some embodiments, the conjugates and particles disclosed herein can reduce the adverse effect associated with systemic administration of an agent in free form (e.g., not coupled to a polymer, conjugate, Brush prodrug or particle described herein).

Without being bound by theory, due to the localized delivery of the compositions described herein (e.g., the agent-containing particles), a lower dose or amount of the agent in the particles can be administered (e.g., through local sustained delivery) compared to the agent in free form. In other embodiments, the agent-containing particles are administered at a dose or amount of the agent that is less than the dose or amount of said agent in free form to have a desired effect (e.g., a desired therapeutic effect).

In some embodiments, the agent is incorporated into a particle at a dose that is less than the dose or amount of said agent in free form to have a desired effect (e.g., a desired therapeutic effect), e.g., the standard of care dose for the intended use of the free agent. In one embodiment, the agent are incorporated into the particles at a dose or amount of the agent that is less than the standard of care dose of the agent for a desired therapy (e.g., a dose that is less than about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, or about 0.95 that of the standard of care dose of the agent).

In some embodiments, the agent is incorporated into a particle at a dose equivalent to the dose or amount of said agent in free form to have a desired effect (e.g., a desired therapeutic effect), e.g., the standard of care dose for the intended use of the free agent. In these embodiments, the particle produces a greater therapeutic effect and/or a less adverse effect than the free agent. In certain embodiments, the particle increases the amount of the agent delivered to a tissue or cell in need thereof and reduces the amount of the agent exposed to a non-target tissue or cell, as compared to the free agent.

In some embodiments, the agent is incorporated into a particle at a dose higher than the dose or amount of said agent in free form to have a desired effect (e.g., a desired therapeutic effect), e.g., the standard of care dose for the intended use of the free agent. In some embodiments, the agent is incorporated into a particle at a dose higher than the dose or amount of said agent in free form that would produce an adverse effect by systemic administration (e.g., a reduction in blood pressure). In some embodiments, since the particle described herein releases the agent at a target site based on pH microenvironment, other non-target sites (e.g., blood vessels) with different pH would be less likely to be exposed to the agent.

In another aspect, provided are kits including a first container comprising a polymer or pharmaceutical composition described herein. In certain embodiments, the kit further comprises instructions for using the polymer or pharmaceutical composition.

In another aspect, provided are kits including a first container comprising a compound described herein. In certain embodiments, the kit further comprises instructions for using the compound.

In another aspect, provided are kits including a first container comprising a conjugate, or a salt thereof, or pharmaceutical composition described herein. In certain embodiments, the kit further comprises instructions for using the conjugate or pharmaceutical composition.

In certain embodiments, the kits are useful for delivering an agent (e.g., to a subject or cell). In certain embodiments, the kits are useful for treating a disease (e.g., proliferative disease, hematological disease, neurological disease, painful condition, psychiatric disorder, or metabolic disorder) in a subject in need thereof. In certain embodiments, the kits are useful for preventing a disease (e.g., proliferative disease, hematological disease, neurological disease, painful condition, psychiatric disorder, or metabolic disorder) in a subject in need thereof. In certain embodiments, the kits are useful for reducing the risk of developing a disease (e.g., proliferative disease, hematological disease, neurological disease, painful condition, psychiatric disorder, or metabolic disorder) in a subject in need thereof. In certain embodiments, the kits are useful for inhibiting the activity (e.g., aberrant activity, such as increased activity) of a protein kinase in a subject or cell.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for delivering an agent. In certain embodiments, the kits and instructions provide for treating a disease (e.g., proliferative disease, hematological disease, neurological disease, painful condition, psychiatric disorder, or metabolic disorder) in a subject in need thereof. In certain embodiments, the kits and instructions provide for preventing a disease (e.g., proliferative disease, hematological disease, neurological disease, painful condition, psychiatric disorder, or metabolic disorder) in a subject in need thereof. In certain embodiments, the kits and instructions provide for reducing the risk of developing a disease (e.g., proliferative disease, hematological disease, neurological disease, painful condition, psychiatric disorder, or metabolic disorder) in a subject in need thereof. In certain embodiments, the kits and instructions provide for inhibiting the activity (e.g., aberrant activity, such as increased activity) of a protein kinase in a subject or cell. A kit described herein may include one or more additional pharmaceutical agents described herein as a separate composition.

Methods of Use and Uses

The present disclosure also provides methods of using the polymers described herein, or a pharmaceutical composition thereof, for delivering an agent. The present disclosure also provides methods of using the polymers described herein, or a pharmaceutical composition thereof, for the treatment or prevention of a disease. In certain embodiments, the disease is a proliferative disease, hematological disease, neurological disease, painful condition, psychiatric disorder, or metabolic disorder. In certain embodiments, the disease is cancer (e.g., lung cancer, large bowel cancer, pancreas cancer, biliary tract cancer, or endometrial cancer), benign neoplasm, angiogenesis, inflammatory disease, autoinflammatory disease, or autoimmune disease.

In another aspect, the present disclosure provides methods of delivering a pharmaceutical agent to a subject in need thereof comprising administering to the subject in need thereof a polymer or a pharmaceutical composition.

In another aspect, the present disclosure provides methods of delivering a pharmaceutical agent to a cell comprising contacting the cell with a polymer or a pharmaceutical composition.

In another aspect, the present disclosure provides methods of treating a disease in a subject in need thereof comprising administering to or implanting in the subject in need thereof a therapeutically effective amount of: a polymer or a pharmaceutical composition; wherein at least one instance of M is a therapeutic agent.

In another aspect, the present disclosure provides methods of preventing a disease in a subject in need thereof comprising administering to or implanting in the subject in need thereof a prophylactically effective amount of: a polymer or a pharmaceutical composition; wherein at least one instance of M is a prophylactic agent.

In another aspect, the present disclosure provides methods of diagnosing a disease in a subject comprising administering to or implanting in the subject a diagnostically effective amount of: a polymer or a pharmaceutical composition; wherein at least one instance of M is a diagnostic agent.

The present disclosure also provides methods of using the conjugates described herein, or a pharmaceutical composition thereof, for delivering an agent. The present disclosure also provides methods of using the conjugates described herein, or a pharmaceutical composition thereof, for the treatment or prevention of a disease. In certain embodiments, the disease is a proliferative disease, hematological disease, neurological disease, painful condition, psychiatric disorder, or metabolic disorder. In certain embodiments, the disease is cancer (e.g., lung cancer, large bowel cancer, pancreas cancer, biliary tract cancer, or endometrial cancer), benign neoplasm, angiogenesis, inflammatory disease, autoinflammatory disease, or autoimmune disease.

In another aspect, the present disclosure provides methods of delivering a pharmaceutical agent to a subject in need thereof comprising administering to the subject in need thereof a conjugate or a pharmaceutical composition.

In another aspect, the present disclosure provides methods of delivering a pharmaceutical agent to a cell comprising contacting the cell with a conjugate or a pharmaceutical composition.

In another aspect, the present disclosure provides methods of treating a disease in a subject in need thereof comprising administering to or implanting in the subject in need thereof a therapeutically effective amount of: a conjugate or a pharmaceutical composition; wherein at least one instance of M is a therapeutic agent.

In another aspect, the present disclosure provides methods of preventing a disease in a subject in need thereof comprising administering to or implanting in the subject in need thereof a prophylactically effective amount of: a conjugate or a pharmaceutical composition; wherein at least one instance of M is a prophylactic agent.

In another aspect, the present disclosure provides methods of diagnosing a disease in a subject comprising administering to or implanting in the subject a diagnostically effective amount of: a conjugate or a pharmaceutical composition; wherein at least one instance of M is a diagnostic agent.

In some embodiments, the polymers or conjugates described herein, or a pharmaceutical composition thereof are useful in treating a cancer. In some embodiments, the polymers or conjugates described herein, or a pharmaceutical composition thereof, are useful to delay the onset of, slow the progression of, or ameliorate the symptoms of cancer. In some embodiments, the polymers or conjugates described herein, or a pharmaceutical composition thereof, are administered in combination with other compounds, drugs, or therapeutics to treat cancer.

In some embodiments, the polymers or conjugates described herein, or a pharmaceutical composition thereof are useful for treating a cancer including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma;

glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarcinoma), Ewing sarcoma, eye cancer (e.g., intraocular melanoma, retinoblastoma), familiar hypercosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM), a.k.a. myelofibrosis (MF), chronic idiopathic myelofibrosis, chronic myelocytic leukemia (CML), chronic neutrophilic leukemia (CNL), hypercosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendocrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), islet cell tumors), penile cancer (e.g., Paget's disease of the penis and scrotum), pincaloma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In some embodiments, the polymers or conjugates described herein, or a pharmaceutical composition thereof, are useful in treating lung cancer, head-and-neck cancer, esophagus cancer, stomach cancer, breast cancer, pancreas cancer, liver cancer, kidney cancer, prostate caner, glioblastomas, metastatic melanomas, peritoneal or pleural mesotheliomas.

In some embodiments, the proliferative disease is a benign neoplasm. All types of benign neoplasms disclosed herein or known in the art are contemplated as being within the scope of the invention. In some embodiments, the proliferative disease is associated with angiogenesis. All types of angiogenesis disclosed herein or known in the art are contemplated as being within the scope of the invention. In certain embodiments, the proliferative disease is an inflammatory disease. All types of inflammatory diseases disclosed herein or known in the art are contemplated as being within the scope of the invention. In certain embodiments, the inflammatory disease is rheumatoid arthritis. In some embodiments, the proliferative disease is an autoinflammatory disease. All types of autoinflammatory diseases disclosed herein or known in the art are contemplated as being within the scope of the invention. In some embodiments, the proliferative disease is an autoimmune disease. All types of autoimmune diseases disclosed herein or known in the art are contemplated as being within the scope of the invention.

In certain embodiments, the methods described herein include administering to a subject with an effective amount of the polymers or conjugates described herein, or a pharmaceutical composition thereof. In certain embodiments, the methods described herein include implanting to a subject with an effective amount of the polymers or conjugates described herein, or a pharmaceutical composition thereof.

In certain embodiments, the polymers or conjugates described herein, or a pharmaceutical composition thereof, are administered in combination with one or more additional pharmaceutical agents described herein. In certain embodiments, the additional pharmaceutical agent is an anti-cancer agent. Anti-cancer agents encompass biotherapeutic anti-cancer agents as well as chemotherapeutic agents. Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g., HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents include, but are not limited to, anti-estrogens (e.g., tamoxifen, raloxifene, and megestrol), LHRH agonists (e.g., goscrclin and leuprolide), anti-androgens (e.g., flutamide and bicalutamide), photodynamic therapies (e.g., vertoporfin (BPD-MA), phthalocyanine, photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosourcas (e.g., carmustinc (BCNU) and lomustine (CCNU)), alkylsulphonates (e.g., busulfan and treosulfan), triazenes (e.g., dacarbazine, temozolomide), platinum containing compounds (e.g., cisplatin, carboplatin, oxaliplatin), vinca alkaloids (e.g., vincristine, vinblastine, vindesine, and vinorelbine), taxoids (e.g., paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonucleotide reductase inhibitors (e.g., hydroxyurea and deferoxamine), uracil analogs (e.g., 5-fluorouracil (5-FU), floxuridine, doxifluridine, raltitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

EXAMPLES

In order that the invention described herein may be more fully understood, the following examples are set forth. The synthetic and biological examples described herein are offered to illustrate the present disclosure and are not to be construed in any way as limiting their scope.

Example 1. Preparation and Characterization of Exemplary Macromonomers and Polymers Described Herein Certain synthetic intermediates were or can be prepared according to reported methods, such as methods described in U.S. patent application publications, 2014/0308234 and 2017/0348431; international PCT application, PCT/US2017/064784, filed Dec. 5, 2017; U.S. provisional patent applications 62/528,010, filed Jun. 30, 2017, and 62/520,473, filed Jun. 15, 2017; the entire contents of each of which are incorporated herein by reference.

Synthesis of T2.
Synthesis of T2-BnOH.

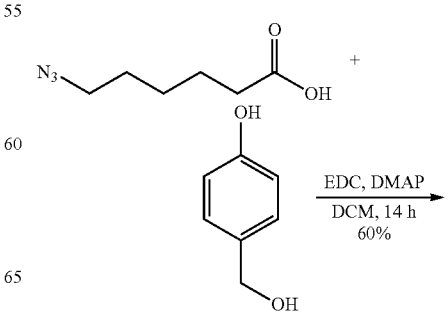

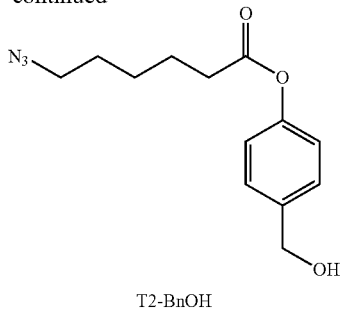

T2-BnOH

To a 100-mL round bottom flask charged with a stir bar was added N₃—C₅H₁₀COOH (CAS 79598-53-1), (1.10 g, 7.0 mmol), 4-hydroxybenzyl alcohol (CAS 623-05-2), (1.74 g, 1.4 mmol), and 4-dimethylaminopyridine, DMAP, (CAS 1122-58-3) (100 mg, 0.8 mmol) followed by DCM (20 mL). To this suspension was then added EDC·HCl (CAS 25952-53-8) (2.0 g, 10.0 mmol), as a solution in DCM (15 mL), dropwise over 1 h. The reaction mixture was stirred at r.t. for 16 h. The reaction mixture was concentrated on rotavap and then directly loaded onto silica column (30%→50% EtOAc/Hex). Isolated product as a clear oil (2.0 g, 60% yield). 1H NMR peaks matched previously reported spectra.

Synthesis of T2-BnCl.

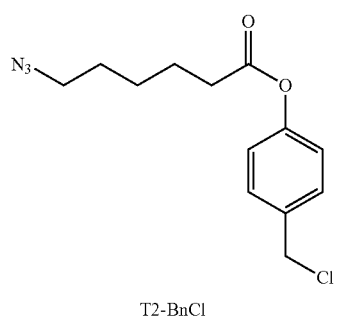

T2-BnOH

To a 50-mL round bottom flask charged with a stir bar was added T2-BnOH (600.0 mg, 2.28 mmol), DMF (0.1 mL), followed by anhydrous DCM (20 mL) under nitrogen. The reaction flask was placed in an ice-bath and after 10 min SOCl₂ (CAS 7719-09-7) (650 mg, 5.46 mmol) was added dropwise. The reaction mixture was initially stirred at 0° C. and then let to warm up to r.t. over 2 h. Upon complete consumption of starting material, as monitored by TLC, the reaction mixture was concentrated on rotavap and loaded directly onto silica column (40% EtOAc/Hex). Isolated product as light oil (610 mg, 95% yield). 1H NMR (400 MHZ, CDCl₃, ppm) δ 7.40 (d, J=8.5 Hz, 2H), 7.07 (d, J=8.5 Hz, 2H), 4.58 (s, 2H), 3.31 (t, J=6.8 Hz, 3H), 2.58 (t, J=7.4 Hz, 2H), 1.79 (p, J=7.4 Hz, 2H), 1.71-1.61 (m, 3H), 1.56-1.43 (m, 2H).

Synthesis of T2-BnI.

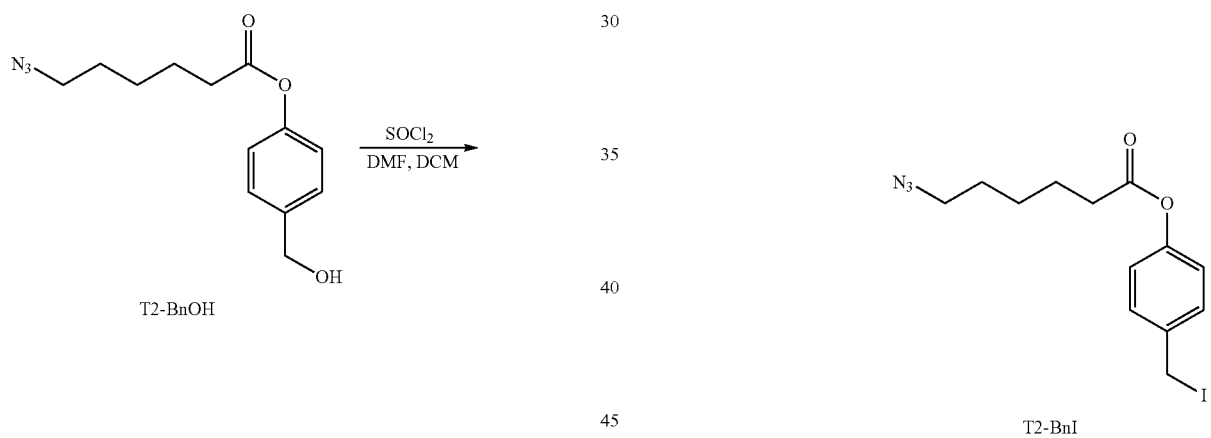

T2-BnCl

T2-BnI

To a 40-mL scintillation vial charged with a stir bar was added T2-BnCl (440 mg, 1.56 mmol), sodium iodide (CAS 7681-82-5) (500 mg, 3.33 mmol) followed by anhydrous acetone (20 mL) under nitrogen. The vial was sealed and the reaction mixture was stirred at 65° C. and monitored by LC-MS. After 1 h, all starting material was consumed and the reaction mixture color was noted as yellow. The reaction was let to cool down and then solvent removed on rotavap. The residue was redissolved in 25% EtOAc/Hex and purified on silica column (30% EtOAc/Hex). Isolated product as clear oil with a tinge of yellow color (420 mg, 72% yield). Note: this compound is not stable and needs to be stored in −20° C. Over time the color changes to brown. It is strongly suggested to repurify the compound before use. ¹H NMR (400 MHZ, CDCl₃, ppm) δ 7.38 (d, J=8.6 Hz, 2H), 7.01 (d, J=8.5 Hz, 2H), 4.44 (s, 2H), 3.30 (t, J=6.8 Hz, 3H), 2.57 (t, J=7.4 Hz, 3H), 1.78 (p, J=7.5 Hz, 3H), 1.66 (p, J=7.0 Hz, 3H), 1.55-1.35 (m, 2H). ¹³C NMR (100 MHz, CDCl₃, ppm) δ 171.71, 150.07, 129.88, 121.92, 51.22, 34.14, 28.57, 26.21, 24.39, 4.64.

Synthesis of T2-N3 Via Quaternary Ammonium Salt Formation

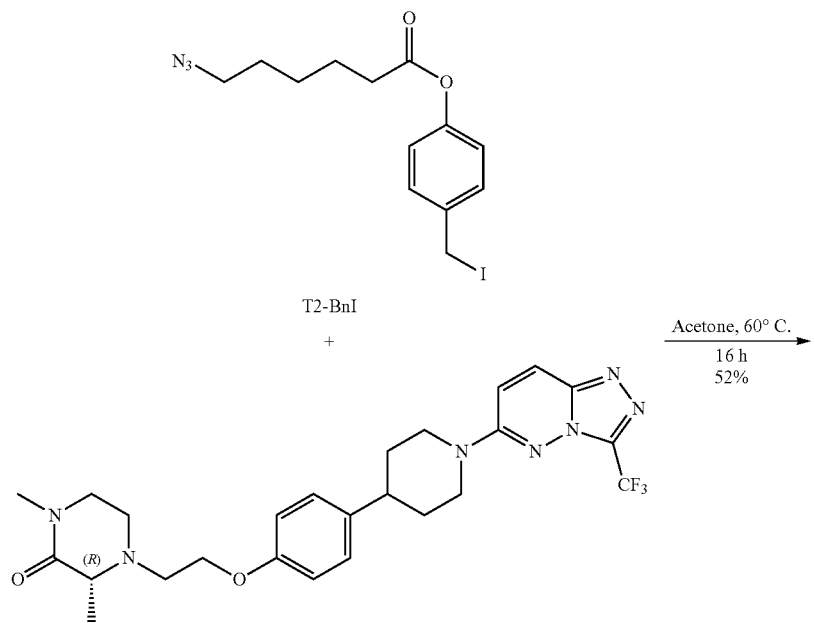

T2-BnI

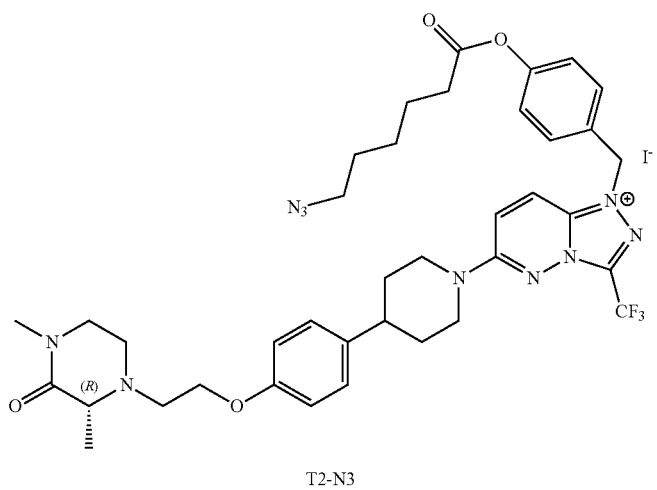

T2-N3

To a 4-mL vial charged with a stir bar was added biBET-CF3 (400.0 mg, 0.77 mmol), T2-BnI (317 mg, 0.189 mmol) followed by anhydrous acetone (0.35 mL) under nitrogen. The reaction mixture was stirred at 65° C. for 16 h. When amount of unconverted biBET-CF3 dropped to <10%, as judged by LC-MS analysis, the reaction mixture was let to cool down and then solvent removed on rotavap. The residue was dissolved in chloroform, filtered through a 0.47-µm nylon filter, and purified using preparatory size exclusion chromatography. Isolated both desired mono-alkylation and bis-alkylation products as bright orange solids (355 mg, 52% isolated yield of mono-alkylation product).

$^1$H NMR (400 MHZ, CDCl$_3$, ppm) δ 9.58 (d, J=10.5 Hz, 1H), 7.99 (d, J=10.6 Hz, 1H), 7.77 (d, J=8.5 Hz, 2H), 7.11 (t, J=8.9 Hz, 4H), 6.84 (d, J=8.6 Hz, 2H), 6.25 (s, 2H), 4.48 (s, 2H), 4.06 (td, J=5.5, 3.2 Hz, 2H), 3.53-3.10 (m, 7H), 3.02 (dt, J=13.9, 5.7 Hz, 1H), 2.94 (s, 3H), 2.90-2.72 (m, 3H), 2.58 (t, J=7.4 Hz, 2H), 2.03 (d, J=13.4 Hz, 2H), 1.83-1.70 (m, 3H), 1.70-1.57 (m, 6H), 1.50 (m, 2H), 1.40 (d, J=6.8 Hz, 3H).

$^{13}$C NMR (125 MHz, CDCl$_3$, ppm) δ 171.69, 170.44, 157.34, 156.18, 151.73, 138.95, 136.96, 136.55, 130.85, 129.84, 129.06, 127.65, 123.44, 122.80, 121.88, 121.26, 117.40, 115.24, 114.64, 66.42, 60.46, 56.75, 52.74, 51.15, 48.14, 46.65, 41.24, 34.47, 34.04, 32.81, 28.51, 26.15, 24.28, 15.33.

$^{19}$F NMR (375 MHz, CDCl$_3$, ppm) δ −64.59.

ESI-MS (M-I$^-$)$^+$: 764.3 m/z.

Synthesis of T2-MM.

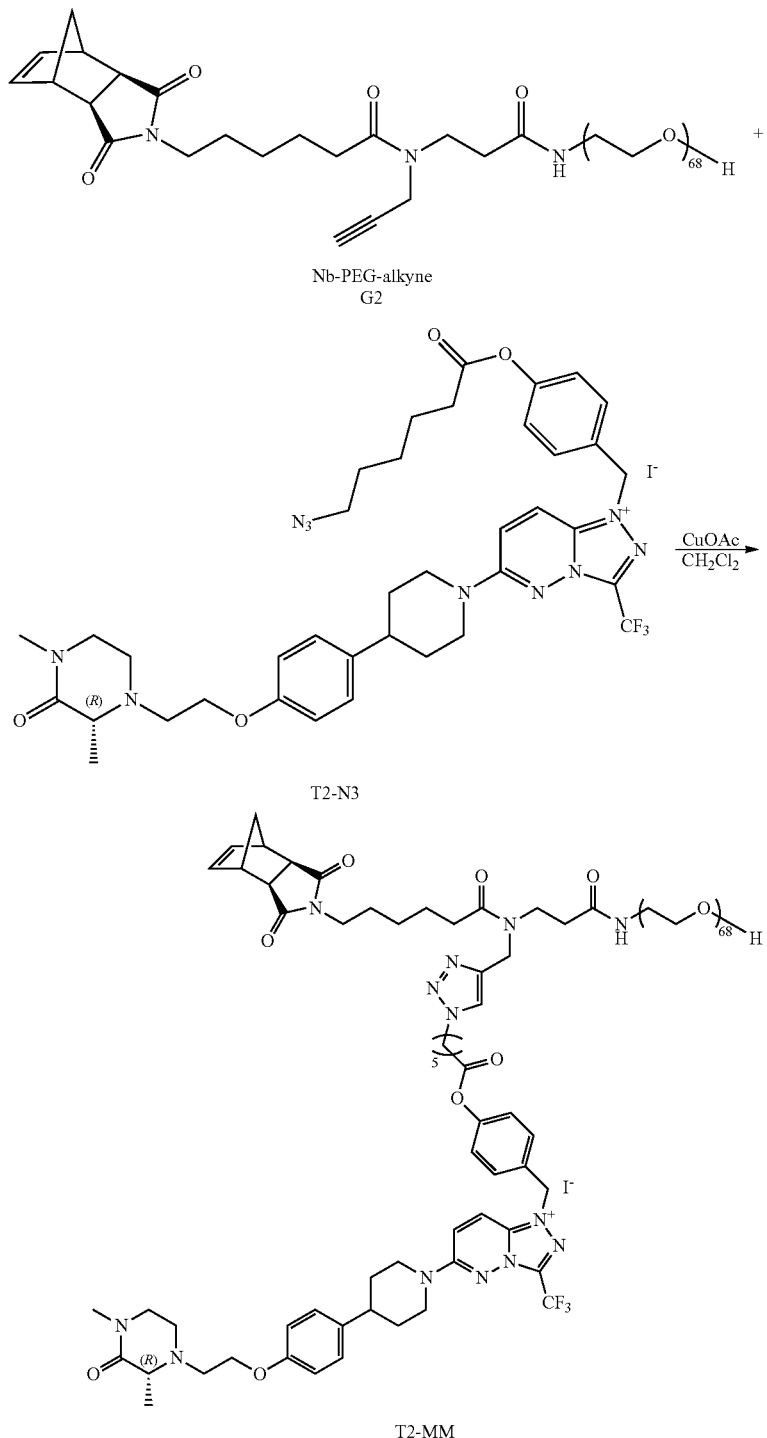

In a nitrogen filled glovebox, to a 20-mL scintillation vial charged with a stir bar containing Nb-PEG-alkyne G2 (1111 mg, 0.327 mmol) was added T2-N3 (320 mg, 0.359 mmol) 5 followed by anhydrous DCM (15 mL). The reaction was started by addition of CuOAc (CAS 598-54-9) (50 mg, 0.41 mmol) and was stirred at room temperature for 1 h. The reaction was monitored by LC-MS and was judged complete after no further consumption of T2-N3 was observed. The reaction was filtered through a 0.45-μm nylon syringe filter (Nalgene) and injected onto preparatory size-exclusion column for purification to give light yellow solid (1205 mg, 75% yield). 1H NMR (400 MHZ, CDCl$_3$, ppm) δ 9.34 (dd, J=29.0, 10.6 Hz, 1H), 8.12 (t, J=11.1 Hz, 1H), 8.01-7.33 (m, 5H), 7.10 (q, J=11.1, 9.8 Hz, 8H), 6.70 (s, 1H), 6.27 (s, 2H), 6.13 (s, 2H), 4.60 (s, 2H), 4.53 (s, 1H), 4.41-4.31 (m, 1H), 4.06 (m, 1H), 3.88-3.10 (m, 377H), 3.06-2.97 (m, 1H), 2.94

Figure 11:
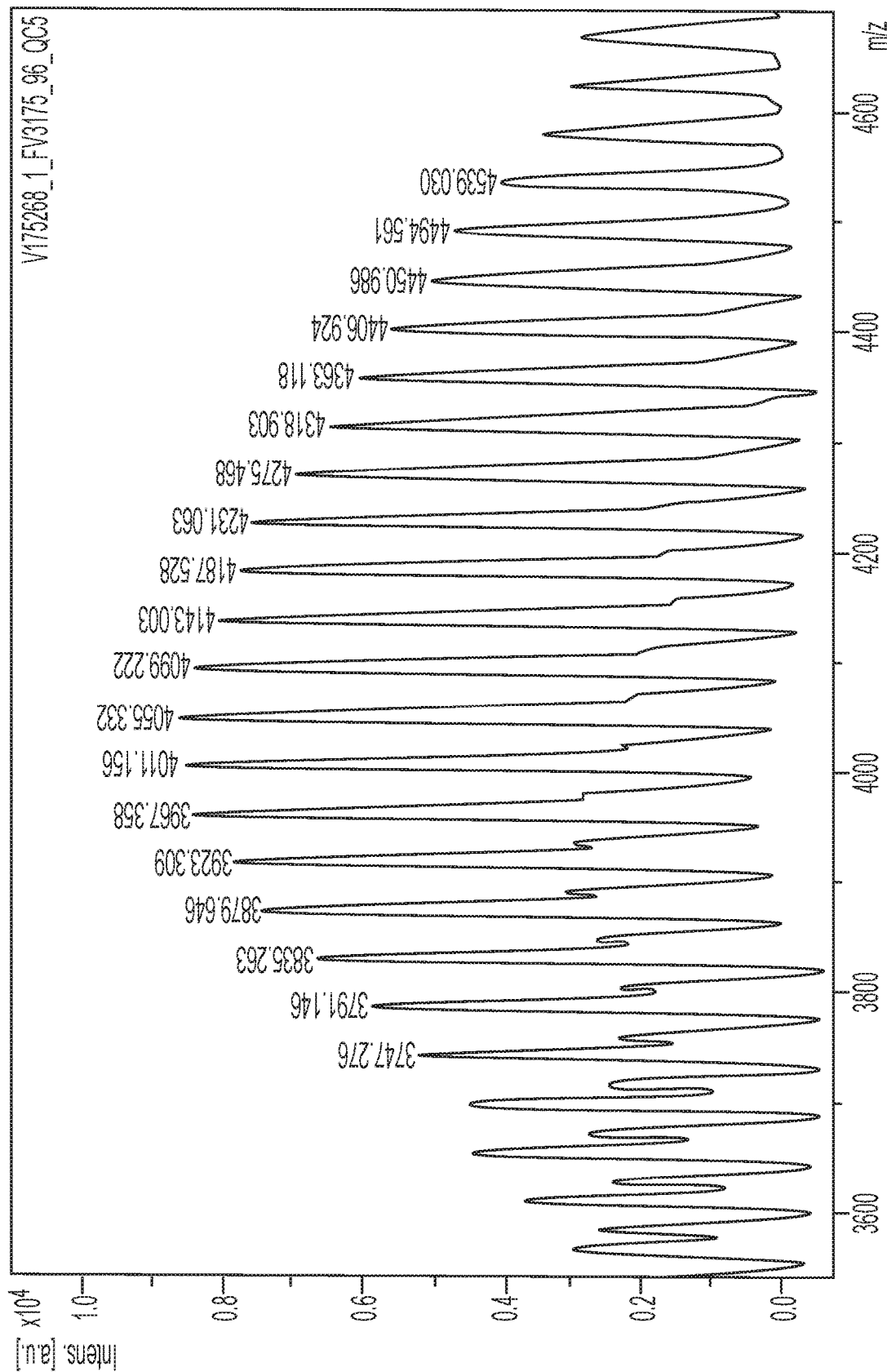
FIG. 11 shows the MALDI-MS spectrum of T2-MM.

(s, 3H), 2.90-2.74 (m, 3H), 2.66 (s, 2H), 2.61-2.51 (m, 4H), 2.48-2.22 (m, 3H), 2.10-1.91 (m, 4H), 1.87-1.69 (m, 11H), 1.65-1.47 (m, 5H), 1.45-1.36 (m, 5H), 1.32-1.17 (m, 17H), 0.97-0.71 (m, 13H). A MALDI-MS spectrum is shown in FIG. 11.

Synthesis T2 Via ROMP.

Figure 9:
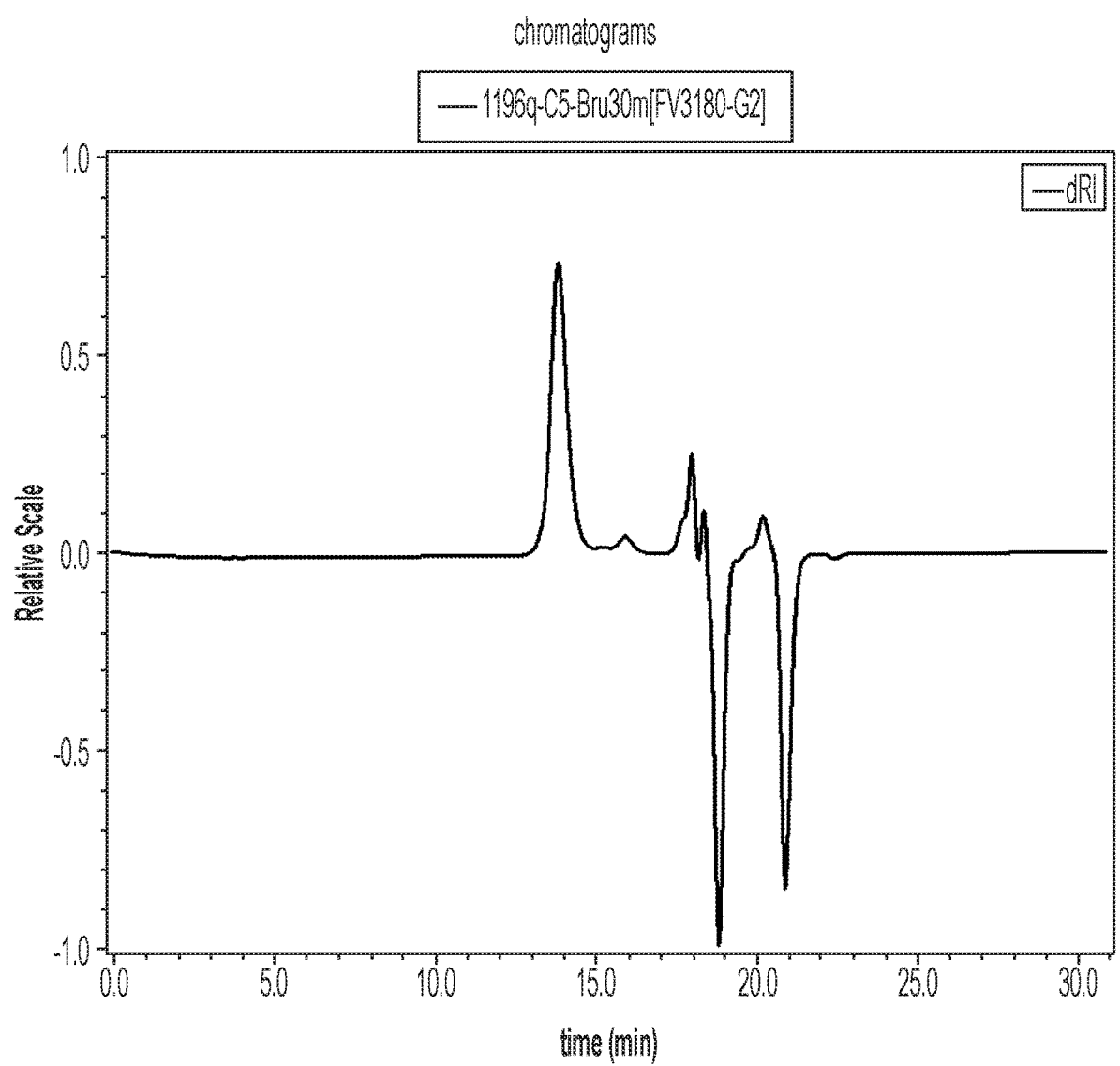
FIG. 9 shows the GPC chromatogram of T2.
Figure 10:
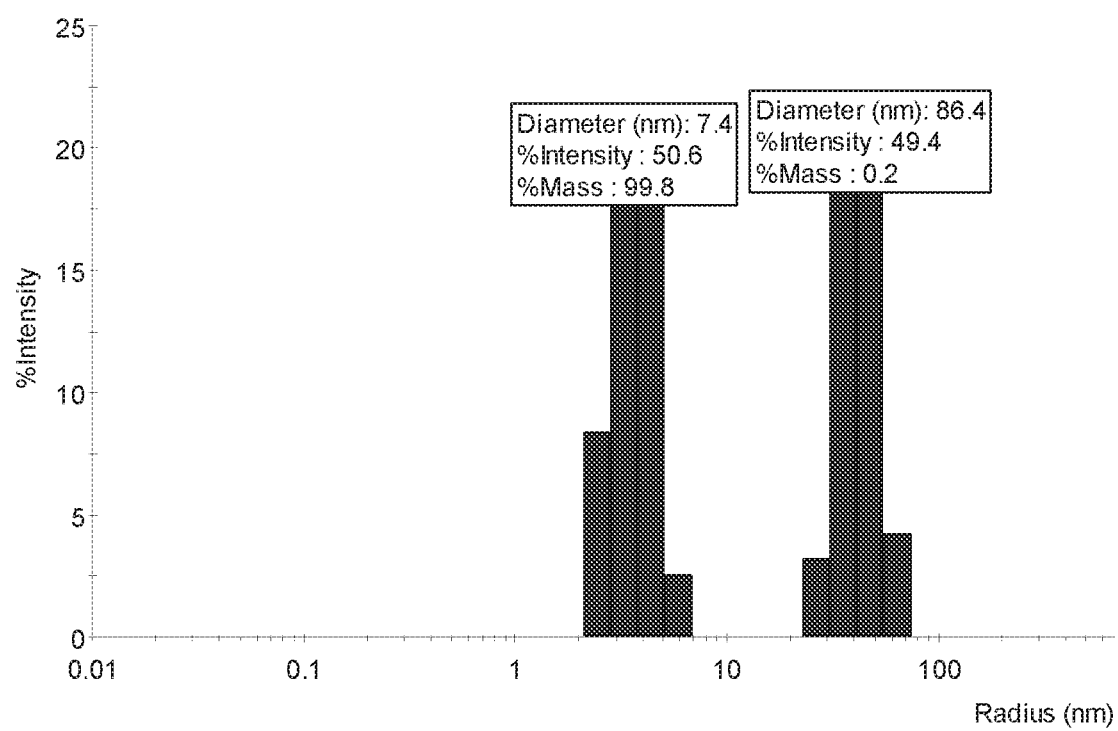
FIG. 10 shows the DLS analysis of ROMP aliquot of T2.

In a nitrogen filled glovebox, to a 4-mL scintillation vial charged with a stir bar and containing T2-MM (289 mg, 0.0674 mmol) was added anhydrous dioxane (CAS 123-91-1) (427 µL). After dissolution of macromonomer, 0.02-M solution of Cy7.5-PEG$_{3K}$ macromonomer in dioxane was added (34 µL, 0.67 µmol). To this mixture then was added Grubbs III catalyst, all at once (247 µL, 6.74 µmol) to give MM: Grubbs III ratio of 10:1. The polymerization reaction was stirred at room temperature for 30 min. Then the reaction mixture was taken out of the glovebox and polymerization quenched by addition of ethyl vinyl ether (CAS 109-92-2) (100 µL, excess) and allowed to stir for 10 min. A 10-µL aliquot was taken out for size exclusion chromatography analysis of polymerization product, after which the brush solution was diluted with milliQ water (6 mL) and transferred into an 8 kD MWCO dialysis tubing (Spectrum Laboratories). The solution was dialyzed against milliQ water (16 L×3, water replaced with fresh milliQ water every 2 h). The brush solution was then filtered through a 0.22-µm nylon filter (Nalgene). A 10 µL aliquot was taken out for dynamic light scattering analysis (FIG. 10). Then the brush solution was flash frozen using liquid nitrogen and lyophilized to afford greenish yellow solid, T2 (265 mg, 91% yield, $M_w/M_n=1.07$ as determined with GPC). An exemplary GPC chromatogram of T2 is shown in FIG. 9.

The theoretical polymerization degree of T2 was 10, and the theoretical $M_w$ of T2 was about 43 KDa. Grubbs III catalyst is known for good control of the polymerization degree in ROMP reactions. In this example, norbornene-terminated macromonomers were almost quantitatively consumed. Therefore, the experimental polymerization degree of T2 should be about the same as the theoretical polymerization degree of T2, and the experimental $M_w$ of T2 should be about the same as the theoretical $M_w$ of T2.

Synthesis of T7

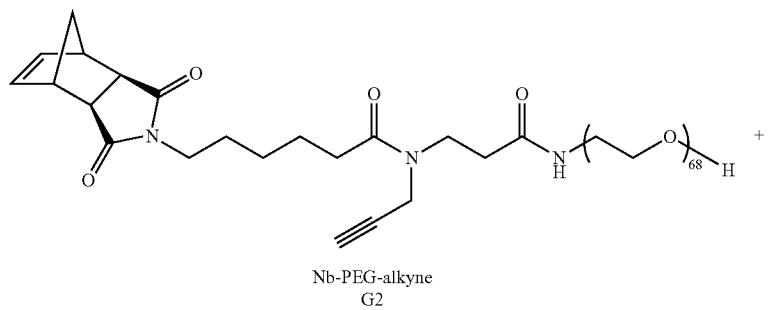

Nb-PEG-alkyne
G2

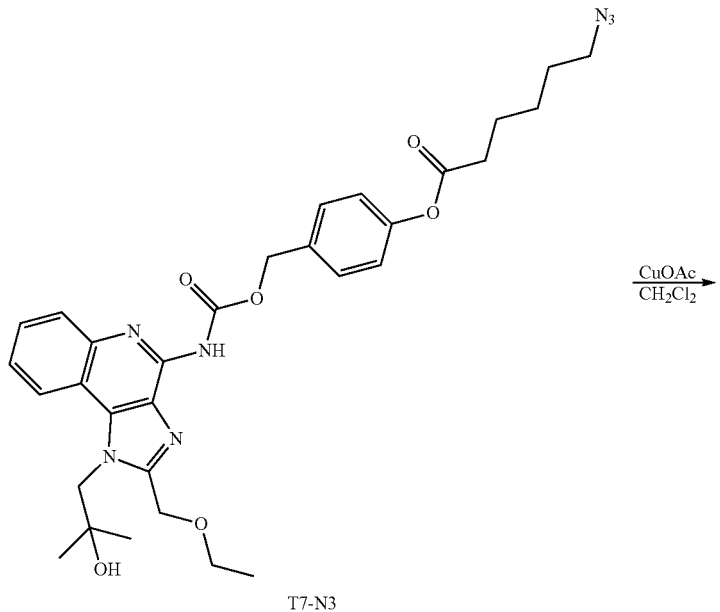

T7-N3

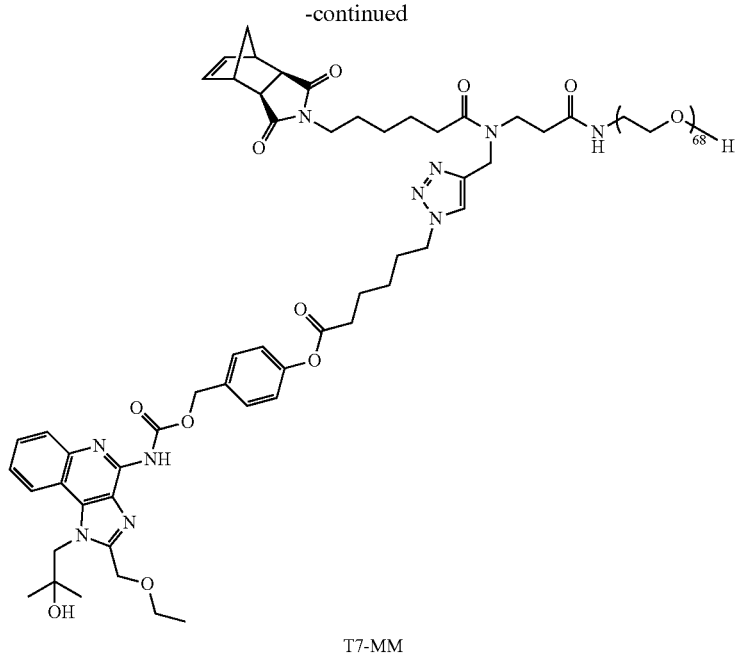
T7-MM
Starting from Nb-PEG-alkyne G2 and T7-N3, T7-MM was prepared in a similar manner to T2-MM. T2, the brush polymer of T7-MM, was synthesized using ROMP following a procedure essentially analogous to the procedure used to synthesize T2.
Synthesis of T8
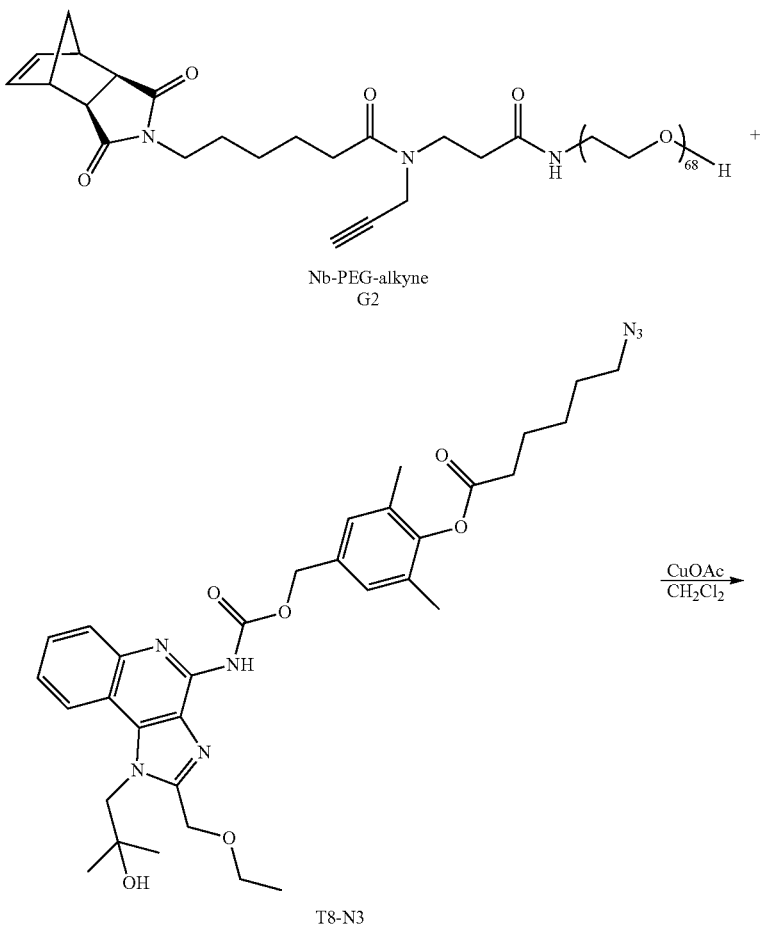

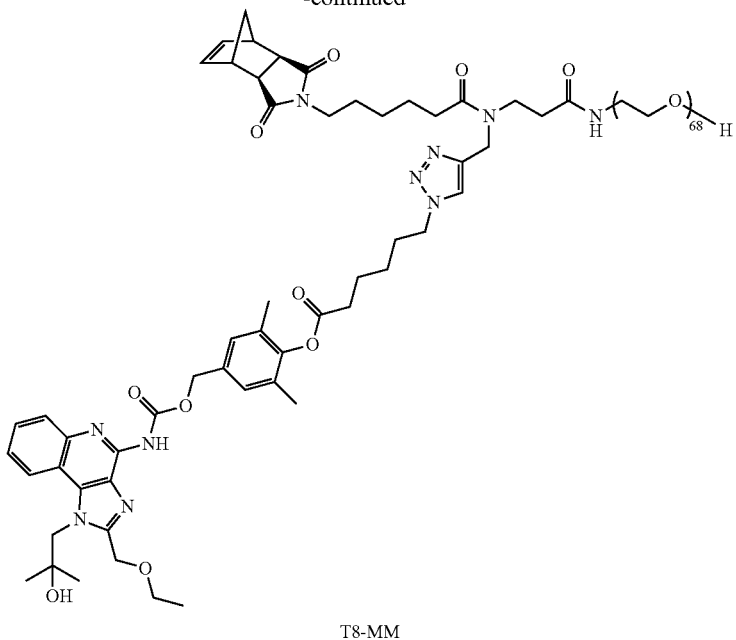
T8-MM
Starting from Nb-PEG-alkyne G2 and T8-N3. T8-MM was prepared in a similar manner to T2-MM. T8, the brush polymer of T8-MM, was synthesized using ROMP following a procedure essentially analogous to the procedure used to synthesize T2.
Synthesis of P1
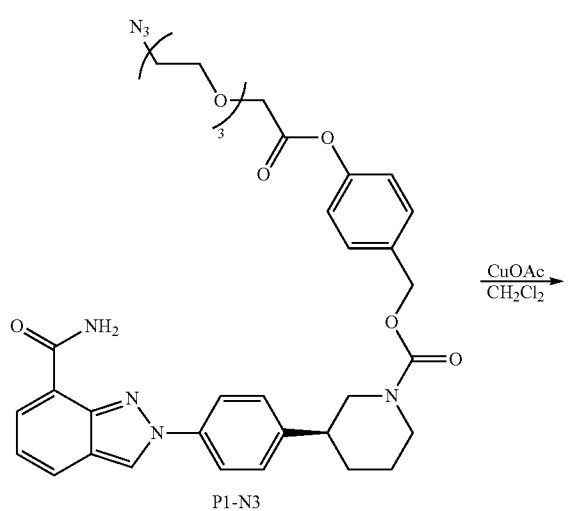

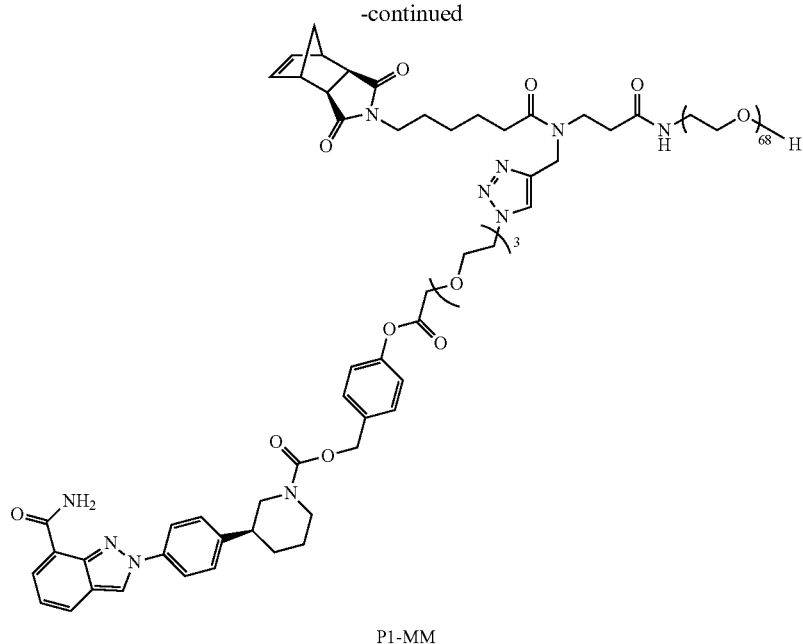
P1-MM
Starting from Nb-PEG-alkyne G2 and P1-N3. P1-MM was prepared in a similar manner to T2-MM. P1, the brush polymer of P1-MM, was synthesized using ROMP following a procedure essentially analogous to the procedure used to synthesize T2.
Synthesis of P2
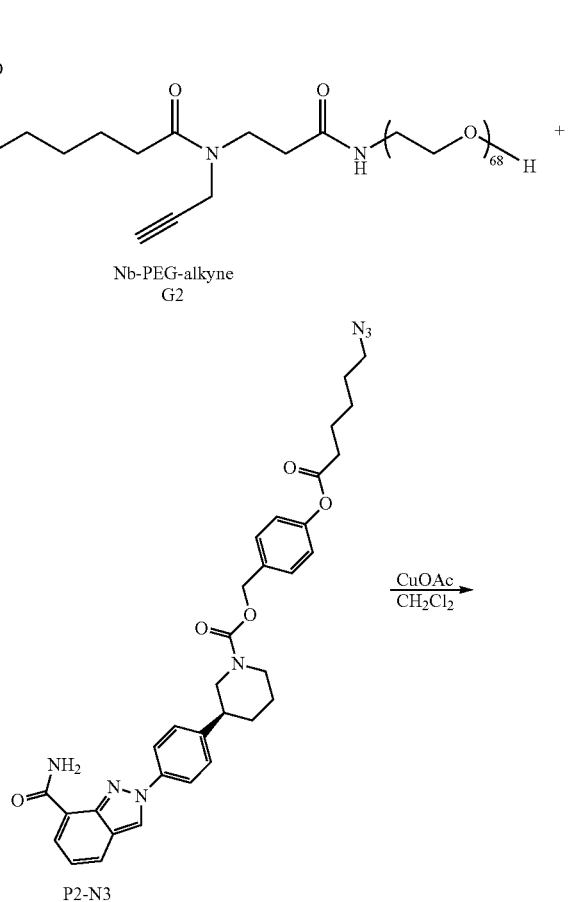

-continued

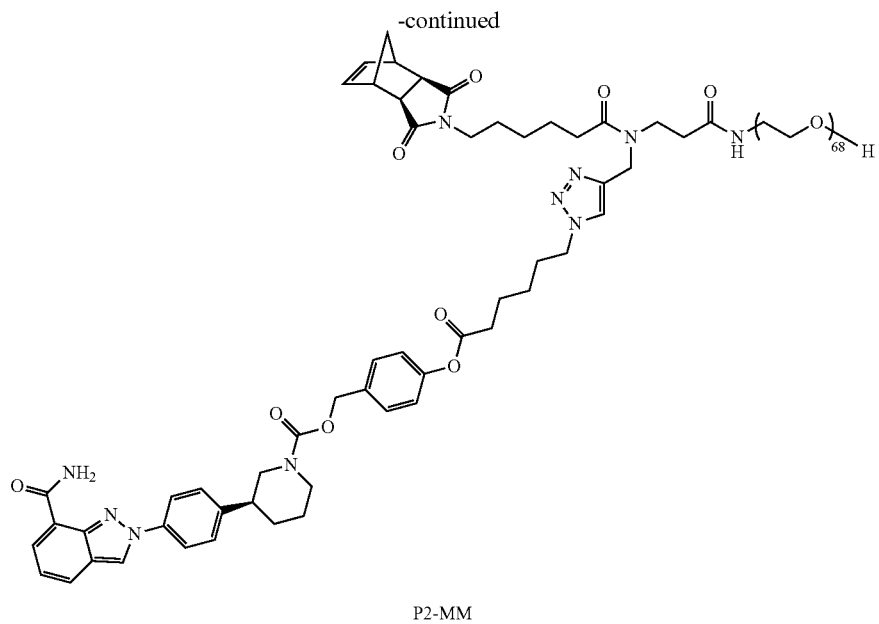

P2-MM

Starting from Nb-PEG-alkyne G2 and P2-N3, P2-MM was prepared in a similar manner to T2-MM. P2, the brush polymer of P2-MM, was synthesized using ROMP following a procedure essentially analogous to the procedure used to synthesize T2.

Figure 8:
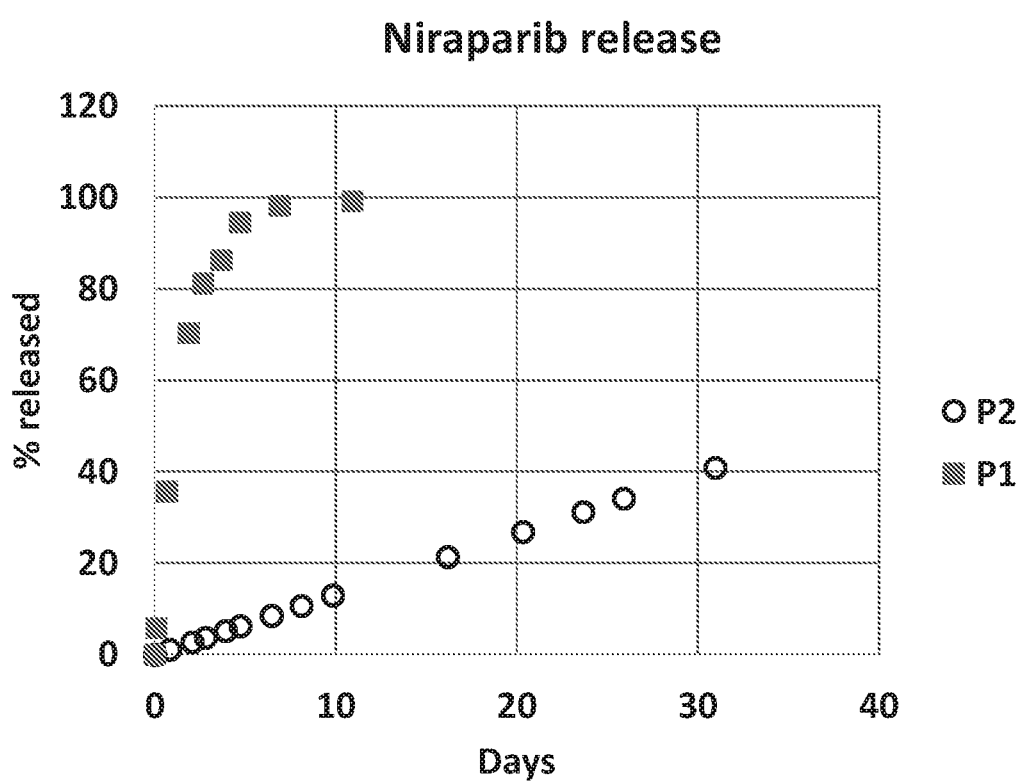
FIG. 8 shows exemplary release of a pharmaceutical agent (niraparib) from two different brush prodrugs, P1 and P2.

Example 2. In Vitro Release Assays of Exemplary Macromonomers and Polymers Described Herein Exemplary macromonomers and brush prodrugs were tested in in vitro release assays. The macromonomers and brush prodrugs were incubated in PBS at 37° C. Aliquots were taken for analysis of drug release (e.g., $t_{1/2}$) by LC-MS. Exemplary results are shown in the figures. Additional results include $t_{1/2}$=~1 week for T7 release of resiquimod, $t_{1/2}$=~1 month for T8 release of resiquimod, $t_{1/2}$=~2 days for P1 release of niraparib (also see FIG. 8), and $t_{1/2}$=~40 days for P2 release of niraparib (also see FIG. 8).

Example 3. Efficacy of Brush Prodrug B4 in Orthotopic, Syngeneic Tumor

B4 was dosed at 125 mpk, 250 mpk, or 500 mpk, twice per week for two weeks for a total of 4 doses, or at 500 mpk every other day for two weeks for a total 6 doses on randomized tumor sizes of 100 mm³. Tumor volumes are calculated after measuring length and width using digital calipers. Tumors were also weighted, and the body weight was measured. Exemplary results are shown FIGS. 5A to 5F.

Example 4. Biodistribution and Pharmacokinetics of Brush Prodrug B4

Biodistribution and pharmacokinetics of Brush prodrug B4 were determined. Exemplary results are shown FIGS. 6A to 6D.

Example 5. Brush Prodrug B4 Offered Efficacy without Systemic Side Effects

Figure 7A:
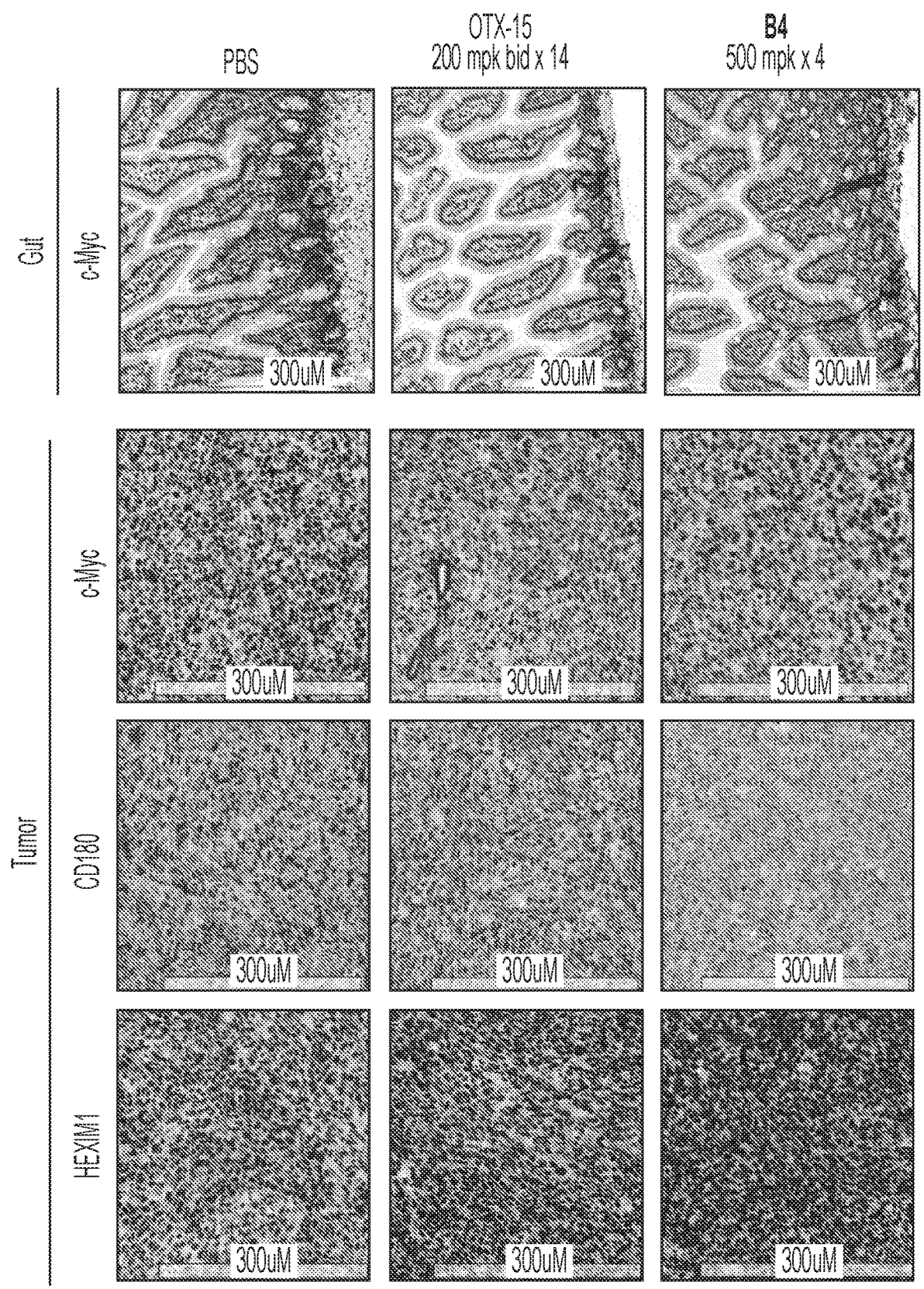
FIGS. 7A and 7B show Brush prodrug B4 offer efficacy without systemic side effects.
Figure 7B:
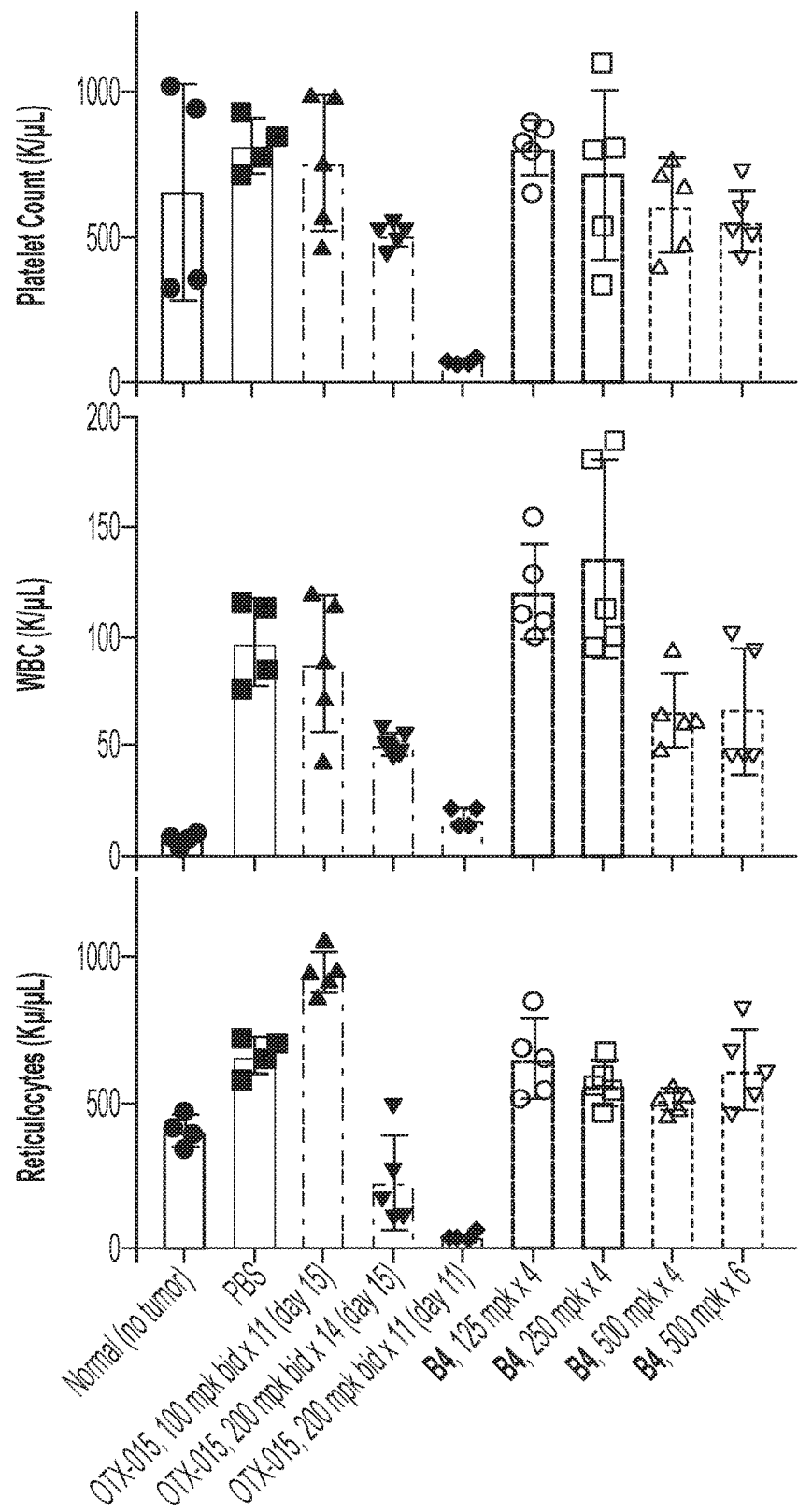

Assays showed Brush prodrug B4 offered efficacy without systemic side effects. Exemplary results are shown FIGS. 7A to 7B.

REFERENCES (1) Rzayev, J.: Molecular Bottlebrushes: New Opportunities in Nanomaterials Fabrication. *ACS Macro Letters* 2012, 1, 1146-1149.
(2) Sheiko, S. S.; Sumerlin, B. S.; Matyjaszewski, K.: Cylindrical molecular brushes: Synthesis, characterization, and properties. *Progress in Polymer Science* 2008, 33, 759-785.
(3) Lee, H.-i.; Pietrasik, J.; Sheiko, S. S.; Matyjaszewski, K.: Stimuli-responsive molecular brushes. *Progress in Polymer Science* 2010, 35, 24-44.
(4) Xia, Y.; Olsen, B. D.; Kornfield, J. A.; Grubbs, R. H.: Efficient Synthesis of Narrowly Dispersed Brush Copolymers and Study of Their Assemblies: The Importance of Side Chain Arrangement. *Journal of the American Chemical Society* 2009, 131, 18525-18532.
(5) Xia, Y.; Kornfield, J. A.; Grubbs, R. H.: Efficient Synthesis of Narrowly Dispersed Brush Polymers via Living Ring-Opening Metathesis Polymerization of Macromonomers. *Macromolecules* 2009, 42, 3761-3766.
(6) Verduzco, R.; Li, X.; Pesck, S. L.; Stein, G. E.: Structure, function, self-assembly, and applications of bottlebrush copolymers. *Chemical Society Reviews* 2015, 44, 2405-2420.
(7) Miyake, G. M.; Piunova, V. A.; Weitekamp, R. A.; Grubbs, R. H.: Precisely Tunable Photonic Crystals From Rapidly Self-Assembling Brush Block Copolymer Blends. *Angewandte Chemie International Edition* 2012, 51, 11246-11248.
(8) Barnes, J. C.; Bruno, P. M.; Nguyen, H. V. T.; Liao, L.; Liu, J.; Hemann, M. T.; Johnson, J. A.: Using an RNAi Signature Assay To Guide the Design of Three-Drug-Conjugated Nanoparticles with Validated Mechanisms, In Vivo Efficacy, and Low Toxicity. *Journal of the American Chemical Society* 2016, 138, 12494-12501.
(9) Kawamoto, K.; Zhong, M.; Gadelrab, K. R.; Cheng, L.-C.; Ross, C. A.; Alexander-Katz, A.; Johnson, J. A.: Graft-through Synthesis and Assembly of Janus Bottlebrush Polymers from A-Branch-B Diblock Macromonomers. *Journal of the American Chemical Society* 2016, 138, 11501-11504.

(10) Ren, J. M.; McKenzie, T. G.; Fu, Q.; Wong, E. H. H.; Xu, J.; An, Z.; Shanmugam, S.; Davis, T. P.; Boyer, C.; Qiao, G. G.: Star Polymers. *Chemical Reviews* 2016, 116, 6743-6836.

(11) Liao, L.; Liu, J.; Dreaden, E. C.; Morton, S. W.; Shopsowitz, K. E.; Hammond, P. T.; Johnson, J. A.: A Convergent Synthetic Platform for Single-Nanoparticle Combination Cancer Therapy: Ratiometric Loading and Controlled Release of Cisplatin, Doxorubicin, and Camptothecin. *Journal of the American Chemical Society* 2014, 136, 5896-5899.

(12) Sveinbjörnsson, B. R.; Weitekamp, R. A.; Miyake, G. M.; Xia, Y.; Atwater, H. A.; Grubbs, R. H.: Rapid self-assembly of brush block copolymers to photonic crystals. *Proceedings of the National Academy of Sciences* 2012, 109, 14332-14336.

(13) Fox, M. E.; Szoka, F. C.; Fréchet, J. M. J.: Soluble Polymer Carriers for the Treatment of Cancer: The Importance of Molecular Architecture. *Accounts of Chemical Research* 2009, 42, 1141-1151.

(14) Peer, D.; Karp, J. M.; Hong, S.; Farokhzad, O. C.; Margalit, R.; Langer, R.: Nanocarriers as an emerging platform for cancer therapy. *Nat Nano* 2007, 2, 751-760.

(15) Maeda, H.; Bharate, G. Y.; Daruwalla, J.: Polymeric drugs for efficient tumor-targeted drug delivery based on EPR-effect. *European Journal of Pharmaceutics and Biopharmaceutics* 2009, 71, 409-419.

(16) Staben, L. R.; Koenig, S. G.; Lehar, S. M.; Vandlen, R.; Zhang, D.; Chuh, J.; Yu, S.-F.; Ng, C.; Guo, J.; Liu, Y.; Fourie-O'Donohue, A.; Go, M.; Linghu, X.; Segraves, N. L.; Wang, T.; Chen, J.; Wei, B.; Phillips, G. D. L.; Xu, K.; Kozak, K. R.; Mariathasan, S.; Flygare, J. A.; Pillow, T. H.: Targeted drug delivery through the traceless release of tertiary and heteroaryl amines from antibody-drug conjugates. *Nature Chemistry* 2016, 8, 1112-1119.

(17) Burke, P. J.; Hamilton, J. Z.; Pires, T. A.; Setter, J. R.; Hunter, J. H.; Cochran, J. H.; Waight, A. B.; Gordon, K. A.; Toki, B. E.; Emmerton, K. K.; Zeng, W.; Stone, I. J.; Senter, P. D.; Lyon, R. P.; Jeffrey, S. C.: Development of Novel Quaternary Ammonium Linkers for Antibody-Drug Conjugates. *Molecular Cancer Therapeutics,* 2016, 15, 938-945.

(18) Tian, L.; Yang, Y.; Wysocki, L. M.; Arnold, A. C.; Hu, A.; Ravichandran, B.; Sternson, S. M.; Looger, L. L.; Lavis, L. D.: Selective esterase-ester pair for targeting small molecules with cellular specificity. *Proceedings of the National Academy of Sciences,* 2012, 109, 4756-4761.

What is claimed is:
1. A macromonomer of Formula (I):

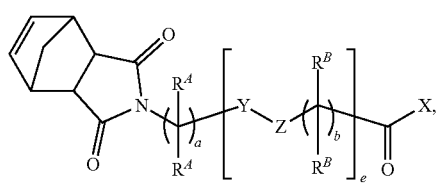

(I)

or a salt thereof, wherein:
each instance of $R^A$ is independently hydrogen, halogen, or substituted or unsubstituted, $C_{1-6}$ alkyl;
a is an integer from 1 to 20, inclusive;
each instance of —Y—Z— is

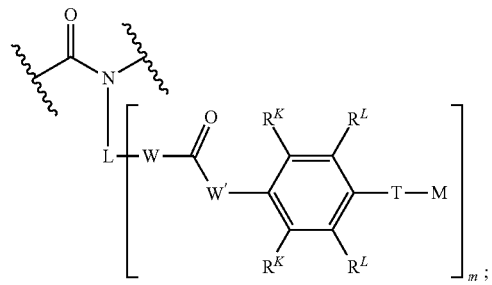

each instance of M is independently hydrogen or a pharmaceutical agent;
each instance of m is independently an integer from 1 to 10, inclusive;
each instance of L is independently substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or substituted or unsubstituted, $C_{2-200}$ heteroalkynylene, wherein:
optionally one or more carbons in each instance of the substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene; and
optionally one or more heteroatoms in each instance of the substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;
each instance of W is independently a single bond, —O—, —S—, or —$NR^E$—;
each instance of $R^E$ is independently hydrogen, substituted or unsubstituted, $C_{1-6}$ alkyl, or a nitrogen protecting group;
each instance of W' is independently —O—, —S—, or —$NR^J$—;
each instance of R' is independently hydrogen, substituted or unsubstituted, $C_{1-6}$ alkyl, or a nitrogen protecting group;
each instance of $R^K$ and $R^L$ is independently hydrogen, halogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 7-membered, monocyclic carbocyclyl, substituted or unsubstituted, 3- to 7-membered, monocyclic heterocyclyl, substituted or unsubstituted phenyl, substituted or unsubstituted, 5- or 6-membered, monocyclic heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC$ (=O)OR$^a$, —NR$^a$C(=O)N(R$^a$)$_2$, —OC(=O)R$^a$, —OC(=O)OR$^a$, or —OC(=O)N(R$^a$)$_2$;

each instance of R$^a$ is independently hydrogen, substituted or unsubstituted, C$_{1-6}$ alkyl, substituted or unsubstituted, C$_{2-6}$ alkenyl, substituted or unsubstituted, C$_{2-6}$ alkynyl, substituted or unsubstituted, 3- to 7-membered, monocyclic carbocyclyl, substituted or unsubstituted, 3- to 7-membered, monocyclic heterocyclyl, substituted or unsubstituted phenyl, substituted or unsubstituted, 5- or 6-membered, monocyclic heteroaryl, an oxygen protecting group when attached to an oxygen atom, a sulfur protecting group when attached to a sulfur atom, or a nitrogen protecting group when attached to a nitrogen atom; or two instances of R$^a$ attached to the same nitrogen atom are joined to form substituted or unsubstituted, 3- to 7-membered, monocyclic heterocyclyl, or substituted or unsubstituted, 5- or 6-membered, monocyclic heteroaryl;

each instance of T is independently a single bond, substituted or unsubstituted, C$_{1-20}$ alkylene, substituted or unsubstituted, C$_{2-20}$ alkenylene, substituted or unsubstituted, C$_{2-20}$ alkynylene, substituted or unsubstituted, C$_{2-20}$ heteroalkylene, substituted or unsubstituted, C$_{2-20}$ heteroalkenylene, or substituted or unsubstituted C$_{2-20}$ heteroalkynylene, wherein:

optionally one or more carbons in each instance of the substituted or unsubstituted, C$_{1-20}$ alkylene, substituted or unsubstituted, C$_{2-20}$ alkenylene, substituted or unsubstituted, C$_{2-20}$ alkynylene, substituted or unsubstituted, C$_{2-20}$ heteroalkylene, substituted or unsubstituted, C$_{2-20}$ heteroalkenylene, and substituted or unsubstituted, C$_{2-20}$ heteroalkynylene are independently replaced with substituted or unsubstituted carbocyclylene, substituted or unsubstituted heterocyclylene, substituted or unsubstituted arylene, or substituted or unsubstituted heteroarylene; and optionally one or more heteroatoms in each instance of the substituted or unsubstituted, C$_{2-20}$ heteroalkylene, substituted or unsubstituted, C$_{2-20}$ heteroalkenylene, and substituted or unsubstituted, C$_{2-20}$ heteroalkynylene are independently replaced with substituted or unsubstituted carbocyclylene, substituted or unsubstituted heterocyclylene, substituted or unsubstituted arylene, or substituted or unsubstituted heteroarylene;

each instance of R$^B$ is independently hydrogen, halogen, or substituted or unsubstituted, C$_{1-6}$ alkyl;

each instance of b is independently an integer from 1 to 20, inclusive;

e is an integer from 1 to 10, inclusive; and

X is —OR$^C$ or —N(R$^D$)$_2$, wherein:

R$^C$ is hydrogen, substituted or unsubstituted, C$_{1-1000}$ alkyl, substituted or unsubstituted, C$_{2-1000}$ alkenyl, substituted or unsubstituted, C$_{2-1000}$ alkynyl, substituted or unsubstituted, C$_{1-1000}$ heteroalkyl, substituted or unsubstituted, C$_{2-1000}$ heteroalkenyl, substituted or unsubstituted, C$_{2-1000}$ heteroalkynyl, an oxygen protecting group, or a leaving group; and each instance of R$^D$ is independently hydrogen, substituted or unsubstituted, C$_{1-1000}$ alkyl, substituted or unsubstituted, C$_{2-1000}$ alkenyl, substituted or unsubstituted, C$_{2-1000}$ alkynyl, substituted or unsubstituted, C$_{1-1000}$ heteroalkyl, substituted or unsubstituted, C$_{2-1000}$ heteroalkenyl, substituted or unsubstituted, C$_{2-1000}$ heteroalkynyl, or a nitrogen protecting group.

2. A method of preparing a macromonomer of claim 1, or a salt thereof, comprising coupling a compound of the formula:

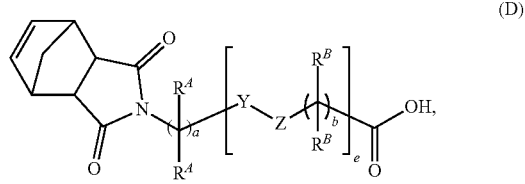

or a salt thereof, with a compound of the formula: HOR$^C$ or HN(R$^D$)$_2$, or a salt thereof.

3. A polymer prepared by polymerizing one or more types of macromonomers of claim 1, or a salt thereof, in the presence of a metathesis catalyst.

4. A method of preparing a polymer of claim 3 comprising polymerizing a macromonomer of Formula (I):

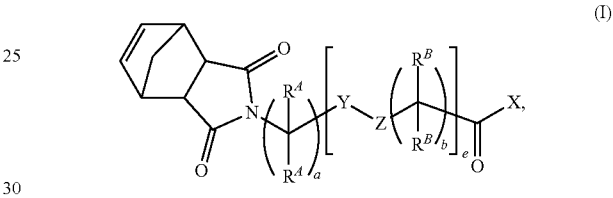

or a salt thereof, in the presence of a metathesis catalyst, wherein:

each instance of R$^A$ is independently hydrogen, halogen, or substituted or unsubstituted, C$_{1-6}$ alkyl;

a is an integer from 1 to 20, inclusive;

each instance of —Y—Z— is

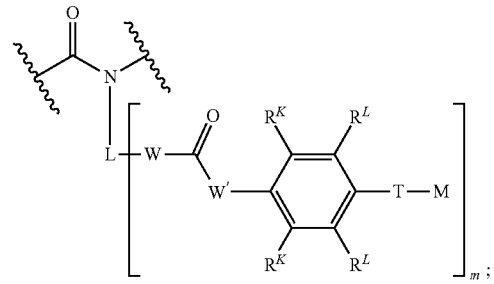

each instance of M is independently hydrogen or a pharmaceutical agent;

each instance of m is independently an integer from 1 to 10, inclusive;

each instance of L is independently substituted or unsubstituted, C$_{1-200}$ alkylene, substituted or unsubstituted, C$_{2-200}$ alkenylene, substituted or unsubstituted, C$_{2-200}$ alkynylene, substituted or unsubstituted, C$_{2-200}$ heteroalkylene, substituted or unsubstituted, C$_{2-200}$ heteroalkenylene, or substituted or unsubstituted, C$_{2-200}$ heteroalkynylene, wherein:

optionally one or more carbons in each instance of the substituted or unsubstituted, C$_{1-200}$ alkylene, substituted or unsubstituted, C$_{2-200}$ alkenylene, substituted or unsubstituted, C$_{2-200}$ alkynylene, substituted or unsubstituted, C$_{2-200}$ heteroalkylene, substituted or unsubstituted, C$_{2-200}$ heteroalkenylene, and substituted or unsubstituted, C$_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene; and optionally one or more heteroatoms in each instance of the substituted or unsubstituted, C$_{2-200}$ heteroalkylene, substituted or unsubstituted, C$_{2-200}$ heteroalkenylene, and substituted or unsubstituted, C$_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;

each instance of W is independently a single bond, —O—, —S—, or —NR$^E$—;

each instance of R$^E$ is independently hydrogen, substituted or unsubstituted, C$_{1-6}$ alkyl, or a nitrogen protecting group;

each instance of W' is independently —O—, —S—, or —NR$^J$—;

each instance of R' is independently hydrogen, substituted or unsubstituted, C$_{1-6}$ alkyl, or a nitrogen protecting group;

each instance of R$^K$ and R$^L$ is independently hydrogen, halogen, substituted or unsubstituted, C$_{1-6}$ alkyl, substituted or unsubstituted, C$_{2-6}$ alkenyl, substituted or unsubstituted, C$_{2-6}$ alkynyl, substituted or unsubstituted, 3- to 7-membered, monocyclic carbocyclyl, substituted or unsubstituted, 3- to 7-membered, monocyclic heterocyclyl, substituted or unsubstituted phenyl, substituted or unsubstituted, 5- or 6-membered, monocyclic heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

each instance of R$^a$ is independently hydrogen, substituted or unsubstituted, C$_{1-6}$ alkyl, substituted or unsubstituted, C$_{2-6}$ alkenyl, substituted or unsubstituted, C$_{2-6}$ alkynyl, substituted or unsubstituted, 3- to 7-membered, monocyclic carbocyclyl, substituted or unsubstituted, 3- to 7-membered, monocyclic heterocyclyl, substituted or unsubstituted phenyl, substituted or unsubstituted, 5- or 6-membered, monocyclic heteroaryl, an oxygen protecting group when attached to an oxygen atom, a sulfur protecting group when attached to a sulfur atom, or a nitrogen protecting group when attached to a nitrogen atom; or two instances of R$^a$ attached to the same nitrogen atom are joined to form substituted or unsubstituted, 3- to 7-membered, monocyclic heterocyclyl, or substituted or unsubstituted, 5- or 6-membered, monocyclic heteroaryl;

each instance of T is independently a single bond, substituted or unsubstituted, C$_{1-20}$ alkylene, substituted or unsubstituted, C$_{2-20}$ alkenylene, substituted or unsubstituted, C$_{2-20}$ alkynylene, substituted or unsubstituted, C$_{2-20}$ heteroalkylene, substituted or unsubstituted, C$_{2-20}$ heteroalkenylene, or substituted or unsubstituted, C$_{2-20}$ heteroalkynylene, wherein:

optionally one or more carbons in each instance of the substituted or unsubstituted, C$_{1-20}$ alkylene, substituted or unsubstituted, C$_{2-20}$ alkenylene, substituted or unsubstituted, C$_{2-20}$ alkynylene, substituted or unsubstituted, C$_{2-20}$ heteroalkylene, substituted or unsubstituted, C$_{2-20}$ heteroalkenylene, and substituted or unsubstituted, C$_{2-20}$ heteroalkynylene are independently replaced with substituted or unsubstituted carbocyclylene, substituted or unsubstituted heterocyclylene, substituted or unsubstituted arylene, or substituted or unsubstituted heteroarylene; and optionally one or more heteroatoms in each instance of the substituted or unsubstituted, C$_{2-20}$ heteroalkylene, substituted or unsubstituted, C$_{2-20}$ heteroalkenylene, and substituted or unsubstituted, C$_{2-20}$ heteroalkynylene are independently replaced with substituted or unsubstituted carbocyclylene, substituted or unsubstituted heterocyclylene, substituted or unsubstituted arylene, or substituted or unsubstituted heteroarylene;

each instance of R$^B$ is independently hydrogen, halogen, or substituted or unsubstituted, C$_{1-6}$ alkyl;

each instance of b is independently an integer from 1 to 20, inclusive;

e is an integer from 1 to 10, inclusive; and

X is —OR$^C$ or —N(R$^D$)$_2$, wherein:

R$^C$ is hydrogen, substituted or unsubstituted, C$_{1-1000}$ alkyl, substituted or unsubstituted, C$_{2-1000}$ alkenyl, substituted or unsubstituted, C$_{2-1000}$ alkynyl, substituted or unsubstituted, C$_{1-1000}$ heteroalkyl, substituted or unsubstituted, C$_{2-1000}$ heteroalkenyl, substituted or unsubstituted, C$_{2-1000}$ heteroalkynyl, an oxygen protecting group, or a leaving group; and each instance of R$^D$ is independently hydrogen, substituted or unsubstituted, C$_{1-1000}$ alkyl, substituted or unsubstituted, C$_{2-1000}$ alkenyl, substituted or unsubstituted, C$_{2-1000}$ alkynyl, substituted or unsubstituted, C$_{1-1000}$ heteroalkyl, substituted or unsubstituted, C$_{2-1000}$ heteroalkenyl, substituted or unsubstituted, C$_{2-1000}$ heteroalkynyl, or a nitrogen protecting group.

5. A method of preparing a polymer of claim 3 comprising polymerizing a first macromonomer of Formula (I):

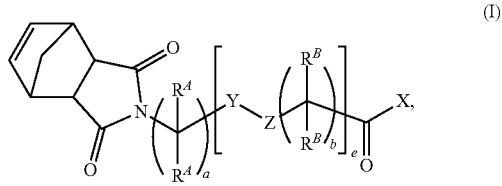

(I)

or a salt thereof, and a second macromonomer of Formula (I), or a salt thereof, in the presence of a metathesis catalyst, wherein at least one instance of M of the first macromonomer is different from at least one instance of M of the second macromonomer, and wherein:

each instance of R$^A$ is independently hydrogen, halogen, or substituted or unsubstituted, C$_{1-6}$ alkyl;

a is an integer from 1 to 20, inclusive;

each instance of —Y—Z— is

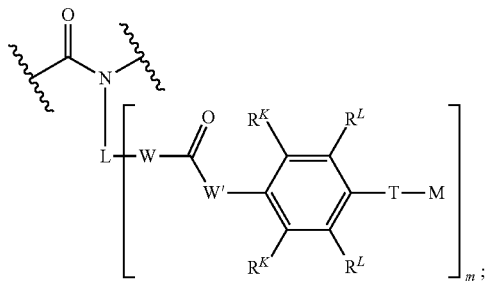

each instance of M is independently hydrogen or a pharmaceutical agent;

each instance of m is independently an integer from 1 to 10, inclusive;

each instance of L is independently substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or substituted or unsubstituted, $C_{2-200}$ heteroalkynylene, wherein:

optionally one or more carbons in each instance of the substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene; and optionally one or more heteroatoms in each instance of the substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;

each instance of W is independently a single bond, —O—, —S—, or —NR$^E$—;

each instance of R$^E$ is independently hydrogen, substituted or unsubstituted, $C_{1-6}$ alkyl, or a nitrogen protecting group;

each instance of W' is independently —O—, —S—, or —NR$^J$—;

each instance of R$^J$ is independently hydrogen, substituted or unsubstituted, $C_{1-6}$ alkyl, or a nitrogen protecting group;

each instance of R$^K$ and R$^L$ is independently hydrogen, halogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 7-membered, monocyclic carbocyclyl, substituted or unsubstituted, 3- to 7-membered, monocyclic heterocyclyl, substituted or unsubstituted phenyl, substituted or unsubstituted, 5- or 6-membered, monocyclic heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

each instance of R$^a$ is independently hydrogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted, 3- to 7-membered, monocyclic carbocyclyl, substituted or unsubstituted, 3- to 7-membered, monocyclic heterocyclyl, substituted or unsubstituted phenyl, substituted or unsubstituted, 5- or 6-membered, monocyclic heteroaryl, an oxygen protecting group when attached to an oxygen atom, a sulfur protecting group when attached to a sulfur atom, or a nitrogen protecting group when attached to a nitrogen atom; or two instances of R$^a$ attached to the same nitrogen atom are joined to form substituted or unsubstituted, 3- to 7-membered, monocyclic heterocyclyl, or substituted or unsubstituted, 5- or 6-membered, monocyclic heteroaryl;

each instance of T is independently a single bond, substituted or unsubstituted, $C_{1-20}$ alkylene, substituted or unsubstituted, $C_{2-20}$ alkenylene, substituted or unsubstituted, $C_{2-20}$ alkynylene, substituted or unsubstituted, $C_{2-20}$ heteroalkylene, substituted or unsubstituted, $C_{2-20}$ heteroalkenylene, or substituted or unsubstituted, $C_{2-20}$ heteroalkynylene, wherein:

optionally one or more carbons in each instance of the substituted or unsubstituted, $C_{1-20}$ alkylene, substituted or unsubstituted, $C_{2-20}$ alkenylene, substituted or unsubstituted, $C_{2-20}$ alkynylene, substituted or unsubstituted, $C_{2-20}$ heteroalkylene, substituted or unsubstituted, $C_{2-20}$ heteroalkenylene, and substituted or unsubstituted, $C_{2-20}$ heteroalkynylene are independently replaced with substituted or unsubstituted carbocyclylene, substituted or unsubstituted heterocyclylene, substituted or unsubstituted arylene, or substituted or unsubstituted heteroarylene; and optionally one or more heteroatoms in each instance of the substituted or unsubstituted, $C_{2-20}$ heteroalkylene, substituted or unsubstituted, $C_{2-20}$ heteroalkenylene, and substituted or unsubstituted, $C_{2-20}$ heteroalkynylene are independently replaced with substituted or unsubstituted carbocyclylene, substituted or unsubstituted heterocyclylene, substituted or unsubstituted arylene, or substituted or unsubstituted heteroarylene;

each instance of R$^B$ is independently hydrogen, halogen, or substituted or unsubstituted, $C_{1-6}$ alkyl;

each instance of b is independently an integer from 1 to 20, inclusive;

e is an integer from 1 to 10, inclusive; and

X is —OR$^C$ or —N(R$^D$)$_2$, wherein:

R$^C$ is hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, an oxygen protecting group, or a leaving group; and each instance of R$^D$ is independently hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, or a nitrogen protecting group.

6. A pharmaceutical composition comprising a polymer of claim 3 and optionally a pharmaceutically acceptable excipient.

7. A kit comprising:
a macromonomer of claim 1, or a salt thereof; and
instructions for using the macromonomer, or a salt thereof.

8. A method of delivering a pharmaceutical agent to a subject in need thereof comprising administering to the subject in need thereof a polymer of claim 3.

9. A method of delivering a pharmaceutical agent to a cell comprising contacting the cell with a polymer of claim 3.

10. A method of treating a disease in a subject in need thereof comprising administering to or implanting in the subject in need thereof a therapeutically effective amount of:
a polymer of claim 3;
wherein at least one instance of M is a therapeutic agent.

11. A method of preventing a disease in a subject in need thereof comprising administering to or implanting in the subject in need thereof a prophylactically effective amount of:
a polymer of claim 3;
wherein at least one instance of M is a prophylactic agent.

12. A method of diagnosing a disease in a subject comprising administering to or implanting in the subject a diagnostically effective amount of:
a polymer of claim 3;
wherein at least one instance of M is a diagnostic agent.

13. A kit comprising:
a polymer of claim 3; and
instructions for using the polymer.

14. The polymer of claim 3, wherein each instance of $R^A$ and $R^B$ is hydrogen.

15. The polymer of claim 14, wherein each instance of —Y—Z— is

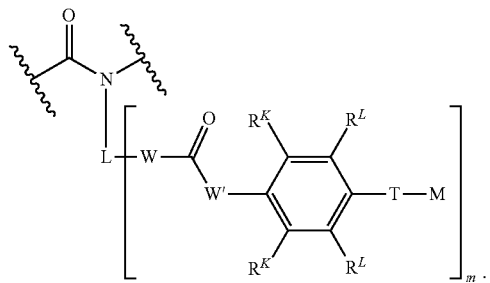

16. The polymer of claim 15, wherein each instance of L is independently substituted or unsubstituted, $C_{1-200}$ alkylene or substituted or unsubstituted, $C_{2-200}$ heteroalkylene, wherein one or more carbons in the $C_{1-200}$ alkylene or $C_{2-200}$ heteroalkylene are replaced with substituted or unsubstituted heteroarylene.

17. The polymer of claim 15, wherein each instance of L is substituted or unsubstituted, $C_{3-30}$ alkylene.

18. The polymer of claim 16, wherein each instance of W is a single bond.

19. The polymer of claim 18, wherein each instance of $R^K$ is hydrogen, and each instance of $R^L$ is hydrogen.

20. The polymer of claim 19, wherein each instance of T is independently a single bond, substituted or unsubstituted, $C_{1-20}$ alkylene, or substituted or unsubstituted, $C_{2-20}$ heteroalkylene, and each instance of M is a pharmaceutical agent.

21. The polymer of claim 20, wherein X is —N($R^D$)$_2$.

22. The polymer of claim 21, wherein each instance of $R^D$ is independently hydrogen or substituted or unsubstituted, $C_{1-1000}$ heteroalkyl, provided that at least one instance of $R^D$ is substituted or unsubstituted, $C_{50-1000}$ heteroalkyl.

23. The polymer of claim 3, wherein the macromonomer is of the formula:

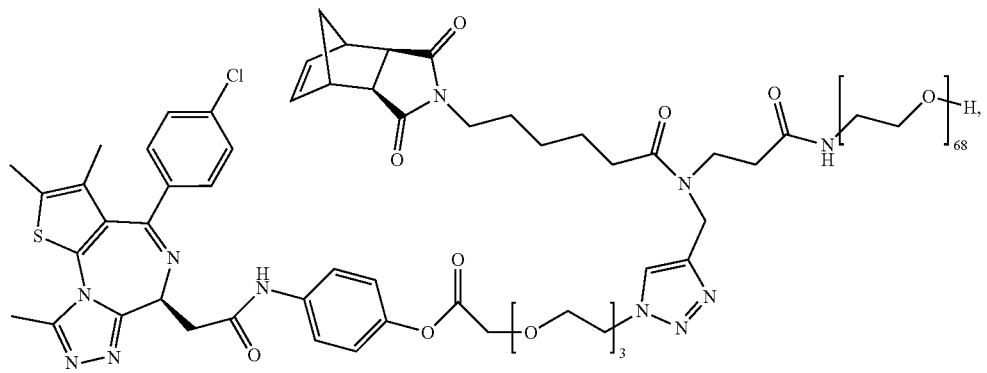

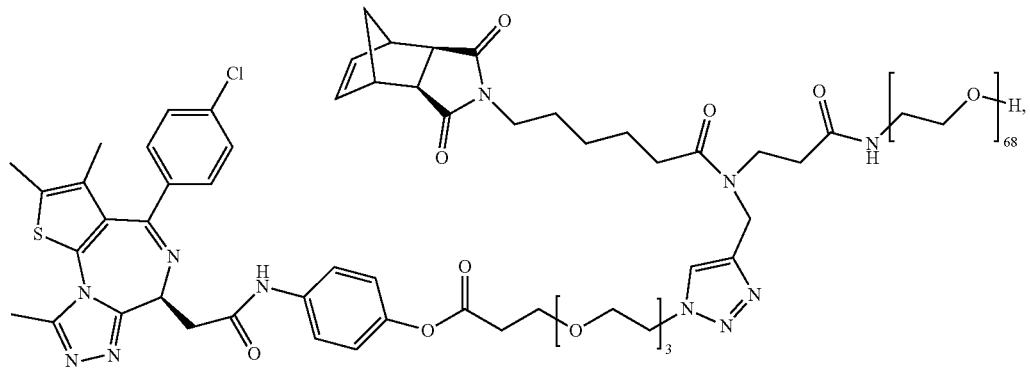

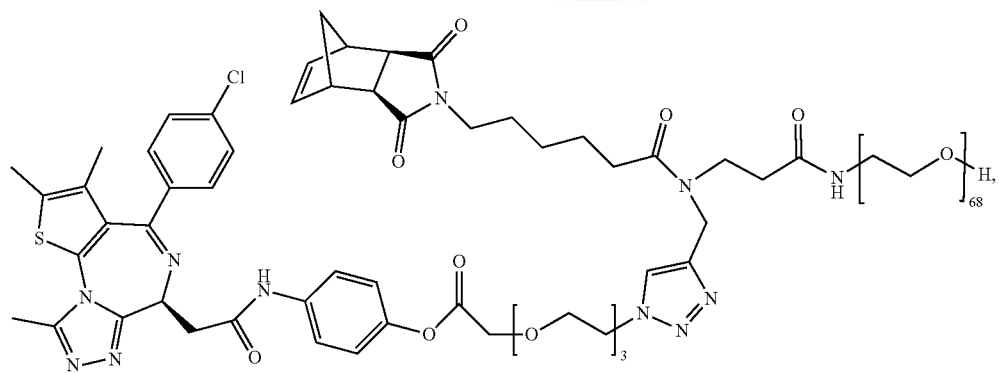
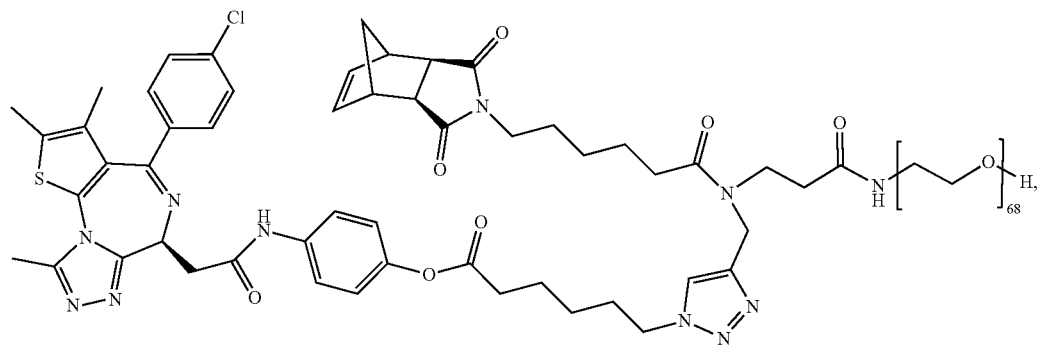
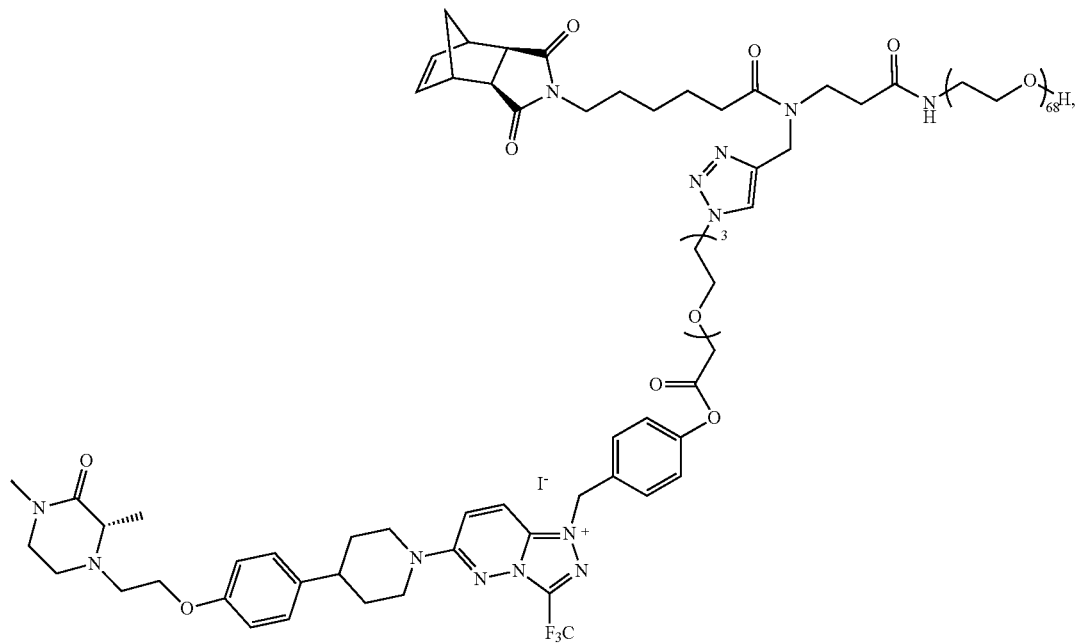

-continued
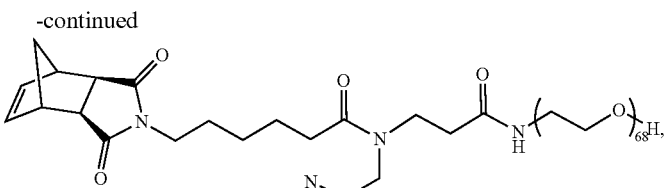
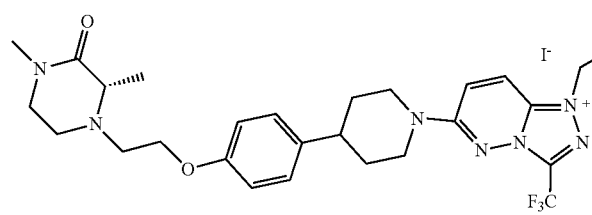
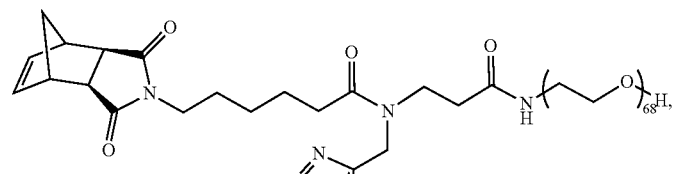
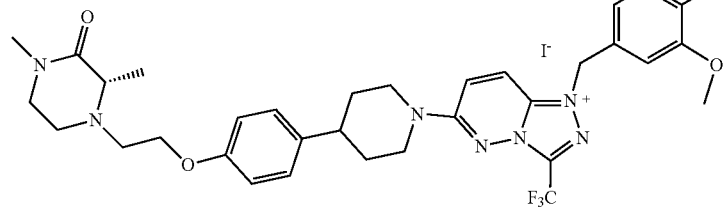

-continued
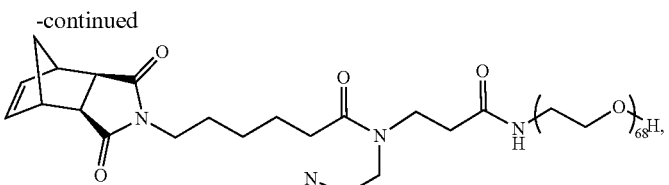
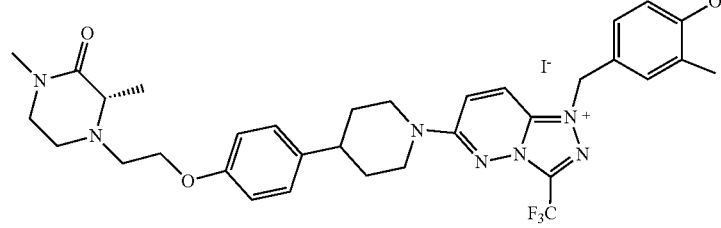
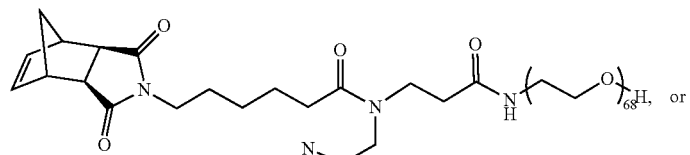
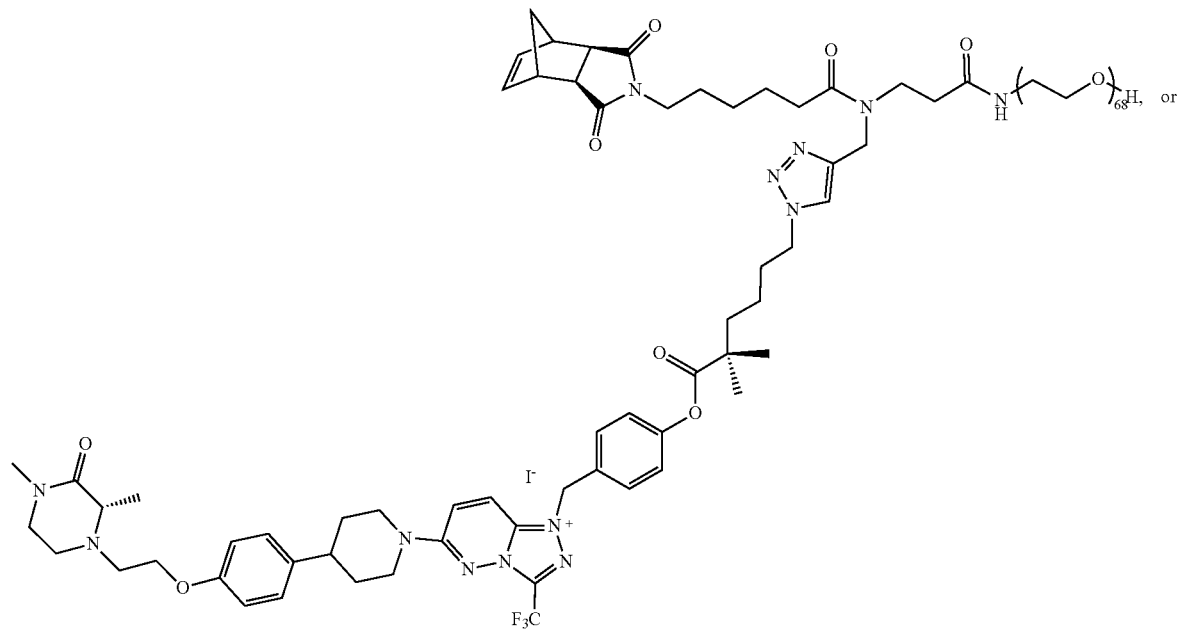

-continued
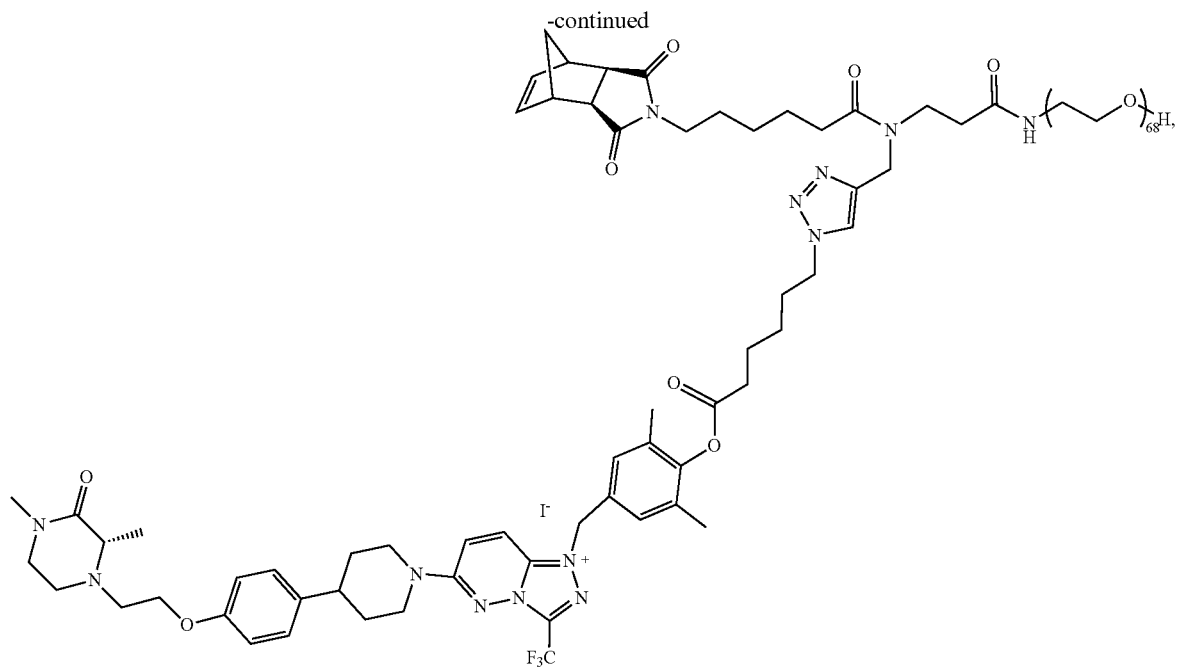
or a salt thereof.
24. The polymer of claim 3, wherein the macromonomer is of the formula:
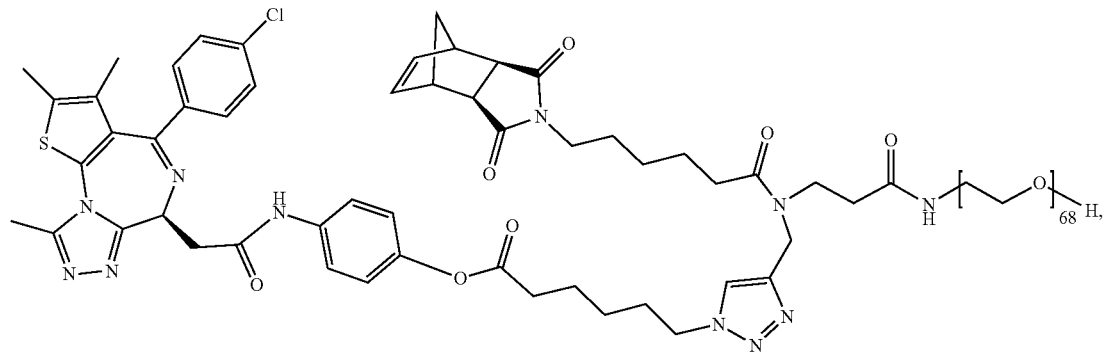
or a salt thereof.
25. The macromonomer of claim 1, or a salt thereof, wherein the macromonomer is of the formula:
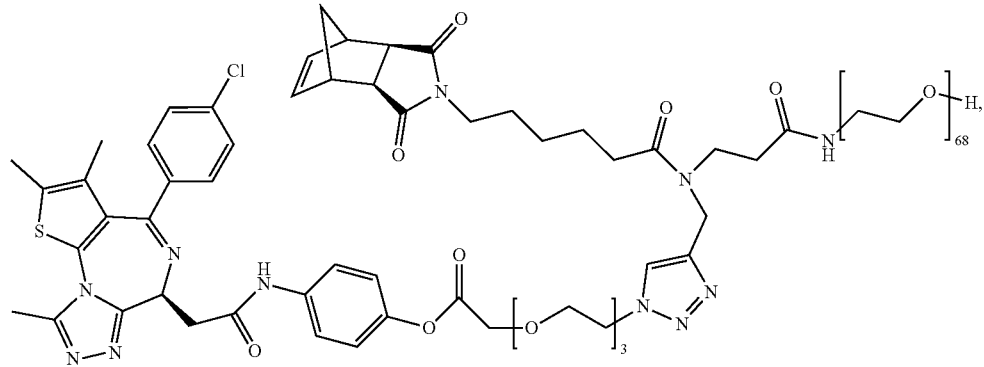

-continued
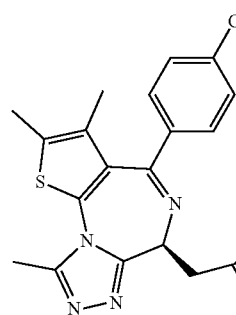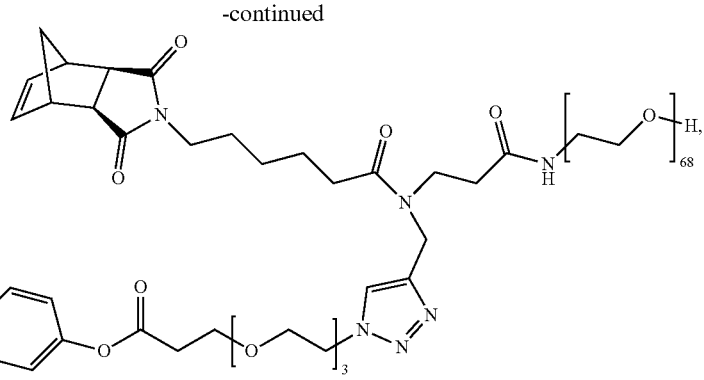
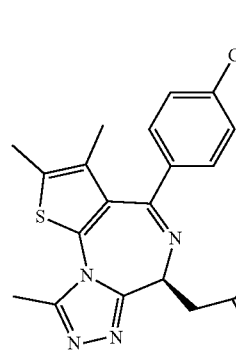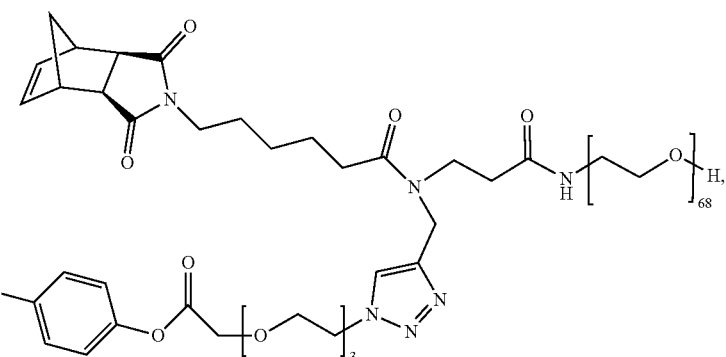
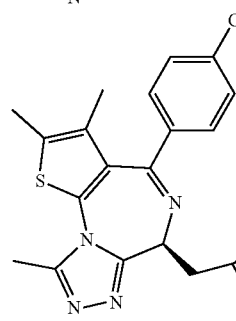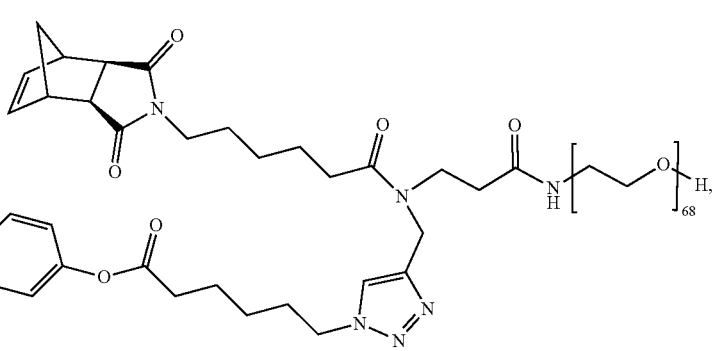
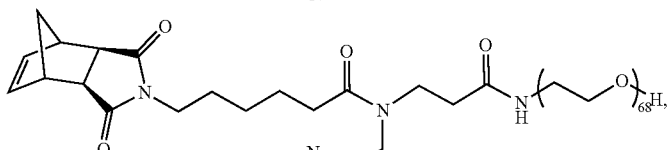
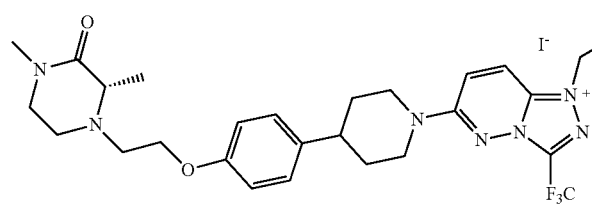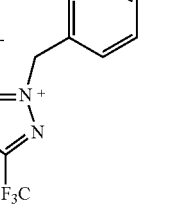

-continued
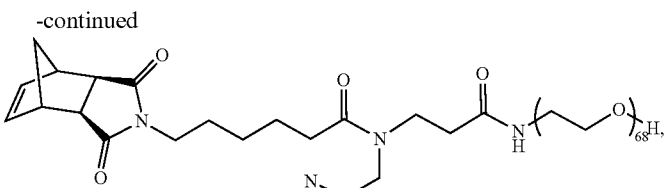
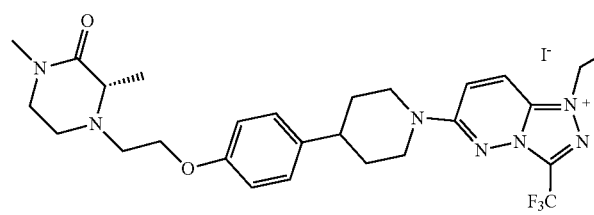
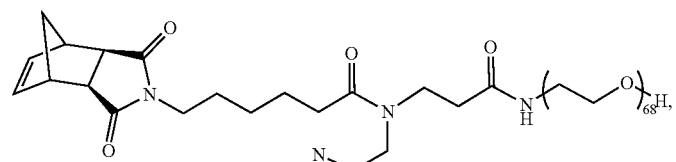
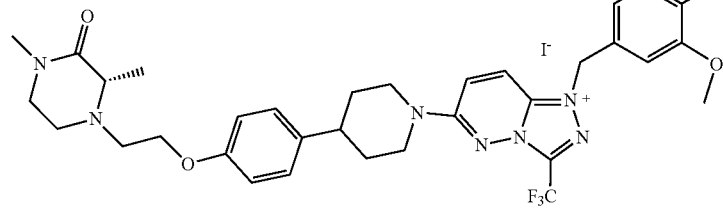

-continued
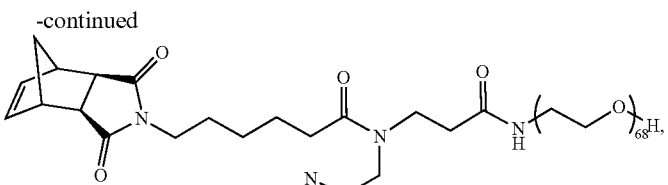
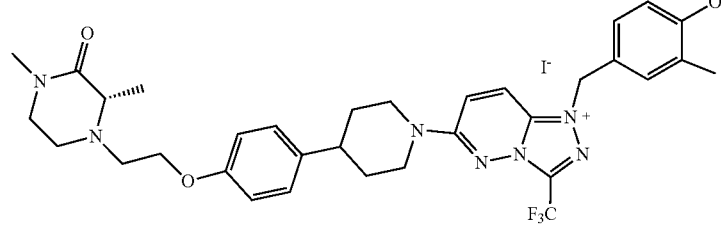
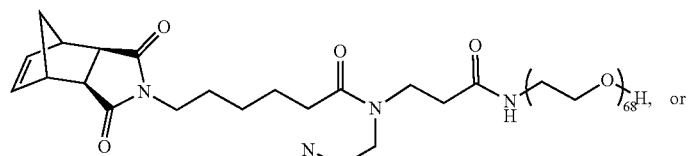
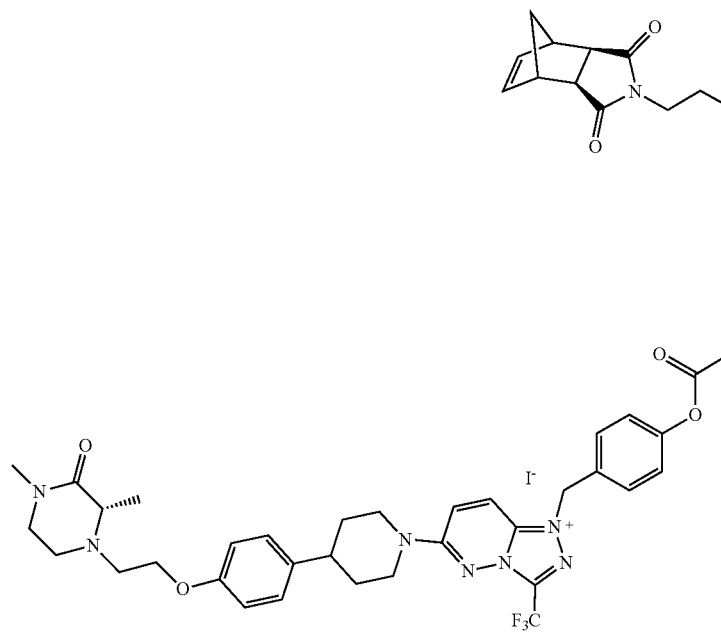

-continued

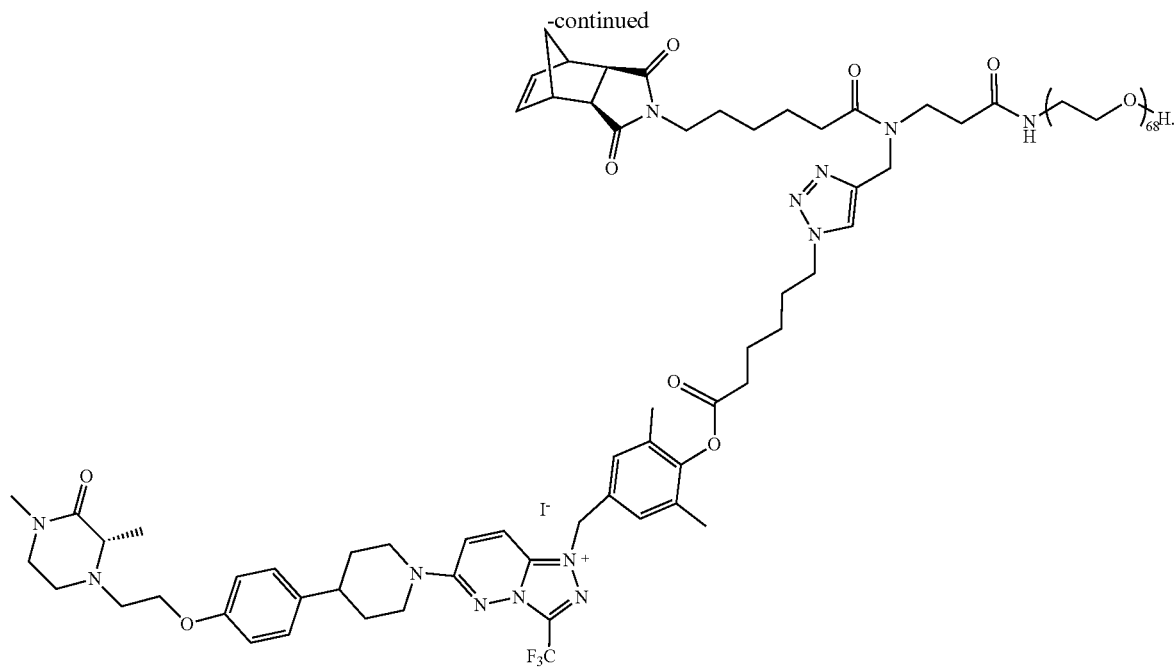

26. The macromonomer of claim 1, or a salt thereof, wherein the macromonomer is of the formula:

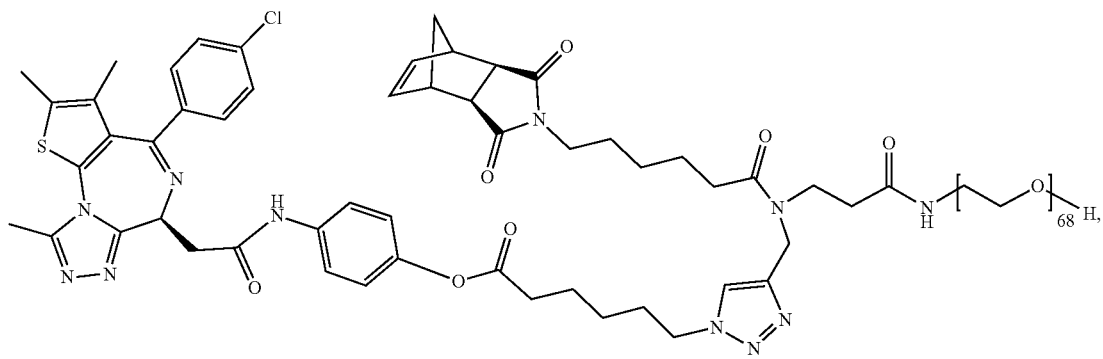

27. The polymer of claim 21, wherein X is

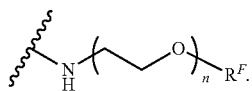

n is an integer from 40 to 100, inclusive; and $R^F$ is hydrogen or unsubstituted $C_{1-6}$ alkyl.

28. The polymer of claim 27, wherein each instance of M is an anti-cancer agent.

29. The polymer of claim 28, wherein each instance of m is independently 1, 2, or 3, and e is 1, 2, or 3.

30. The macromonomer of claim 1, or a salt thereof, wherein each instance of $R^A$ and $R^B$ is hydrogen.

31. The macromonomer of claim 30, or a salt thereof, wherein each instance of —Y—Z— is

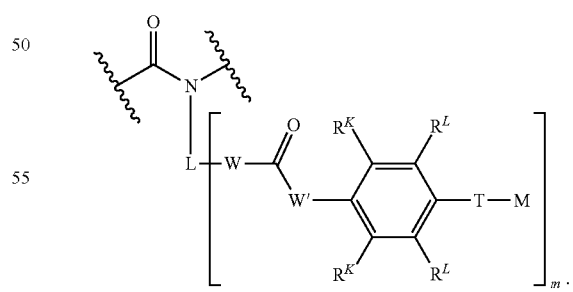

32. The macromonomer of claim 31, or a salt thereof, wherein each instance of L is independently substituted or unsubstituted, $C_{1-200}$ alkylene or substituted or unsubstituted, $C_{2-200}$ heteroalkylene, wherein one or more carbons in the $C_{1-200}$ alkylene or $C_{2-200}$ heteroalkylene are replaced with substituted or unsubstituted heteroarylene.

33. The macromonomer of claim 31, or a salt thereof, wherein each instance of L is substituted or unsubstituted, $C_{3-30}$ alkylene.

34. The macromonomer of claim 32, or a salt thereof, wherein each instance of W is a single bond.

35. The macromonomer of claim 34, or a salt thereof, wherein each instance of $R^K$ is hydrogen, and each instance of $R^L$ is hydrogen.

36. The macromonomer of claim 35, or a salt thereof, wherein each instance of T is independently a single bond, substituted or unsubstituted, $C_{1-20}$ alkylene, or substituted or unsubstituted, $C_{2-20}$ heteroalkylene, and each instance of M is a pharmaceutical agent.

37. The macromonomer of claim 36, or a salt thereof, wherein X is $-N(R^D)_2$.

38. The macromonomer of claim 37, or a salt thereof, wherein each instance of $R^D$ is independently hydrogen or substituted or unsubstituted, $C_{1-1000}$ heteroalkyl, provided that at least one instance of $R^D$ is substituted or unsubstituted, $C_{50-1000}$ heteroalkyl.

39. The macromonomer of claim 37, or a salt thereof, wherein X is

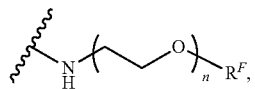

n is an integer from 40 to 100, inclusive; and $R^F$ is hydrogen or unsubstituted $C_{1-6}$ alkyl.

40. The macromonomer of claim 39, or a salt thereof, wherein each instance of M is an anti-cancer agent.

41. The macromonomer of claim 40, or a salt thereof, wherein each instance of m is independently 1, 2, or 3, and e is 1, 2, or 3.

* * * * *